US007951384B2

(12) United States Patent
Morrison et al.

(10) Patent No.: US 7,951,384 B2
(45) Date of Patent: May 31, 2011

(54) VIRUS-LIKE PARTICLES AS VACCINES FOR PARAMYXOVIRUS

(75) Inventors: Trudy Morrison, Northborough, MA (US); Homer D. Pantua, Worcester, MA (US)

(73) Assignee: University of Massachusetts, Boston, MA (US)

( * ) Notice: Subject to any disclaimer, the term of this patent is extended or adjusted under 35 U.S.C. 154(b) by 950 days.

(21) Appl. No.: 11/497,888

(22) Filed: Aug. 2, 2006

(65) Prior Publication Data

US 2007/0178120 A1    Aug. 2, 2007

(51) Int. Cl.
*A61K 39/17* (2006.01)
*C12P 21/00* (2006.01)
*C12N 7/04* (2006.01)

(52) U.S. Cl. ............... 424/214.1; 435/69.1; 435/236; 530/350

(58) Field of Classification Search .............. None
See application file for complete search history.

(56) References Cited

U.S. PATENT DOCUMENTS

| | | | |
|---|---|---|---|
| 4,774,339 A | 9/1988 | Haugland et al. | 548/405 |
| 5,098,825 A | 3/1992 | Tchen et al. | 435/6 |
| 5,187,288 A | 2/1993 | Kang et al. | 548/110 |
| 5,248,782 A | 9/1993 | Haugland et al. | 548/110 |
| 5,274,113 A | 12/1993 | Kang et al. | 548/405 |
| 5,433,896 A | 7/1995 | Kang et al. | 252/700 |
| 5,451,663 A | 9/1995 | Kang et al. | 530/367 |
| 5,690,938 A | 11/1997 | Ermak et al. | 424/215.1 |
| 5,804,196 A | 9/1998 | Mazzara et al. | 424/208.1 |
| 5,916,879 A | 6/1999 | Webster | 514/44 |
| 6,013,772 A | 1/2000 | Barnett et al. | 530/387.7 |
| 6,328,972 B1 | 12/2001 | Rock | 424/196.11 |
| 6,602,705 B1 | 8/2003 | Barnett et al. | 435/320.1 |
| 6,875,592 B2 | 4/2005 | Rothschild et al. | 435/91.1 |
| 6,913,881 B1 | 7/2005 | Aizenstein et al. | 435/6 |
| 2004/0009193 A1 | 1/2004 | Morikawa | 424/208.1 |
| 2004/0105871 A1 | 6/2004 | Robinson et al. | 424/199.1 |
| 2005/0002953 A1 | 1/2005 | Herold | 424/186.1 |

OTHER PUBLICATIONS

Schmitt et al. (Journal of Virology, Apr. 2002, vol. 76, No. 8, pp. 3952-3964).*
Hui et al. (Journal of Virology, Jun. 2003, vol. 77, No. 12, pp. 7078-7092).*
Ong et al. (Cytotechnology, 2000, vol. 32, pp. 243-251).*
Maeda A, et al., Isolation and characterization of defective interfering particle of Newcastle disease virus. Microbiol Immunol. 1978 vol. 22(12):775-84. Abstract only.*
Alexander D.J., "Newcastle disease, other avian paramyxoviruses, and pneumovirus infections,"In *Diseases of Poultry*, Barnes et al. Editors 11th Ed., Ch. 2, pp. 63-99 (2003).
Ali et al., Assembly of Sendai virus: M protein interacts with F and HN proteins and with the cytoplasmic tail and transmembrane domain of F protein *Virology* 276:289-303 (2000).

Aslanidis et al., "Ligation-independent cloning of PCR products (LIC-PCR)" *Nucleic Acids Res.* 18:6069-6074 (1990).
Babst et al., "ESCRT-III: an endosome-associated heterooligomeric protein complex required for MBV sorting" *Dev Cell* 3:271-282 (2002).
Belyaev et al., "High-level expression of five foreign genes by a single recombinant baculovirus," *Gene* 156:229-233 (1995).
Belyaev et al., "Development of baculovirus triple and quadruple expression vectors: co-expression of three or four bluetongue virus proteins and the synthesis of blue tongue virus-like particles in insect cells," *Nucleic Acids Res.* 21:1219-1223 (1993).
Bieniasz, P. D., "Late budding domains and host proteins in enveloped virus release" *Virology* 344:55-63 (2006).
Boublik et al., "Eukary virus diaplay: engineering the major surface glycoprotein of the autographa californica nuclear polyhedrosis virus (AcNPV) for the presentation of foreign proteins on the virus surface,"*Bio/Technology* 13:1079-1084 (1995).
Carter, C. A., "Tsg101: HIV-1 's ticket to ride," *Trends Microbiol.* 10:203-205 (2002).
Cathomen et al., "A matrix-less measles virus is infectious and elicits extensive cell fusion: consequences for propagation in the brain," *EMBO J.* 17:3899-3908 (1998).
Chanock, et al., Parainfluenza Viruses, in Fields Virology, Ed. Knipe, D. and Howley, P. Lippincott Williams and Wilkins, Chapter 24, pp. 1341-1379 (2001), Chapter 42.
Chen et al., "Functions of early (AP-2) and late (AIPI/ALIX) endocytic proteins in equine infectious anemia virus budding," *J Biol Chem* , 280:40474-40480 (2005).
Chubet et al., "Vectors for expression and secretion of FLAG epitope-tagged proteins in mammalian cells" *Biotechniques* 20:136-41 (1996).
Collins, et al, Respiratory Syncytial Virus, in Fields Virology, Ed. Knipe, D. and Howley, P. Lippincott Williams and Wilkins, 2001, p. 1443.
Coronel et al., "Human parainfluenza virus type 1 matrix and nucleoprotein genes transiently expressed in 12 mammalian cells induce the release of virus-like particles containing 13 nucleocapsid-like structures," *J. Virol.* 73:7035-8 (1999).
Delchambre et al., "The GAG precursor of simian immunodeficiency virus assembles into virus-like particles," *EMBO J* 8:2653-60 (1989).
Demirov et al., "Retrovirus budding," *Virus Res* 106:87-102 (2004).
DiCesare et al., "A high-sensitivity electrochemiluminescence-based detection system for automated PCR product quantitation," *BioTechniques* 15:152-59 (1993).
Dolganiuc et al., "Role of the cytoplasmic domain of the Newcastle disease virus fusion protein in association with lipid rafts," *J Virol* 77:12968-12979 (2003).

(Continued)

Primary Examiner — Zachariah Lucas
Assistant Examiner — Myron G Hill
(74) Attorney, Agent, or Firm — Medlen & Carroll, LLP

(57) ABSTRACT

The present invention discloses the method of making and using a novel, non-infective, paramyxovirus vaccine. Paramyxovirus structural proteins within a virus-like particle (VLP) comprise one example of such a vaccine. It is observed that the presence of matrix protein, alone, is sufficient and necessary to provide an effective VLP release. Co-expression of four paramyxovirus structural proteins, however, result in the release of non-infective VLPs with densities and efficiencies of release similar to that of infective particles. Representative diseases wherein a VLP vaccine might be useful include, but are not limited to, Newcastle disease, measles, respiratory syncytial virus infection, and parainfluenza 3 virus infection.

45 Claims, 91 Drawing Sheets
(1 of 91 Drawing Sheet(s) Filed in Color)

OTHER PUBLICATIONS

Duck et al., "Probe amplifier system based on chimeric cycling oligonucleotides," *BioTech.*, 9:142-147 (1990).
Faeberg et al., "Strain variation and nuclear association of 20 NDV matrix protein," *J Virol.* 62:586-593 (1988).
Freed, E. O., "Mechanisms of enveloped virus release," *Virus Res* 106:85-86 (2004).
Freed, E. O., "Viral late domains," *J. Virol.* 76:4679-87 (2002).
Freed, E. O., "The HIV-TSG101 interface: recent advances in a budding field," *Trends Microbiol.* 11:56-9 (2003).
Garoff et al., "Virus Maturation by Budding," *Microbiol Mol Biol Rev* 62:1171-1190 (1998).
Garrus et al., "Tsg101 and the vacuolar protein sorting pathway are essential for HIV-1 budding," *Cell* 107:55-65 (2001).
Gheysen et al., "Assembly and release of HIV-1 precursor Pr55$^{gag}$ virus-like particles from recombinant baculovirus-infected insect cells," *Cell* 59:103-12 (1989).
Ghildyal et al., "Interaction between the respiratory syncytial virus G glycoprotein cytoplasmic domain and the matrix protein," *J Gen Virol* 86:1879-1884 (2005).
Gomez-Puertas et al., "Influenza virus matrix protein is the major driving force in virus budding," *J. Virol.*74:11538-47 (2000).
Gonzalez-Reyes, et al, "Cleavage of the human respiratory syncytial virus fusion protein at two distinct sites is required for activation of membrane fusion," PNAS 98:9859-9864 (2001).
Greenberg et al., "Immunization against viral respiratory disease: A review," *Pediatr Infect Dis J .* 23(11):S254-61 (2004).
Henderson et al., "Sorting of the respiratory syncytial virus matrix protein into detergent-resistant structures is dependent on cell-surface expression of the glycoproteins," *Virology* 300:244-254 (2002).
Herbst et al., "HAM: a new epitope-tag for in vivo protein labeling," *Mol Biol Rep.* 27:203-8 (2000).
Huang et al., "p6$^{Gag}$ is required for particle production from full-length human immunodeficiency virus type 1 molecular clones expressing protease," *J Virol* 69:6810-6818 (1995).
Hui et al., "YRKL sequence of influenza virus M1 functions as the L domain motif and interacts with VPS28 and Cdc42," *J Virol* 80:2291-2308 (2006).
Inoue et al., "A new Sendai virus vector deficient in the matrix gene does not form virus particles and shows extensive cell-to-cell spreading," *J. Virol.* 77:6419-29 (2003).
Irie et al., "Budding of PPxY-containing rhabdoviruses is not dependent on host proteins TGS101 and VPS4A," *J Virol* 78:2657-2665 (2004).
Jasenosky et al., "Ebola virus VP40-induced particle formation and association with the lipid bilayer," *J. Virol.* 75:5205-14 (2001).
Jasenosky et al., "Filovirus budding," *Virus Res*. 106:181-188 (2004).
Jayakar et al., "Rhabdovirus assembly and budding," *Virus Res*. 106:117-32 (2004).
Jiang et al., "Multivesicular bodies: a mechanism to package lytic and storage functions in one organelle?," *Trends Cell Biol.* 12:362-7 (2002).
Katzmann et al., "Ubiquitin-dependent sorting into the multivesicular body pathway requires the function of a conserved endosomal protein sorting complex, ESCRT-1," *Cell* 106:145-55 (2001).
Katzmann et al., "Vps27 recruits ESCRT machinery to endosomes during MVB sorting," *J Cell Biol.* 162:413-23 (2003).
Kennedy et al., "Measles virus infection and vaccination: potential role in chronic illness and associated adverse events," *Crit Rev Immunol.* 24(2):129-56 (2004).
Kitts et al., "A method for producing recombinant baculovirus expression vectors at high frequency," *BioTechniques* 14:810-817 (1993).
Lamb et al., "Paramyxoviridae: The Viruses and Their Replication" Chapter 41, pp. 1305-1340. In: *Fields Virology, Third Edition*, vol. 1., Eds: D. M. K. &. P. M. Howley, LippincottWilliams & Wilkins, Philadelphia (2001).
Levinson et al., "Radiation studies of avian tumor viruses and Newcastle disease virus," *Virology* 28:533-542 (1966).
Li et al., "Effect of cleavage mutants on syncytium formation directed by the wild-type fusion protein of Newcastle disease virus," *J. Virol.* 72:3789-95 (1998).
Li et al., "Viral liposomes released from insect cells infected with recombinant baculovirus expressing the matrix protein of vesicular stomatitis virus," *J. Virol.* 67:4415-20 (1993).
Martindale, D., "Budding viral hijackers co-opt the endocytic machinery to make a getaway," *J Biol.* 3:2-2.5 (2003).
Martin-Serrano et al., "Role of ESCRT-1 in retroviral budding," *J Virol* 77:4794-4804 (2003).
McGinnes et al., "Newcastle disease virus HN protein alters the conformation of the F protein at cell surfaces," *J. Virol.* 76:12622-33 (2002).
McGinnes et al., "Role of carbohydrate processing and calnexin binding in the folding and activity of the HN protein of Newcastle disease virus," *Virus Res* 53:175-85 (1998).
Mebatsion et al., "Matrix protein of rabies virus is responsible for the assembly and budding of bullet-shaped particles and interacts with the transmembrane spike glycoprotein G," *J. Virol.* 73:242-50 (1999).
Miyazaki et al., "Expression vector system based on the chicken beta-actin promoter directs efficient production of interleukin-5," *Gene* 79:269-77 (1989).
Morita et al., "Retrovirus budding," *Annu Rev Cell Dev Biol* 20:395-425 (2004).
Nagy et al., "Synthesis of newcastle disease virus (NDV)-like envelopes in insect cells infected with a recombinant baculovirus expressing the haemagglutinin-neuraminidase of NDV," *J Gen Virol.* 72:753-756 (1991).
Nayak et al., "Assembly and budding of influenza virus," *Virus Res* 106:147-65 (2004).
Niwa et al., "Efficient selection for high-expression transfectants with a novel eukaryotic vector," *Gene* 108:193-9 (1991).
Noad et al., "Virus-like particles as immunogens," *Trends Microbiol* 11:438-444 (2003).
Panch et al., "In vivo oligomerization and raft localization of Ebola virus protein VP40 during vesicular budding," *PNAS, USA* 100:15936-41 (2003), Panchal.
Patterson et al., "Evidence that the hypermutated M protein of a subacute sclerosing panencephalitis measles virus actively contributes to the chronic progressive CNS disease," *Virology* 291:215-25 (2001).
Peeples M. E., "Paramyxovirus M proteins: pulling it all together and taking it on the road," Chapter 16, pp. 427-456. In: *The Paramyxoviruses*, Ed: D. W. Kingsbury, Plenum, New York, N. Y (1991).
Pornillos et al., "Mechanisms of enveloped RNA virus budding," *Trends Cell Biol.* 12:569-79 (2002).
Pornillos et al., "HIV Gag mimics the Tsg101-recruiting activity of the human Hrs protein," *J Cell Biol* 162:425-34 (2003).
Puffer et al., "Equine infectious anemia virus utilizes a YXXL motif within the late assembly domain of the Gag p9 protein," *J Virol* 71:6541-6546 (1997).
Raiborg et al., "Protein sorting into multivesicular endosomes," *Curr Opin Cell Biol* 15:446-55 (2003).
Richards et al., In: *The Enzymes*, Bovine Pancreatic Ribonuclease vol. IV (Boyer, P.D., Ed.), Ch. 24, pp. 647-806, Academic Press, New York (1971).
Sakaguchi et al., "Double-layered membrane vesicles released from mammalian cells infected with Sendai virus expressing the matrix protein of vesicular stomatitis virus," *Virology* 263:230-43 (1999).
Sanderson et al., "Sendai virus assembly:M protein binds to viral glycoproteins in transit through the secretory pathway," *J Virol* 67:651-663 (1993).
Schmitt et al., "Escaping from the cell: assembly and budding of negative-strand RNA viruses," *Curr Top Microbiol Immunol* 283:145-96 (2004).
Schmitt et al., "Evidence for a new viral late-domain core sequence, FPIV, necessary for budding of a paramyxovirus," *J. Virol.* 79:2988-97 (2005).
Schmitt et al., "Requirements for budding of paramyxovirus simian virus 5 virus-like particles," *J Virol* 76:3952-64 (2002).
Simons et al., "The budding mechanisms of enveloped animal viruses," *J. Gen. Virol.* 50:1-21 (1980).
Strack et al., "AIP1/ALIX is a binding partner for HIV-1 p6 and EIAV p9 functioning in virus budding," *Cell* 114:689-699 (2003).

Stricker et al., "The Sendai virus matrix protein appears to be recruited in the cytoplasm by the viral nucleocapsid to function in viral assembly and budding," *J Gen Virol* 75 (Pt 5):1031-1042 (1994).

Sugahara et al., "Paramyxovirus Sendai virus-like particle formation by expression of multiple viral proteins and acceleration of its release by C protein," *Virology* 325:1-10 (2004).

Takimoto et al., "Molecular mechanism of paramyxovirus budding," *Virus Res.* 106:133-45 (2004).

Takimoto et al., "Role of matrix and fusion proteins in budding of Sendai virus," *J. Virol.* 75: 11384-91 (2001).

Terpe K., "Overview of tag protein fusions: from molecular and biochemical fundamentals to commercial systems," *Appl Microbiol Biotechnol.* 60:523-33 (2003).

Timmins et al., "Vesicular release of Ebola virus matrix protein VP40," *Virology* 283: 1-6 (2001).

Urdea et al., "A novel method for the rapid detection of specific nucleotide sequences in crude biological samples without blotting or radioactivity; application to the analysis of hepatitis B virus in human serum," *Gene* 61:253-264 (1987).

Vana et al., "Role of Nedd4 and ubiquitination of *Rous sarcoma* virus Gag in budding of virus-like particles from cells," *J Virol* 78:13943-13953 (2004).

Varshney et al., "Direct analysis of aminoacylation levels of tRNA in vitro," *J. Biol. Chem.* 266:24712-24718 (1991).

Vincent, et al., "Inefficient measles virus budding in murine L.CD46," *Virology* 265:185-195 (1999).

von Schwedler et al., "The protein network of HIV budding," *Cell* 114:701-13 (2003).

Weyer et al., "A baculovirus dual expression vector derived from the autographa californica nuclear polyhedrosis virus polyhedrin and p10 promoters: co-expression of two influenza virus genes in insect cells," *J. Gen. Virol.* 72:2967-2974 (1991).

Willenbrink et al., "Long-term replication of sendai virus defective interfering particle nucleocapsids in stable helper cell lines," *J. Virol.* 68:8413-8417 (1994).

Wunderlich et al., "Use of recombinant fusion proteins for generation and rapid characterization of monoclonal antibodies," *J. Immunol. Methods* 147:1-11 (1992.

Xiang et al., "Fine mapping and characterization of the *Rous sarcoma* virus Pr76$^{gag}$ late assembly domain," *J Virol* 70:5695-5700 (1996).

Yoshida et al., "Membrane (M) protein of HVJ (sendai virus): Its role in virus assembly" *Virology* 71:143-161 (1976).

Fouillot-Coriou et al., "Structure-Function Analysis of the Sendai Virus F and HN Cytoplasmic Domain: Different Role for the Two Proteins in the Production of Virus Particle," *Virology*. 270: 464-475 (2000).

Li et al., "Mumps Virus Matrix, Fusion, and Nucleocapsid Proteins Cooperate for Efficient Production of Virus-Like Particles," *J. Virol.* 1-37 (2009).

Sugahara et al., "Paramyxovirus Sendai virus-like particle formation by expression of multiple viral proteins and acceleration of its release by C protein" Virology 325:1-10 (2004).

Teng et al., "Identification of the Respiratory Syncytial Virus Proteins Required for Formation and Passage of Helper-Dependent Infectious Particles," *J. Virology.* 72: 5707-5716 (1998).

Hui et al., "Basic Residues Of The Helix Six Domain Of Influenza Virus M1 Involved in Nuclear Translocation of M1 Can Be Replaced by PTAP and YPDL Late Assembly Domain Motifs" *J. Virology* 80:10289 (2006).

Pantua et al., "Requirements For The Assembly And Release Of Newcastle Disease Virus-Like Particles" *J. Virology.* 80:11062-11073 (2006).

Coronel et al., "Human Parainfluenza Virus Type 1 Matrix And Nucleoprotein Genes Transiently Expressed In Mammalian Cells Induce The Release Of Virus-Like Particles Containing Nucleocapsid-Like Structures" *J. Virology.* 73: 7035-7038 (1999).

Cathomen et al., "A matrix-less measles virus is infectious and elicits extensive cell fusion: consequences for propagation in the brain" *The EMBO Journal* 17:3899-3908 (1998).

* cited by examiner

PARAMYXOVIRUS VIRIONS

MEMBRANE COMPONENTS

CORE COMPONENTS

HN, H, G (ATTACHMENT PROTEIN)

F (FUSION PROTEIN)

M (MEMBRANE PROTEIN)

LIPID

RNA+NP (NUCLEOCAPSID PROTEIN)

P (PHOSPHOPROTEIN)

L (LARGE

FIG. 6

PARAMYXOVIRUS INFECTIOUS CYCLE

VIRUS ENTRY

FUSION

ATTACHMENT

VIRUS REPLICATION

INFECTED CELL

ASSEMBLY

VIRUS PARTICLES ARE RELEASED FROM INFECTED CELL SURFACES

BUDDING

RELEASE

VIRION FORMATION

FIG. 7

MSSVFDEYEQLLAAQTRPNGTHGGGEKGSTLKVEVPVFTLNSDD
PEDRWNFAVFCLRIAVSEDANKPLRQGALISLLCSHSQVMRNHVALAGKQNEATLAVL
EIDSFADSVPQFNNRSGVSEERAQRFMVIAGSLPRACSNGTPFVTAGVEDDAPEDITD
TLERILSIQAQVWVTVAKAMTAYETADESETRRINKYMQQGRVQKKYILHPVCRSAIQ
LTIRHSLAVRIFLVSELKRGRNTAGGSSTYYNLVGDVDSYIRNTGLTAFFLTLKYGIN
TKTSALALSSLTGDIQKMKQLMRLYRMKGENAPYMTLLGDSDQMSFAPAEYAQLYSFA
MGMASVLDKGTGKYQFARDFMSTSFWRLGVEYAQAQGSSINEDMAAELKLNPAARRGL
AAAAQRVSEEIGNMDIPTQQAGVLTGLSDKGPRAPQGGPSRSQGQPDAGDGETQFLDL
MRAVANSMREAPNSAQSTIHPEPLPTHGPSQDNDTDWGY

FIG. 8A

```
   1 atgtcgtccg tatttgacga atacgagcag ctcctcgctg ctcagacccg ccctaacgga
  61 actcatggag ggggagagaa agggagcact ttaaaagttg aggtcccagt atttaccctt
 121 aacagtgatg atccagagga tagatggaat tttgcggtat tctgtcttcg gattgctgtt
 181 agcgaggatg ccaacaaacc actcaggcaa ggtgctctta tatcccctctt atgctcccat
 241 tctcaggtga tgagaaacca cgttgcccctt gcagggaaac agaatgaggc tacactggct
 301 gttcttgaga tcgatagttt tgccgacagt gtgccccagt tcaacaatag gagtggagtg
 361 tctgaggaaa gagcacagag attcatggta atagcaggat ctctccctcg ggcatgcagc
 421 aacggtactc cgttcgtcac agctggggtt gaagatgatg caccagaaga tatcactgac
 481 actctggaaa gaatcctatc tatccaggct caggtatggg tcacagtagc aaaggccatg
 541 actgcatatg agacagcaga tgagtcggaa acaagaagaa taaataagta tatgcagcaa
 601 ggtagagtcc agaagaaata catccttcac cctgtatgca ggagtgcaat tcaactcaca
 661 atcagacatt ctctggcagt ccgtattttc ctagttagtg agctcaagag gggccgcaat
 721 acagcaggtg ggagctccac atattacaac ttggtcgggg atgtagactc atacatcaga
 781 aacaccgggc ttactgcatt tttcctaaca ctcaaatatg gaatcaatac caagacgtca
 841 gccctcgcac tcagcagcct cacaggtgat atccaaaaaa tgaaacagct catgcgttta
 901 tatcggatga aggtgaaaa tgcaccatac atgacattgt taggtgacag tgaccagatg
 961 agctttgcac cagctgagta tgcacaactt tattcttttg ccatgggcat ggcatcagtc
1021 ttagataagg gaactggcaa ataccaattc gccagagact tcatgagcac atcattctgg
1081 agactcgggg tggagtatgc tcaggctcag gaagtagca tcaatgaaga tatggctgct
1141 gaattgaaac ttaacccagc agcaaggagg ggcctggcag ctgctgccca acgagtatct
1201 gaggaaattg gcaacatgga tattcctact caacaggccg ggtccttac tgggctcagc
1261 gacaaaggtc cccgagctcc acaggtggat ccgagcaggt cgcaagggca accggacgcc
1321 ggggatgggg agacccaatt cctggatctg atgagagcag tggcaaacag catgcgagaa
1381 gcgccaaatt ctgcacagag caccattcac ccggagcctc tcccaactca tgggccatct
1441 caagacaacg acaccgactg ggggtactga
```

FIG. 8B

MDRVVSRVVLENEEREAKNTWRLVFRIAVLSLVVMTLAISVATL
VYSMEASTPGDLAGISTVISKAEDKVISLLSSNQDVVDRVYKQVALESPLALLNTESV
IMNAITSLSYQINGAANNSGCGAPVHDPDYVGGVGKELIVDDTSDVTSFYPSAYQEHL
NFIPAPTTGSGCTRIPSFDMSATHYCYTHNVILSGCRDHSHSHQYLALGVLRTSATGR
VFFSTLRSINLDDTQNRKSCSVSATPLGCDMLCSKVTEIEEEDYKSATPTSMVHGRLG
FDGQYHEKDLDVTALFKDWVANYPGVGGGSLIGDRVWFPVYGGLKPNSPSDIAQEGRY
VIYKRYNNTCPDEQDYQVRMAKSSYKPGRFGGKRVQQAILSIKVSVSLGEDPVLTVPP
NTVTLMGAEGRVLTVGTSHFLYQRGSSYFSPALLYPMTIHNKTATLHSPYTFNAFTRP
GSVPCQASARCPNSCITGVYTDPYPVVFHKNHTLRGVFGTMLDNEQARFNPVSAVFDY
TSRSRITRVSSSSTKAAYTTSTCFKVVKTNKIYCLSIAEISNTLFGEFRIVPLLVEIL
KDDRV

FIG. 9A

```
   1 acgggtagaa cggtgggaga ggccacccct tagtggggaa ccaagcttct taacgtccgt
  61 tctaccgcat taccaatagc ataccttagt catggatcgt gtagttagta gggttgtact
 121 agagaatgag gaaagagaag caaagaacac atggcgcctg gtttttcgga tcgcagtctt
 181 atctctagta gtaatgactt tagctatctc tgttgccacc ctagtataca gcatggaggc
 241 tagcacaccg ggcgatctgg cgggcatatc gacggtgatc tctaaggcag aggataaggt
 301 gatatctcta ctcagttcaa atcaagatgt ggtagatagg gtatataaac aggtggccct
 361 tgagtcccca ctggcattgc tgaatactga gtctgtaatt atgaatgcaa taacttctct
 421 ctcctatcaa attaacggag ccgcaaataa tagtgggtgt ggggcacctg ttcatgaccc
 481 agattacgtt gggggagtag gcaaagagct catagtagat gacacaagtg atgtcacatc
 541 attctaccct tcagcatacc aagaacacct gaattttatc ccggcgccta ctacaggatc
 601 aggctgcact cggataccct cgttcgacat gagcgctacc cattattgtt atactcacaa
 661 tgtaatatta tctggttgca gagatcactc acactcacat cagtatttag cactaggtgt
 721 acttcggaca tctgcaacag ggagggtatt cttttctact ctgcgctcca tcaatttgga
 781 tgacacccaa aatcggaagt cttgcagtgt gagtgcgact cctttaggtt gtgatatgct
 841 gtgctctaaa gtcacagara ttgaagagga ggattataag tcagctactc ccacatcaat
 901 ggtgcatgga aggttaggrt ttgacggtca gtatcatgag aaggacttag acgtcacagc
 961 cttatttaag gattgggttg caaattatcc aggagtggga ggagggtctc ttattggcga
1021 ccgtgtatgg ttcccagttt atggagggct taaacccaat tcgcctagtg acattgcaca
1081 agaggggaga tatgtaatat ataagcgcta taataacaca tgccccgatg aacaggatta
1141 ccaagttcgg atggctaagt cttcatataa gcctggacgg tttggtggaa agcgcgtaca
1201 gcaagccatc ttatctatca agtatcagt atctttgggc gaggacccgg tgctaaccgt
1261 accccctaat acagttacac tcatggggc cgaaggcagg gtcctcacag tagggacatc
1321 tcacttcttg taccaacgag ggtcttcata cttctctccc gccttactat accctatgac
1381 aatacacaac aaaacagcta ctcttcatag tccctataca ttcaatgctt tcactcggcc
1441 aggcagtgtc cctgccagg catcagcaag gtgccccaac tcatgcatca ctggagtcta
1501 tactgatcca tatcctgtgg tctttcataa gaatcacacc ctgcgagggg tattcgggac
1561 gatgcttgat aatgaacaag caaggttcaa ccctgtatct gcagtatttg attacacatc
1621 tcgcagtcgc ataacccggg taagttcgag cagcaccaag cagcataca cgacatcgac
1681 atgttttaaa gttgtcaaga ccaataaaat ttattgtctt agcattgcag aaatatccaa
1741 tacctatttt ggggaattca ggattgtccc tctactggtt gagatcctca aggatgatag
1801 ggtttaagag gctaagttca gccggccggg tcaaccacga ggaagacggg aagatggcgt
1861 tgtgtcacct accctctgca atgccaagga tcaagcggaa taataatact agcccgaatc
1921 tcatgctatc agacagcctt aatcggataa tgctgacacg atcagcttga atcctgtcaa
1981 tagtcactct gtttagaaaa aatatgagag gtggtgggat ataagagaaa caacttaca
2041 gaagatagca cgggtaggac atggcgggct ccggtcccga aagggcagag caccagatta
2101 tcctaccaga gtcacacctg
```

FIG. 9B

MGSKPSTRIPVPMMLITQIVLILSCICLTSSLDGRPLAAAGIVV
TGDKAVNIYTSSQTGSIIVKLLPNMPKDKEACAKAPLEAYNRTLTTLLTPLGDSIRRI
QGSVSTSRGRRQKRFIGAIIGSVALGVATSAQITAAAALIQANQNAANILRLKESIAA
TNEAVHEVTDGLSQLAVAVGKMQQFVNDQFNNTARELDCIKITQQVGIELNLYLTELT
TVFGPQITSPALTQLTIQALYNLAGGNMDYLLTKLGVG

FIG. 10A

```
  1 tgaggttact tctactaggt tagagaagag gcacaccatt gctaaataca atcctttcaa
 61 gaagtaagtt gcgtccctga gactgcgatc cacccacttt cctggatcat cgcaacgcaa
121 aataatgatc tgtctcgatt gcttgcagtt ggttcacctg tctatctagt tagaaaaaac
181 acgggtagaa gagtctggat cccagctggc acattcaagg tgcagtatgg gctctaaacc
241 ttctaccagg atcccagtac ctatgatgct gatcacccaa attgtgttga tactgagctg
301 tatctgtctg acaagctccc ttgacggcag gcctcttgca gctgcgggga ttgtggtaac
361 aggagataaa gcagtcaata tatacacctc atctcagacg gggtcaatca tagtcaagtt
421 gctcccaaat atgcccaagg ataaagaggc gtgtgcaaaa gccccgttag aagcatacaa
481 cagaacactg accactttac tcaccccctc tggtgattcc atccgcagga tacaagggtc
541 tgtgtccaca tcaagaggaa ggagacagaa acgctttata ggtgccatta tcggcagtgt
601 agctcttggg gtcgcaacat cggcacagat aacagcagct gcggccctaa tacaagccaa
661 ccagaatgcc gccaacatcc tccggcttaa ggagagcatt gctgcaacca atgaagctgt
721 gcatgaggtc accgacggat tatcgcaact agcagtggca gttgggaaga tgcagcagtt
781 tgttaatgac caatttaata atacggcgcg agaattggac tgtatcaaaa ttacacaaca
841 agtcggtata gaactcaacc tatacctaac tgagttgact acagtgttcg ggccacaaat
901 cacttcccct gccctaactc agctgactat ccaggcactt tataatttag ctggtggcaa
961 catggattac ttgttgacta agttaggcgt agg
```

FIG. 10B

MDSSRTIGLYFDSALPSSNLLAFPIVLQDTGDGKKQFAPQYRIQ
RLDSWTDSKEDSVFITTYGFIFQVGDEEATVGMINDEPKRELLSAAMLCLGSVPNVGD
LVELARACLTMAVTCKKSATNTERMVFSVVQAPQVLQSCRVVANKYSSVNAVKHVKAP
EKIPGSGTLEYKVNFVSLTVVPRKDVYKIPTAALKVSGSSLYNLALNVTIDVEVDPKS
PLVKSLSKSDSGYYANLFLHIGLMSTVDKKGKKVTFDKLEKKIRRLDLSVGLSDVLGP
SVLVKARGARTKLMAPFFSSSGTACYPIANASPQVAKILWSQTAHLRSVKVIIQAGTQ
RAVAVTADHEATSTKLEKGHTHSKYNPFKK

FIG. 11A

```
   1 atggactcat ctaggacaat cggactgtac tttgattctg cccttccttc tagcaacttg
  61 ttagcattcc cgatcgtcct acaggacaca ggagatggaa agaagcaatt cgccccgcaa
 121 tataggatcc agcgtcttga ctcgtggacc gatagtaaag aagactcagt attcatcaca
 181 acctatggat tcatcttcca ggtcggggat gaggaagcca ctgtcggtat gatcaatgat
 241 gaacccaagc gcgagttact ttctgctgca atgctctgtc taggaagtgt cccaaacgtc
 301 ggagatctcg ttgagctggc aagggcctgt ctcaccatgg cagtcacatg caagaagagt
 361 gcaactaata ctgagaggat ggttttctca gtggtgcagg caccacaagt gctgcagagc
 421 tgcagggttg tggcaaataa atattcgtca gtgaatgctg ttaagcacgt gaaggcgcca
 481 gagaagatcc ctggaagcgg gaccctagag tacaaggtga actttgtctc cttgaccgtg
 541 gtaccgagaa aggatgtcta caagatccca accgcagcat gaaggtttc tggttcgagt
 601 ctgtataatc ttgcgctcaa tgtcaccatt gatgtggagg tggatccgaa gagcccgttg
 661 gttaaatcgc tatctaagtc tgacagtggc tattacgcta atctcttctt gcatattgga
 721 cttatgtcca ctgtagataa gaaggggaag aaagtgacat tgacaaatt ggaaaagaag
 781 ataaggagac ttgatctatc tgtcgggctc agtgacgtgc ttggaccttc cgtgttggtg
 841 aaggcaagag gtgcacggac caaattgatg gcacctttct cctccagtag tggaacagcc
 901 tgctacccca tagcgaatgc ctctcctcag gtagccaaga tactctggag tcaaaccgcg
 961 cacctgcgga gtgtgaaagt catcatccaa gcaggcaccc aacgcgccgt cgcagtgact
1021 gctgaccacg aggctacatc caccaagctg gaaaaggggc atacccattc caaatacaat
1081 ccttttcaaga aatag
```

FIG. 11B

```
   1 ttctctgtca cagaatgaaa attttctgt catctcttcg ttattaatgt tgtaattga
  61 ctgaatatca acgcttattt gcagcctgaa tggcgaatgg gacgcgccct gtagcggcgc
 121 attaagcgcg gcgggtgtgg tggttacgcg cagcgtgacc gctacacttg ccagcgccct
 181 agcgcccgct cctttcgctt tcttcccttc ctttctcgcc acgttcgccg gctttccccg
 241 tcaagctcta aatcggggc tccctttagg gttccgattt agtgctttac ggcacctcga
 301 ccccaaaaaa cttgattagg gtgatggttc acgtagtggg ccatcgccct gatagacggt
 361 ttttcgccct tgacgttgg agtccacgtt ctttaatagt ggactcttgt tccaaactgg
 421 aacaacactc aaccctatct cggtctattc ttttgattta taagggattt tgccgatttc
 481 ggcctattgg ttaaaaatg agctgattta acaaaattt aacgcgaatt taacaaaat
 541 attaacgttt acaatttcag gtggcacttt tcggggaaat gtgcgcggaa ccctatttg
 601 tttatttttc taaatacatt caaatatgta tccgctcatg agacaataac cctgataaat
 661 gcttcaataa tattgaaaaa ggaagagtat gagtattcaa catttccgtg tcgcccttat
 721 tcccttttt gcggcatttt gccttcctgt ttttgctcac cagaaacgc tggtgaaagt
 781 aaaagatgct gaagatcagt tgggtgcacg agtgggttac atcgaactgg atctcaacag
 841 cggtaagatc cttgagagtt ttcgccccga agaacgtttt ccaatgatga gcacttttaa
 901 agttctgcta tgtggcgcgg tattatcccg tattgacgcc gggcaagagc aactcggtcg
 961 ccgcatacac tattctcaga atgacttggt tgagtactca ccagtcacag aaaagcatct
1021 tacggatggc atgacagtaa gagaattatg cagtgctgcc ataaccatga gtgataacac
1081 tgcggccaac ttacttctga caacgatcgg aggaccgaag gagctaaccg cttttttgca
1141 caacatgggg gatcatgtaa ctcgccttga tcgttgggaa ccggagctga atgaagccat
1201 accaaacgac gagcgtgaca ccacgatgcc tgtagcaatg gcaacaacgt tgcgcaaact
1261 attaactggc gaactactta ctctagcttc ccggcaacaa ttaatagact ggatggaggc
1321 ggataaagtt gcaggaccac ttctgcgctc ggcccttccg gctggctggt ttattgctga
1381 taaatctgga gccggtgagc gtgggtctcg cggtatcatt gcagcactgg ggccagatgg
1441 taagccctcc cgtatcgtag ttatctacac gacggggagt caggcaacta tggatgaacg
1501 aaatagacag atcgctgaga taggtgcctc actgattaag cattggtaac tgtcagacca
1561 agtttactca tatatacttt agattgattt aaaacttcat ttttaattta aaaggatcta
1621 ggtgaagatc ctttttgata atctcatgac caaaatccct taacgtgagt tttcgttcca
1681 ctgagcgtca gaccccgtag aaaagatcaa aggatcttct tgagatcctt ttttctgcg
1741 cgtaatctgc tgcttgcaaa caaaaaaacc accgctacca gcggtggttt gtttgccgga
1801 tcaagagcta ccaactcttt ttccgaaggt aactggcttc agcagagcgc agataccaaa
1861 tactgtcctt ctagtgtagc cgtagttagg ccaccacttc aagaactctg tagcaccgcc
1921 tacataccct gctctgctaa tcctgttacc agtggctgct gccagtggcg ataagtcgtg
1981 tcttaccggg ttggactcaa gacgatagtt accggataag gcgcagcggt cgggctgaac
2041 ggggggttcg tgcacacagc ccagcttgga gcgaacgacc tacaccgaac tgagatacct
2101 acagcgtgag cattgagaaa gcgccacgct tcccgaaggg agaaaggcgg acaggtatcc
2161 ggtaagcggc agggtcggaa caggagagcg cacgagggag cttccagggg gaaacgcctg
2221 gtatctttat agtcctgtcg ggtttcgcca cctctgactt gagcgtcgat ttttgtgatg
2281 ctcgtcaggg gggcggagcc tatggaaaaa cgccagcaac gcggcctttt tacgttcct
2341 ggcctttgc tggcctttg ctcacatgtt ctttcctgcg ttatcccctg attctgtgga
2401 taaccgtatt accgcctttg agtgagctga taccgctcgc cgcagccgaa cgaccgagcg
2461 cagcgagtca gtgagcgagg aagcggaaga gcgcctgatg cggtattttc tccttacgca
2521 tctgtgcggt atttcacacc gcagaccagc cgcgtaacct ggcaaatcg gttacggttg
2581 agtaataaat ggatgccctg cgtaagcggg tgtgggcgga caataaagtc ttaaactgaa
2641 caaaatagat ctaaactatg acaataaagt cttaaactag acagaatagt tgtaaactga
2701 aatcagtcca gttatgctgt gaaaaagcat actggacttt tgttatggct aaagcaaact
2761 cttcattttc tgaagtgcaa attgcccgtc gtattaaaga gggcgtggc caagggcatg
2821 gtaaagacta tattcgcggc gttgtgacaa tttaccgaac aactccgcgg ccgggaagcc
2881 gatctcggct tgaacgaatt gttaggtggc ggtacttggg tcgatatcaa agtgcatcac
2941 ttcttcccgt atgcccaact tgtatagag agccactgcg gatcgtcac cgtaatctgc
3001 ttgcacgtag atcccataag caccaagcgc gttggcctca tgcttgagga gattgatgag
3061 cgcggtggca atgccctgcc tccggtgctc gccggagact gcgagatcat agatatagat
3121 ctcactacgc ggctgctcaa acctgggcag aacgtaagcc gcgagagcgc caacaaccgc
```

FIG. 12A

```
3181 ttcttggtcg aaggcagcaa gcgcgatgaa tgtcttacta cggagcaagt tcccgaggta
3241 atcggagtcc ggctgatgtt gggagtaggt ggctacgtct ccgaactcac gaccgaaaag
3301 atcaagagca gcccgcatgg atttgacttg gtcagggccg agcctacatg tgcgaatgat
3361 gcccatactt gagccaccta actttgtttt agggcgactg ccctgctgcg taacatcgtt
3421 gctgctgcgt aacatcgttg ctgctccata acatcaaaca tcgacccacg gcgtaacgcg
3481 cttgctgctt ggatgcccga ggcatagact gtacaaaaaa acagtcataa caagccatga
3541 aaaccgccac tgcgccgtta ccaccgctgc gttcggtcaa ggttctggac cagttgcgtg
3601 agcgcatacg ctacttgcat tacagtttac gaaccgaaca ggcttatgtc aactgggttc
3661 gtgccttcat ccgtttccac ggtgtgcgtc acccggcaac cttgggcagc agcgaagtcg
3721 aggcatttct gtcctggctg gcgaacgagc gcaaggtttc ggtctccacg catcgtcagg
3781 cattggcggc cttgctgttc ttctacggca aggtgctgtg cacggatctg ccctggcttc
3841 aggagatcgg tagacctcgg ccgtcgcggc gcttgccggt ggtgctgacc ccggatgaag
3901 tggttcgcat cctcggtttt ctggaaggcg agcatcgttt gttcgcccag gactctagct
3961 atagttctag tggttggcct acgtacccgt agtggctatg gcagggcttg ccgccccgac
4021 gttggctgcg agccctgggc cttcacccga acttggggt tggggtgggg aaaaggaaga
4081 aacgcgggcg tattggtccc aatggggtct cggtggggta tcgacagagt gccagccctg
4141 ggaccgaacc ccgcgtttat gaacaaacga cccaacaccc gtgcgtttta ttctgtcttt
4201 ttattgccgt catagcgcgg gttccttccg gtattgtctc cttccgtgtt tcagttagcc
4261 tcccccatct cccggtaccg catgctatgc atcggccgct ttacttgtac agctcgtcca
4321 tgccgagagt gatcccggcg gcggtcacga actccagcag gaccatgtga tcgcgcttct
4381 cgttggggtc tttgctcagg gcggactggg tgctcaggta gtggttgtcg ggcagcagca
4441 cggggccgtc gccgatgggg gtgttctgct ggtagtggtc ggcgagctgc acgctgccgt
4501 cctcgatgtt gtggcggatc ttgaagttca ccttgatgcc gttcttctgc ttgtcggcca
4561 tgatatagac gttgtggctg ttgtagttgt actccagctt gtgccccagg atgttgccgt
4621 cctccttgaa gtcgatgccc ttcagctcga tgcggttcac cagggtgtcg ccctcgaact
4681 tcacctcggc gcgggtcttg tagttgccgt cgtccttgaa gaagatggtg cgctcctgga
4741 cgtagccttc gggcatggcg gacttgaaga agtcgtgctg cttcatgtgg tcggggtagc
4801 ggctgaagca ctgcacgccg taggtcaggg tggtcacgag ggtgggccag ggcacgggca
4861 gcttgccggt ggtgcagatg aacttcaggg tcagcttgcc gtaggtggca tcgccctcgc
4921 cctcgccgga cacgctgaac ttgtggccgt ttacgtcgcc gtccagctcg accaggatgg
4981 gcaccacccc ggtgaacagc tcctcgccct tgctcaccat ggctcgagat cccgggcgtt
5041 taaattgtgt aatttatgta gctgtaattt ttaccttatt aatatttttt acgctttgca
5101 ttcgacgact gaactcccaa atatatgttt aactcgtctt ggtcgtttga attttgttg
5161 ctgtgtttcc taatattttc catcaccta aatatgttat tgtaatcctc aatgttgaac
5221 ttgcaattgg acacggcata gttttccata gtcgtgtaaa acatggtatt ggctgcattg
5281 taatacatcc gactgagcgg gtacggatct atgtgtttga gcagccgtt caaaaactct
5341 gcatcgtcgc aaaacggaat ttggtacccg ggcgtatact ccggaatatt aatagatcat
5401 ggagataatt aaaatgataa ccatctcgca aataaataag tattttactg ttttcgtaac
5461 agttttgtaa taaaaaaacc tataaatatt ccggattatt cataccgtcc caccatcggg
5521 cgccatggat cccggtccga agcgcgcgga attcaaaggc ctacgtcgac gagctcacta
5581 gtcgcggccg ctttcgaatc tagagcctgc agtctcgaca agcttgtcga gaagtcatag
5641 aggatcataa tcagccatac cacatttgta gaggttttac ttgctttaaa aaacctccca
5701 cacctccccc tgaacctgaa acataaaatg aatgcaattg ttgttgttaa cttgtttatt
5761 gcagcttata atggttacaa ataaagcaat agcatcacaa atttcacaaa taaagcattt
5821 ttttcactgc attctagttg tggtttgtcc aaactcatca atgtatctta tcatgtctgg
5881 atctgatcac tgcttgagcc taggagatcc gaaccagata agtgaaatct agttccaaac
5941 tattttgtca tttttaattt tcgtattagc ttacgacgct acaccagtt cccatctatt
6001 ttgtcactct tccctaaata atccttaaaa actccatttc caccccctccc agttcccaac
6061 tattttgtcc gcccacagcg gggcatttt cttcctgtta tgtttttaat caaacatcct
6121 gccaactcca tgtgacaaac cgtcatcttc ggctacttt
```

FIG. 12B

MNRAVCQVALENDEREAKNTWRLVFRIAILLLTVMTLAISAAAL
AYSMEASTPGDLVSIPTAISRAEGKITSALGSNQDVVDRIYKQVALESPLALLNTESI
IMNAITSLSYQINGAANNSGCGAPVHEPDYIGGIGKELIVDDTSDVTSFYPSAFQEHL
NFIPAPTTGSGCTRIPSFDMSATHCYTHNVIFSGCRHHSHSHQYLALGVLRTSATGRV
FFSTLRSINLDDTQNRKSCSVSATPLGCDMLCSKVTETEEQDYNSVIPTSMVHGRLGF
DGQYHEKDLDVTTLFGDWVANYPGVGGGSFIDNRVWFPVYGGLKPSSPSDTGQEGRYV
IYKRYNDTCPDEQDYQIRMAKSSYKPGRFGGKRVQQAILSIKVSTSLGEDPVLTIPPN
TVTLMGAEGRVLTVGTSHFLYQRGSSYFSPALLYPMTVNNNTATLHSPYTFNAFTRPG
SVPCQASARCPNSCVTGVYTDPYPLVFHRNHTLRGVFGTMLDDEQARLNLVSAVFDNI
SRSRITRVSSSRTKAAYTTSTCFKVVKTNKTYCLSIAEISNTLFGEFRIVPLLVEILK
DDGV

FIG. 20A

```
   1 acgggtagaa cggtcggaga ggccacccct caatcgggag tcggacctca caacttccat
  61 tctgccgcat caccagtagc ggtcttcagt catgaaccgc gcagtttgcc aagttgcgct
 121 agagaatgat gaaagggaag cgaagaatac atggcgcttg gtattccgga tcgcaatctt
 181 acttttaaca gtaatgacct tagccatctc tgcagccgcc ctggcatata gtatggaggc
 241 tagcacacct ggcgaccttg taagcatacc aactgcgatc tctagggcag agggaaagat
 301 tacatctgca ctcggttcca atcaggatgt agtagatagg atatacaagc aggtggctct
 361 tgaatctccg ttggcattgc taaacaccga atctataatt atgaatgcaa taacatccct
 421 ctcttatcaa atcaatggag ctgcaaataa cagcggtgtg ggggcacctg ttcatgaccc
 481 agattacatc gggggggatag gtaaagaact tattgtggat gatactagtg atgtcacatc
 541 attctatccc tctgcgttcc aagaacacct gaattttatc ccggcaccca ctacaggatc
 601 aggttgcact cggataccct cattcgacat gagtgctacc cactgttata ctcacaatgt
 661 gatattttct ggttgcagac accattcaca ctcacatcag tatttagcac tgggtgtgct
 721 tcggacatct gcaacaggga gggtattctt ttctaccctg cgttccatca atttggatga
 781 cacccaaaat cggaagtctt gcagtgtgag tgcaactccc ttaggttgtg atatgctgtg
 841 ctctaaagtc acagagactg aggaacagga ttataattca gttatcccca catcgatggt
 901 acatggaagg ttagggtttg acggccaata ccatgagaag gacctagacg tcacaacatt
 961 atttggggac tgggtggcaa attacccagg agtgggaggt gggtctttta ttgacaaccg
1021 cgtatggttc ccagtctacg gagggctaaa acccagttcg cctagtgaca ctggacaaga
1081 agggagatat gtaatatata agcgatacaa tgacacatgc ccagatgagc aagattacca
1141 gattcggatg gctaagtctt cgtataagcc tgggcggttt ggtggaaagc gtgtacagca
1201 ggccatctta tctatcaagg tgtcaacatc cttgggtgag gacccggtgc tgactatacc
1261 gcccaacaca gtcacactca tggggccgga aggcagagtt ctcacagtag gacatctca
1321 tttcttgtac cagcgagggt catcatattt ctctcctgct ttattatacc ctatgacagt
1381 caacaacaac acagccactc ttcatagtcc ttatacattc aatgctttca ctcggccagg
1441 tagtgtccct tgccaggctt cagcaagatg ccctaactca tgtgtcactg ggtctatac
1501 tgatccatat cccttagtct tccataggaa ccacaccttg cgagggtat tcgggacaat
1561 gcttgatgat gaacaagcaa gactcaacct tgtatctgca gtatttgata acatatcccg
1621 cagtcgcata acccgggtaa gttcaagcag aaccaaggca gcatacacga catcaacgtg
1681 ttttaaagtt gtcaagacca ataaaaccta ttgcctcagc attgcagaaa tatccaatac
1741 cctctttggg gaattcagga tcgtcccttt actagttgag attctcaagg atgatggggt
1801 ttagaaagcc aggtctagcc ggttgagcca actgtgagag ggttggaaag atgacattgt
1861 gtcacctatc ttttgtagcg ccaagaatca aactgaatac cggccacgag ctcgaatcct
1921 ccgctgccag tcggtcataa tcactagtgc taatgtgatt agtctgaatc ttgtcgatag
1981 tcacttgatt aag
```

FIG. 20B

MDRAVSQVALENDEREAKNTWRLIFRIAILFLTVVTLAISVASL
LYSMGASTPSDLVGIPTRISRAEEKITSTLGSNQDVVDRIYKQVALESPLALLNTETT
IMNAITSLSYQINGAANNSGWGAPIHDPDYIGGIGKELIVDDASDVTSFYPSAFQEHL
NFIPAPTTGSGCTRIPSFDMSATHYCYTHNVILSGCRDHSHSHQYLALGVLRTSATGR
VFFSTLRSINLDDTQNRKSCSVSATPLGCDMLCSKATETEEEDYNSAVPTRMVHGRLG
FDGQYHEKDLDVTTLFGDWVANYPGVGGGSFIDSRVWFSVYGGLKPNTPSDTVQEGKY
VIYKRYNDTCPDEQDYQIRMAKSSYKPGRFGGKYIQQAILSIKVSTSLGEDPVLTVPP
NTVTLMGAEGRILTVGTSHFLYQRGSSYFSPALLYPMTVSNKTATLHSPYTFNAFTRP
GSIPCQASARCPNSCVTGVYTDPYPLIFYRNHTLRGVFGTMLDGEQARLNPASAVFDS
TSRSRITRVSSSSIKAAYTTSTCFKVVKTNKTYCLSIAEISNTLFGEFRIVPLLVEIL
KDDGVREARSG

FIG. 21A

```
   1 atggaccgcg ccgttagcca agttgcgtta gagaatgatg aaagagaggc aaaaaataca
  61 tggcgcttga tattccggat tgcaatctta ttcttaacag tagtgacctt ggctatatct
 121 gtagcctccc ttttatatag catgggggct agcacaccta gcgatcttgt aggcataccg
 181 actaggattt ccagggcaga agaaaagatt acatctacac ttggttccaa tcaagatgta
 241 gtagatagga tatataagca agtggccctt gagtctccat tggcattgtt aaatactgag
 301 accacaatta tgaacgcaat aacatctctc tcttatcaga ttaatggagc tgcaaacaac
 361 agcggtgggg ggcacctat tcatgaccca gattatatag ggggatagg caaagaactc
 421 attgtagatg atgctagtga tgtcacatca ttctatccct ctgcatttca agaacatctg
 481 aatttatcc cggcgcctac tacaggatca ggttgcactc gaataccctc atttgacatg
 541 agtgctaccc attactgcta cacccataat gtaatattgt ctggatgcag agatcactca
 601 cactcacatc agtatttagc acttggtgtg ctccggacat ctgcaacagg gagggtattc
 661 ttttctactc tgcgttccat caacctggac gacacccaaa atcggaagtc ttgcagtgtg
 721 agtgcaactc ccctggggtt tgatatgctg tgctcgaaag ccacggagac agaggaagaa
 781 gattataact cagctgtccc tacgcggatg gtacatggga ggttagggtt cgacggccaa
 841 tatcacgaaa aggacctaga tgtcacaaca ttattcgggg actgggtggc caactaccca
 901 ggagtagggg gtggatcttt tattgacagc cgcgtatggt tctcagtcta cggagggtta
 961 aaacccaata cacccagtga cactgtacag aagggaaat atgtgatata caagcgatac
1021 aatgacacat gcccagatga gcaagactac cagattcgaa tggccaagtc ttcgtataag
1081 cctggacggt tggtgggaa acgcatacag caggctatct tatctatcaa agtgtcaaca
1141 tccttaggcg aagacccggt actgactgta ccgcccaaca cagtcacact catgggggcc
1201 gaaggcagaa ttctcacagt agggacatcc catttcttgt atcagcgagg gtcatcatac
1261 ttctctcccg cgttattata tcctatgaca gtcagcaaca aaacagccac tcttcatagt
1321 ccttatacat tcaatgcctt cactcggcca ggtagtatcc cttgccaggc ttcagcaaga
1381 tgccccaact cgtgtgttac tggagtctat acagatccat atcccctaat cttctataga
1441 aaccacacct gcgagggggt attcgggaca atgcttgatg gtgaacaagc aagacttaac
1501 cctgcgtctg cagtattcga tagcacatcc cgcagtcgca taactcgagt gagttcaagc
1561 agcatcaaag cagcatacac aacatcaact tgttttaaag tggtcaagac caataagacc
1621 tattgtctca gcattgctga aatatctaat actctcttcg gagaattcag aatcgtcccg
1681 ttactagttg agatcctcaa agatgacggg gttagagaag ccaggtctgg ctag
```

FIG. 21B

MGPRSSTRIPIPLMLTIRIALALSCVHLASSLDGRPLAAAGIVV
TGDKAVNIYTSSQTGSIIVKLLPNMPKDKEACAKAPLEAYNRTLTTLLTPLGDSIRRI
QESVTTSGGRRQKRFIGAIIGSVALGVATAAQITAASALIQANQNAANILRLKESITS
TNEAVHEVTDGLSQLAVAVGKMQQFVNDQFNNTAQELDCIKITQQVGVELNLYLTELT
TVFGPQITSPALTQLTIQALYNLAGGNMDYLLTKLGVGNNQLSSLIGSGLITGNPILY
DSQTQLLGIQVTLPSVGNLNNMRATYLETLSVSTTKGFASALVPKVVTQVGSVIEELD
TSYCIETDLDLYCTRIVTFPMSPGIYSCLNGNTSACMYSKTEGALTTPYMTLKGSVIA
NCKMTTCRCADPPGIISQNYGEAVSLIDRHSCNVLSLDGITLRLSGEFDATYQKNISI
LDSQVIVTGNLDISTELGNVNNSISNALDKLEESNSKLDKVNVKLTSTSALITYIALT
AISLVCGILSLVLACYLMYKQKAQQKTLLWLGNNTLGQMRATTKM

FIG. 22A

```
   1 acgggtagaa gagtttggat cccggttggc gcattcaagg cgcaagatgg gccccagatc
  61 ttctaccagg atcccaatac ctctgatgtt gaccatccgg atcgcgctgg cactgagttg
 121 tgtccatctg gcaagttctc ttgatggcag gcctcttgca gctgcaggga tcgtggtaac
 181 aggggataaa gcagtcaaca tatacacctc atcccagaca gggtcaatca tagtcaagtt
 241 actcccaaat atgcccaagg ataaagaggc gtgtgcaaaa gccccgttgg aggcatacaa
 301 caggacactg actactttgc tcacccccct tggtgattct atccgcagga tacaagagtc
 361 tgtgactaca tccggaggaa ggagacagaa acgctttata ggtgctatta tcggcagtgt
 421 agctcttggg gttgcaacag ctgcacagat aacagcagcc tcggccctga tacaagccaa
 481 tcagaatgct gccaacatcc tccggcttaa ggagagcatt actgcaacca atgaagctgt
 541 acatgaggtc actgacggat tatcacaact agcagtggca gttgggaaga tgcagcagtt
 601 tgttaatgac cagtttaata acacagctca ggaattggac tgtataaaaa ttacacagca
 661 ggttggtgta gaactcaacc tgtacctaac tgaattgact acagtattcg ggccacaaat
 721 aacttcccct gccttaactc agctgactat ccaggcgctt tacaacctag ctggtggtaa
 781 tatggattac ttgttgacta agttaggtgt agggaacaac caactcagct cattaattgg
 841 tagcggcttg atcaccggca accctattct gtacgactca cagactcaac tcttgggtat
 901 acaggtaact ttaccctcag tcggaaacct aaataatatg cgtgccacct acctggagac
 961 cttgtctgta agcacaacca agggatttgc ctcagcactc gtcccaaaag tggtgacaca
1021 ggtcggttct gtgatagaag aacttgacac ttcatactgt atagagaccg atttggattt
1081 gtattgtaca agaatagtga cattccctat gtctcctggt atttattcct gtttgaacgg
1141 caatacatcg gcttgcatgt attcaaagac tgaaggcgca cttactacgc catacatgac
1201 tctcaaaggc tcagttattg ccaattgcaa gatgacaaca tgcagatgtg cagaccccc
1261 gggtatcata tcgcaaaatt atggagaagc tgtgtctcta atagataggc actcatgcaa
1321 tgtcttatcc ttggacggga taactttgag gctcagtggg gaatttgatg caacttatca
1381 aaagaatatc tcaatactag attctcaagt aatagtgaca ggcaatctcg atatctcaac
1441 tgagcttggg aatgtcaaca actcgataag taatgctttg gataagttag aggaaagcaa
1501 cagcaaacta gacaaagtca atgtcaaact gaccagcaca tctgctctca ttacctatat
1561 cgctttaact gccatatctc ttgtttgcgg tatacttagt ctggttctag catgctacct
1621 aatgtacaag caaaaggcgc aacaaagac cttgttatgg cttgggaata atccctggg
1681 tcagatgaga gccactacaa aaatgtgaat gcagatgaga ggcggaggta tccccaatag
1741 caatttgtgt gcaaattct
```

FIG. 22B

```
  1 mgsrpftknp apmmltirva lvlscicpan sidgrpfaaa givvtgdkav niytssqtgs
 61 iivkllpnlp kdkeacakap ldaynrtltt lltplgdsir riqesvttsg ggrqgrliga
121 iiggvalgva taaqitaaaa liqakqnaan ilrlkesiaa tneavhevtd glsqlavavg
181 kmqqfvndqf nktaqeldci kiaqqvgvel nlyltelttv fgpqitspal nkltiqalyn
241 laggnmdyll tklgignnql ssligsglit gnpilydsqt qllgiqvtlp svgnlnnmra
301 tyletlsvst trgfasalvp kvvtqvgsvi eeldtsycie tdldlyctri vtfpmspgiy
361 sclsgntsac mysktegalt tpymtikgsv ianckmttcr cvnppgiisq nygeavslid
421 kqscnvlslg gitlrlsget dvtyqknisi qdsqviitgn ldistelgnv nnsisnalnk
481 leesnrkldk vnvkltstsa lityivltii slvfgilsli lacylmykqk aqqktllwlg
541 nntldqmrat tkm
```

FIG. 23

MSSVFDEYEQLLAAQTRPNGAHGGGEKGSTLKVDVPVFTLNSDD
PEDRWSFVVFCLRIAVSEDANKPLRQGALISLLCSHSQVMRNHVALAGKQNEATLAVL
EIDGFANGTPQFNNRSGVSEERAQRFAMIAGSLPRACSNGTPFVTAGAEDDAPEDITD
TLERILSIQAQVWVTVAKAMTAYETADESETRRINKYMQQGRVQKKYILYPVCRSTIQ
LTIRQSLAVRIFLVSELKRGRNTAGGTSTYYNLVGDVDSYIRNTGLTAFFLTLKYGIN
TKTSALALSSLSGDIQKMKQLMRLYRMKGDNAPYMPLLGDSDQMSFAPAEYAQLYSFA
MGMASVLDKGTGKYQFAKDFMSTSFWRLGVEYAQAQGSSINEDMAAELKLTPAARRGL
AAAAQRVSEVTSSIDMPTQQVGVLTGLSEGGSQALQGGSNRSQGQPEAGDGETQFLDL
MRAVANSMREAPNSAQGTPQSGPPPTPGPSQDNDTDWGY

FIG. 24A

```
   1 gccaaaatgt cttccgtatt cgacgagtac gaacagctcc tcgcggctca gactcgcccc
  61 aatggagctc atggaggggg ggagaaaggg agtaccttaa aagtagacgt cccggtattc
 121 actcttaaca gtgatgaccc agaagatagg tggagctttg tggtattctg cctccggatt
 181 gctgttagcg aagatgccaa caaaccactc aggcaaggtg ctctcatatc tcttttatgc
 241 tcccactcac aggtaatgag gaaccatgtt gcccttgcag ggaaacagaa tgaagccaca
 301 ttggccgtgc ttgagattga tggctttgcc aacggcacgc ccagttcaa caataggagt
 361 ggagtgtctg aagagagagc acagagattt gcgatgatag caggatctct ccctcgggca
 421 tgcagcaacg gcaccccgtt cgtcacagcc ggggctgaag atgatgcacc agaagacatc
 481 accgataccc tggagaggat cctctctatc caggctcaag tatgggtcac agtagcaaaa
 541 gccatgactg cgtatgagac tgcagatgag tcggaaacaa ggcgaatcaa taagtatatg
 601 cagcaggcca gggtccaaaa gaaatacatc ctctaccccg tatgcaggag cacaatccaa
 661 ctcacgatca gacagtctct tgcagtccgc atcttttgg ttagcgagct caagagaggc
 721 cgcaacacgg caggtggtac ctctacttat tataacctag tagggacgt agactcatat
 781 atcaggaata ccgggcttac tgcattcttc ttgacactca agtacggaat caacaccaag
 841 acatcagccc ttgcacttag tagcctctca ggcgacatcc agaagatgaa gcagctcatg
 901 cgtttgtatc ggatgaaagg agataatgcg ccgtacatga cattacttgg tgatagtgac
 961 cagatgagct ttgcgcctgc cgagtatgca caactttact cctttgccat gggtatggca
1021 tcagtcctag ataaaggtac tgggaaatac caatttgcca aggactttat gagcacatca
1081 ttctggagac ttggagtaga gtacgctcag gctcagggaa gtagcattaa cgaggatatg
1141 gctgccgagc taaagctaac cccggcagca aggagggggcc tgccagctgc tgcccaacga
1201 gtctccgagg tgaccagcag catagacatg cctactcaac aagtcggagt cctcactggg
1261 cttagcgagg ggggatccca agccctacaa ggcggatcga atagatcgca agggcaacca
1321 gaagccgggg atggggagac ccaattcctg gatctgatga gagcggtagc aaatagcatg
1381 agggaggcgc aaactctgc acaggcact ccccaatcgg ggcctccccc aactcctggg
1441 ccatcccaag ataacgacac cgactggggg tattgattga caaaacccag cctgcttcta
1501 caagaacatc ccaatgctct cacccgtagt cgacc
```

FIG. 24B

MDSSRTIGLYFDSALPSSNLLAFPIVLQDIGDGKKQIAPQYRIQ
RLDSWTDSKEDSVFITTYGFIFQVGNEEVTVGMISDNPKHELLSAAMLCLGSVPNVGD
LVELARACLTMVVTCKKSATDTERMVFSVVQAPQVLQSCRVVANKYSSVNAVKHVKAP
EKIPGSGTLEYKVNFVSLTVVPRKDVYKIPTAALKVSGSSLYNLALNVTIDVEVDPKS
PLVKSLSKSDSGYYANLFLHIGLMSTVDKKGKKVTFDKLERKIRRLDLSVGLSDVLGP
SVLVKARGARTRLLAPFFSSSGTACYPISNASPQVAKILWSQTARLRSVKVIIQAGTQ
RAVAVTADHEVTSTKIEKRHTIAKYNPFKK

FIG. 25A

```
   1 acgggtagaa tcggagtgcc ctgattgtgc caagatggac tcatctagga caatagggct
  61 atactttgat tctgcccttc cttctagcaa cctgttagca ttcccgatcg tcctacaaga
 121 cataggagat gggaagaagc aaatcgcccc gcaatatagg atccagcgtc ttgactcgtg
 181 gacagacagt aaagaagact cggtattcat caccacctat ggattcatct tccaggttgg
 241 gaatgaagaa gtcactgtcg gcatgatcag cgataatccc aagcacgagt tactttcagc
 301 tgcgatgctc tgcctaggaa gtgtcccgaa tgtcggagat cttgttgagt tggcaagggc
 361 ctgcctcact atggtggtaa catgcaagaa gagtgcaact gatactgaga gaatggtctt
 421 ctcggtagta caggcgcccc aggtgctgca aagctgtagg gtcgtggcaa acaaatactc
 481 gtcagtgaat gcagttaagc acgtgaaagc accagagaag atccctggga gcggaaccct
 541 agagtacaag gtgaattttg tctctttgac tgtggtgcca aggaaggatg tctacaaaat
 601 cccaaccgca gcattgaagg tatctggctc gagcctgtac aatcttgcgc tcaatgtcac
 661 tattgatgtg gaggtagacc caaagagccc gttagtcaaa tctctttcaa agtccgacag
 721 tggatactat gctaatcttt tcttacatat cggacttatg tccactgtag ataagaaggg
 781 aaagaaagtg acatttgaca agctggagag gaagataaga agactcgatt tatctgtcgg
 841 gctcagtgat gtgctcggac cttccgtgct tgtgaaggcg agaggtgcac ggactaggct
 901 gctggcacct tcttctcta gcagtgggac agcctgctat cctatatcaa atgcctctcc
 961 tcaggtagct aagatactct ggagtcaaac tgcgcgcctg cggagtgtaa aagtcattat
1021 tcaagcgggc acccaacgcg ctgtcgcggt gaccgctgac cacgaggtca cctctactaa
1081 gatagaaaag aggcatacca ttgctaaata caatcctttt aagaaataag ctgcatctct
1141 gagactgcaa tccgcccgct ttcccgaatc atcacgacgc ttaataatgg atctgtcctg
1201 attactcaca
```

FIG. 25B

MDSSRTIGLYFDSAHSSSNLLAFPIVLQDTGDGKKQIAPQYRIQ
RLDSWTDSKEDSVFITTYGFIFQVGNEEATVGMIDDKPKRELLSAAMLCLGSVPNTGD
LVELTRACLTMMVTCKKSATNTERMVFSVVQAPQVLQSCRVVPNKYSSVNAVKHVKAP
EKIPGSGTLEYKVNFVSLTVVPKKDVYKIPAAVLKISGSSLYNLALNVTINVEVDPRS
PLVKSLSKSDSGYYANLFLHIGLMTTVDRKGKKVTFDKLEKKIRSLDLSVGLSDVLGP
SVLVKARGARTKLLAPFFSSSGTACYPIANASPQVAKILWSQTACLRSVKIIIQAGTQ
RAVAVTADHEVTSTKLEKGHTLAKYNPFKK

FIG. 26A

```
   1 tgtgccaaga tggactcatc taggacaatt gggctgtact ttgattctgc ccattcttct
  61 agcaacctgt tagcatttcc gatcgtccta caagacacag gagatgggaa gaagcaaatc
 121 gccccgcaat ataggatcca gcgccttgac tcgtggactg atagtaagga agactcagta
 181 ttcatcacca cctatggatt catctttcaa gttgggaatg aggaagccac tgtcggcatg
 241 atcgatgata acccaagcg cgagttactt ccgctgcga tgctctgcct aggaagcgtc
 301 ccaaataccg gagaccttgt tgagctgaca agggcctgtc tcactatgat ggtcacatgc
 361 aagaagagtg caactaatac tgagagaatg gttttctcag tagtgcaggc accccaagtg
 421 ctgcaaagct gtagggttgt gccaaacaaa tactcatcag tgaatgcagt caagcacgtg
 481 aaagcgccag agaagatccc cgggagtgga ccctagaat acaaggtgaa ctttgtctcc
 541 ttgactgtgg taccgaagaa ggatgtctac aagatcccag ctgcagtatt gaagatttct
 601 ggctcgagtc tgtacaatct gcgctcaat gtcactatta atgtggaggt agacccgagg
 661 agtcctttgg ttaaatctct gtctaagtct gacagcggat actatgctaa cctcttcttg
 721 catattggac ttatgaccac cgtagatagg aaggggaaga aagtgacatt tgacaagctg
 781 gaaaagaaaa taaggagcct tgatctatct gtcgggctca gtgatgtgct cgggccttcc
 841 gtgttggtaa aagcaagagg tgcacggact aagcttttgg caccttctt ctctagcagt
 901 gggacagcct gctatcccat agcaaatgct ctcctcagg tggccaagat actctggagc
 961 caaaccgcgt gcctgcggag cgttaaaatc attatccaag caggtaccca acgcgctgtc
1021 gcagtgaccg ctgaccacga ggttacctct actaagctgg agaagggggca cacccttgcc
1081 aaatacaatc cttttaagaa ataagctgcg tctctgagat tgcgctccgc ccactcaccc
1141 agatcatcat gacacaaaaa actaatctgt cttgattatt tacagttagt ttacctgtcc
1201 atcaagttag aaaaaacacg ggt
```

FIG. 26B

```
   1 accaaacaga gaatcggtga gttacgataa aaggcgaagg agcaattgaa gtcgcacggg
  61 tagaaggtgt gaatctcgag tgcgagcccg aagcacaaac tcgaggaagc cttctgccaa
 121 catgtcttcc gtattcgacg agtacgaaca gctcctcgcg gctcagactc gccccaatgg
 181 agctcatgga gggggggaga aagggagtac cttaaaagta gacgtcccgg tattcactct
 241 taacagtgat gacccagaag ataggtggag cttttgtggta ttctgcctcc ggattgctgt
 301 tagcgaagat gccaacaaac cactcaggca aggtgctctc atatctcttt tatgctccca
 361 ctcacaggta atgaggaacc atgttgccct tgcagggaaa cagaatgaag ccacattggc
 421 cgtgcttgag attgatggct ttgccaacgg cacgcccag ttcaacaata ggagtggagt
 481 gtctgaagag agagcacaga gatttgcgat gatagcagga tctctccctc gggcatgcag
 541 caacggcacc ccgttcgtca gccggggc tgaagatgat gcaccagaag acatcaccga
 601 taccctggag aggatcctct ctatccaggc tcaagtatgg gtcacagtag caaaagccat
 661 gactgcgtat gagactgcag atgagtcgga aacaaggcga atcaataagt atatgcagca
 721 aggcagggtc caaaagaaat acatcctcta ccccgtatgc aggagcacaa tccaactcac
 781 gatcagacag tctcttgcag tccgcatctt tttggttagc gagctcaaga gaggccgcaa
 841 cacggcaggt ggtacctcta cttattataa cctagtaggg gacgtagact catatatcag
 901 gaataccggg cttactgcat tcttcttgac actcaagtac ggaatcaaca ccaagacatc
 961 agcccttgca cttagtagcc tctcaggcga catccagaag atgaagcagc tcatgcgttt
1021 gtatcggatg aaaggagata atgcgccgta catgacatta cttggtgata gtgaccagat
1081 gagctttgcg cctgccgagt atgcacaact ttactccttt gccatgggta tggcatcagt
1141 cctagataaa ggtactggga ataccaatt tgccaaggac tttatgagca catcattctg
1201 gagacttgga gtagagtacg ctcaggctca gggaagtagc attaacgagg atatggctgc
1261 cgagctaaag ctaaccccgg cagcaaggag gggcctggca gctgctgccc aacgagtctc
1321 cgaggtgacc agcagcatag acatgcctac tcaacaagtc ggagtcctca ctgggcttag
1381 cgaggggga tcccaagccc tacaaggcgg atcgaataga tcgcaagggc aaccagaagc
1441 cggggatggg gagacccaat tcctggatct gatgagagcg gtagcaaata gcatgaggga
1501 ggcgccaaac tctgcacagg gcactcccca atcggggcct cccccaactc ctgggccatc
1561 ccaagataac gacaccgact gggggtattg attgacaaaa cccagcctgc ttctacaaga
1621 acatcccaat gctctcaccc gtagtcgacc cctcgatttg cggctctata tgaccacacc
1681 ctcaaacaaa catcccctc tttcctccct ccccctgctg tacaactccg cacgccctag
1741 gcaacagagg cacaatgcgg ctcactaaca atcaaaacag agccgaggga attagaaaaa
1801 agtacgggta gaagagggat attcagagat cagggcaagt ctcccgagtc tctgctctct
1861 cctctacctg atagaccagg acaaacatgg ccaccttttac agatgcagag atcgacgagc
1921 tatttgagac aagtggaact gtcattgaca acataattac agcccaggt aaaccagcag
1981 agactgttgg aaggagtgca atcccacaag gcaagaccaa ggtgctgagc gcagcatggg
2041 agaagcatgg gagcatccag ccaccggcca gtcaagacaa ccccgatcga caggacagat
2101 ctgacaaaca accatccaca cccgagcaaa cgaccccgca tgacagcccg ccggccacat
2161 ccgctgacca gccccccacc caggccacag acgaagccgt cgacacacag ctcaggaccg
2221 gagcaagcaa ctctctgctg ttgatgcttg acaagctcag caataaatcg tccaatgcta
2281 aaaagggccc atggtcgagc cccaagagg ggaatcacca acgtccgact caacagcagg
2341 ggagtcaacc cagtcgcgga aacagtcagg aaagaccgca gaaccaagtc aaggccgccc
2401 ctggaaacca gggcacagac gtgaacacag catatcatgg acaatgggag gagtcacaac
2461 tatcagctgg tgcaacccct catggtctcc gatcaaagca gagccaaaac aatacccctg
2521 tttctgcgga tcatttccac ccacctgtag actttgtgca agcgatgatg tctattatgg
2581 agggatttc ccaaagagta agtaaggttg cctatcaggt agatcttgtt tttaaacaga
2641 catcctccat ccctatgatg gggtccgaaa tccaacagct gaaaacattt gttgcagtca
2701 tggaagccaa cttgggaatg atgaagattt ggatcccgg ttgtgccaac atttcatctt
2761 tgagtgatct acgggcagtt gcccgatctc acccggtttt agtttcaggc cctgagacc
2821 catctcccta tgtgatacaa ggaggcgaaa tggcacttaa taaactttcg caaccagtgc
2881 cacatccatc tgaattgatt aaacccgcca ctgcatgcgg gcctgatata ggagtggaga
2941 gggacactgt ccgtgcattg atcatgtcac gcccaatgca cccgagttct tcagccaagc
3001 tcctaagcaa gttagatgca gccgggtcga tcgaggaaat caggaaaatc aagcgccttg
3061 ctctaaatgg ctaattacta ctgccacacg tagcgggtcc ctgtccactc ggcatcacac
3121 ggaatctgca ccgagttccc ccccgcagac ccaaggtcca actctccaag cggcaatcct
3181 ctctcgcttc ctcagcccca ctgaatgatc gcgcaaccgc aattaatcta gctacattaa
3241 ggattaagaa aaaatacggg tagaattgga gtgccccaat tgtgccaaga tggactcatc
```

FIG. 27A

```
3301 taggacaatt gggctgtact ttgattctgc ccattcttct agcaacctgt tagcatttcc
3361 gatcgtccta caagacacag gagatgggaa gaagcaaatc gccccgcaat ataggatcca
3421 gcgccttgac ttgtggactg atagtaagga agactcagta ttcatcacca cctatggatt
3481 catctttcaa gttgggaatg aagaagccac tgtcggcatt atcgatgata aacccaagcg
3541 cgagttactt tccgctgcga tgctctgcct aggaagcgtc ccaaataccg gagaccttat
3601 tgagctggca agggcctgtc tcactatgat ggtcacatgc aagaagagtg caactaatac
3661 tgagagaatg gtttctcag tagtgcaggc accccaagtg ctgcaaagct gtagggttgt
3721 ggcaaacaaa tactcatcag tgaatgcagt caagcacgtg aaagcgccag agaagatccc
3781 cgggagtgga accctagaat acaaggtgaa ctttgtctcc ttgactgtgg taccgaagaa
3841 ggatgtctac aagatcccag ctgcagtatt gaagatttct ggctcgagtc tgtacaatct
3901 tgcgctcaat gtcactatta atgtggaggt agacccgagg agtcctttgg ttaaatctct
3961 gtctaagtct gacagcggat actatgctaa cctcttcttg catattggac ttatgaccac
4021 cgtagatagg aaggggaaga aagtgacatt tgacaagctg gaaaagaaaa taaggagcct
4081 tgatctatct gtcgggctca gtgatgtgct cgggccttcc gtgttggtaa aagcaagagg
4141 tgcacggact aagcttttgg cacctttctt ctctagcagt gggacagcct gctatcccat
4201 agcaaatgct tctcctcagg tggccaagat actctggagt caaaccgcgt gcctgcggag
4261 cgttaaaatc attatccaag caggtaccca acgcgctgtc gcagtgaccg ctgaccacga
4321 ggttacctct actaagctgg agaaggggca caccctttgcc aaatacaatc cttttaagaa
4381 ataagctgcg tctctgagat tgcgctccgc ccactcaccc agatcatcat gacacaaaaa
4441 actaatctgt cttgattat tacagttagt ttacctgtcc atcaagttag aaaaaacacg
4501 ggtagaagac tctggatccc ggttggcgcc ctccaggtgc aggatgggct ccagaccttt
4561 taccaagaac ccagcaccta tgatgctgac tatccgggtc gcgctggtat tgagttgcat
4621 ctgtccggca aactccattg atggcaggcc ttttgcagct gcaggaattg tggttacagg
4681 agacaaagca gtcaacatat acacctcatc ccagacagga tcaatcatag ttaagctcct
4741 cccgaatctg cccaaggata aggaggcatg tgcgaaagcc cccttggatg catcaacag
4801 gacattgacc actttgctca ccccccttgg tgactctatc cgtaggatac aagagtctgt
4861 gactacatct ggaggggga gacagggcg ccttataggc gccattattg gcggtgtggc
4921 tcttggggtt gcaactgccg cacaaataac agcggccgca gctctgatac aagccaaaca
4981 aaatgctgcc aacatcctcc gacttaaaga gagcattgcc gcaaccaatg aggctgtgca
5041 tgaggtcact gacggattat cccaactagc agtggcagtt gggaagatgc agcagtttgt
5101 taatgaccaa tttaataaaa cagctcagga attagactgc ataaaaattg cacagcaagt
5161 tggtgtagag ctcaacctgt acctaaccga attgactaca gtattcggac cacaaatcac
5221 ttcacctgcc ttaaacaagc tgactattca ggcactttac aatctagctg gtgggaatat
5281 ggattactta ttgactaagt taggtatagg gaacaatcaa ctcagctcat taatcggtag
5341 cggcttaatc accggtaacc ctattctata cgactcacag actcaactct tgggtataca
5401 ggtaactcta ccttcagtcg ggaacctaaa taatatgcgt gccacctact tggaaacctt
5461 atccgtaagc acaaccaggg gatttgcctc ggcacttgtc ccaaaagtgg tgacacaggt
5521 cggttctgtg atagaagaac ttgacacctc atactgtata gaaactgact tagatttata
5581 ttgtacaaga atagtaacgt tccctatgtc ccctggtatt tactcctgct tgagcggcaa
5641 tacatcggcc tgtatgtact caaagaccga aggcgcactt actacaccat atatgactat
5701 caaaggctca gtcatcgcta actgcaagat gacaacatgt agatgtgtaa acccccgggg
5761 tatcatatcg caaaactatg gagaagccgt gtctctaata gataaacaat catgcaatgt
5821 tttatcctta ggcgggataa ctttaaggct cagtggggaa ttcgatgtaa cttatcagaa
5881 gaatatctca atacaagatt ctcaagtaat aataacaggc aatcttgata tctcaactga
5941 gcttgggaat gtcaacaact cgatcagtaa tgctttgaat aagttagagg aaagcaacag
6001 aaaactagac aaagtcaatg tcaaactgac cagcacatct gctctcatta cctatatcgt
6061 tttgactatc atatctcttg tttttggtat acttagcctg attctagcat gctacctaat
6121 gtacaagcaa aaggcgcaac aaaagaccttt attatggctt gggaataata ccctagatca
6181 gatgagagcc actacaaaaa tgtgaacaca gatgaggaac gaaggtttcc ctaatagtaa
6241 tttgtgtgaa agttctggta gtctgtcagt tcggagagtt aagaaaaaac taccggttgt
6301 agatgaccaa aggacgatat acgggtagaa cggtaagaga ggccgccccc caattgcgag
6361 ccagacttca caacctccgt tctaccgctt caccgacaac agtcctcaat catggaccgc
6421 gccgttagcc aagttgcgtt agagaatgat gaaagagagg caaaaaatac atggcgcttg
6481 atattccgga ttgcaatctt attcttaaca gtagtgacct tggctatatc tgtagcctcc
6541 ctttatatta gcatgggggc tagcacacct agcgatcttg taggcatacc gactaggatt
```

```
6601 tccagggcag aagaaaagat tacatctaca cttggttcca atcaagatgt agtagatagg
6661 atatataagc aagtggccct tgagtctcca ttggcattgt taaatactga gaccacaatt
6721 atgaacgcaa taacatctct ctcttatcag attaatggag ctgcaaacaa cagcgggtgg
6781 ggggcaccta ttcatgaccc agattatata gggggatag gcaaagaact cattgtagat
6841 gatgctagtg atgtcacatc attctatccc tctgcatttc aagaacatct gaattttatc
6901 ccggcgccta ctacaggatc aggttgcact cgaatacct catttgacat gagtgctacc
6961 cattactgct acacccataa tgtaatattg tctggatgca gagatcactc acactcatat
7021 cagtatttag cacttggtgt gctccggaca tctgcaacag ggagggtatt cttttctact
7081 ctgcgttcca tcaacctgga cgacacccaa aatcggaagt cttgcagtgt gagtgcaact
7141 cccctgggtt gtgatatgct gtgctcgaaa gccacggaga cagaggaaga agattataac
7201 tcagctgtcc ctacgcggat ggtacatggg aggttagggt tcgacggcca atatcacgaa
7261 aaggacctag atgtcacaac attattcggg gactggtgg ccaactaccc aggagtaggg
7321 ggtggatctt ttattgacag ccgcgtatgg ttctcagtct acggagggtt aaaacccaat
7381 tcacccagtg acactgtaca ggaagggaaa tatgtgatat acaagcgata caatgacaca
7441 tgcccagatg agcaagacta ccagattcga atggccaagt cttcgtataa gcctggacgg
7501 tttggtggga aacgcataca gcaggctatc ttatctatca aagtgtcaac atccttaggc
7561 gaagacccgg tactgactgt accgcccaac acagtcacac tcatggggc cgaaggcaga
7621 attctcacag tagggacatc ccatttcttg tatcagcgag ggtcatcata cttctctccc
7681 gcgttattat atcctatgac agtcagcaac aaaacagcca ctcttcatag tccttataca
7741 tcaatgcct tcactcggcc aggtagtatc ccttgccagg cttcagcaag atgccccaac
7801 tcgtgtgtta ctggagtcta tacagatcca tatccctaa tcttctatag aaaccacacc
7861 ttgcgagggg tattcgggac aatgcttgat ggtgaacaag caagacttaa ccctgcgtct
7921 gcagtattcg atagcacatc ccgcagtcgc ataactcgag tgagttcaag cagcatcaaa
7981 gcagcataca caacatcaac ttgttttaaa gtggtcaaga ccaataagac ctattgtctc
8041 agcattgctg aaatatctaa tactctcttc ggagaattca gaatcgtccc gttactagtt
8101 gagatcctca agatgacgg ggttagagaa gccaggtctg gctagttgag tcaactatga
8161 aagagttgga aagatggcat tgtatcacct atcttctgcg acatcaagaa tcaaaccgaa
8221 tgccggcgcg tgctcgaatt ccatgtcgcc agttgaccac aatcagccag tgctcatgcg
8281 atcagattaa gccttgtcaa tagtctcttg attaagaaaa aatgtaagtg gcaatgagat
8341 acaaggcaaa acagctcatg gtaaataata cgggtaggac atggcgagct ccggtcctga
8401 aagggcagag catcagatta tcctaccaga gtcacacctg tcttccacat tggtcaagca
8461 caaactactc tattattgga aattaactgg gctaccgctt cctgatgaat gtgacttcga
8521 ccacctcatt ctcagccgac aatggaaaaa aatacttgaa tcggcctctc ctgatactga
8581 gagaatgata aaactcggaa gggcagtaca ccaaactctt aaccacaatt ccagaataac
8641 cggagtactc caccccaggt gtttagaaga actggctaat attgaggtcc ctgattcaac
8701 caacaaattt cggaagattg agaagaagat ccaaattcac aacacgagat atggagaact
8761 gttcacaagg ctgtgtacgc atatagagaa gaaactgctg gggtcatctt ggtctaacaa
8821 tgtcccccgg tcagaggagt tcagcagcat tcgtacggat ccggcattct ggtttcactc
8881 aaaatggtcc acagccaagt tgcatggct ccatataaaa cagatccaga ggcatctgat
8941 tgtggcagct aggacaaggt ctgcggccaa caaattggtg atgctaaccc ataaggtagg
9001 ccaagtcttt gtcactcctg aacttgttgt tgtgacgcat acgaatgaga acaagttcac
9061 atgtcttacc caggaacttg tattgatgta tgcagatatg atggagggca gagatatggt
9121 caacataata tcaaccacgg cggtgcatct cagaagctta tcagagaaaa ttgatgacat
9181 tttgcggtta atagacgctc tggcaaaaga cttgggtaat caagtctacg atgttgtatc
9241 actaatggag ggatttgcat acggagctgt ccagctactc gagccgtcag gtacatttgc
9301 gggagatttc ttcgcattca acctgcagga gcttaaagac attctaattg gcctcctccc
9361 caatgatata gcagaatccg tgactcatgc aatcgctact gtattctctg gtttagaaca
9421 gaatcaagca gctgagatgt tgtgcctgtt gcgtctgtgg ggtcacccac tgcttgagtc
9481 ccgtattgca gcaaaggcag tcaggagcca aatgtgcgca ccgaaaatgg tagactttga
9541 tatgatcctt caggtactgt ctttcttcaa gggaacaatc atcaacggat acagaaagaa
9601 gaatgcaggt gtgtggccgc gagtcaaagt ggatacaata tgggaagg tcattgggca
9661 actacatgca gattcagcag agatttcaca cgatatcatg ttgagagagt ataagagttt
9721 atctgcactt gaatttgagc catgtataga atacgaccct gtcactaacc tgagcatgtt
9781 cctaaaagac aaggcaatcg cacacccaa cgataattgg cttgcctcgt ttaggcggaa
9841 ccttctctcc gaagaccaga agaaacatgt aaaggaagcg acttcgacta accgcctctt
```

FIG. 27C

```
 9901 gatagagttt ttagagtcaa atgattttga tccatataaa gagatggaat atctgacgac
 9961 ccttgagtac cttagagatg acaatgtggc agtatcatac tcgctcaaag agaaggaagt
10021 gaaagttaat ggacggatct tcgctaagct gacaaagaag ttaaggaact gtcaggtgat
10081 ggcggaaggg atcctagccg atcagattgc acctttcttt cagggaaatg gagtcattca
10141 ggatagcata tccttgacca agagtatgct agcgatgagt caactgtctt ttaacagcaa
10201 taagaaacgt atcactgact gtaaagaaag agtatcttca aaccgcaatc atgatccgaa
10261 aagcaagaac cgtcggagag ttgcaacctt cataacaact gacctgcaaa agtactgtct
10321 taattggaga tatcagacga tcaaattgtt cgctcatgcc atcaatcagt tgatgggcct
10381 acctcatttc ttcgagtgga ttcacctaag actgatggac actacgatgt tcgtaggaga
10441 cccttcaat cctccaagtg accctactga ctgtgacctc tcaagagtcc ctaatgatga
10501 catatatatt gtcagtgcca gaggggtat cgaaggatta tgccagaagc tatggacaat
10561 gatctcaatt gctgcaatcc aacttgctgc agctagatcg cattgtcgtg ttgcctgtat
10621 ggtacagggt gataatcaag taatagcagt aacgagagag gtaagatcag atgactctcc
10681 ggagatggtg ttgacacagt tgcatcaagc cagtgataat ttcttcaagg aattaatcca
10741 tgtcaatcat ttgattggcc ataatttgaa ggatcgtgaa accatcaggt cagacacatt
10801 cttcatatac agcaaacgaa tcttcaaaga tggagcaatc ctcagtcaag tcctcaaaaa
10861 ttcatctaaa ttagtgctag tgtcaggtga tctcagtgaa acaccgtaa tgtcctgtgc
10921 caacattgcc tctactgtag cacggctatg cgagaacggg cttcccaaag acttctgtta
10981 ctatttaaac tatataatga gttgtgtgca gacatacttt gactctgagt tctccatcac
11041 caacaattcg caccccgatc ttaatcagtc gtggattgag gacatctctt ttgtgcactc
11101 atatgttctg actcctgccc aattaggggg actgagtaac cttcaatact caaggctcta
11161 cactagaaat atcggtgacc cggggactac tgcttttgca gagatcaagc gactagaagc
11221 agtgggacta ctgagtccta acattatgac taatatctta actaggccgc ctgggaatgg
11281 agattgggcc agtctgtgca acgacccata ctctttcaat tttgagactg ttgcaagccc
11341 aaatattgtt cttaagaaac atacgcaaag agtcctattt gaaacttgtt caaatcccct
11401 attgtctgga gtgcacacag aggataatga ggcagaagag aaggcattgg ctgaattctt
11461 gcttaatcaa gaggtgattc atccccgcgt tgcgcatgcc atcatggagg caagctctgt
11521 aggtaggaga aagcaaattc aagggcttgt tgacacaaca aacactgtaa ttaagattgc
11581 gcttactagg aggccattag gcatcaagag gctgatgcgg atagtcaatt attctagcat
11641 gcatgcaatg ctgtttagag acgatgtttt ttcctctagt agatccaacc accccttagt
11701 ctcttctaat atgtgttctc tgacactggc agactatgca cggaatagaa gctggtcacc
11761 tttgacggga ggcaggaaaa tactgggtgt atctaatcct gatacgatag aactcgtaga
11821 gggtgagatt cttagtgtaa gcggagggtg tacaagatgt gacagcggag atgaacaatt
11881 tacttggttc catcttccaa gcaatataga attgaccgat gacaccagca agaatcctcc
11941 gatgagggta ccatatctcg ggtcaaagac acaggagagg agagctgcct cacttgcgaa
12001 aatagctcat atgtcgccac atgtgaaggc tgccctaagg gcatcatccg tgttgatctg
12061 ggcttatggg gataatgaag taaattggac tgctgctctc acgattgcaa aatctcggtg
12121 taatgtaaac ttagagtatc ttcggttact gtccccttta cccacggctg ggaatcttca
12181 acatagacta gatgatggta taactcagat gacattcacc cctgcatctc tctacaggtg
12241 tcaccttaca ttcacatatc caatgattct caaaggctgt tcactgaaga aggagtcaaa
13201 gagggaatg tggtttacca acagagtcat gctcttgggt ttatctctaa tcgaatcgat
12361 ctttccaatg acaacaacca gaacatatga tgagatcaca ctgcacctac atagtaaatt
12421 tagttgctgt atcagggaag cacctgttgc ggttcctttc gagctacttg gggtggcacc
12481 ggaactgagg acagtgacct caaataagtt tatgtatgat cctagccctg tatcggaggg
12541 agactttgcg agacttgact tagctatctt caagagttat gagcttaatc tggagtcata
12601 tcccacgata gagctaatga acattctttc aatatccagc gggaagttga ttggccagtc
12661 tgtggttcct tatgatgaag atacctccat aaagaatgat gccataatag tgtatgacaa
12721 tacccgaaat tggatcagtg aagctcagaa ttcagatgtg gtccgcctat tgaatatgc
12781 agcacttgaa gtgctcctcc accgttctta ccaactctat tacctgagag taagaggcct
12841 agacaatatt gtcttatata tgggtgattt ataaagaat atgccaggaa ttctactttc
12901 caacattgca gctacaatat ctcatcctgt cattcattca aggttacatg cagtgggcct
12961 ggtcaaccat gacggatcac accaacttgc agatacggat tttatcgaaa tgtctgcaaa
13021 actgttagta tcttgcaccc gacgtgtgat ctccggctta tattcaggaa ataagtatga
13081 tctgctgttc ccatctgtct tagatgataa cctgaatgag aagatgcttc agctgatatc
13141 ccggttatgc tgtctgtaca cggtactctt tgctacaaca agagaaatcc cgaaaataag
```

FIG. 27D

```
13201 aggcttaact gcagaagaga aatgttcaat actcactgag tatttactgt cggatgctgt
13261 gaaaccatta cttagccccg atcaagtgag ctctatcatg tctcctaaca taattacatt
13321 cccagctaat ctgtactaca tgtctcggaa gagcctcaat ttgatcaggg aaagggagga
13381 cagggatact atcctggcgt tgttgttccc ccaagagcca ttattagagt tcccttctgt
13441 gcaagatatt ggtgctcgag tgaaagatcc attcacccga caacctgcgg cattttttgca
13501 agagttagat ttgagtgctc cagcaaggta tgacgcattc acacttagtc agattcatcc
13561 tgaactcaca tctccaaatc cggaggaaga ctacttagta cgatacttgt tcagagggat
13621 agggactgca tcttcctctt ggtataaggc atcccatctc ctttctgtac ccgaggtaag
13681 atgtgcaaga cacgggaact cttatactt ggctgaagga agcggagcca tcatgagtct
13741 tcttgaactg catgtaccac atgaaactat ctattacaat acgctctttt caaatgagat
13801 gaaccccccg caacgacatt cgggccgac cccaactcag ttttttgaatt cggttgttta
13861 taggaatcta caggcggagg taacatgcaa ggatggattt gtccaagagt tccgtccatt
13921 atggagagaa aatacagagg aaagtgacct gacctcagat aaagcagtgg ggtatattac
13981 atctgcagta ccctacagat ctgtatcatt gctgcattgt gacattgaaa ttcctccagg
14041 gtccaatcaa agcttactag atcaactagc tatcaattta tctctgattg ccatgcattc
14101 tgtaagggag ggcggggtag taatcatcaa agtgttgtat gcaatgggat actactttca
14161 tctactcatg aacttgtttg ctccgtgttc cacaaaagga tatattctct ctaatggtta
14221 tgcatgtcga ggggatatgg agtgttacct ggtatttgtc atgggttacc tgggcgggcc
14281 tacatttgta catgaggtgg tgaggatggc aaaaactctg gtgcagcggc acggtacgct
14341 cttgtctaaa tcagatgaga tcacactgac caggttattc acctcacagc ggcagcgtgt
14401 gacagacatc ctatccagtc ctttaccaag attaataaag tacttgagga agaatattga
14461 cactgcgctg attgaagccg ggggacagcc cgtccgtcca ttttgtgcgg aaagtttggt
14521 gagcacgcta gcgaacataa ctcagataac ccagattatc gctagtcaca ttgacacagt
14581 catccggtct atgatatata tggaagctga gggtgatctc gctgacacag tatttctatt
14641 taccccttac aatctctcta ctgacgggaa aaagaggaca tcacttaaac agtgcacgag
14701 acagatccta gaggttacaa tactaggtct tagagtcgaa atctcaata aaataggcga
14761 tataatcagc ctagtgctta aaggcatgat ctccatggag gaccttatcc cactaaggac
14821 atacttgaag catagtacct gccctaaata tttgaaggct gtcctaggta ttaccaaact
14881 caaagaaatg tttacagaca cttctgtact gtacttgact cgtgctcaac aaaaattcta
14941 catgaaaact ataggcaatg cagtcaaagg atattacagt aactgtgact cctaacgaaa
15001 atcacatatt aataggctcc ttttttggcc aattgtattc ttgttgattt aattatatta
15061 tgttagaaaa aagttgaact ctgactcctt aggactcgaa ttcgaactca aataaatgtc
15121 tttaaaaaag gttgcgcaca attattcttg agtgtagtct cgtcattcac caaatctttg
15181 tttggt
```

FIG. 27E

PCR PRODUCT

|       | START         | INSERT   | STOP            |
|-------|---------------|----------|-----------------|
| 5'    | GACGACGACAAGATG | ...SENSE... | TAACCGGGCTTCTCCTC 3' |
| 3'    | CTGCTGCTGTTCTAC | ...ANTI...  | ATTGGCCCGAAGAGGAG 5' |

↓ T4 DNA pol + dATP

```
GACGACGACAAGATG...SENSE...TAA
            AC...ANTI...ATTGGCCCGAAGAGGAG 5
```

+

```
 GAT                        CCGGGCTTCTCCTCA
CTACTGCTGCTGTTCT                           T
```

*pBAC LIC TRANSFER PLASMID*

↓ ANNEALING

```
              ek
AspAspAspAspLysMet    INSERT  STOP
GATGACGACGACAAGATG...SENSE..TAACCGGGCTTCTCCTCA
CTACTGCTGCTGTTCTAC...ANTI...ATTGGCCCGAAGAGGAGT
```

*pBAC RECOMBINANT*

FIG. 29

MSPQRDRINAFYKDNPHPKGSRIVINREHLMIDRPYVLLAVLFV
MFLSLIGLLAIAGIRLHRAAIYTAEIHKSLSTNLDVTNSIEHQVKDVLTPLFKIIGDE
VGLRTPQRFTDLVKFISDKIKFLNPDREYDFRDLTWCINPPERIKLDYDQYCADVAAE
ELMNALVNSTLLEARATNQFLAVSKGNCSGPTTIRGQFSNMSLSLLDLYLSRGYNVSS
IVTMTSQGMYGGTYLVEKPNLSSKGSELSQLSMHRVFEVGVIRNPGLGAPVFHMTNYF
EQPVSNDFSNCMVALGELKFAALCHREDAITIPYQGSGKGVSFQLVKLGVWKSPTDMQ
SWVPLSTDDPVIDRLYLSSHRGVIADNQAKWAVPTTRTDDKLRMETCFQQACKGKIQA
LCENPEWAPLKDNRIPSYGVLSVNLSLTVELKIKIASGFGPLITHGSGMDLYKSNHNN
VYWLTIPPMKNLALGVINTLEWVPRFKVSPNLFTVPIKEAGEDCHAPTYLPAEVDGDV
KLSSNLVILPGQDLQYVLATYDTSRVEHAVVYYVYSPSRSFSYFYPFRLPIKGFPIEL
QVECFTWDQKLWCRHFCVLADSESGGHITHSGMVGMGVSCTVTREDGTNRR

FIG. 32A

```
   1 atgtcaccac aacgagaccg gataaatgcc ttctacaaag acaacccca tcctaaggga
  61 agtaggatag ttattaacag agaacatctt atgattgata gaccttatgt tttgctggct
 121 gttctgttcg tcatgtttct gagcttgatc gggctgctag ccattgcagg cattagactg
 181 catcgggcag ccatctacac cgcagagatc cataaaagcc tcagcaccaa tctagatgta
 241 actaactcaa tcgagcatca ggtcaaggac gtgctgacac cactcttcaa gatcattggt
 301 gatgaagtgg gcctgaggac acctcagaga ttcactgatc tagtgaaatt catctctgac
 361 aagattaaat tccttaatcc ggatagggag tacgacttca gagatctcac ttggtgtatc
 421 aacccgccag agagaatcaa attggattat gaccaatact gtgcagatgt ggctgctgaa
 481 gaactcatga atgcattggt gaactcaact ctactggaag ccagggcaac caatcagttc
 541 ctagctgtct caaagggaaa ctgctcaggg cccactacaa tcagaggtca attctcaaac
 601 atgtcgctgt ccctgttgga cttgtatta agtcgaggtt acaatgtgtc atctatagtc
 661 actatgacat cccagggaat gtacgggga acttacctag tggaaaagcc taatctgagc
 721 agcaaaggtt cggagttgtc acaactgagc atgcaccgag tgtttgaagt aggtgttatc
 781 agaaatccgg gtttggggc tccggtgttc catatgacaa actatttga gcaaccagtc
 841 agtaatgatt tcagcaactg catggtggct ttaggagagc tcaaattcgc agcccttgt
 901 cacagggagg atgctatcac aattccctat cagggatcag ggaaaggtgt cagcttccag
 961 ctcgtcaagc taggtgtctg gaaatcccca accgacatgc aatcctgggt cccctatca
1021 acggatgatc cagtgataga caggctttac ctctcatctc acagaggcgt tatcgctgac
1081 aatcaagcaa aatgggctgt cccgacaaca cggacagatg acaagttgcg aatggagaca
1141 tgcttccagc aggcgtgtaa gggtaaaatc caagcactct gcgagaatcc cgagtgggca
1201 ccattgaagg ataacaggat tccttcatac ggggtcttgt ctgttaatct gagtctgaca
1261 gttgagctta aaatcaaaat tgcttcagga ttcgggccat tgatcacaca cggttcaggg
1321 atggacctgt acaaatccaa ccacaacaat gtgtattggc tgactatccc gccaatgaag
1381 aacctagcct taggtgtaat caacacattg gagtgggtac cgagattcaa ggttagtccc
1441 aacctcttca ctgttccaat caaggaagca ggcgaggact gccatgcccc aacataccta
1501 cctgcggagg tggatggtga tgtcaaactc agttccaatc tggtgattct acctggtcaa
1561 gacctccaat atgttttggc aacctacgat acttccagag tgagcatgc tgtggtttat
1621 tacgtttaca gcccaagccg ctcatttct tactttatc cttttaggtt gcctataaag
1681 gggttcccca tcgaattaca ggtggaatgc ttcacttggg accaaaaact ctggtgccgt
1741 cacttctgtg tgcttgcgga ctcagaatct ggtggacata tcactcactc tgggatggtg
1801 ggcatgggag ttagctgtac agtcactcga agagatggaa ccaaccgcag atag
```

FIG. 32B

MSPQRDRINAFYKDNPHPKGSRIVINREHLMIDRPYVLLAVLFV
MFLSLIGLLAIAGIRLHRAAIYTAEIHKSLSTNLDVTNSIEHQVKDVLTPLFKIIGDE
VGLRTPQRFTDLVKFISDKIKFLNPDREYDFRDLTWCINPPERIKLDYDQYCADVAAE
ELMNALVNSTLLEARATNQFLAVSKGNCSGPTTIRGQFSNMSLSLLDLYLSRGYNVSS
IVTMTSQGMYGGTYLVEKPNLSSKGSELSQLSMHRVFEVGVIRNPGLGAPVFHMTNYF
EQPVSNDFSNCMVALGELKFAALCHREDSITIPYQGSGKGVSFQLVKLGVWKSPTDMQ
SWVPLSTDDPVIDRLYLSSHRGVIADNQAKWAVPTTRTDDKLRMETCFQQACKGKIQA
LCENPEWAPLKDNRIPSYGVLSVNLSLTVELKIKIASGFGPLITHGSGMDLYKSNHNN
VYWLTIPPMKNLALGVINTLEWVPRLKVSPNLFTVPIKEAGEDCHAPTYLPAEVDGDV
KLSSNLVILPGQDLQYVLATYDTSRVEHAVVYYVYSPSRSFSYFYPFRLPIKGFPIEL
QVECFTWDQKLWCRHFCVLADSETGGHITHSGMVGMGVSCTVTREDGTNRR

FIG. 33A

```
   1 atgtcaccac aacgagaccg gataaatgcc ttctacaaag acaaccccca tcctaaggga
  61 agtaggatag ttattaatag agaacatctt atgattgata gaccttatgt tttgctggct
 121 gttctattcg tcatgtttct gagcttgatc gggctgctag ccattgcagg cattagactg
 181 catcgggcag ccatctacac cgcagagatc cataaaagcc tcagcaccaa tctagatgta
 241 actaactcaa tcgagcatca ggtcaaggac gtgctgacac cactcttcaa gatcatcggt
 301 gatgaagtgg gcctgaggac acctcagaga ttcactgacc tagtgaaatt catctctgac
 361 aagattaaat tccttaatcc ggataggag tacgacttca gagatctcac ttggtgtatc
 421 aacccgccag agagaatcaa attggattat gaccaatact gtgcagatgt ggctgctgaa
 481 gaactcatga atgcattggt gaactcaact ctactggagg ccagggcaac caatcagttc
 541 ttagctgtct caaagggaaa ctgctcaggg cccactacaa tcagaggtca attctcaaac
 601 atgtcgctgt ccctgttgga cttgtattta agtcgaggtt acaatgtgtc atctatagtc
 661 actatgacat cccagggaat gtacggggga acttacctag tggaaaagcc taatctgagc
 721 agcaaagggt cagagttgtc acaactgagc atgcaccggg tgtttgaggt aggtgttatc
 781 agaaatccgg gtttgggggc tccagtgttc catatgacaa actattttga gcaaccagtc
 841 agtaatgatt tcagcaactg catggtggct taggggagc tcaaattcgc agccctttgt
 901 cacagggagg attctatcac aattccctat caagggtcag ggaaaggtgt cagcttccag
 961 ctcgtcaagc taggtgtctg gaaatcccca accgacatgc aatcctgggt cccctatca
1021 acggatgatc cagtgataga caggctttac ctctcatctc acagaggcgt tatcgctgac
1081 aatcaagcaa aatgggctgt cccgacaaca cggacagatg acaagttgcg aatggagaca
1141 tgcttccagc aggcgtgtaa gggtaaaatc caagcactct gcgagaatcc cgagtgggca
1201 ccattgaagg ataacaggat tccttcatac ggggtcttgt ctgttaatct gagtctgaca
1261 gttgagctta aaatcaaaat tgcttcagga ttcgggccat tgatcacaca cggttcaggg
1321 atggacctgt acaagtccaa ccacaacaat gtgtattggc tgactatccc gccaatgaag
1381 aacctagcct taggtgtaat caacacattg gaatgggtac cgagactcaa ggttagtccc
1441 aacctcttca ctgttccaat caaggaggca ggcgaggact gccatgcccc gacatacct a
1501 cctgcggagg tggatggtga tgtcaaactc agttccaatc tggtgattct acctggtcaa
1561 gacctccaat atgttttggc aacctacgat acttccagag ttgaacatgc tgtggtttat
1621 tacgtttaca gcccaagccg ctcatttct tactttatc cttttaggtt gcctataaag
1681 ggggtcccca tcgaattaca ggtggaatgc ttcacatggg accaaaaact ctggtgccgt
1741 cacttctgtg tgcttgcgga ctcagaaact ggtggacata tcactcactc tgggatggtg
1801 ggcatgggag tcagctgcac agtcactcgg gaagatggaa ccaaccgcag atag
```

FIG. 33B

```
MSLQRDRINAFYKDNPHPKGSRIVINREHLMIDRPYVLLAVLFV
MFLSLIGLLAIAGIRLHRAAIYTAEIHKSLSTNLDVTNSIEHQVKDVLTPLFKIIGDE
VGLRTPQRFTDLVKFISDKIKFLNPDREYDFRDLTWCINPPERIKLNYDQYCADVAAE
ELMNALVNSTLLETRTTNQFLAVSKGNCSGPTTIRGQFSNMSLSLLDLYLSRGYNVSS
IVTMTSQGMYGGTYLVEKPNLNSKGSELSQLSMYRVFEVGVIRNPGLGAPVFHMTNYF
EQPISNDLSNCMVALGELKLAALCHGGDSITIPYQGSGKGVSFQLVKLGVWKSPTDMQ
SWVPLSTDDPVIDRLYLSSHRGVITDNQANWAVPTTRTDDKLRMETCFQQACKGKIQA
LCENPEWAPLKDSRIPSYGVLSVNLSLAAEPKIKIASGFGPLITHGSGMDLYKSNHNN
VYWLTIPPMKNLALGVINTLEWIPRLKVSPNLFTVPIKEAGENCHAPTYLPAEVDGDV
KLSSNLVILPGQDLQYVLATYDTSRVEHAVVYYVYSPSRSFSYFYPFRLPIKGTPIEL
QVECFTWDQRLWCRHFCVLADSESGGHITHSGMVGMGVSCTVNREDEANRR
```

FIG. 34A

```
   1 atgtcactgc aacgagaccg gataaatgcc ttctacaaag ataaccctca ttccaaagga
  61 agtaggatag ttattaacag agaacatctc atgattgata gaccttatgt tttgctggct
 121 gttctgttcg tcatgtttct gagcttgatc gggttgctgg ccattgcagg cattaggctt
 181 catcgggcag ctatctacac tgcagagatc cataaaagcc tcagcaccaa tctagatgta
 241 actaactcaa tcgagcatca ggtcaaggat gtgctgacac cgctcttcaa aatcatcggt
 301 gatgaagtgg gcctgagaac acctcagaga ttcactgacc tagtgaaatt catctctgac
 361 aagatcaaat tccttaatcc ggatagggag tatgacttca gagatctcac ttggtgtatc
 421 aacccgccag agagaatcaa attgaattat gatcaatact gtgcagatgt ggctgctgaa
 481 gagctcatga atgcattagt gaactcaact ctactggaga ccagaacaac caatcagttc
 541 ctagctgtct caaagggaaa ctgctcaggg cccactacca tcagaggtca attctcaaac
 601 atgtcgctgt ctctgttaga cttatattta agtcgaggtt acaatgtgtc atctatagtc
 661 actatgacgt cccagggaat gtatggggga acttacctag ttgaaaagcc aatctgaac
 721 agcaaaggat cagaattatc acaactgagc atgtaccgag tgtttgaagt aggtgttata
 781 agaaatccag gcttgggggc tccggtgttc catatgacaa actatttga acaaccaatc
 841 agcaaggatc tcagcaactg catggtagct tggggggagc tcaaactcgc agccctttgt
 901 cacgggggag attccatcac aattccctat cagggatcag ggaaaggtgt cagcttccaa
 961 ctcgtcaagc taggtgtctg gaaatcccca accgacatgc aatcctgggt ccccctatca
1021 acggatgacc cagtgataga caggctttac ctctcatctc acagaggtgt catcactgac
1081 aatcaagcaa attgggctgt tccgacaaca cgaacagatg ataagttgcg gatggagaca
1141 tgcttccagc aggcgtgcaa gggcaaaatc caagcactct gtgaaaatcc cgagtgggca
1201 ccgttgaagg acagcaggat tccttcatac ggggtcttgt ctgtcgacct gagtctggca
1261 gctgagccca aaatcaaaat tgcttcggga ttcggtccat tgatcactca cggttcaggg
1321 atggacctat acaaatccaa ccacaacaat gtgtattggc tgactatccc gccaatgaag
1381 aacttagcct taggtgtaat caacacattg gagtggatac cgagactcaa ggttagtccc
1441 aacctcttca ctgtcccaat taaggaagct ggcgagaact gccatgcccc aacataccta
1501 cctgcggagg tggatggtga tgtcaaactc agttccaatc tggtgatttt acctggtcaa
1561 gatctccaat atgttttggc aacctacgat acttccagag ttgaacatgc tgtggtttat
1621 tacgtttaca gcccaagccg ctcattctct tactttatc cctttaggtt acctataaag
1681 gggatcccca tcgaattaca agtggaatgc ttcacatggg accaaagact ctggtgccgt
1741 cacttctgtg tgcttgctga ctcggaatct ggtggacata tcacccactc tgggatggtg
1801 ggcatgggag tcagctgcac agtcaaccgg gaagacgaag ccaatcgcag atag
```

FIG. 34B

MGLKVNVSAIFMAVLLLQTPTGQIHWGNLSKIGVVGIGSASYK
VMTRSSHQSLVIKLMPNITLLNNCTRVEIAEYRRLLRTVLEPIRDALNAMTQNIRPFQ
SVASSRRHKRFAGVVLAGAALGVATAAQITAGIALHQSMLNSQAIDNLRASLETTNQA
IEAIRQAGQEMILAVQGVQDYINNELIPSMNQLSCDLIGQKLGLKLLRYYTEILSLFG
PSLRDPISAEISIQALSYALGGDINKVLEKLGYSGGDLLGILESRGIKARITHVDTES
YFIVLSIAYPTLSEIKGVIVHRLEGVSYNIGSQEWYTTVPKYVATQGYLISNFDESSC
TFNPEGTVCSQNALYPMSPLLQECLRGSTKSCARTLVSGSFGNRFILSQGNLIANCAS
ILCKCYTTGTIINQDPDKILTYIAADHCPVVEVNGVTIQVGSRRYPDAVYLHRIDLGP
PISLERLDVGTNLGNAIAKLEDAKELLESSDQILRSMKGLSSTSIVYILIAVCLGGLI
GIPALICCCRGRCNKKGEQVGMSRPGLKPDLTGTSKSYVRSL

FIG. 35A

```
   1 cttagggtca aggaacatac acacccaaca gaacccagac cccgacccac ggcgccgcgc
  61 ccccaacccc cgacaaccag agggagcccc caaccaatcc cgccggctcc ctcggtgccc
 121 acagacaggc acaccaaccc ccgaacaggc ccagtgccca gccatcgaca atctaagacg
 181 ggggggcccc ccccaaaaaa agcccccagg ggccgacagc cagcaccgcg cggaagccca
 241 cccaccccac acacgaccac gacaaccaaa ccagaatcca gaccaccctg ggccgccagc
 301 tcccagactc ggccatcacc ccgcagaaag gaaagggcac aacccgcgca ccccagcccc
 361 gatccggcgg gcagccaccc aacccgaacc ggcacccaag agcgatcccc gaaggacccc
 421 cgagccgcaa aggacatcag tatcccacag cctctccaag tccctggtc tcttcctctt
 481 ctcgaaggga ccaaaagatc aatccaccac atccgacgac actcaactcc caccccctaa
 541 aggagacacc gggagtcctg gaatcaagac tcatccaatg tccatcatgg gtctcaaggt
 601 gaacgtctct gccatattca tggcagtact gttaactctc caaacaccca ccggtcaaat
 661 ccattggggc aatctctcta agatagggt ggtaggaata ggaagtgcaa gctacaaagt
 721 tatgactcgt tccagccatc aatcattagt cataaaatta atgcccaata taactctcct
 781 caataactgc acgagggtag agattgcaga atacaggaga ctactgagaa cagttttgga
 841 accaattaga gatgcactta atgcaatgac ccagaatata agaccgtttc agagtgtagc
 901 ttcaagtagg agacacaaga gatttgcggg agtagtcctg gcaggtgcgg ccctaggcgt
 961 tgccacagct gctcagataa cagccggcat tgcacttcac cagtccatgc tgaactctca
1021 agccatcgac aatctgagag caagtctgga aactactaat caggcaattg aggcaatcag
1081 acaagcaggg caggagatga tattggctgt tcagggtgtc caagactaca tcaataatga
1141 gctgataccg tctatgaacc aactatcttg tgatttaatc ggccagaagc tcgggctcaa
1201 attgctcaga tactatacag aaatcctgtc attatttggc cctagcttac gggaccccat
1261 atctgcggag atatctatcc aggctttgag ctatgcgctc ggaggagata tcaataaggt
1321 gttagaaaag ctcggatata gcggaggtga tttactgggc atcttagaga gcagaggaat
1381 aaaggcccgg ataactcacg tcgacacaga gtcctactc attgtcctca gtatagctta
1441 tccgacgctg tccgagatca agggggtgat tgtccaccgg ctcgaggggg tctcgtacaa
1501 cataggctct caagagtggt atacgactgt gcccaagtat gttgcaaccc aagggtacct
1561 tatctcgaat tttgatgagt catcgtgtac ttttatgcca gaggggactg tgtgcagcca
1621 aaatgccttg tacccgatga gtcctctgct ccaagaatgc tccgggggt ccaccaagtc
1681 ctgtgctcgt acactcgtat ctgggtcttt tgggaaccgg tttattttgt cacaagggaa
1741 cctaatagcc aattgtgcat cgatcctttg caagtgttac acaacaggaa cgatcattaa
1801 tcaagaccct gacaagatcc taacatacat tgctgcagat cactgcccgg tagtcgaagt
1861 gaacggcgtg accatccaag tcgggagcag gaggtatcca gacgctgtgt acttgcacag
1921 aattgacctc ggtcctccca tcattggga gaggttggac gtagggacaa atctgggaa
1981 tgcaattgct aagttggagg atgccaaaga attgttggag tcatcggacc agatattgag
2041 gagtatgaaa ggtttgtcga gcactagcat agtctacatc ctgattgcag tgtgtcttgg
2101 agggttgata gggatccccg ctttaatatg ttgctgcagg gggcgttgta acaaaaggg
2161 agaacaagtt ggtatgtcaa gaccaggcct aaagcctgat cttacaggaa catcaaaatc
2221 ctatgtaagg tcgctctgat cctctacaac tcttggaaca caaatgtccc acaagtctcc
2281 tcttcgtcat caagcaacca ccgcatccag catcaagccc acctgaaatt atctccggct
2341 tccctttggc cgaacaatat cggcagttaa ttaaaactta ggg
```

FIG. 35B

MSIMGLKVNVSAIFMAVLLTLQTPTGQIHWGNLSKIGVVGIGSA
SYKVMTRSSHQSLVIKLMPNITLLNNCTRVEIAEYRRLLRTVLEPIRDALNAMTQNIR
PVQSVASSRRHKRFAGVVLAGAALGVATAAQITAGIALHQSMLNSQAIDNLRASLETT
NQAIEAIRQAGQEMILAVQGVQDYINNELIPSMNQLSCDLIGQKLGLKLLRYYTEILS
LFGPSLRDPISAEISIQALSYALGGDINKVLEKLGYSGGDLLGILESRGIKARITHVD
TESYFIVLSIAYPTLSEIKGVIVHRLEGVSYNIGSQEWYTTVPKYVATQGYLISNFDE
SSCTFMPEGTVCSQNALYPMSPLLQECLRGSTKSCARTLVSGSFGNRFILSQGNLIAN
CASILCKCYTTGTIINQDPDKILTYIAADHCPVVEVNGVTIQVGSRRYPDAVYLHRID
LGPPISLERLDVGTNLGNAIAKLEDAKELLESSDQILRSMKGLSSTSIVYILIAVCLG
GLIGIPALICCCRGRCNKKGEQVGMSRPGLKPDLTGTSKSYVRSL

FIG. 36A

```
   1 tcgagggcca aggaacatac acacccaaca gaacccagac cccggcccac ggcgccgcgc
  61 ccccaacccc cgacaaccag agggagcccc caaccaatcc gccggctccc ccggtgccca
 121 caggcaggga caccaacccc cgaacagacc cagcacccaa ccatcgacaa tccaagacgg
 181 gggggccccc ccaaaaaaaa ggccccccagg ggccgacagc cagcaccgcg aggaagccca
 241 cccaccccac acacgaccac ggcaaccaaa ccagaaccca gaccaccctg ggtcaccagc
 301 tccagacctc ggtcatcacc ccgcagaaag gaaaggcaca acccgcgacc ccagccccga
 361 tccggcgggg agccacccaa cccgaaccag cacccaagag cgatccccga aggaccccccg
 421 aaccgcaaag gacatcagta tcccacagcc tctccaagtc ccccggtctc ctcctcttct
 481 cgaagggacc aaaagatcaa tccaccacca cacacccgac gacactcaac tccccacccc
 541 taaaggagac accgggaatc ccagaatcaa gactcatcca atgtccatca tgggtctcaa
 601 ggtgaacgtc tctgccatat tcatggcagt actgttaact ctccaaacac ccaccggtca
 661 aatccattgg ggcaatctct ctaagatagg ggtggtagga ataggaagtg caagctacaa
 721 agttatgact cgttccagcc atcaatcatt agtcataaaa ttaatgccca atataactct
 781 cctcaataac tgcacgaggg tagagattgc agaatacagg agactactga gaacagtttt
 841 ggaaccaatt agagatgcac ttaatgcaat gacccagaat ataagaccgg ttcagagtgt
 901 agcttcaagt aggagacaca agagatttgc gggagtagtc ctggcaggtg cggccctagg
 961 cgttgccaca gctgctcaga taacagccgg cattgcactt caccagtcca tgctgaactc
1021 tcaagccatc gacaatctga gagcgagcct ggaaactact aatcaggcaa ttgaggcaat
1081 cagacaagca gggcaggaga tgatattggc tgttcagggt gtccaagact acatcaataa
1141 tgagctgata ccgtctatga accaactatc ttgtgattta atcggccaga agctcgggct
1201 caaattgctc agatactata cagaaatcct gtcattattt ggccccagct acgggaccc
1261 catatctgcg gagatatcta tccaggctt gagctatgcg cttggaggag acatcaataa
1321 ggtgttagaa aagctcggat acagtggagg tgatttactg ggcatcttag agagcagagg
1381 aataaaggcc cggataactc acgtcgacac agagtcctac ttcattgtcc tcagtatagc
1441 ctatccgacg ctgtccgaga ttaaggggggt gattgtccac cggctagagg gggtctcgta
1501 caacataggc tctcaagagt ggtataccac tgtgcccaag tatgttgcaa cccaagggta
1561 ccttatctcg aattttgatg agtcatcgtg tactttcatg ccagagggga ctgtgtgcag
1621 ccaaaatgcc ttgtacccga tgagtcctct gctccaagaa tgcctccggg gtccaccaa
1681 gtcctgtgct cgtacactcg tatccgggtc ttttgggaac cggttcattt tatcacaagg
1741 gaacctaata gccaattgtg catcaatcct ttgcaagtgt tacacaacag gaacgatcat
1801 taatcaagac cctgacaaga tcctaacata cattgctgcc gatcactgcc cggtagtcga
1861 ggtgaacggc gtgaccatcc aagtcgggag caggaggtat ccagactgtg tacttgca
1921 cagaattgac ctcggtcctc ccatatcatt ggagaggttg gacgtaggga caaatctggg
1981 gaatgcaatt gctaagttgg aggatgccaa ggaattgttg gagtcatcgg accagatatt
2041 gaggagtatg aaaggttat cgagcactag catagtctac atcctgattg cagtgtgtct
2101 tggagggttg atagggatcc ccgctttaat atgttgctgc aggggggcgtt gtaacaaaaa
2161 gggagaacaa gttggtatgt caagaccagg cctaaagcct gatcttacgg gaacatcaaa
2221 atcctatgta aggtcgctct gatcctctac aactcttgaa acacaaatgt tcccacaagt
2281 ctcctcttcg tcatcaagca accaccgcac ccagcatcaa gcccacctga accagctaaa
2341 ttatctccgg cttccctctg gccgaacaat atcggtagtt aatt
```

FIG. 36B

MSIMGLKVNVSAIFMAVLLTLQTPAGQIHWGNLSKIGVVGIGSA
SYKVMTRSSHQSLVIKLIPNITLLNNCTRVEIAEYRRLLRTVLEPIRDALNAMTQNIR
PVQSVASSMRHKRFAGVVLAGAALGVATAAQITAGIALHRSMLNSQAIDNLRASLETT
NQAIEAIRQAGQEMILAVQGVQDYINNELIPSMNQLSCDLIGQKLGLKLLRYYTEILS
LFGPSLRDPISAEISIQALSYALGGDINKVLEKLGYSGGDLLGILESRGIKARITHVD
TESYFIVLSIAYPTLSEIKGVIVHRLEGVSYNIGSQEWYTTVPKYVATQGYLISNFDE
SSCTFMPEGTVCSQNALYPMSPLLQECLRGSTKSCARTLVSGSFGNRFILSQGNLIAN
CASILCKCYTTGTIINQDPDKILTYIAADHCPVVEVNGVTIQVGSRRYPDAVYLHRID
LGPPISLERLDVGTNLGNAIAKLEDAKELLESSDQILRSMKGLSSTSIVYILIAVCLG
GLIGIPTLICCCRGRCNKKGEQVGMSRPGLKPDLTGTSKSYVRSL

FIG. 37A

```
   1 atgtccatca tgggtctcaa ggtgaacgtc tctgccatat tcatggcagt actgttaact
  61 ctccaaacac ccgccggtca aatccattgg ggcaatctct ctaagatagg ggtagtagga
 121 ataggaagtg caagctacaa agttatgact cgttccagcc atcaatcatt agtcataaaa
 181 ttaattccca atataactct cctcaataac tgcacgaagg tagagattgc agagtacagg
 241 agactactaa gaacagtttt ggaaccaatt agagatgcac ttaatgcaat gacccagaac
 301 ataaggccgg ttcagagcgt agcttcaagt atgagacaca gagatttgc gggagtagtc
 361 ctggcaggtg cggccctagg cgttgccaca gctgctcaga taacagccgg cattgcactt
 421 caccggtcca tgctgaactc tcaagccatc gacaatctga gagcgagcct ggaaactact
 481 aatcaggcaa ttgaggcaat cagacaagca gggcaggaga tgatcttggc tgttcagggg
 541 gtccaagact acatcaataa tgagctgata ccatctatga accagctatc ttgtgattta
 601 atcgggcaga agctcgggct caaattgctc agatactata cagaaatcct gtcattattt
 661 ggccccagcc tacgagaccc catatctgcg agatatctca tccaggcctt gagctatgca
 721 cttggaggag atatcaataa ggtgttagaa aagctcggat acagtggagg cgatttactg
 781 ggcatcttag agagcagagg aataaaggct cggataactc acgtcgacac agagtcctac
 841 ttcattgtcc tcagtatagc ctatccgaca ctgtccgaga ttaaggggt gattgtccat
 901 cggctagagg gggtctcgta acatagc tctcaagagt ggtataccac tgtgcccaag
 961 tatgttgcaa cccaagggta ccttatctcg aattttgatg agtcatcgtg taccttcatg
1021 ccagagggga ctgtgtgcag ccaaaatgcc ttgtacccga tgagtcctct gctccaagaa
1081 tgcctccggg ggtccaccaa gtcctgtgct cgtacactcg tatccgggtc ttttgggaac
1141 cggttcattt tatcacaagg gaacctaata gccaattgtg catcaattct ttgcaagtgt
1201 tacacaacag gaacgatcat taatcaagac cctgacaaga ttctaacata catcgctgcc
1261 gatcgctgcc cggtagtcga ggtaaacggc gtgaccatcc aagtcgggag caggaggtat
1321 ccagacgctg tgtatttgca cagaattgac ctcggtcctc ccatatcatt ggagaggttg
1381 gacgtaggga caaatctggg gaatgcaatt gccaaattgg aggatgccaa ggaattgttg
1441 gagtcatcgg accagatatt gaggagtatg aaaggtttat cgagcactag catagtctac
1501 atcctgattg cagtgtgtct tggagggctg ataggatcc ccactttaat atgttgctgc
1561 aggggggcgtt gtaacaaaaa gggagaacaa gttggtatgt caagaccagg cctaaagcct
1621 gatcttacag gaacatcaaa atcatatgta aggtcgctct ga
```

FIG. 37B

MATLLRSLALFKRNKDKPPITSGSGGAIRGIKHIIIVPIPGDSS
ITTRSRLLDRLVRLIGNPDVSGPKLTGALIGILSLFVESPGQLIQRITDDPDVSIRLL
EVVQSDQSQSGLTFASRGTNMEDEADQYFSHDDPSSSDQSRFGWFENKEISDIEVQDP
EGFNMILGTILAQIWVLLAKAVTAPDTAADSELRRWIKYTQQRRVVGEFRLERKWLDV
VRNRIAEDLSLRRFMVALILDIKRTPGNKPRIAEMICDIDTYIVEAGLASFILTIKFG
IETMYPALGLHEFAGELSTLESLMNLYQQMGETAPYMVILENSIQNKFSAGSYPLLWS
YAMGVGVELENSMGGLNFGRSYFDPAYFRLGQEMVRRSAGKVSSTLASELGITAEDAR
LVSEIAMHTTEDRISRAVGPRQSQVSFLHGDQNENELPRWGGKEDMRVKQSRGEARES
YRETRPSRASDARATHPPTDTPLDIDTASESSQDPQDSRRSADALLRLQAMAGISEEQ
GSDTDTPRVYNDRDLLD

FIG. 38A

```
   1 aggattcaag atcctattat cagggacaag agcaggatta gggatatccg agatggccac
  61 acttctaagg agcttagcat tgttcaaaag aaacaaggac aaaccaccca ttacatcagg
 121 atccggtgga gccatcagag gaatcaaaca cattattata gtaccaatcc cgggagattc
 181 ctcaattacc actcgatcta gacttctgga ccggttggtc aggttaattg gaaacccgga
 241 tgtgagcggg cccaaactaa cagggcact  aataggtata ttatccttat ttgtggagtc
 301 tccaggtcaa ttgattcaga ggatcaccga tgaccctgac gttagcataa ggctgttaga
 361 ggttgtccag agtgaccagt cacaatctgg ccttaccttc gcatcaagag gtaccaacat
 421 ggaggatgag gcggaccaat attttcaca  tgatgatcca agtagtagtg atcaatccag
 481 gttcggatgg ttcgagaaca aggaaatctc agatattgaa gtgcaagacc ctgagggatt
 541 caacatgatt ctgggtacca tcctagctca aatttgggtc ttgctcgcaa aggcggttac
 601 ggccccagac acggcagctg attcggagct aagaaggtgg ataaagtaca cccaacaaag
 661 aagggtagtt ggtgaattta gattggagag aaaatggttg gatgtggtga ggaacaggat
 721 tgccgaggac ctctccttac gccgattcat ggtcgctcta atcctggata tcaagagaac
 781 acccgggaac aaacccagga ttgctgaaat gatatgtgac attgatacat atatcgtaga
 841 ggcaggatta gccagtttta tcctgactat taagtttggg atagaaacta tgtatcctgc
 901 tcttggactg catgaatttg ctggtgagtt atccacactt gagtccttga tgaatcttta
 961 ccagcaaatg ggggaaactg caccatacat ggtaatcctg agaactcaa  ttcagaacaa
1021 gttcagtgca ggatcatacc ctctgctctg gagctatgcc atgggagtag gagtggaact
1081 tgaaaactcc atgggaggtt tgaactttgg ccgatcttac ttcgatccag catatttag
1141 actagggcaa gagatggtga ggaggtcagc tggaaaggtc agttccacat ggcatctga
1201 actcggtatc actgccgaag atgcaaggct tgtttcagag atcgcaatgc atactacaga
1261 ggacaggatc agtagagcgg ttggacccag acaatcccaa gtgtcattcc tacacggtga
1321 tcaaaatgaa aatgagctac gagatgggg  gggtaaggaa gatatgaggg tcaaacagag
1381 tcggggagaa gccagagaga gctacagaga aaccaggccc agcagagcaa gtgacgcgag
1441 agctacccat cctccaaccg acacacctt  agacattgac actgcatcgg agtccagcca
1501 agatccgcag gacagtcgaa ggtcagctga cgccctgctc aggctgcaag ccatggcagg
1561 aatctcggaa gaacaaggct cagacacgga cacccctaga gtgtacaatg acagagatct
1621 tctagactag gtgcaagagg ccgaggacca gaacaacatc cgcctaccct ccatcattgt
1681 tataa
```

FIG. 38B

MATLLRSLALFKRNKDKPPITSGSGGAIRGIKHIIIVPIPGDSS
ITTRSRLLDRLVRLIGNPDVSGPKLTGALIGILSLFVESPGQLIQRITDDPDVSIRLL
EVVQSDQSQSGLTFASRGTNMEDEADQYFLHDDSSSGDQFRSGWFENKEISDIEVQDP
EGFNMILGTILAQIWVLLAKAVTAPDTAADSELRRWIKYTQQRRVVGEFRLERKWLDV
VRNRIAEDLSLRRFMVALILDIKRTPGNKPRIAEMICDIDTYIVEAGLASFILTIKFG
IETMYPALGLHEFAGELSTLESLMNLYQQMGETAPYMVILENSIQNKFSAGSYPLLWS
YAMGVGVELENSMGGLNFGRSYFDPAYFRLGQEMVRRSAGKVSSTLASELGITAEDAR
LVSEIAMHTTEDRISRAVGPRQAQVSFLHGDQSENELPGLGGKEDKRVKQSRGEARES
YRETGHSRANDARAADLPTDTPLDIDTASESSQDPQDSRRSADALLRLQAMAGIPEEQ
GSDMDTPRVYNDRDLLD

FIG. 39A

```
   1 atggccacgc tattaaggag cttagcattg ttcaaaagaa acaaggacaa accacccatt
  61 acatcaggat ccggtggggc catcagaggg atcaaacaca ttattatagt accaatccct
 121 ggagactcct caattaccac tcgatccaga cttctggacc ggttggtcag gctaattgga
 181 aacccggatg tgagtgggcc taaattaaca ggggcactaa taggtatatt gtccttattt
 241 gtggagtctc caggtcaatt gattcagaga atcaccgatg accctgacgt tagcataagg
 301 ctgttagagg ttgtccagag cgaccagtca caatctggcc ttacctttgc atcaagaggt
 361 accaacatgg aggatgaggc ggaccaatac ttttttacatg atgattcaag tagcggtgat
 421 caattcaggt ccggatggtt cgagaacaag gaaatctcag atattgaagt gcaggaccct
 481 gagggattca acatgattct gggtaccatc ctagctcaaa tttgggtctt gctcgcaaag
 541 gcggttacgg ccccagacac ggcagctgat tcggagctaa gaaggtggat aaaatacacc
 601 caacaaagaa gggtagtcgg tgaattcaga ttggagagaa aatggttgga tgtagtgagg
 661 aacaggattg ccgaggacct ctccttacgc cggttcatgg tcgctctaat cctggatatc
 721 aagagaacac ccgggaacaa acccaggatt gctgaaatga tatgtgacat tgacacatat
 781 atcgtggagg caggattagc cagttttatc cttactatta gtttgggat agaaaccatg
 841 tatcctgctc ttggactgca tgaatttgct ggtgagttat caacacttga gtccttgatg
 901 aacctttatc agcaaatggg ggaaactgca ccctacatgg tcattctgga gaactcaatt
 961 cagaacaagt tcagtgcagg atcataccct gctctctgga gctatgccat gggagtagga
1021 gtggaactcg aaaactccat gggagtttg aactttggcc gatcttactt tgatccagca
1081 tattttagat taggacaaga gatggtcagg aggtcagctg gaaggtcag ttccacattg
1141 gcatctgaac tcggtatcac ggccgaggat gcaaggcttg tttcagagat tgcaatgcat
1201 actactgagg acaggatcag tagagcggtt ggacccaggc aagcccaagt gtcatttcta
1261 cacggtgatc aaagtgagaa tgagctaccg ggattgggag gtaaggaaga taagagagtc
1321 aaacagagtc gaggagaagc cagggagagc tatagagaaa ctgggcacag cagagcaaat
1381 gatgcgagag ctgctgacct tccaaccggc acacccctag acattgacac tgcatcggag
1441 ttcagccaag acccacagga cagtcgaagg tcagctgacg ccctgctcag gctgcaagcc
1501 atggcaggga tcccggaaga acaaggctca gacatggaca ccctagagt gtacaatgac
1561 agagatcttc tagactag
```

FIG. 39B

MATLLRSLALFKRNKDKPPITSGSGGAIRGIKHIIIVPIPGDSS
ITTRSRLLDRLVRLIGNPDVSGPKLTGALIGILSLFVESPGQLIQRITDDPDVSIRLL
EVVQSDQSQSGLTFASRGTNMEDEADQYFSHDDPISSDQSRFGWFENKEISDIEVQDP
EGFNMILGTILAQIWVLLAKAVTAPDTAADSELRRWIKYTQQRRVVGEFRLERKWLDV
VRNIIAEDLSLRRFMVALILDIKRTPGNKPRIAEMICDIDTYIVEAGLASFILTIKFG
IETMYPALGLHEFAGELSTLESLMNLYQQMGKPAPYMVNLENSIQNKFSAGSYPLLWS
YAMGVGVELENSMGGLNFGRSYFDPAYFRLGQEMVRRSAGKVSSTLASELGITAEDAR
LVSEIAMHTTEDRISRAVGPRQAQVSFLQGDQSENELPRLGGKEDRRVKQSRGEARES
YRETGPSRASDARAAHLPTGTPLDIDTASESSQDPQDSRRSAEPLLSCKPWQESRKNK
AQTRTPLQCTMTEIF

FIG. 40A

```
   1 atggccacgc ttttaaggag cttagcattg ttcaaaagaa acaaggacaa accacccatt
  61 acatcaggat ccggtggagc catcagagga atcaaacaca ttattatagt accaatccct
 121 ggagattcct caattaccac tcgatccaga cttctggacc ggttggtcag gttaattgga
 181 aacccggatg tgagcgggcc caaactaaca ggggcactaa taggtatatt gtccttattt
 241 gtggagtctc caggtcaatt gattcagagg atcaccgatg accctgacgt agcataagg
 301 ctgttagagg ttgtccagag tgaccagtca aatctggcc ttaccttcgc atcaagaggt
 361 accaacatgg aggatgaggc ggaccaatac ttttcacatg atgatccaat tagcagtgat
 421 caatccaggt tcggatggtt cgagaacaag gaaatctcag atattgaagt gcaagaccct
 481 gagggattca acatgattct gggtaccatc ctagcccaaa tttgggtctt gctcgcaaag
 541 gcggttacgg ccccagacac ggcagctgat tcggagctaa gaaggtggat aaagtacacc
 601 caacaaagaa gggtagttgg tgaatttaga ttggagagaa aatggttgga tgtggtgagg
 661 aacattattg ccgaggacct ctccttacgc cgattcatgg tcgctctaat cctggatatc
 721 aagagaacac ccggaaacaa acccaggatt gctgaaatga tatgtgacat tgatacatat
 781 atcgtagagg caggattagc cagttttatc ctgactatta gtttgggat agaaactatg
 841 tatcctgctc ttggactgca tgaatttgct ggtgagttat caacacttga gtccttgatg
 901 aacctttacc agcaaatggg gaaacctgca cctacatgg tcaacctgga gaactcaatt
 961 cagaacaagt tcagtgcagg atcataccct ctgctctgga gctatgccat gggagtagga
1021 gtggaacttg aaaactccat gggaggtttg aactttggcc gatcttactt tgatccagca
1081 tattttagat tagggcaaga gatggtaagg aggtcagctg gaaaggtcag ttccacatta
1141 gcatctgaac tcggtatcac tgccgaggat gcaaggcttg tttcagagat tgcaatgcat
1201 actactgagg acaagatcag tagagcggtt ggacccagac aagcccaagt atcatttcta
1261 cagggtgatc aaagtgagaa tgagctaccg cgattggggg caaggaaga taggagggtc
1321 aaacagagtc gaggagaagc cagggagagc tacagagaaa ccgggcccag cagagcaagt
1381 gatgcgagag ctgcccatct tccaaccggc acacccctag acattgacac tgcatcggag
1441 tccagccaag atccgcagga cagtcgaagg tcagctgagc ccctgcttag ctgcaagcca
1501 tggcaggaat ctcggaagaa caaggctcag acacggacac cctacagtg tacaatgaca
1561 gaaatcttct agactaggtg cgagaggccg agggccagaa caacatccgc ctaccctcca
1621 tcattgttat a
```

FIG. 40B

MHMFPLGVVEDSDPPGPPIGRASGSPPPGAGRSTAKPEELLKEA
TEANIVVRRTAGLNEKLAFHNNTPPTLPTPRRKAPTTGSVLNANQACNAVNLAPLDTP
QRFRVVYMSITRPLDNGYYTVPRRMLEFRSVNAVAFNLLVTLRIDKAIGPGKIIDNAE
QLPEATFMVHIGDFRRKKSEVYSADYCKMKIEKMGLVFALGGIGGTSLHTRSTGKMSK
TLHAQLGFKKTSCYPPMDINEDLNRLLWRSRCKIVRIQAVLQPSVPQELRIYDDVIIN
DDQGVFKVLQTVVPSNARKRPPSQ

FIG. 41A

```
   1 aggagcaaag tgattgcctc ccaagctcca caacgacaga gatccacgac ctcgacaagt
  61 cggcatggga catcaagggg tcgatcgctc cgacacaacc caccacccac agtgatggca
 121 ggctggtgcc ccaggccaga gccacagatc ctggtctagg cgacaggaag ggcgaacgcc
 181 ccatgcacat gtttccgctg ggggtcgttg aggacagcga ccccccaggg cctccaatcg
 241 ggcgagcatc cgggtccccg cccccaggcg ctggcagatc cacagcaaaa cccgaagaac
 301 tcctcaaaga ggccaccgag gccaacatag tcgtcagacg cacagcaggg ctcaacgaaa
 361 aactggcgtt ccacaacaat accccaccaa ctctccccac accccggaga aaggccccaa
 421 caacagggag cgtcctcaac gcaaaccaag cgtgcaatgc ggtcaatctg caccgctgg
 481 acaccccgca gaggttccgt gttgtctaca tgagcatcac ccgtcccttg acaacgggt
 541 actacaccgt tcccagaaga atgctggaat caggtcggt caatgcagtg gccttcaacc
 601 tgctggtgac ccttagaatt gacaaggcga ttggccctgg aagatcatc gacaatgcag
 661 agcaacttcc tgaggcaaca ttcatggtcc acatcgggga cttcaggaga aagaagagcg
 721 aagtctactc tgccgactat gcaagatga aaatcgaaaa gatgggcctg gtttttgcac
 781 ttggtgggat agggggcacc agtcttcaca ctagaagcac aggcaaaatg agcaagactc
 841 tccatgcaca actcgggttc aagaagacct catgttaccc accaatggat atcaatgaag
 901 acctcaatcg actactctgg aggagcagat gcaagatagt aagaatccag gcagttctgc
 961 agccatcagt tccccaagaa ctccgcattt acgacgacgt gatcataaat gatgaccaag
1021 gagtattcaa agttctgcag accgtggtgc cagcaatgc cgaaaacga ccccccctcac
1081 aatgacagcc aaaaggcccg gacaaaaaaa cccccccga aaaactccac ggaccaagcg
1141 agaggccagc cagcagctga cggcaagcgc gaacaccagg cggccccagc acagaacagc
1201 cccgacacaa ggccaccacc agccagccca atctgcatcc tcctcgtggg accccggagg
1261 accaaccccc aaagttgccc ccgacccaaa ccaccaaccg catccccacc cccctgggga
1321 agaaaccccc cagcaactgg aaggccccctt ccccccctccc tcaacacaag aaccccacaa
1381 ccgaaccgca caagcgaccg aggtgaccca accgcaggca cccgactccc tagatagatc
1441 ctctccccc gggc
```

FIG. 41B

MHMFPLGVVEDSDPPGPPIGRASGSPPPGAGRSTAKPEELLKEA
TEANIVVRRTAGLNEKLAFHNNTPPTLPTPRRKAPTTGSVLNANQACNAVNLAPLDTP
QRFRVVYMSITRPLDNGYYTVPRRMLEFRSVNAVAFNLLVTLRIDKAIGPGKIIDNAE
QLPEATFMVHIGDFRRKKSEVYSADYCKMKIEKMGLVFALGGIGGTSLHTRSTGKMSK
TLHAQLGFKKTSCYPPMDINEDLNRLLWRSRCKIVRIQAVLQPSVPQELRIYDDVIIN
DDQGVFKVLQTVVPSNARK

FIG. 42A

```
   1 aggagcaaag tgattgcctc ccaagctcca caacgacaga gatccacgac ctcgacaagt
  61 cggcatggga catcaagggg tcgatcgctc cgacacaacc caccacccac agtgatggca
 121 ggctggtgcc ccaggccaga gccacagatc ctggtctagg cgacaggaag ggcgaacgcc
 181 ccatgcacat gtttccgctg ggggtcgttg aggacagcga ccccccaggg cctccaatcg
 241 ggcgagcatc cgggtccccg cccccaggcg ctggcagatc cacagcaaaa cccgaagaac
 301 tcctcaaaga ggccaccgag gccaacatag tcgtcagacg cacagcaggg ctcaacgaaa
 361 aactggcgtt ccacaacaat accccaccaa ctctccccac accccggaga aaggccccaa
 421 caacagggag cgtcctcaac gcaaaccaag cgtgcaatgc ggtcaatctg gcaccgctgg
 481 acaccccgca gaggttccgt gttgtctaca tgagcatcac ccgtcccttg acaacgggt
 541 actacaccgt tcccagaaga atgctggaat tcaggtcggt caatgcagtg gccttcaacc
 601 tgctggtgac ccttagaatt gacaaggcga ttggccctgg gaagatcatc gacaatgcag
 661 agcaacttcc tgaggcaaca ttcatggtcc acatcgggga cttcaggaga aagaagagcg
 721 aagtctactc tgccgactat gcaagatga aaatcgaaaa gatgggcctg ttttttgcac
 781 ttggtgggat aggggcacc agtcttcaca ctagaagcac aggcaaaatg agcaagactc
 841 tccatgcaca actcgggttc aagaagacct catgttaccc accaatggat atcaatgaag
 901 acctcaatcg actactctgg aggagcagat gcaagatagt aagaatccag gcagttctgc
 961 agccatcagt tccccaagaa ctccgcattt acgacgacgt gatcataaat gatgaccaag
1021 gagtattcaa agttctgcag accgtggtgc ccagcaatgc ccgaaaatga ccccctcac
1081 aatgacaacc aaaaggcccg gacaaaaaaa cccccccga aaaactccac ggaccaagcg
1141 agaggccagc cagcagctga cggcaagcgc gaacaccagg cggccccagc acagaacagc
1201 cccgacacaa ggccaccacc agccagccca atctgcatcc tcctcgtggg accccggagg
1261 accaaccccc aaagttgccc ccgacccaaa ccaccaaccg catccccacc accccgga
1321 aagaaacccc cagcaactgg aaggccccct tccccctccc tcaacacaag aaccccacaa
1381 ccgaaccgca caagcgaccg aggtgaccca accgcaggca cccgactccc tagatagatc
1441 ctctcccccc gggc
```

FIG. 42B

MTEIYDFDKSAWDIKGSIAPIQPTTYSDGRLVPQVRVIDPGLGD
RKDECFMYMFLLGVVEDSDSLGPPIGRAFGSLPLGVGRSTAKPEKLLKEATELDIVVR
RTAGLNEKLVFYNNTPLTLLTPWRKVLTTGSVFNANQVCNAVNLIPLDTPQRFRVVYM
SITRLSDNGYYTVPRRILEFRSVNAVAFNLLVTLRIDKAIGPGKIIDNTEQLPEATFM
VHIGNFMRNKSEVYSADYCKMKIEKMGLVFALGGIGGTSLHIRSTGKMSKTLHAQLGF
KKTLCYPLIDINEDLNRLLWRSRCKIVRIQAVLQPSVPQEFRIYDDVIINDDQGLFKV
L

FIG. 43A

```
  1 atgacagaga tctacgactt cgacaagtcg gcatgggaca tcaaagggtc gatcgctccg
 61 atacaaccca ccacctacag tgatggcagg ctggtgcccc aggtcagagt catagatcct
121 ggtctaggcg acaggaagga tgaatgcttt atgtacatgt ttctgctggg ggttgttgag
181 gacagcgatt ccctagggcc tccaatcggg cgagcatttg gtccctgcc cttaggtgtt
241 ggcagatcca cagcaaagcc cgaaaaactc ctcaaagagg ccactgagct tgacatagtt
301 gttagacgta cagcagggct caatgaaaaa ctggtgttct acaacaacac cccactaact
361 ctcctcacac cttggagaaa ggtcctaaca acagggagtg tcttcaacgc aaaccaagtg
421 tgcaatgcgg ttaatctgat accgctcgat accccgcaga ggttccgtgt tgtttatatg
481 agcatcaccc gtctttcgga taacgggtat tacaccgttc ctagaagaat actggaattc
541 agatcggtca atgcagtggc cttcaacctg ctggtgaccc ttaggattga caaggcgata
601 ggccctggga agatcatcga caatacagag caacttcctg aggcaacatt tatggtccac
661 atcgggaact tcatgagaaa taagagtgaa gtctactctg ccgattattg caaaatgaaa
721 atcgaaaaga tgggcctggt ttttgcactt ggtgggatag ggggcaccag tcttcacatt
781 agaagcacag gcaaaatgag caagactctc catgcacaac tcgggttcaa gaagaccta
841 tgttacccgc tgatagatat caatgaagac cttaatcgat tactctggag gagcagatgc
901 aagatagtaa gaatccaggc agttttgcag ccatcagttc ctcaagaatt ccgcatttac
961 gacgacgtga tcataaatga tgaccaagga ctattcaaag ttctgtag
```

FIG. 43B

MSNHTHQLKFKTLKRAWKASKYFIVGLSCLYKFNLKSLVQTALT
TLAMITLTSLVITAIIYISVGNAKAKPTFKPTIQQTQQPQNHTSPLFTEHNHKSTHTS
IQSTTLSQPLNIDTTRGTTYSHSTDETQNRKNKSQSTLPANRQPPINPSGSNPPENHQ
DHNNSQTLPYVPCSTCKGNLACSSLCQIGLERAPSRAPTITLKRASKPKTTKKPTKTT
THHRTSPEAKLQPKNNTAAPQQGILSSPEHHTDQSTTQI

FIG. 44A

```
  1 atgtccaacc atacccatca acttaaattc aagacattaa agagggcttg gaaagcctca
 61 aaatacttca tagtaggatt atcatgttta tataagttca atttaaaatc ccttgtccaa
121 acggctttga ccaccttagc tatgataacc ttgacatcac tcgtcataac agccattatt
181 tacattagtg tgggaaatgc taaagccaag cccacattca aaccaaccat ccaacaaaca
241 caacagcccc aaaaccatac ctcacctctt ttcacagagc acaaccacaa atcaactcac
301 acatcaatcc aaagcaccac actatcccaa ccactaaaca tagacaccac tagaggaact
361 acatacagtc actcaaccga tgaaacccaa aatagaaaaa acaaaagcca atccactcta
421 cctgccaaca gacaaccacc aatcaaccca tcgggaagca accccctga aaaccaccaa
481 gaccacaaca actcccaaac actcccctat gtgccttgca gtacatgtaa aggcaatctt
541 gcttgctcat cactctgcca aatcgggctg gagagagcac caagcagagc ccccacaatc
601 accctaaaaa gggcgtcaaa acccaaaacc accaaaaaac caaccaagac aacaacccac
661 cacagaacta gccctgaagc caaactgcaa cccaaaaaca cacggcagc tccacaacaa
721 ggcatcctct cttcaccaga gcaccacaca gatcaatcaa ctacacagat ctaa
```

FIG. 44B

MSKNKNQRTARTLEKTWDTLNHLIVISSCLYRLNLKSIAQIADS
VLAMIISTSLIIAAIIFIISANHKVTPTTVTVQTIKNHTEKNITTYLTHVSPERVSPS
KQPTTTLPIHTNSATISPNTKSETHHTTAQTKGIITTPTQTNKPSTKPRPKNPPKKPK
DDYHFEVFNFVPCSICGNNQLCKSICKTIPSNKPKKKPTIKPTNKPTTKTTNKRDPKT
LAKTLKKENTTNPTKKPTLKTTERDTSTPQSTVLDTTTSKHTIQQQSLHSTTPENTPN
STQIPTASEPSTSNSTQKI

FIG. 45A

```
  1 ggggcaaatg caaccatgtc caaaaacaag aatcaacgca ctgccaggac tctagaaaag
 61 acctgggata ctcttaatca tctaattgtg atatcctctt gtttatacag attaaattta
121 aaatctatag cacaaatagc actatcagtt ttggcaatga taatctcaac ctctctcata
181 attgcagcca taatattcat catctctgcc aatcacaaag ttacaccaac aacggtcaca
241 gttcaaacaa taaaaaacca cactgaaaaa aacatcacca cttaccttac tcatgtctca
301 ccagaaaggg ttagcccatc caaacaaccc acaaccacac taccaatcca cacaaactca
361 gccacaatat cacctaatac aaaatcagaa acacaccata caacagcaca aaccaaaggc
421 ataatcacca ctccaacaca gaccaacaag ccaagcacaa aaccacgtcc aaaaaatcca
481 ccaaaaaaac aaaagatga ttaccatttt gaagtgttca cttcgttcc ctgtagtata
541 tgtggcaaca accaactttg caaatccatc tgcaaaacaa taccaagcaa caaaccaaag
601 aaaaaaccaa ccatcaaacc cacaaacaaa ccaaccacca aaccacaaa caaaagagac
661 ccaaaaacac tagccaaaac gctgaaaaaa gaaaacacca ccaacccaac aaaaaaacca
721 accctcaaga ccacagaaag agacaccagc actccacaat ccaccgtgct cgacacaacc
781 acatcaaaac acacaatcca acagcaatcc ctccactcaa ccaccccga aaacacaccc
841 aactccacac aaatacccac agcatccgag ccctccacat caaattccac ccaaaaaatc
901 tagtcacatg cttagttatt c
```

FIG. 45B

MSKNKNQRTARTLEKTWDTLNHLIVISSCLYRLNLKSIAQIALS
VLAMIISTSLIIAAIIFIISANHKVTLTTVTVQTIKNHTEKNITTYLTQVSPERVSPS
KQPTTTPPIHTNSATISPNTKSETHHTTAQTKGRITTPTQNNKPSTKPRPKNPPKKPK
DDYHFEVFNFVPCSICGNNQLCKSICKTIPSNKPKKKPTIKPTNKPPTKTTNKRDPKT
LAKTLKKETTTNPTKKPTPKTTEGDTSTPQSTVLDTTTSKHTERDTSTSQSTVLDTTT
SKHTIQQQSLYSTTPENTPNSTQTPTASEPSTSNSTQKL

FIG. 46A

```
  1 ggggcaaatg caaccatgtc caaaaacaag aatcaacgca ctgccaggac tctagaaaag
 61 acctgggata ctcttaatca tctaattgta atatcctctt gtttatacaa attaaattta
121 aaatctatag cacaaatagc actatcagtt ttggcaatga taatctcaac ctctctcata
181 attgcagcca taatattcat catctctgcc aatcacaaag ttacactaac aactgtcaca
241 gttcaaacaa taaaaaacca cactgaaaaa aacatcacca cttaccttac tcaagtctca
301 ccagaaaggg ttagcccatc caaacaaccc acaaccacac caccaatcca cacaaactca
361 gccacaatat cacctaatac aaaatcagaa acacaccata aacagcaca aaccaaaggc
421 agaaccacca ctccaacaca gaacaacaag ccaagcacaa aaccacgtcc aaaaaatcca
481 ccaaaaaaac caaaagatga ttaccatttt gaagtattca acttcgttcc ctgtagtata
541 tgtggcaaca accaactctg caaatccatc tgcaaaacaa taccaagcaa taaaccaaag
601 aaaaaaccaa ccataaaacc cacaaacaaa ccacccacca aaccacaaa caaaagagac
661 ccaaaaactc tagccaaaac actgaaaaaa gaaaacacca tcaacccaac aaaaaaacca
721 accccccaaga ccacagaagg agacaccagc acctcacaat ccactgtgct cgacacaacc
781 acatcaaaac acacagaaag agacaccagc acctcacaat ccactgtgct aaacacaccc
841 acctccaaac acacaatcca acagcaatcc ctctactcaa ccaccctga aaacacaccc
901 aactccacac aaacacccac agcatccgag ccctccacat caattccac ccaaaaactc
961 tagtcatatg cttagttatt c
```

FIG. 46B

MELPILKTNAITTILAAVTLCFASSQNITEEFYQSTCSAVSKGY
LSALRTGWYTSVITIELSNIKENKCNGTDAKAKLIKQELDKYKNAVTELQLLMQSTPA
ANNRARRELPRFMNYTLNNTKNTNVTLSKKRKRRFLGFLLGVGSAIASGIAVSKVLHL
EGEVNKIKSALLSTNKAVVSLSNGVSVLTSKVLHLKNYIDKQFLPIVNKQSCSISNIA
TVIEFQQKNNRLLEITREFSVNAGVTTPVSTYMLTNSELLSLINDMPITNDQKKLMSN
NVQIVRQQSYSIMSIIKEEVLAYVVQLPLYGVMDTPCWKLHTSPLCTTNTKEGSNICL
TRTDRGWYCDNAGSVSFFPQAETCKVQSNRVFCDTMSSLTLPSEVNLCNIDIFNPKYD
CKIMTSKTDVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKINQSLAFIRK
SDELLHNVNAGKSTINIMITTIIIVIIVILLSLIAVGLLLYCKARSTPVTLSKDQLSG
INNIAFSS

FIG. 47A

```
   1 cgcgcaaata acaatggagt tgccaatcct caaaacaaat gctattacca caatccttgc
  61 tgcagtcaca ctctgtttcg cttccagtca aaacatcact gaagaatttt atcaatcaac
 121 atgcagtgca gttagcaaag gctatcttag tgctctaaga actggttggt atactagtgt
 181 tataactata gaattaagta atattaaaga aaataagtgt aatggaacag acgccaaggc
 241 aaaattgata aacaagaat tagataaata taaaaatgct gtaacagaat gcagttgct
 301 catgcaaagt actccagcag ccaacaatcg agccagaaga gaactaccaa ggtttatgaa
 361 ttatacactc aacaatacca aaaacaccaa tgtaacatta agcaagaaaa ggaaaagaag
 421 atttcttggt tttttgttag gtgttggatc tgcaatcgcc agtggcattg ccgtatccaa
 481 ggtcctacac ctagaagggg aagtgaacaa atcaaaagt gctctactat ccacaaacaa
 541 ggctgtagtc agcttatcaa atggagtcag tgttttaacc agcaaagtgt tacatctcaa
 601 aaactatata gataaacagt tcttacctat tgtgaacaag caaagctgca gcatatcaaa
 661 cattgcgact gtgatagagt tccaacaaaa gaacaacaga ctactagaga ttaccaggga
 721 atttagtgtt aatgcaggcg taactacacc tgtaagtact tatatgttaa ctaatagtga
 781 attattatca ttaatcaatg atatgcctat aacaaatgat cagaaaaagt taatgtccaa
 841 caatgtccaa atagttagac agcaaagtta ctctatcatg tccataataa aggaggaagt
 901 cttagcatat gtagtacaat taccactata tggtgtaatg gatacacctt gttggaaact
 961 gcacacatcc cctctatgta caaccaacac aaaggaaggg tccaacatct gcttaacaag
1021 aaccgacaga ggatggtact gtgacaatgc aggatcagta tctttcttcc cacaagctga
1081 aacatgtaaa gttcaatcga atcgggtatt tgtgacaca atgaacagtt aacattacc
1141 aagtgaggta aatctctgca cattgacat attcaacccc aaatatgatt gtaaaattat
1201 gacttcaaaa acagatgtaa gcagctccgt tatcacatct ctaggagcca ttgtgtcatg
1261 ctatggcaaa actaaatgta cagcatccaa taaaaatcgt gggatcataa agacatttc
1321 taacgggtgt gattatgtat caaataaggg ggtggatact gtgtctgtag taatacatt
1381 atattatgta aataagcaag aaggcaaaag tctctatgta aaggtgaac caataataaa
1441 tttctatgac ccattagtgt tcccctctga tgaatttgat gcatcaatat ctcaagtcaa
1501 tgagaagatt aaccagagtc tagcatttat tcgtaaatca gatgaattat tacataatgt
1561 aaatgctggt aaatccacca ttaatatcat gataactact ataattatag tgattatagt
1621 aatattgtta tcattaattg cagttggact gcttctatac tgcaaggcca gaagcacacc
1681 agtcacacta agtaaggatc aactgagtgg tataaataat attgcattta gtagctgaat
1741 aaaaatagca cttaatcata ttcttacaat ggttcactat ctgaccatag ataacccatc
1801 tatcattgga ttttcttaaa atttgaactt catcacaact ttcatctata aaccatctca
1861 cttacactat ttaagtagat tcctagttta tagttatat
```

FIG. 47B

MELPILKANAITTILAAVTFCFASSQNITEEFYQSTCSAVSKGY
LSALRTGWYTSVITIELSNIKENKCNGTDAKVKLMKQELDKYKNAVTELQLLMQSTPA
ANNRARRELPRFMNYTLNNTKNTNVTLSKKRKRRFLGFLLGVGSAIASGIAVSKVLHL
EGEVNKIKSALLSTNKAVVSLSNGVSVLTSKVLDLKNYIDKQLLPIVNKQSCRISNIE
TVIEFQQKNNRLLEITREFSVNAGVTTPVSTYMLTNSELLSLINDMPITNDQKKLMSN
NVQIVRQQSYSIMSIIKEEVLAYVVQLPLYGVIDTPCWKLHTSPLCTTNTKEGSNICL
TRTDRGWYCDNAGSVSFFPQAETCKVQSNRVFCDTMSSLTLPSEVNLCNVDIFNPKYD
CKIMTSKTDVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKINQSLAFIRK
SDELLHNVNAGKSTTNIMITTIIIVIIVILLSLIAVGLLLYCKARSTPVTLSKDQLSG
INNIAFSN

FIG. 48A

```
   1 taacaatgga gttgccaatc ctcaaagcaa atgcaattac cacaatcctc gctgcagtca
  61 cattttgctt tgcttctagt caaaacatca ctgaagaatt ttatcaatca acatgcagtg
 121 cagttagcaa aggctatctt agtgctctaa gaactggttg gtatactagt gttataacta
 181 tagaattaag taatatcaag gaaaataagt gtaatggaac agatgctaag gtaaaattga
 241 tgaaacaaga attagataaa tataaaaatg ctgtaacaga attgcagttg ctcatgcaaa
 301 gcacaccagc agcaaacaat cgagccagaa gagaactacc aaggtttatg aattatacac
 361 tcaacaatac caaaaaaacc aatgtaacat taagcaagaa aaggaaaaga agatttcttg
 421 gttttttgtt aggtgttgga tctgcaatcg ccagtggcat tgctgtatct aaggtcctgc
 481 acttagaagg agaagtgaac aagatcaaaa gtgctctact atccacaaac aaggccgtag
 541 tcagcttatc aaatggagtt agtgtcttaa ccagcaaagt gttagacctc aaaaactata
 601 tagataaaca attgttacct attgtgaata agcaaagctg cagaatatca aatatagaaa
 661 ctgtgataga gttccaacaa aagaacaaca gactactaga gattaccagg gaatttagtg
 721 ttaatgcagg tgtaactaca cctgtaagca cttacatgtt aactaatagt gaattattgt
 781 cattaatcaa tgatatgcct ataacaaatg atcagaaaaa gttaatgtcc aacaatgttc
 841 aaatagttag acagcaaagt tactctatca tgtccataat aaaagaggaa gtcttagcat
 901 atgtagtaca attaccacta tatggtgtga tagatacacc ttgttggaaa ttacacacat
 961 cccctctatg tacaaccaac acaaaagaag ggtcaaacat ctgtttaaca agaactgaca
1021 gaggatggta ctgtgacaat gcaggatcag tatcttttt cccacaagct gaaacatgta
1081 aagttcaatc gaatcgagta ttttgtgaca caatgaacag tttaacatta ccaagtgaag
1141 taaatctctg caatgttgac atattcaatc ccaaatatga ttgtaaaatt atgacttcaa
1201 aaacagatgt aagcagctgg gttatcacat ctctaggagc cattgtgtca tgctatggca
1261 aaactaaatg tacagcatcc aataaaaatc gtggaatcat aaagacattt tctaacgggt
1321 gtgattatgt atcaaataaa ggggtggaca ctgtgtctgt aggtaacaca ttatattatg
1381 taaataagca agaaggcaaa agtctctatg taaaaggtga accaataata aatttctatg
1441 acccattagt attcccctct gatgaatttg atgcatcaat atctcaagtc aatgagaaga
1501 ttaaccagag tttagcattt attcgtaaat ccgatgaatt attacataat gtaaatgctg
1561 gtaaatcaac cacaaatatc atgataacta ctataattat agtgattata gtaatattgt
1621 tatcattaat tgctgttgga ctgctcctat actgtaaggc cagaagcaca ccagtcacac
1681 taagcaagga tcaactgagt ggtataaata atattgcatt tagtaactga ataaaaatag
1741 cacctaatca tgttcttaca atggtttact atctgctcat agacaaccca tctatcattg
1801 gattttctta aaatctgaac ttcatcgaaa ctcttatcta taaccatct cacttacact
1861 attt
```

FIG. 48B

MDVRICLLLFLISNPSSCIQETYNEESCSTVTRGYKSVLRTGWY
TNVFNLEIGNVENITCNDGPSLIDTELVLTKNALRELKTVSADQVAKESRLSSPRRRR
FVLGAIALGVATAAAVTAGVALAKTIRLEGEVKAIKNALRNTNEAVSTLGNGVRVLAT
AVNDLKEFISKKLTPAINQNKCNIADIKMAISFGQNNRRFLNVVRQFSDSAGITSAVS
LDLMTDDELVRAINRMPTSSGQISLMLNNRAMVRRKGFGILIGVYDGTVVYMVQLPIF
GVIETPCWRVVAAPLCRKEKGNYACILREDQGWYCTNAGSTAYYPNKDDCEVRDDYVF
CDTAAGINVALEVEQCNYNISTSKYPCKVSTGRHPVSMVALTPLGGLVSCYESVSCSI
GSNKVGIIKQLGKGCTHIPNNEADTITIDNTVYQLSKVVGEQRTIKGAPVVNNFNPIL
FPEDQFNVALDQVFESIDRSQDLIDKSNDLLGADAKSKAGIAIAIVVLVILGIFFLLA
VIYYCSRVRKTKPKHDYPATTGHSSMAYVS

FIG. 49A

```
   1 gggacaagta ggatggatgt aagaatctgt ctcctattgt tccttatatc taatcctagt
  61 agctgcatac aagaaacata caatgaagaa tcctgcagta ctgtaactag aggttataag
 121 agtgtgttaa ggacagggtg gtatacgaat gtatttaacc tcgaaatagg gaatgttgag
 181 aacatcactt gcaatgatgg acccagccta attgacactg agttagtact cacaaagaat
 241 gctttgaggg agctcaaaac agtgtcagct gatcaagtgg ctaaggaaag cagactatcc
 301 tcacccagga gacgtagatt tgtactgggt gcaatagcac ttggtgttgc gacagctgct
 361 gccgtaacag ctggtgtagc acttgcaaag acaattagat tagagggaga ggtgaaggca
 421 attaagaatg ccctccggaa cacaaatgag gcagtatcca cattagggaa tggtgtgagg
 481 gtactagcaa ctgcagtcaa tgacctcaaa gaatttataa gtaaaaaatt gactcctgct
 541 attaaccaga acaaatgcaa tatagcagat ataaagatgg caattagttt tggccaaaat
 601 aacagaaggt tcctgaatgt ggtgaggcaa ttctctgata gtgcaggtat cacatcagct
 661 gtgtctcttg atttaatgac agatgatgaa cttgttagag caattaacag aatgccaact
 721 tcatcaggac agattagttt gatgttgaac aatcgtgcca tggttagaag gaaggggttt
 781 ggtatattga ttggtgttta tgatggaacg gtcgtttata tggtacaact gcccatattc
 841 ggcgtgattg agacaccttg ttggagggtg gtggcagcac cactctgtag gaaagagaaa
 901 ggcaattatg cttgtatact gagagaagat caagggtggt actgtacaaa tgctggctct
 961 acagcttatt atcctaataa agatgattgt gaggtaaggg atgattatgt attttgtgac
1021 acagcagctg gcattaatgt ggccctagaa gttgaacagt gcaactataa catatcgact
1081 tctaaatacc catgcaaagt cagcacaggt agacaccctg tcagtatggt agccttaacc
1141 cccctagggg gtctagtgtc ttgttatgag agtgtaagtt gctccatagg tagcaataaa
1201 gtagggataa taaaacagct aggcaaaggg tgcacccaca ttcccaacaa cgaagctgac
1261 acgataacca ttgataacac tgtgtaccaa ttgagcaagg ttgtaggcga acagaggacc
1321 ataaaaggag ctccagttgt gaacaatttt aacccaatat tattccctga ggatcagttc
1381 aatgttgcac ttgaccaagt atttgagagt atagatagat ctcaggactt aatagataag
1441 tctaacgact tgctaggtgc agatgccaag agcaaggctg gaattgctat agcaatagta
1501 gtgctagtca ttctaggaat cttcttttta cttgcagtga tatattactg ttccagagtc
1561 cggaagacca aaccaaagca tgattacccg gccacgacag gtcatagcag catggcttat
1621 gtcagttaag ttattt
```

FIG. 49B

METYVNKLHEGSTYTAAVQYNVLEKDDDPASLTIWVPMFQSSIS
ADLLIKELINVNILVRQISTLKGPSLKIMINSRSAVLAQMPNKFTISANVSLDERSKL
AYDITTPCEIKACSLTCLKVKNMLTTVKDLTMKTFNPTHEIIALCEFENIMTSKKVVI
PTFLRSINVKAKDLDSLENIATTEFKNAITNAKIIPYAGLVLVITVTDNKGAFKYIKP
QSQFIVDLGAYLEKESIYYVTTNWKHTATRFSIKPIED

FIG. 50A

```
  1 ggggcaaata tggagacata cgtgaacaaa ctccatgaag ggtcaacata cacagctgct
 61 gtccaataca atgttctaga aaaggatgat gatcctgcat ctctcacgat atgggttcct
121 atgtttcaat catccatttc tgctgactta ctcataaagg agttaatcaa tgtgaacata
181 ttagtacgac aaatttctac tctgaaaggc ccatcattaa aaattatgat aaactctaga
241 agtgctgtac tagctcaaat gcccaacaag tttactataa gtgcaaatgt gtcattggat
301 gaacggagca agttggcata tgacataacc accccttgtg agatcaaagc ttgcagtttg
361 acatgcttaa aagtaaaaaa tatgctcact actgtaaaag atcttactat gaaaacattc
421 aatcccactc atgaaatcat tgcactgtgt gaatttgaaa atattatgac gtctaagaaa
481 gttgtaatac caacttttt aaggtctatt aatgtgaagg caaaggattt agattcactg
541 gaaaacatag ctacaacaga gtttaaaaat gccatcacta atgctaaaat tataccttac
601 gctgggttag tgttagtcat taccgtaact gacaacaaag gagcatttaa gtatatcaag
661 ccacaaagcc aatttatagt tgatcttggt gcatatcttg aaaaagagag catatattat
721 gtaactacaa attggaaaca cacagccact agattctcca tcaaacctat agaagattaa
781 atcctaaaca aattatcttg ccaaaataga acactctatt aagaacctac aaaacaccat
841 tgaaatcaaa tcctattgat actccattga acatcactgt cacacattcc caatctggtc
901 aattcacttg atcatctatt ctgttaatta tacctctatt agataaat
```

FIG. 50B

MSRRNPCKYEIRGHCLNGKKCHFSHNYFEWPPHALLVRQNFMLN
KILKSMDRSNDTLSEISGAAELDRTEEYALGVIGVLESYLGSVNNITKQSACVAMSKL
LGEINSDDIKGLRNKELPTSPKIRIYNTVISYIDSNKRNPKQTIHLLKRLPADVLKKT
IKNTIDIHNEINVNNPSDIGVNEQNE

FIG. 51A

```
  1 ggggcaaata tgtcacgaag aaatccctgc aaatatgaga tcaggggaca ttgcttaaat
 61 ggcaaaaaat gccatttcag ccataattac tttgaatggc ctccacatgc tttattagtg
121 aggcaaaatt ttatgttaaa caagatatta aagtctatgg ataggagcaa tgatactctg
181 tcagagataa gtggagctgc agaattagat agaacagagg aatatgcatt aggtgtgata
241 ggagttttag aaagttactt gggctctgtt aataacataa caaaacaatc agcttgtgtt
301 gctatgagta aattattagg tgagattaat agtgatgaca tcaaaggatt aagaaacaaa
361 gaattgccaa cttcacctaa gataagaata tataacacag ttatatcata tattgatagc
421 aacaagagaa acccaaaaca aactatacat ttacttaaaa gattgcctgc agatgtgctt
481 aagaagacca tcaagaatac aatagatatt cacaatgaaa taaatgttaa taatccaagt
541 gacataggtg ttaatgaaca aaatgaataa ttccaatatc attattttcc cagagaaata
601 tccttgtagt atatcttctt tgttaatcag agatgagaat aatgttattg tattaaatca
661 tcagaatatt tttgactgct cacagtctca acatccatgt gatatgtatc ctcaaaatca
721 tatacttgac tatacctatt ggacatcaca ggaattgatt gacgatgtac taagattct
781 tcacctttct agcatcccca taaataggta tgtggtctat gtcttagtgc tgtagtatgt
841 aaatcattta actttcaatc attatctata tatttctcct tgtagccgga aatacaccag
901 aggacaaaat ggactcactc attcatgaaa actcaaccaa tgtatactta acagatagtt
961 attt
```

FIG. 51B

MALSKVKLNDTFNKDQLLSTSKYTIQRSTGDNIDIPNYDVQKHL
NKLCGMLLITEDANHKFTGLIGMLYAMSRLGREDTLKILKDAGYQVKANGVDVITHRQ
DVNGKEMKFEVLTLVSLTSEVQVNIEVESRKSYKKMLKEMGEVAPEYRHDSPDCGMIV
LCIAALVIAKLAAGDRSGLTAVIRRANNVLKNEIERYKGLIPKDVANSFYEVFEKYPH
YIDVFVHFGIAQSSTRGGSRVEGIFAGLFMNAYGAGQVMLRWGVLAKSVKNIMLGHAS
VQAEMEQVVEVYEYAQKLGGEAGFYHILNNPKASLLSLTQFPNFSSVVLGNAAGLGIM
GEYRGTPRNQDLYDAAKAYAEQLKENGVINYSVLDLTTEELEAIKNQLNPKDNDVEL

FIG. 52A

```
   1 ggggcaaata caaaaatggc tctcagcaag gttaaactga atgacacctt caacaaagat
  61 caattgctat caactagcaa atataccatc caacgtagca ctggagataa tattgacata
 121 cctaattatg atgtacaaaa gcatctcaat aaattgtgtg gtatgctgct aataacagaa
 181 gatgctaatc acaaatttac aggattaata ggtatgttat atgccatgtc tcgattggga
 241 agggaagata ccctcaaaat actcaaggat gcaggttacc aagtaaaggc aatggagtt
 301 gatgtaatta cacatcgaca agatgtaaat ggaaaagaaa tgaaatttga agtgctaaca
 361 ctagtcagct taacatcaga agttcaagtt aacattgagg tagaatcaag gaaatcttac
 421 aaaaagatgc taaagagat gggagaggta gctccagaat acagacatga ttctcctgat
 481 tgtggtatga tagtgctatg tattgctgct tggttatag caaaattagc agcagggat
 541 agatcaggcc tcaccgcagt catcagaaga gccaacaatg tgcttaagaa tgaaatagag
 601 cgatacaagg gacttatacc aaaggatgta gccaacagct ctatgaagt atttgaaaag
 661 tatcctcatt atatagacgt atttgtacat tttggaattg ctcagtcctc aacaagagga
 721 ggtagtaggg tagaggggat ctttgcaggg ttattcatga atgcgtatgg agcaggtcaa
 781 gtaatgttaa gatggggtgt attagccaaa tcagtcaaga atatcatgct tggtcatgcc
 841 agtgtgcaag ctgaaatgga acaagttgta gaagtctatg aatatgcaca aaaattagga
 901 ggagaagcag gtttctacca catattaaac aacccaaaag catcattatt gtcccttaca
 961 cagtttccta acttctccag tgtagtccta ggtaatgctg ctggtttggg aataatgggt
1021 gagtatagag gtacacctag gaatcaggat ttatatgatg ctgccaaagc atatgcagaa
1081 caactgaaag agaatggagt catcaattac agtgtattag atctaactac agaggaatta
1141 gaggcaatca gaaccagct aaatcccaag gataatgatg tggaactgtg agttaat
```

FIG. 52B

MALSKVKLNDTLNKDQLLSTSKYTIQRSTGDSIDTPNYDVQKHI
NKLCGMLLITEDANHKFTGLIGMLYAMSRLGREDTLKILKDAGYHVKANGVDVITHRQ
DINGKEMKFEVLTLASLTTEIQINIEIESRKSYKKMLKEMGEVAPEYRHDSPDCGMII
LCIAALVITKLAAGDRSGLTAVIRRANNVLKNEMKRYKGLIPKDIANSFYEVFEKHPH
FIDVFVHFGIAQSSTRGGSRVEGIFAGLFMNAYGAGQVMLRWGVLAKSVKNIMLGHAS
VQAEMEQVVEVYEYAQKLGGEAGFYHILNNPKASLLSLTQFPHFSSVVLGNAAGLGIM
GEYRGTPRNQDLYDAAKAYAEQLKENGVINYSVLDLTAEELTLKTTKKDPKPQTTKSK
EVPTTKPTEEPTINTTKTNIITTLLTSNTTGNPELTSQMETPHSTSSEGNPSPSQVST
TSEYPSQPSSPPNTPRQ

FIG. 53A

```
   1 caaatacaaa gatggctctt agcaaagtca agttgaatga tacactcaac aaagatcaac
  61 ttctgtcatc cagcaaatac accatccaac ggagcacagg agatagtatt gatactccta
 121 attatgatgt gcagaaacac atcaataagt tatgtggcat gttattaatc acagaagatg
 181 ctaatcataa attcactggg ttaataggta tgttatatgc gatgtctagg ttaggaagag
 241 aagacaccat aaaaatactc agagatgcgg gatatcatgt aaaagcaaat ggagtagatg
 301 taacaacaca tcgtcaagac attaatggaa aagaaatgaa atttgaagtg ttaacattgg
 361 caagcttaac aactgaaatt caaatcaaca ttgagataga atctagaaaa tcctacaaaa
 421 aaatgctaaa agaaatggga gaggtagctc cagaatacag gcatgactct cctgattgtg
 481 ggatgataat attatgtata gcagcattag taataactaa attagcagca ggggacagat
 541 ctggtcttac agccgtgatt aggagagcta ataatgtcct aaaaaatgaa atgaaacgtt
 601 acaaaggctt actacccaag gacatagcca acagcttcta tgaagtgttt gaaaaacatc
 661 cccactttat agatgttttt gttcattttg gtatagcaca atcttctacc agaggtggca
 721 gtagagttga agggattttt gcaggattgt ttatgaatgc ctatggtgca gggcaagtga
 781 tgttacggtg gggagtctta gcaaaatcag ttaaaaatat tatgttagga catgctagtg
 841 tgcaagcaga aatggaacaa gttgttgagg tttatgaata tgcccaaaaa ttgggtggtg
 901 aagcaggatt ctaccatata ttgaacaacc caaaagcatc attattatct ttgactcaat
 961 ttcctcactt ctccagtgta gtattaggca atgctgctgg cctaggcata atgggagagt
1021 acagaggtac accgaggaat caagatctat atgatgcagc aaaggcatat gctgaacaac
1081 tcaaagaaaa tggtgtgatt aactacagtg tactagactt gacagcagaa gaactaaccc
1141 tcaagacaac caaaaaagat cccaaacctc aaaccactaa atcaaaggaa gtacccacca
1201 ccaagcccac agaagagcca accatcaaca ccaccaaaac aaacatcata actacactac
1261 tcacctccaa caccacagga atccagaac tcacaagtca aatggaaacc ttccactcaa
1321 cttcctccga aggcaatcca agcccttctc aagtctctac aacatccgag tacccatcac
1381 aaccttcatc tccacccaac acaccacgcc agtagttact t
```

FIG. 53B

MALSKVKLNDTFNKDQLLSTSKYTIQRSTGDNIDTPNYDVQKHL
NKLCGMLLITEDANHKFTGLIGMLYAMSRLGREDTLKILKDAGYQVRANGVDVITHRQ
DVNGKEMKFEVLTLVSLTSEVQGNIEIESRKSYKKMLKEMGEVAPEYRHDSPDCGMIV
LCVAALVITKLAAGDRSGLTAVIRRANNVLRNEMKRYKGLIPKDIANSFYEVFEKYPH
FIDVFVHFGIAQSSTRGGSRVEGIFAGLFMNAYGAGQVMLRWGVLAKSVKNIMLGHAS
VQAEMEQVVEVYEYAQKLGGEAGFYHILNNPKASLLSLTQFPHFSSVVLGNAAGLGIM
GEYRGTPRNQDLYDAAKAYAEQLKENGVINYSVLDLTAEELEAIKNQLNPKDNDVEL

FIG. 54A

```
   1 ngggcaaata caaaaatggc tcttagcaag gtcaaactaa atgacacttt caacaaggac
  61 caactgttgt caaccagcaa atatactatt caacgtagta caggtgacaa cattgatata
 121 cccaattacg atgtgcaaaa acatctcaat aagttgtgtg gtatgctatt aataacagaa
 181 gatgccaatc ataaatttac aggactgata ggtatgttat atgctatgtc ccgattgggg
 241 agagaagata cccttaaaat actcaaagat gcaggctacc aagtgagggc aatggggtt
 301 gatgtgataa cacatcgaca ggatgtgaat ggaaaagaaa tgaaatttga agtgctaaca
 361 ttagtcagct aacatcaga agttcaaggt aatatagaaa tagagtcaag gaagtcttac
 421 aaaaagatgc taaaagagat gggagaggta gctccagaat acagacatga ctttcctgat
 481 tgtggtatga tagtgctatg tgttgctgct tggttataa caaaattagc agcaggtgat
 541 aggtcaggcc tcactgcagt cattaggaga gccaacaatg tactaaggaa tgaaatgaaa
 601 cgatacaaag gactcatccc gaaagatata gccaacagct ctatgaagt atttgaaaag
 661 taccctcatt acatagatgt attcgtacat tttggcattg ctcaatcctc aactagagga
 721 ggtagtaggg tagaaggaat ctttgcaggg ttattcatga atgcatatgg agcaggtcaa
 781 gtgatgttaa gatgggtgt gctagccaaa tcagtcaaga acattatgct tggtcatgcc
 841 agcgtacaag cagaaatgga acaggttgta gaagtctatg aatatgcaca aaagttaggt
 901 ggagaagctg gttttatca catactgaac aatcctaaag catcattgtt atccttgaca
 961 caattcccca acttctctag tgtagtccta ggcaatgctg caggactagg tataatgggt
1021 gagtatagag gtacaccaag aaaccaagac ttgtatgatg ctgccaaagc atatgcagaa
1081 caactaaaag agaatggggt catcaattac agtgtgttgg atctgactac agaggaatta
1141 gaggcaatca gaaccaatt gaatcccaaa gataatgatg tggaattgtg agttaat
```

FIG. 54B

MLSLFDTFNARRQENITKSAGGAIIPGQKNTVSIFALGPTITDD
NEKMTLALLFLSHSLDNEKQHAQRAGFLVSLLSMAYANPELYLTTNGSNADVKYVIYM
IEKDLKRQKYGGFVVKTREMIYEKTTEWIFGSDLDYDQETMLQNGRNNSTIEDLVHTF
GYPSCLGALIIQIWIVLVKAITSISGLRKGFFTRLEAFRQDGTVQAGLVLSGDTVDQI
GSIMRSQQSLVTLMVETLITMNTSRNDLTTIEKNIQIVGNYIRDAGLASFFNTIRYGI
ETRMAALTLSTLRPDINRLKALMELYLSKGPRAPFICILRDPIHGEFAPGNYPAIWSY
AMGVAVVQNRAMQQYVTGRSYLDIDMFQLGQAVARDAEAQMSSTLEDELGVTHEAKES
LKRHIRNINSSETSFHKPTGGSAIEMAIDEEPEQFEHRADQEQDGEPQSSIIQYAWAE
GNRSDDRTEQATESDNIKTEQQNIRDRLNKRLNDKKQGSQPSTNPTNRTNQDEIDDL
FNAFGSN

FIG. 55A

```
   1 gaggattaaa gacattgact agaaggtcaa gaaaagggaa ctctataatt tcaaaaatgt
  61 tgagcctatt tgatacattt aatgcacgta ggcaagaaaa cataacaaaa tcagctggtg
 121 gagctatcat tcctggacag aaaaatactg tctccatatt tgcccttgga ccgacaataa
 181 ctgatgacaa tgagaaaatg acattagctc ttctatttct atctcattca ctagataatg
 241 agaaacaaca tgcacaaagg gcagggttct ggtgtctttt attgtcaatg cttatgcca
 301 atccagagct ttacctgaca acaaatggaa gtaatgcaga tgttaaatat gtcatatata
 361 tgattgagaa agatctaaaa cggcaaaagt atggaggatt tgtggttaag acgagagaga
 421 tgatatatga aaagacaact gagtggatat ttggaagtga cctggattat gaccaggaaa
 481 ctatgctgca gaacggcaga aacaattcaa cgattgaaga tcttgttcac acatttgggt
 541 atccatcatg tttaggagct cttataatac agatctggat agttttggtc aaagccatca
 601 ctagcatctc agggttaaga aaaggctttt tcactcgatt agaggctttc agacaagatg
 661 gaacagtgca agcagggctg gtattgagcg gtgacacagt ggatcagatt gggtcaatca
 721 tgcggtctca acagagcttg gtaactctta tggttgagac attaataaca atgaatacta
 781 gcagaaatga cctcacaacc atagaaaaga atatacaaat tgttggtaac tacataagag
 841 atgcaggtct tgcttcattc ttcaatacaa tcaggtatgg aattgagact agaatggcag
 901 ctttgactct atctactctc agaccagata tcaatagatt aaaagctctg atggaattgt
 961 atttatcaaa gggaccacgc gctccttta tctgtatcct cagagatcct atacatggtg
1021 agttcgcacc aggcaactat cctgccatat ggagttatgc aatgggggtg gcagttgtac
1081 aaaacagagc catgcaacag tatgtgacgg gaagatcata tctagatatt gatatgttcc
1141 agctgggaca agcagtagca cgtgatgctg aagctcagat gagctcaaca ctggaagatg
1201 aacttggagt gacacacgaa gccaagaaa gcttgaaaag acatataagg aacataaaca
1261 gttcagagac atctttccac aaaccaacag gcggatcagc catagagatg caatagatg
1321 aagagccaga acaatttgaa cacagagcag atcaagaaca agatggagaa cctcaatcat
1381 ctataatcca atatgcttgg gcagaaggaa acagaagtga tgatcggacc gagcaagcta
1441 cagaatccga caatatcaag actgaacaac aaaacatcag agacagacta acaagagac
1501 tcaacgacaa gaagaaacaa ggcagtcaac catccaccaa tcccacaaac agaacgaacc
1561 aggacgaaat agacgatctg ttcaatgcat ttggaagcaa ctaactgagt caacattttg
1621 atctaaatca ataataaata ag
```

FIG. 55B

MPTSILLIITTMIMASFCQIDITKLQHVGVLVNSSKGMKISQNF
ETRYLILSLIPKIEDSNSCGDQQIKQYKRLLDRLIIPLYDGLRLQKDVIVSNQESNEN
TDPRTKRFFGGVIGTIALGVATSAQITAAVALVEAKQARSDIEKLKEAIRDTNKAVQS
VQSSIGNLIVAIKSVQDYVNKEIVPSIARLGCEAAGLQLGIALTQHYSELTNIFGDNI
GSLQEKGIKLQGIASLYRTNITEIFTTSTVDKYDIYDLLFTESIKVRVIDVDLNDYSI
ALQVRLPLLTRLLNTQIYRVDSISYNIQNREWYIPLPSHIMTKGAFLGGADVKECIEA
FSSYICPSDPGFVLNHEMESCLSGNISQCPRTVVKSDIVPRYAFVNGGVVANCITTTC
TCNGIGNRINQPPDQGVKIITHKECNTIGINGMLFNTNKEGTLAFYTPNDITLNNSVA
LDPIDISIELNKAKSDLEESKEWIRRSNQKLDSIGNWHQSSTTIIIVLIMIIILFIIN
VTIIIIAVKYYRIQKRNRVDQNDKPYVLTNK

FIG. 56A

```
   1 aggacaaaag aagtcaatac caacaactat tagcagccac actcgctgga acaagaaaga
  61 agggataaaa aaagtttaac agaagaaaca aaaacaaaaa gcacagaaca ccagaacaac
 121 aagatcaaaa cacccaaccc actcaaaacg aaaatctcaa aagagattgg caacacaaca
 181 aacactgaac atcatgccaa cctcaatact gctaattatt acaaccatga ttatggcatc
 241 tttctgccaa atagatatca caaaactaca gcatgtaggt gtattggtta acagttccaa
 301 agggatgaag atatcacaaa actttgaaac aagatatcta attttgagcc tcataccaaa
 361 aatagaagat tctaactctt gtggtgacca acagatcaag caatacaaga ggttattgga
 421 tagactgatc attcctttat atgatggatt aagattacag aaggatgtga tagtgtccaa
 481 tcaagaatcc aatgaaaaca ctgacccag aacaaaacga ttctttggag gggtaattgg
 541 aactattgct ctgggagtgg caacctcagc acaaattaca gcggcagttg ctctggttga
 601 agccaagcag gcaagatcag acattgaaaa actcaaggaa gcaatcaggg acacaaacaa
 661 agcagtgcag tcagtccaga gctccatagg aaatttgata gtagcaatta atcggtcca
 721 ggattatgtc aacaaagaaa tcgtgccatc aattgcgaga ttaggttgtg aagcagcagg
 781 acttcagtta ggaattgcat taacacagca ttactcagaa ttaacaaaca tattcggtga
 841 taacatagga tcgttacaag aaaaagggat aaaattacaa ggtatagcat cattataccg
 901 cacaaatatc acagagatat tcacaacatc aacagttgat aaatatgata tttatgatct
 961 attatttaca gaatcaataa aggtgagagt tatagatgtt gacttgaatg attactcgat
1021 cgccctccaa gtcagactcc ctttattaac tagactgctg aacacccaga tttacagagt
1081 agattccata tcatataaca tccaaaacag gaatggtat atccctcttc ccagccacat
1141 catgacaaaa ggggcatttc taggtggagc agatgtcaaa gaatgtatag aagcattcag
1201 cagttatata tgcccttctg atccaggatt tgtactaaac catgaaatgg agagctgttt
1261 atcaggaaac atatcccaat gtccaagaac cgtggttaaa tcagacattg ttccaagata
1321 tgcatttgtc aatggaggag tggttgcaaa ttgtataaca accacatgta catgcaacgg
1381 tatcggtaat agaatcaatc aaccacctga tcaaggagta aaaattataa cacataaaga
1441 atgtaataca ataggtatca acggaatgct gttcaataca aataaagaag aactcttgc
1501 attttacaca ccaaatgata taacattaaa caattctgtt gcacttgatc caattgacat
1561 atcaatcgag ctcaataagg ccaaatcaga tctagaagag tcaaaagaat ggataagaag
1621 gtcaaatcaa aaactagatt ccattggaaa ttggcatcaa tctagcacca aatcataat
1681 tgttttgata atgataatta ttgtttat aattaatgta acgataatta taattgcagt
1741 taagtattac agaattcaaa agagaaatcg agtggatcaa aatgataaac catatgtatt
1801 aacaaacaaa tgacagatct atagatcatt agatattaaa attat
```

FIG. 56B

MPISILLIITTMIMASFCQIDITKLHHVGVLVNSPKGMKISQNF
ETRYLILSLIPKIEDSNSCGDQQIRQYKKLLDRLIIPLYDGLRLQKDVIVTNQESNEN
TDPRTKRFFGGVIGTIALGVATSAQITAAVALVEAKQARSDIEKLKEAIRDTNKAVQS
VQSSIGNLIVAIKSVQDYVNKEIVPSIARLGCEAAGLQLGIALTQHYSELTNIFGDNI
GSLQEKGIKLQGIASLYRTNITEIFTTSTVDKYDIYDLLFTESIKVRVIDVDLNDYSI
TLQVRLPLLTRLLNTQIYKVDSISYNIQNREWYIPLPSHIMTKGAFLGGADVKECIEA
FSSYICPSDPGFVLNHEIESCLSGNISQCPRTTVTSDIVPRYAFVNGGVVANCITTTC
TCNGIGNRINQPPDQGIKIITHKECSTIGINGMLFNTNKEGTLAFYTPNDITLNNSVA
LDPIDISIELNKAKSDLEESKEWIRRSNQKLDSIGNWHQSSTTIIIILIMIIILFIIN
VTIITIAIKYYRIQKRNRVDQNDEPYVLTNK

FIG. 57A

```
   1 aggacaaaag aggtcaatac caacaactat tagcagtcat actcacaaga ataagaaaga
  61 agggatttaa aaagttaaat aggagaaata aaaacaaaaa gtacagaaca ccagagcgat
 121 aaaatcaaaa catctaactc actcaaaaca aaaattccaa aagagaccgg taatacaaca
 181 agcactgagc acaatgccaa tttcaatact gctgattatt acaaccatga tcatggcatc
 241 cttctgtcaa atagatatca caaaactaca tcatgtaggt gtattggtca atagtcccaa
 301 agggatgaag atatcacaaa actttgaaac aagatatctg attttgagcc tcataccaaa
 361 aatagaagac tctaactctt gtggtgacca acagatcagg caatacaaga agctattgga
 421 tagactgatc atcccttat atgatggatt aagattacag aaagatgtga tagtaactaa
 481 tcaagaatcc aatgaaaaca ctgatcctag aacaaaacga ttctttggag gggtaattgg
 541 aactattgct ctgggagtag caacctcagc acaaattaca gcagcagttg ctttggtcga
 601 agccaagcag gcaagatcag acatcgaaaa acttaaagaa gcaattaggg acacaaataa
 661 agcagtgcag tcagttcaga gctccatagg aaatctaata gtagcaatta atcagtcca
 721 ggattatgtc aacaaagaaa tcgtgccatc gattgcaagg ctaggttgtg aagcagcagg
 781 acttcaatta ggaattgcat taacacagca ttactcagaa ttaacaaaca tatttggtga
 841 taacatagga tcgttacaag aaaaaggaat aaaattacaa ggtatagcat cattataccg
 901 cacaaacatc acagaaatat tcacaacatc aacagttgat aaatatgata tttatgatct
 961 attatttaca gaatcaataa aggtgagagt tatagatgtt gacttgaatg attactcaat
1021 cacccctcca gtcagactcc cttattaac tagactgctg aacactcaga tctacaaagt
1081 agattccata tcatacaaca tccaaaacag gaatggtat atccctcttc ccagccacat
1141 catgacgaaa ggggcatttc taggtggagc agatgtcaaa gaatgcatag aagcattcag
1201 cagctatata tgcccttctg atccaggatt tgtactaaac catgaaatag agagctgctt
1261 atcaggaaac atatctcaat gtccaagaac cacagtcaca tcagacattg ttccaagata
1321 tgcatttgtc aatggaggag tggttgcaaa ctgtataaca accacttgta catgcaacgg
1381 aatcggtaat agaatcaatc aaccacctga tcaaggaata aaaattataa cacataaaga
1441 atgtagtaca ataggtatca acggaatgct gttcaataca aataaagaag gaactcttgc
1501 attctacaca ccaaatgata taacactaaa caattctgtt gcacttgatc caattgacat
1561 atcaatcgag ctcaacaagg ccaaatcaga tctaaaagaa tcaaaagaat ggataagaag
1621 gtcaaatcaa aaactagatt ccattggaaa ttggcatcaa tctagcacta caatcataat
1681 tattttgata atgatcatta tatttat aattaatgta acgataatta caattgcaat
1741 taagtattac agaattcaaa agagaaatcg agtggatcaa aatgatgagc catatgtact
1801 aacaaacaaa taacatatct acagatcatt agatattaaa attataaaaa a
```

FIG. 57B

MSITNSAIYTFPESSFSENGHIEPLPLKVNEQRKAVPHIRVAKI
GNPPKHGSRYLDVFLLGFFEMERIKDKYGSVNDLDNDPGYKVCGSGSLPIGLVKYTGN
IQELLQAATKLDIEVRRTVKAKEMIVYTVQNIKPELYPWSSRLRKGMLFDANKVALAP
QCLPLDRSIKFRVIFVNCTAIGSITLFKIPKSMASLSLPSTISINLQVHIKTGVQTDS
KGIVQILDEKGEKSLNFMVHLGLIKRKVGRMYSVEYCKQKIEKMRLIFSLGSVGGISL
HVNATGSISKTLASQLVFKREICYPLMDLNPHLNLVIWASSVEITRVDAIFQPSLPGE
FRYYPNIIAKGVGKIKQWN

FIG. 58A

```
   1 aggattaaag aataaattaa tccttgtcca aaatgagtat aactaactct gcaatataca
  61 cattcccgga gtcatcattc tctgagaatg gtcatataga accattacca ctcaaagtca
 121 atgaacagag aaaagcagta cctcacatta gagttgccaa aatcggaaat ccaccaaaac
 181 atggatcccg gtatttggat gtcttcttac tcggcttctt cgagatggaa cgaatcaaag
 241 acaaatacgg gagtgtgaat gatcttgaca atgacccggg ttacaaagtt tgtggctctg
 301 gatcattacc aatcggatta gttaaataca ctgggaatat ccaggaatta ttacaggcag
 361 caactaaact ggacatagaa gtgagaagaa cagtcaaagc gaaagaaatg attgtttata
 421 cggtacaaaa tataaaacca gaactgtacc catggtccag tagactaaga aaaggaatgt
 481 tgttcgatgc caacaaagtt gctcttgctc ctcaatgtct tccactagat aggagcataa
 541 aattcagagt aatcttcgtt aattgtacgg caattggatc aataaccttg tttaaaattc
 601 ccaagtcaat ggcatcacta tctctaccca gcacaatatc aatcaatctg caggtacaca
 661 tcaaaacagg ggttcagact gattctaaag ggatagttca aatttggat gagaagggtg
 721 aaaaatcact gaatttcatg gtccatctc  gattgatcaa agaaaagta ggcagaatgt
 781 actctgtcga gtactgtaaa cagaaaatcg agaaatgag attgatattt tctttgggat
 841 cagttggagg aatcagtctt catgtcaatg caactggatc tatatcaaaa acactagcaa
 901 gtcagctggt attcaaaagg gagatttgtt atcccttaat ggatctaaat ccacatctca
 961 atctagttat ctgggcttca tcagtagaga ttacaagagt ggatgcaatt ttccaacctt
1021 ctttacctgg cgagttcaga tactatccta acattattgc aaaaggagtt gggaaaatca
1081 aacaatggaa ctagtaatct ctattttgat ctggatatat ctattaagcc aaagcaaata
1141 agagataatc
```

FIG. 58B

MEYWKHTNHGKDAGNEPETSTATNGNKLTNKITYILWTITLMLL
SIIFIIVLINSIKSEKARESLLQDINNEFMEVTEKIQVASDNTNDLIQSGVNTRLLTI
QSHVQNYIPISLTQQISDLRKFISEITIRNDNQEVPPQRITHDVGIKPLNPDDFWRCT
SGLPSLMKTPKIRLMPGPGLLAMPTTVDGCVRTPSLVINDLIYAYTSNLITRGCQDIG
KSYQVLQIGIITVNSDLVPDLNPRISHTFNINDNRKSCSLALLNTDVYQLCSTPKVDE
RSDYASSGIEDIVLDIVNYDSSISTTRFKNNNISFDQPYAALYPSVGPGIYYKGKIIF
LGYGGLEHPINENAICNTTGCPGKTQRDCNQASHSPWFSDRRMVNSIIVVDKGLNSVP
KLKVWTISMRQNYWGSEGRLLLLGNKIYIYTRSTSWHSKLQLGIIDITDYSDIRIKWT
WHNVLSRPGNNECPWGHSCPDGCITGVYTDAYPLNPTGSIVSSVILDSQKSRVSPVIT
YSTATERVNELAIRNKTLSAGYTATSCITHYNKGYCFHIVEINHKSLITFQPMLFKTE
IPKSCS

FIG. 59A

```
   1 atggaatact ggaagcacac caatcacgga aaggatgctg gtaatgagcc ggagacatcc
  61 acagccacta atggcaacaa gctcaccaac aagataacat atatattatg gacgataacc
 121 ctgatgttat tatcaataat cttcatcata gtgctaatta attccatcaa aagtgaaaag
 181 gcccgcgaat cattgctaca agacataaat aatgagttta tggaagttac agaaaagatc
 241 caagtggcat cggataatac taatgatcta atacaatcag gagtaaatac aaggcttctt
 301 acaattcaga gtcatgtcca gaattatata ccaatatcat tgacacaaca aatatcggat
 361 cttaggaaat tcattagtga aattacaatt agaaatgata atcaagaagt gccaccacaa
 421 agaataacac atgatgtggg tataaaacct ttaaatccag atgatttctg gagatgcaca
 481 tctggtcttc catctttgat gaaaactcca aaaataagat tattgccggg gccaggatta
 541 ttagctatgc caacgactgt tgatggctgt gtcagaactc cgtccttagt gataaatgat
 601 ctgatttatg cttacacctc aaatctaatc actcgaggtt gccaagatat agggaaatca
 661 tatcaagtgt tacagatagg gataataact gtaaactcag acttggtacc tgacttaaat
 721 cccaggatct ctcatacctt caacataaat gacaatagaa agtcatgttc tctagcactc
 781 ctaaacacag atgtatatca actgtgttca actcccaaag ttgatgaaag atcagattat
 841 gcatcatcag gcatagaaga tattgtactt gatattgtca attatgatag ctcaatctca
 901 acaacaagat ttaagaataa taatataagt tttgaccaac catatgcggc attataccca
 961 tctgttggac cagggatata ctacaaaggc aaaataatat tcttgggta tggaggtctt
1021 gaacatccaa taaatgagaa tgcaatctgc aacacaactg ggtgtcctgg aaaaacacag
1081 agagactgca tcaagcatc tcatagtcca tggttttcag atagaaggat ggtcaactct
1141 atcattgttg ttgacaaggg tttaaactca gttccaaaat gaaggtatg gacgatatcg
1201 atgagacaaa attactgggg gtcagaagga agattacttc tactaggtaa caagatctac
1261 atatacacaa gatctacaag ttggcacagc aagttacaat taggaataat tgacattact
1321 gactacagtg atataaggat aaaatggaca tggcataatg tgctatcaag accaggaaac
1381 aatgaatgtc catggggaca ttcatgtccg gatggatgta taacaggagt atatactgat
1441 gcatatccac tcaatcccac aggaagcatt gtatcatctg tcatattaga ctcacaaaaa
1501 tcgagagtca gcccagtcat aacttactca acagcaaccg aaagggtaaa cgagctggcc
1561 atccgaaaca aaacactctc agctgggtat acagcaacaa gctgcattac acactataac
1621 aaaggatatt gttttcatat agtagaaata aatcataaaa gcttaatcac atttcaacct
1681 atgttgttca aaacagagat tccaaaaagc tgcagttaa
```

FIG. 59B

MEYWKHTNHGKDVGNELETSTATHGNKLTNKITYILWTITLVLL
SIVFIIVLINSIKSEKARESLLQDINNEFMEVTEKIQVASDNTNDLIQSGVNTRLLTI
QSHVQNYIPISLTQQISDLRKFISEITIRNDNQEVPPQRITHDVGIKPLNPDDFWRCT
SGLPSLMKTPKIRLMPGPGLLAMPTTVDGCVRTPSLVINDLIYAYTSNLITRGCQDIG
KSYQVLQIGIITVNSDLVPDLNPRISHTFNINDNRKSCSLALLNTDVYQLCSTPKVDE
RSDYASSGIEDIVLDIVNYDGSISTTRFKNNNISFDQPYAALYPSVGPGIYYKGKIIF
LGYGGLEHPINENAICNTTECPGKTQRDCNQASHSPWFSDRRMVNSIIVVDKGLNSVP
KLKVWSISMRQNYWGSEGRLLLLGNKIYIYTRSTSWHSKLQLGIIDITDYSDIRIKWT
WHNVLSRPGNNECPWGHSCPDGCITGVYTDAYPLNPTGSIVSSVILDSQKSRVNPVIT
YSTATERVNELAIRMETLSAGYTTTSCITHYNKGYCFHIVEINHKSLNTFQPMLFKTE
IPKSCS

FIG. 60A

```
   1 atggaatact ggaagcacac caaccacgga aaggatgttg gtaatgagct ggaaacatcc
  61 acagccacta atggcaacaa gctcaccaac aagataacat atatattatg gacgataacc
 121 ctggtgttat tatcaatagt cttcatcata gtgctaacta attccatcaa aagtgaaaag
 181 gcccgcgaat cattgctaca agacataaat aatgagttta tggaagttac agaaaagatc
 241 caagtggcat ctgataatac taatgatcta atacagtcag gagtgaatac aaggcttctt
 301 acaattcaga gtcatgtcca gaattatata ccaatatcat tgacacaaca aatatcggat
 361 cttaggaaat tcattagtga aattacaatt agaaatgata atcaagaagt gccaccacaa
 421 agaataacac atgatgtagg tataaaacct ttaaatccag atgatttctg gagatgcaca
 481 tctggtcttc catctttaat gaaaactcca aaaataagat taatgccggg cccaggatta
 541 ttagctatgc caacgactgt tgatggctgt gtcagaaccc cgtccttagt gataaatgat
 601 ctgatttatg cttacacctc aaatctaatt actcgaggtt gccaggatat agggaaatca
 661 tatcaagtat tacagatagg gataataact gtaaactcag acttggtacc tgacttaaat
 721 cctaggatct ctcataccTT caacataaat gacaatagaa agtcatgttc tctagcactc
 781 ctaaatacag atgtatatca actgtgttca actccaaaag ttgatgaaag atcagattat
 841 gcatcatcag gcatagaaga tattgtactt gatattgtca attatgatag ctcaatctca
 901 acaacaagat ttaagaataa taatataagt tttgatcaac catatgcggc attataccca
 961 tctgttggac cagggatata ctacaaagc aaaataatat ttctcgggta tggaggtctt
1021 gaacatccaa taaatgagaa tgcaatctgc aacacaactg agtgtcctgg aaaacacag
1081 agagactgca atcaggcatc tcacagtcca tggttttcag atagaaggat ggtcaactct
1141 ataattgttg ttgacaaggg tttaaactca gttccaaaat gaaggtatg gtcgatatct
1201 atgagacaaa attactgggg gtcagaagga agattacttc tactaggtaa caagatctac
1261 atatacacaa gatctacaag ttggcacagc aagttacaat taggaataat tgacattact
1321 gactacagtg atataaggat aaaatggaca tggcataatg tgctatcaag accaggaaac
1381 aatgaatgtc catggggaca ttcatgtccg gatggatgta acgggagt atatactgat
1441 gcatatccac tcaatcccac aggaagcatt gtatcatctg tcatattgga ctcacaaaaa
1501 tcgagagtca acccagtcat aacttactca acagcaaccg aaagggtaaa cgagctggcc
1561 atccgaaaca aaacactctc agctgggtat acaacaacaa gttgcattac acactataac
1621 aaagggtatt gttttcatat agtagaaata aatcataaaa gcttaaacac atttcaaccc
1681 atgttgttca aaacagagat tccaaaaagc tgcagttaa
```

FIG. 60B

MEYWKHTNHGKDAGNELETSMATNGNKLTNKITYILWTITLVLL
SIVFIIVLINSIKSEKAHESLLQDINNEFMEITEKIQMASDNTNDLIQSGVNTRLLTI
QSHVQNYIPISLTQQMSDLRKFISEITIRNDNQEVLPQRITHDVGIKPLNPDDFWRCT
SGLPSLMKTPKIRLMPGPGLLAMPTTVDGCIRTPSLVINDLIYAYTSNLITRGCQDIG
KSYQVLQIGIITVNSDLVPDLNPRISHTFNINDNRKSCSLALLNTDVYQLCSTPKVDE
RSDYASSGIEDIVLDIVNYDGSISTTRFKNNNISFDQPYAALYPSVGPGIYYKGKIIF
LGYGGLEHPINENVICNTTGCPGKTQRDCNQASHSPWFSDRRMVNSIIVVDKGLNSIP
KLKVWTISMRQNYWGSEGRLLLLGNKIYIYTRSTSWHSKLQLGIIDITDYSDIRIKWT
WHNVLSRPGNNECPWGHSCPDGCITGVYTDAYPLNPTGSIVSSVILDSQKSRVNPVIT
YSTATERVNELAIRNRTLSAGYTTTSCITHYNKGYCFHIVEINQKSLNTLQPMLFKTE
VPKSCS

FIG. 61A

```
   1 gacaaatcca aattcgagat ggaatactgg aagcatacca atcacggaaa ggatgctggc
  61 aatgagctgg agacgtccat ggctactaat ggcaacaagc tcaccaataa gataacatat
 121 atattatgga caataatcct ggtgttatta tcaatagtct tcatcatagt gctaattaat
 181 tccatcaaaa gtgaaaaggc tcatgaatca ttgctgcaag acataaataa tgagtttatg
 241 gaaattacag aaaagatcca aatggcatcg gataatacca atgatctaat acagtcagga
 301 gtgaatacaa ggcttcttac aattcagagt catgtccaga attatatacc aatatcactg
 361 acacaacaga tgtcagatct taggaaattc attagtgaaa ttacaattag aaatgataat
 421 caagaagtgc tgccacaaag aataacacat gatgtgggta taaaaccttt aaatccagat
 481 gattttttgga gatgcacgtc tggtcttcca tctttaatga aaactccaaa aataaggtta
 541 atgccagggc cgggattatt agctatgcca acgactgttg atggctgtat cagaactccg
 601 tccttagtta taaatgatct gatttatgct tatacctcaa atctaattac tcgaggttgt
 661 caggatatag aaaaatcata tcaagtctta cagatagggg taataactgt aaactcagac
 721 ttggtacctg acttaaatcc caggatctct catactttta acataaatga caataggaag
 781 tcatgttctc tagcactcct aaatacagat gtatatcaac tgtgttcaac tcccaaagtt
 841 gatgaaagat cagattatgc atcatcaggc atagaagata ttgtacttga tattgtcaat
 901 tatgatggct caatctcaac aacaagattt aagaataata acataagctt tgatcaacct
 961 tatgctgcac atacccatc tgttggacca gggatatact acaaaggcaa aataatattt
1021 ctcgggtatg gaggtcttga acatccaata aatgagaatg taatctgcaa cacaactggg
1081 tgtcccggga aaacacagag agactgcaat caggcatctc atagtccatg gttttcagat
1141 aggaggatgg tcaactctat cattgttgtt gacaaaggct aaactcaat tccaaaattg
1201 aaggtatgga cgatatctat gagacagaat tactgggggt cagaaggaag gttacttcta
1261 ctaggtaaca agatctatat atatacaaga tccacaagtt ggcatagcaa gttacaatta
1321 ggaataattg atattactga ttacagtgat ataaggataa aatggacatg cataatgtg
1381 ctatcaagac caggaaacaa tgaatgtcca tggggacatt catgtccaga tggatgtata
1441 acaggagtat atactgatgc atatccactc aatcccacag ggagcattgt gtcatctgtc
1501 atattagatt cacaaaaatc gagagtgaac ccagtcataa cttactcaac agcaaccgaa
1561 agagtaaacg agctggccat ccgaaacaga acactctcag ctggatatac aacaacaagc
1621 tgcatcacac actataacaa aggatattgt tttcatatag tagaaataaa tcagaaaagc
1681 ttaaacacac ttcaacccat gttgttcaag acagaggttc caaaagctg cagttaatca
1741 taattaaccg caatatgcat taacctatct ataatacaag tatatgataa gtaatcagca
1801 atcagacaat agacaaaagg gaaatataaa aa
```

FIG. 61B

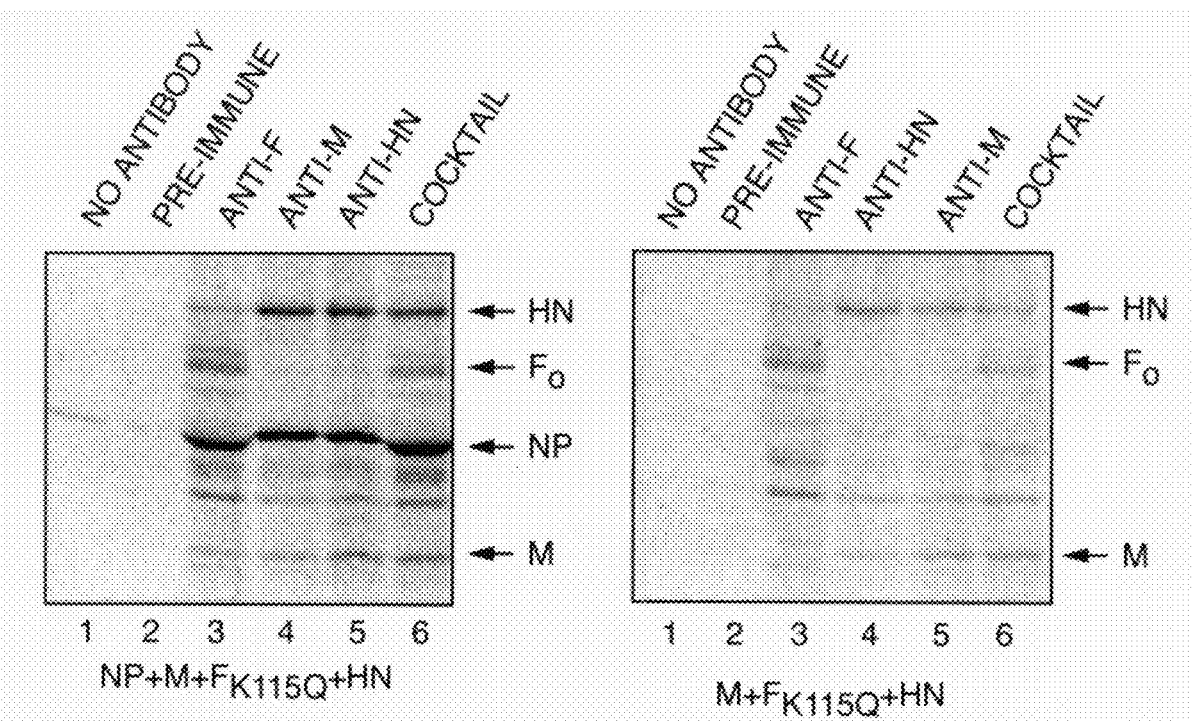
FIG. 65A
FIG. 65B
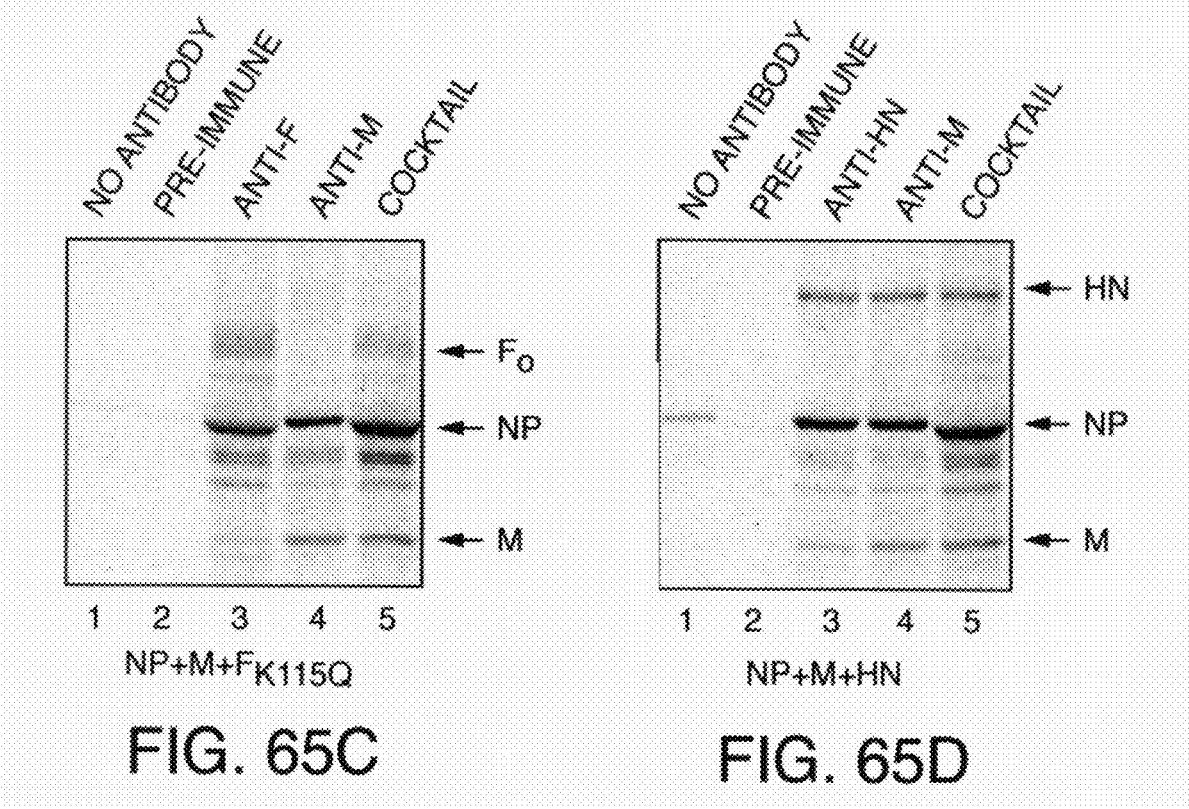
FIG. 65C
FIG. 65D

VIRUS-LIKE PARTICLES AS VACCINES FOR PARAMYXOVIRUS

STATEMENT OF GOVERNMENT SUPPORT

This invention was made with government support under grant no. AI030572 awarded by the National Institutes of Health. The government has certain rights in the invention.

FIELD OF INVENTION

The present invention relates to the field of viral vaccines. In one embodiment, the present invention contemplates a paramyxoviral vaccine effective against diseases such as, but not limited to, Newcastle disease, measles, parainfluenza virus 3, and respiratory syncytial virus. In one embodiment, the present invention contemplates a vaccine comprising Newcastle disease virus (NDV)-like particles (VLP). In one embodiment, the present invention contemplates a method comprising transfecting avian cells with cDNAs encoding major NDV structural proteins. In another embodiment, a method wherein particles resembling infectious virions are released with nearly 100% efficiency. In one embodiment, the particles are non-infectious and provide a safe and effective NDV vaccine.

BACKGROUND

Over the last decade, a number of concerns have arisen related to safety issues regarding paramyxovirus vaccines that have had an adverse effect on the public's trust. These concerns affect not only parents whose children are the primary recipient of childhood disease vaccines, but also ranchers devoted to raising animals susceptible to various types of paramyxoviruses.

Historically, Newcastle disease has been a devastating disease of poultry, and in many countries the disease remains one of the major problems affecting existing or developing poultry industries. Even in countries where Newcastle disease may be considered to be controlled, an economic burden is still associated with vaccination and/or maintaining strict biosecurity measures. The variable nature of Newcastle disease virus strains in terms of virulence for poultry and the different susceptibilities of the different species of birds mean that for control and trade purposes, Newcastle disease requires careful definition. Confirmatory diagnosis of Newcastle Disease requires the isolation and characterization of the virus involved. Currently Newcastle disease control is limited to prevention of introduction and spread, good biosecurity practices and/or live attenuated virus vaccination. Newcastle disease viruses may infect humans, usually causing transient conjunctivitis, but human-to-human spread has never been reported. Alexander D. J., "Newcastle disease and other avian paramyxoviruses" Rev Sci Tech. 19(2):443-62 (2000).

Historically, the live attenuated measles virus (MV) vaccine and the combination multivalent measles, mumps, and rubella (MMR) vaccine have had a positive impact on the health of children worldwide by preventing infectious disease. The induction of an effective antiviral immune response using these live attenuated virus vaccines, however, are known to result in a significant rate of adverse events (i.e., for example, autism). Kennedy et al., "Measles virus infection and vaccination: potential role in chronic illness and associated adverse events" Crit Rev Immunol. 24(2):129-56 (2004).

Healthy, and at risk, children are susceptible to the morbidity and mortality associated with viral-induced respiratory diseases, including respiratory syncytial virus (RSV) and influenza. Currently, the World Health Organization is attempting to develop and distribute effective vaccines to prevent/reduce key viral respiratory diseases. The progress, however, is slow and the risk/benefit ratio is high. A vaccination program for viral respiratory infections should include the prevention of lower respiratory tract infections and prevention of infection-associated morbidities, hospitalization and mortality. Presently, there are two influenza vaccines; i) a trivalent inactivated vaccine, and ii) a live, cold-adapted, attenuated vaccine. Compliancy, however, is relatively low (i.e., 10-30%). Because it is believed that the low compliancy is related to the known high risk of contaminated vaccines, those in the art recommend that research should continue into safe and effective vaccines for all childhood viral illnesses. Greenberg et al., "Immunization against viral respiratory disease: A review" Pediatr Infect Dis J. 23(11 Suppl):S254-61 (2004).

What is needed in the art is a low risk, highly effective paramyxovirus vaccine that is compatible with population-wide distribution marketing goals of low cost and high production rates.

SUMMARY

The present invention relates to the field of viral vaccines. In one embodiment, the present invention contemplates a paramyxoviral vaccine effective against diseases such as, but not limited to, Newcastle disease, measles, parainfluenza virus 3, and respiratory syncytial virus. In one embodiment, the present invention contemplates a vaccine comprising Newcastle disease virus-like particles (VLP). In one embodiment, the present invention contemplates a method comprising transfecting avian cells with cDNAs encoding major NDV structural proteins. In another embodiment, a method wherein particles resembling infectious virions are released with nearly 100% efficiency. In one embodiment, the particles are non-infectious and provide a safe and effective NDV vaccine.

In one embodiment, the present invention contemplates a method, comprising; a) providing, i) an expression vector comprising DNA sequences encoding a Newcastle disease matrix protein; ii) a cell capable of being transfected by said vector; b) transfecting said cell with said vector under conditions such that Newcastle disease virus-like particles are generated. In one embodiment, the method further comprises the step c) harvesting said virus-like particles so as to create a cell-free preparation of particles. In one embodiment, the method further comprises the step d) administering a vaccine comprising said preparation of particles to a chicken. In one embodiment, the cell is part of a cell culture and said harvesting comprises obtaining said particles from the supernatant of said culture. In one embodiment, the cell culture comprises sub-confluent avian cells. In one embodiment, the vector further comprises DNA sequences encoding additional Newcastle disease viral proteins selected from the group consisting of a nucleocapsid protein, a fusion protein, and a hemagglutinin-neuraminidase protein. In one embodiment, the particles are free of Newcastle disease viral DNA.

In one embodiment, the present invention contemplates a transfected cell comprising an expression vector comprising DNA sequences encoding a Newcastle disease matrix protein capable of generating Newcastle disease virus-like particles.

In one embodiment, the present invention contemplates a cell-free preparation of virus like particles harvested from a transfected cell comprising an expression vector comprising DNA sequences encoding a Newcastle disease matrix protein capable of generating Newcastle disease virus-like particles.

In one embodiment, the present invention contemplates a method, comprising; a) providing, i) a vaccine comprising Newcastle disease virus-like particles, said particles comprising a Newcastle disease viral matrix protein; ii) a host susceptible to Newcastle disease; b) immunizing said host with said vaccine under conditions such that antibodies directed to said virus-like particle are produced. In one embodiment, the host is selected from the group consisting of avian, murine, and human. In one embodiment, the particles further comprise one or more additional Newcastle disease viral proteins selected from the group consisting of a fusion protein, a nucleocapsid protein and a hemagglutinin-neuraminidase protein.

In one embodiment, the present invention contemplates a vaccine comprising Newcastle disease virus-like particles, said particles comprising a Newcastle disease viral matrix protein. In one embodiment, the particles are free of Newcastle disease viral DNA. In one embodiment, the particles further comprise one or more additional viral proteins selected from the group consisting of a fusion protein, nucleocapsid protein and a hemagglutinin-neuraminidase protein.

In one embodiment, the present invention contemplates a vaccine comprising a Newcastle disease virus-like particle and a Newcastle disease matrix protein. In one embodiment, the vaccine further comprises at least two viral glycoproteins. In one embodiment, the glycoproteins are selected from the group consisting of a fusion protein and a hemagglutinin-neuraminidase protein. In one embodiment, the vaccine further comprises a nucleocapsid protein. In one embodiment, the matrix protein comprises a Late Domain. In one embodiment, the Late Domain comprises an FPIV sequence (SEQ ID NO:1). In one embodiment, the Late Domain comprises a PXXP sequence (SEQ ID NO:2). In one embodiment, the Late Domain comprises an YXXL sequence (SEQ ID NO:3). In one embodiment, the vaccine is non-infectious.

One embodiment of the present invention contemplates an avian vaccine comprising a Newcastle disease virus-like particle and a Newcastle disease matrix protein. In one embodiment, the vaccine further comprises at least two viral glycoproteins. In one embodiment, said glycoproteins are selected from the group comprising a fusion protein and a hemagglutinin-neuraminidase protein. In one embodiment, the vaccine further comprises a nucleocapsid protein. In one embodiment, said virus-like particle comprises a Paramyxovirus virus-like particle. In one embodiment, said Paramyxovirus virus-like particle comprises a Newcastle disease virus-like particle. In one embodiment, said matrix protein comprises a Late Domain. In one embodiment, said Late Domain comprises an FPIV sequence (SEQ ID NO:1). In one embodiment, said Late Domain comprises a PXXP sequence (SEQ ID NO:2). In one embodiment, said Late Domain comprises an YXXL sequence (SEQ ID NO:3). In one embodiment, said virus-like particle is non-infectious.

In one embodiment, the present invention contemplates a method, comprising; a) providing, i) an expression vector comprising cDNA sequences encoding a Newcastle disease virus matrix protein and at least two viral glycoproteins; ii) a cell capable of being transfected by said vector; b) transfecting said cell by said vector under conditions that generate a Newcastle disease virus-like particle, wherein said particle comprises said matrix protein. In one embodiment, the cell comprises sub-confluent avian cells. In one embodiment, the expression vector comprises pCAGGS. In one embodiment, the glycoproteins are selected from the group consisting of a fusion protein and a hemagglutinin-neuraminidase protein. In one embodiment, the expression vector further comprises a cDNA sequence encoding a nucleocapsid protein. In one embodiment, the method further comprises releasing said virus-like particle at an efficiency of at least 85%. In one embodiment, the virus-like particle further comprises said at least two viral glycoproteins.

One embodiment of the present invention contemplates a method, comprising; a) providing, i) an expression vector comprising cDNA sequences encoding a Newcastle disease virus matrix protein and at least two viral glycoproteins; ii) a cell capable of being transfected by said vector; and b) transfecting said cell by said vector under conditions that generate an avian vaccine comprising a virus-like particle. In one embodiment, said cell comprises sub-confluent avian cells. In one embodiment, said cell comprises human cells. In one embodiment, said expression vector comprises pCAGGS. In one embodiment, said glycoproteins are selected from the group comprising a fusion protein and a hemagglutinin-neuraminidase protein. In one embodiment, the vector further comprises a cDNA sequence encoding a nucleocapsid protein. In one embodiment, the method further comprises releasing said virus-like particle at an efficiency of at least 85%. In one embodiment, said virus-like particle comprises said matrix protein and said at least two viral glycoproteins.

In one embodiment, the present invention contemplates a method, comprising; a) providing, i) a vaccine comprising a Newcastle disease virus-like particle and a Newcastle disease virus matrix protein and at least two viral glycoproteins; ii) a host capable of immunization by said virus-like particle; b) immunizing said host by said virus-like particle under conditions such that antibodies directed to said virus-like particle are produced. In one embodiment, the host is selected from the group consisting of avian, murine, and human. In one embodiment, the glycoproteins are selected from the group consisting of a fusion protein, and a hemagglutinin-neuraminidase protein. In one embodiment, the vaccine further comprises a nucleocapsid protein.

One embodiment of the present invention contemplates a method, comprising; a) providing, i) an avian vaccine comprising a Newcastle disease virus virus-like particle, a Newcastle disease virus matrix protein and at least two viral glycoproteins; ii) a host capable of immunization by said virus-like particle; b) immunizing said host by said vaccine under conditions such that antibodies directed to said virus-like particle are produced. In one embodiment, said host is selected from the group comprising avian, murine, and human. In one embodiment, said virus-like particle comprises a Newcastle disease virus-like particle. In one embodiment, said glycoproteins are selected from the group comprising a fusion protein, and a hemagglutinin-neuraminidase protein. In one embodiment, the vaccine further comprises a nucleocapsid protein.

In one embodiment, the present invention contemplates an VLP vaccine expression system comprising a first cDNA encoding a first viral protein gene from a first Newcastle disease virus strain; a second cDNA encoding a second viral protein gene from a second Newcastle disease virus strain; and a third cDNA encoding a third viral protein gene from a third strain. In one embodiment, the first viral protein gene is selected from the group comprising HN protein, F protein, NP protein or M protein. In one embodiment, the first strain is selected from the group comprising strain Hertz, strain AV, or strain B1. In one embodiment, the second viral protein gene is selected from the group comprising HN protein, F protein, NP protein or M protein. In one embodiment, the second strain is selected from the group comprising strain Hertz, strain AV, or strain B1. In one embodiment, the third viral protein gene is selected from the group comprising HN protein, F protein, NP protein or M protein. In one embodiment, the third strain is selected from the group comprising strain Hertz, strain AV, or strain B1. In one embodiment, the present invention contemplates a method for detecting a viral protein gene incorporated into a VLP vaccine comprising contacting the viral protein gene with strain specific antibodies or incorporated sequence tags.

Definitions

The terms used within the present invention are generally used according to those definitions accepted by one having ordinary skill in the art, with the following exceptions:

The term "virus-like particle" as used herein, refers to a non-infective viral subunit either with, or without, viral proteins. For example, a virus-like particle may completely lack the DNA or RNA genome. Further, a virus-like particle comprising viral capsid proteins may undergo spontaneous self-assembly. Preparations of virus-like particles are contemplated in one embodiment, where the preparation is purified free of infectious virions (or at least substantially free, such that the preparation has insufficient numbers to be infectious).

The term "matrix protein", "membrane protein", or "M protein" as used herein, means any protein localized between the envelope and the nucleocapsid core and facilitates the organization and maintenance of the virion structure and budding processes.

The term "fusion protein" or "F protein" as used herein, means any protein that projects from the envelope surface and mediates host cell entry by inducing fusion between the viral envelope and the cell membrane. However, it is not intended that the present invention be limited to functional F proteins. For example, an F protein may be encoded by a mutant F gene such as, but not limited to, F-K115Q. F-K115Q is believed to eliminate the normal cleavage and subsequent activation of the fusion protein. F-K115Q mimics naturally occurring F-protein mutations in avirulent NDV strains, and in cell culture, eliminates any potential side effects of cell-cell fusion on the release of VLPs.

The term "nucleocapsid protein" or "NP protein" as used herein, means any protein that associates with genomic RNA (i.e., for example, one molecule per hexamer) and protects the RNA from nuclease digestion.

The term "haemagglutinin-neuraminidase protein", "HN protein", or G protein as used herein, means any protein that spans the viral envelope and projects from the surface as spikes to facilitate cell attachment and entry (i.e., for example, by binding to sialic acid on a cell surface). These proteins possess both haemagglutination and neuraminidase activity.

The term "glycoprotein" as used herein, refers to any protein conjugated to a nonprotein group that comprises a carbohydrate.

The term "paramyxovirus" as used herein, refers to any virus of the Paramyxoviridae family of the Mononegavirales order; that are negative-sense single-stranded RNA viruses responsible for a number of human and animal diseases (i.e., for example, Newcastle disease). Paramyxoviruses include, but are not limited to, for example, Sendai virus, Newcastle disease virus, Mumps virus, Measles virus, Respiratory syncytial (RS) virus, rinderpest virus, distemper virus, simian parainfluenza virus (SV5), type I, II, and III human parainfluenza viruses, etc. Sendai viruses may be wild-type strains, mutant strains, laboratory-passaged strains, artificially constructed strains, or so on. Incomplete viruses such as the DI particle (J. Virol., 1994, 68, 8413-8417), synthesized oligonucleotides, and so on, may also be utilized as material for producing the vaccine of the present invention.

The term "Late Domain" as used herein, refers to any region in a viral protein that is involved in the budding of virus particles from a cell's plasma membrane. Late Domains comprise highly conserved motifs known to mediate protein-protein interactions between cellular proteins. For example, at least three classes of motifs comprise PTAP (SEQ ID NO:4), PPXY (SEQ ID NO:5), or YXXL (SEQ ID NO:3)(i.e., for example, a YANL sequence).

The term "vector" as used herein, refers to any nucleotide sequence comprising exogenous operative genes capable of expression within a cell. For example, a vector may comprise a nucleic acid encoding a viral matrix protein and at least two glycoproteins that are expressed within a human, avian, or insect cell culture system. For example, a baculovirus vector may be used to transfect various *Lepidoptera* species.

The term "transfect" or "transfecting" as used herein, refers to any mechanism by which a vector may be incorporated into a host cell. A successful transfection results in the capability of the host cell to express any operative genes carried by the vector. Transfections may be stable or transient. One example of a transient transfection comprises vector expression within a cell, wherein the vector is not integrated within the host cell genome. Alternatively, a stable transfection comprises vector expression within a cell, wherein the vector is integrated within the host cell genome.

The term "host" as used herein, refers to any organism capable of becoming infected by a virus and immunized by a virus-like particle. A host may be an avian host (i.e., for example, a chicken) or a mammalian host (i.e., for example, human, mouse, dog, rat, cow, sheep, etc.).

The term "sequence tag" as used herein, refers to any atom or molecule that can be used to provide a detectable (preferably quantifiable) signal, and that can be attached to a nucleic acid or protein. "Sequence tags" may provide signals detectable by fluorescence, radioactivity, colorimetry, gravimetry, X-ray diffraction or absorption, magnetism, enzymatic activity, and the like. A "sequence tag" may be a charged moiety (positive or negative charge) or alternatively, may be charge neutral. "Sequence tags" can include or consist of a nucleic acid or protein sequence, so long as the sequence comprising the "sequence tag" is detectable.

The term "adjuvant" as used herein, refers to any compound which enhances or stimulates the immune response when administered with an antigen(s).

BRIEF DESCRIPTION OF THE FIGURES

The patent or application file contains at least one drawing executed in color. Copies of this patent or patent application publication with color drawing(s) will be provided by the Office upon request and payment of the necessary fee.

The following figures are presented only as an illustration of specific embodiments of the present invention and are not intended to be limiting.

Panel A: avian cells, co-transfected with pCAGGS(-NP), (-M), (F-K115Q), and (-HN), were radioactively labeled with $^{35}$S-methionine and $^{35}$S-cysteine for 4 hours (P) and then chased in non-radioactive medium for 8 hours (C).

Panel B: avian cells, infected with NDV, strain AV, with a Multiplicity Of Infection (MOI) of 5 pfu for 5 hours, were pulse-labeled for 30 minutes and chased in non-radioactive medium for 8 hours.

Panel C shows the quantitation of efficiency of virion and VLP release as determined by the amount of M protein in the pulse and chase cell extracts. The results of 3 separate experiments were averaged and the standard deviation is shown.

Figure 2A:
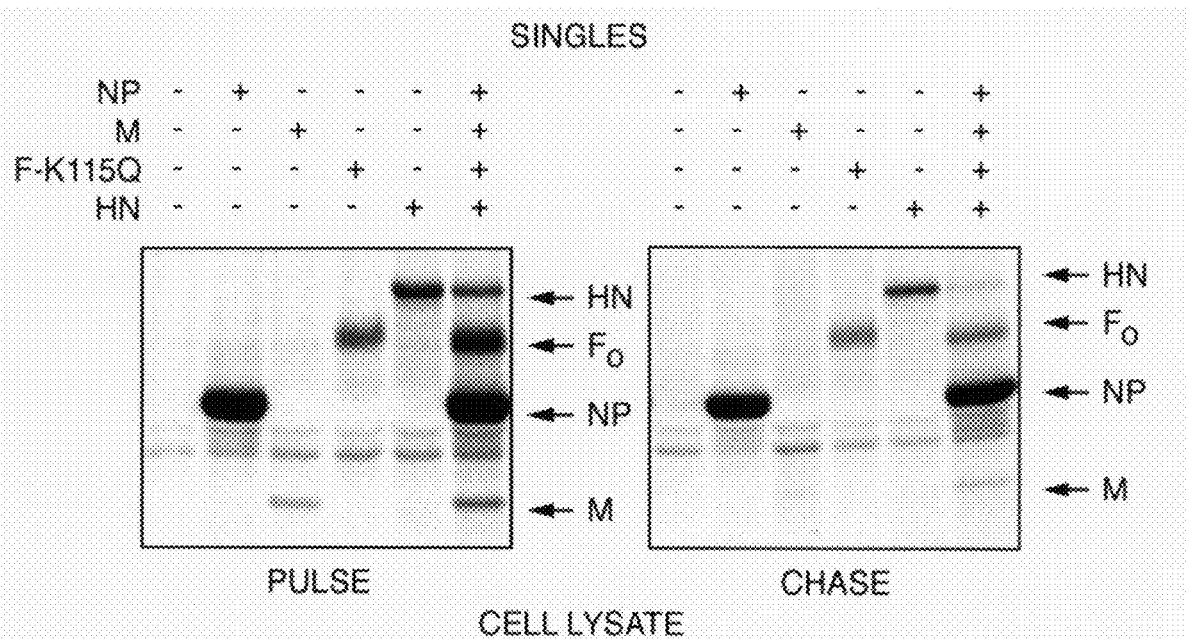
Figure 2B:
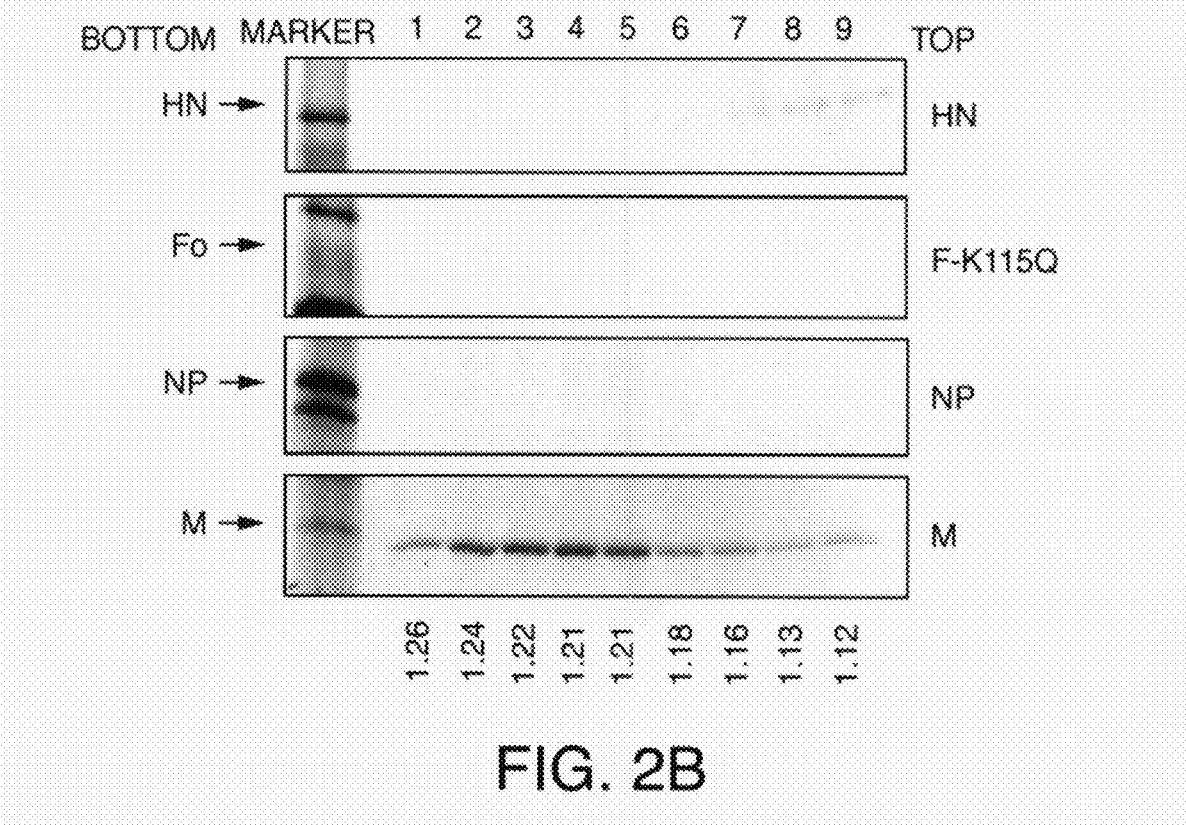
Figure 2C:
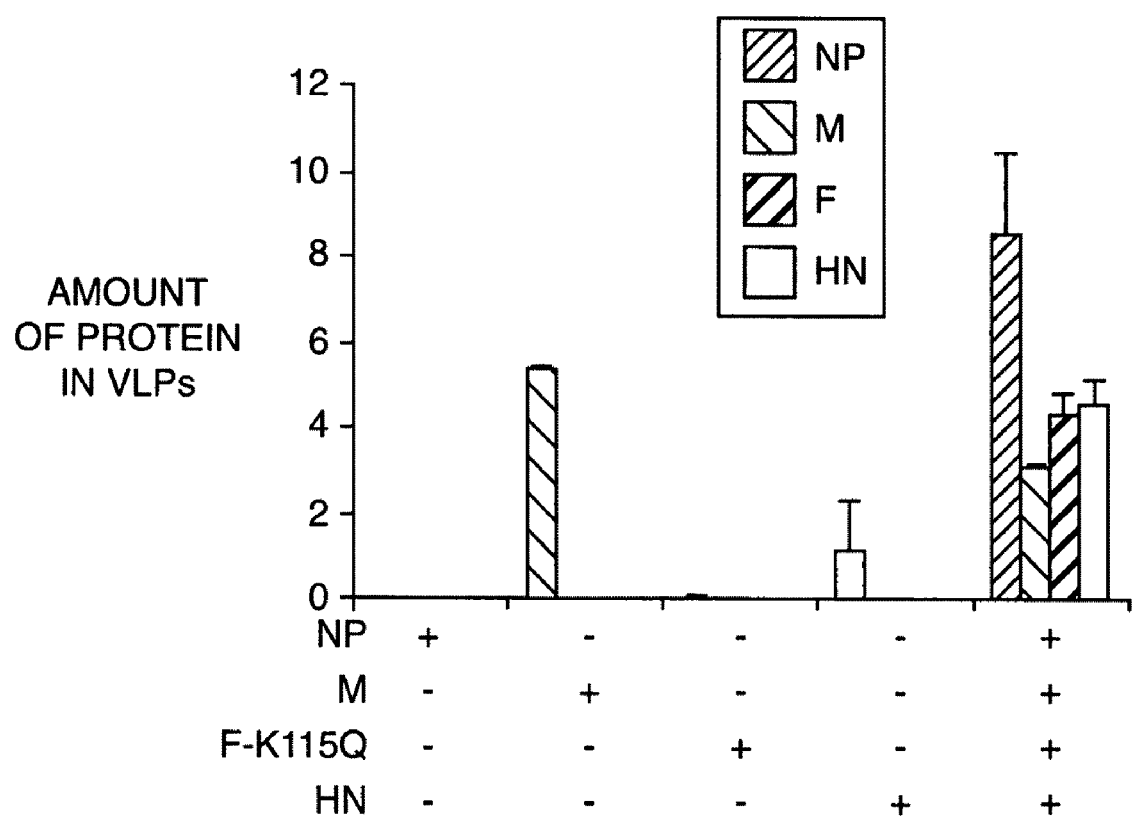

FIG. 2 presents exemplary data showing that M protein is sufficient for VLP release. Avian cells were transfected with pCAGGS-NP, -M, -F-K115Q, and -HN individually.

Figure 1C:
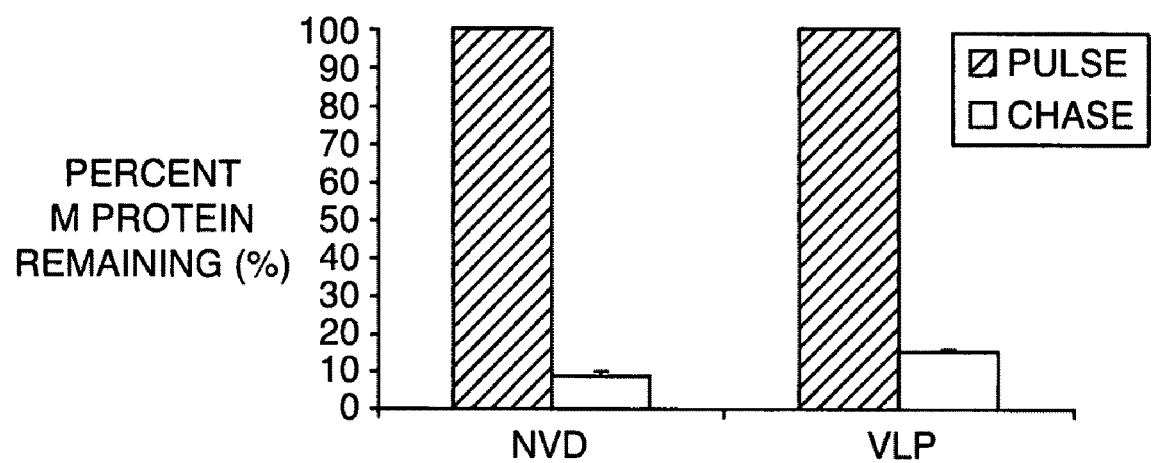
FIG. 1 presents exemplary data showing co-expression of NP, F, HN, and M proteins resulted in VLP formation and release. Radioactively labeled proteins in both the transfected (Panel A) and infected (Panel B) extracts were immunoprecipitated with a cocktail of antibodies specific for all viral proteins and precipitated labeled proteins are shown on the left side of each panel. VLP particles in cell supernatants were purified as described in Example 4. After flotation into sucrose gradients, each gradient fraction was immunoprecipitated with antibody cocktail (right side of each panel). The density of each fraction (g/cc) is shown at the bottom.

Panel A shows radioactively labeled proteins in the extracts at time of pulse (left) and chase (right). Particles in the supernatants of avian cells expressing NP, M, F, and HN individually, were concentrated and floated into sucrose gradients as described above in FIG. 1.

Panel B shows the distribution in the gradients of radioactively labeled proteins derived from each supernatant.

Panel C shows the quantification of the amounts of each protein in VLPs. The results of three separate experiments were averaged and the standard deviation is shown.

Figures 3A, 3B:
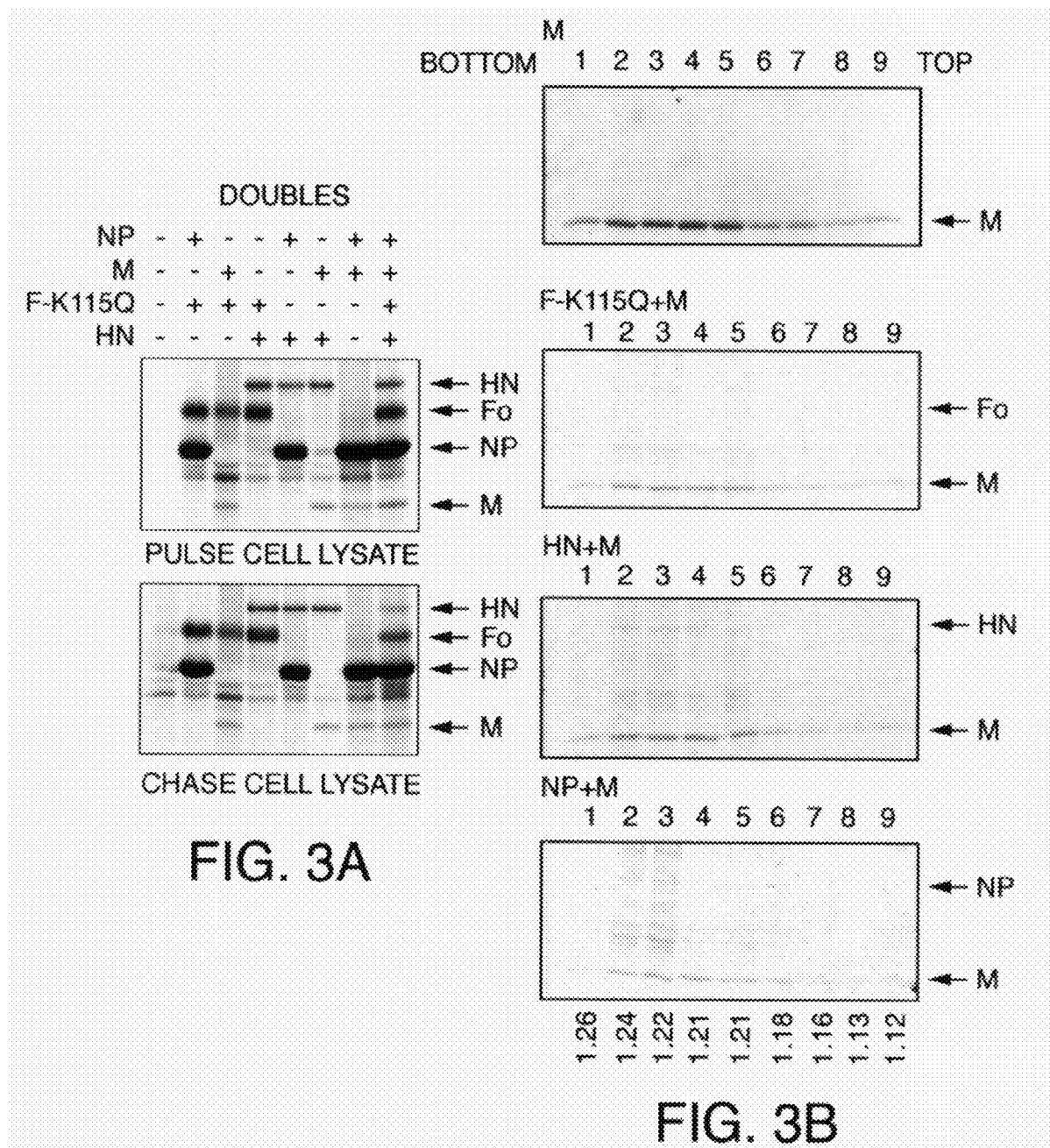
Figure 3C:
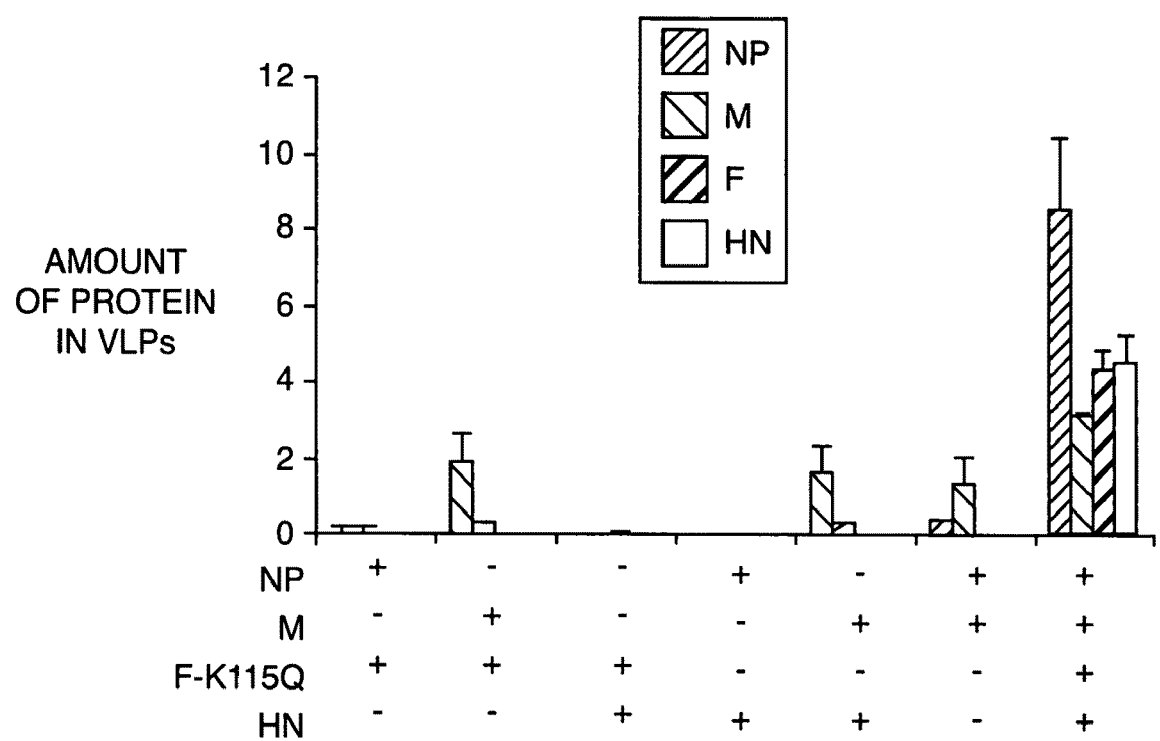

FIG. 3 presents exemplary data showing effects of NP, F, or HN protein co-expression with M protein on VLP release. Avian cells, transfected with all possible combinations of two NDV structural protein genes (i.e., pair wise combinations including, but not limited to, F+NP, F+M, F+HN, HN+NP, HN+M and NP+M, wherein F is F-K115Q). Labeling in a pulse-chase protocol is as described in FIG. 1. Particles present in the supernatants were concentrated and then floated into sucrose gradients as described in Example 4.

Panel A shows labeled proteins in cell extracts at time of pulse (top) and chase (bottom).

Panel B shows the proteins present in each gradient fraction after immunoprecipitation of each fraction with an antibody cocktail. Densities (g/cc) of the fractions are shown at the bottom. Gradients from transfections that did not contain M protein are not shown since there were no radioactively labeled proteins in those gradients.

Panel C shows the quantification of each protein in VLPs released from transfected avian cells. Results are the average of three experiments and the standard deviation is shown.

Figure 4C:
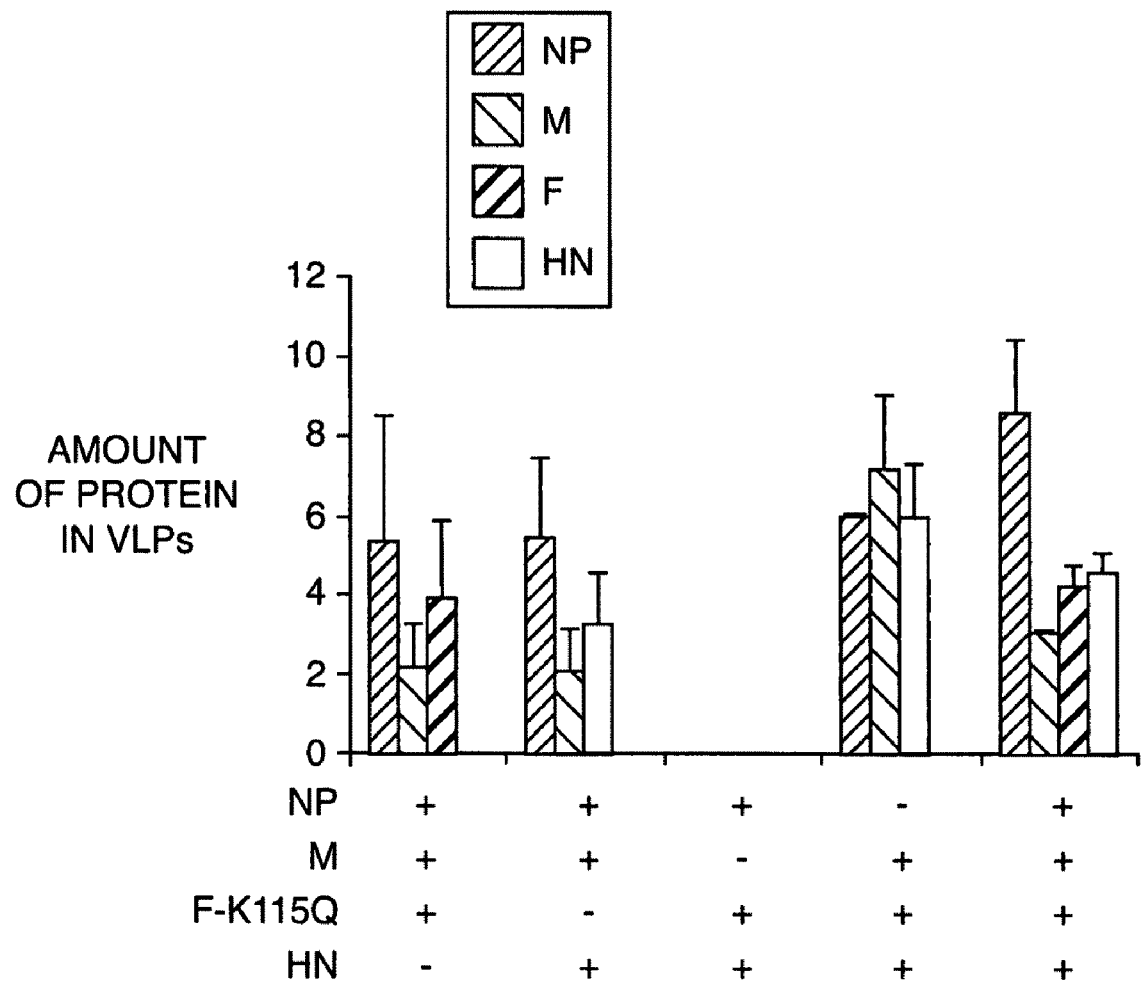
Figure 4D:
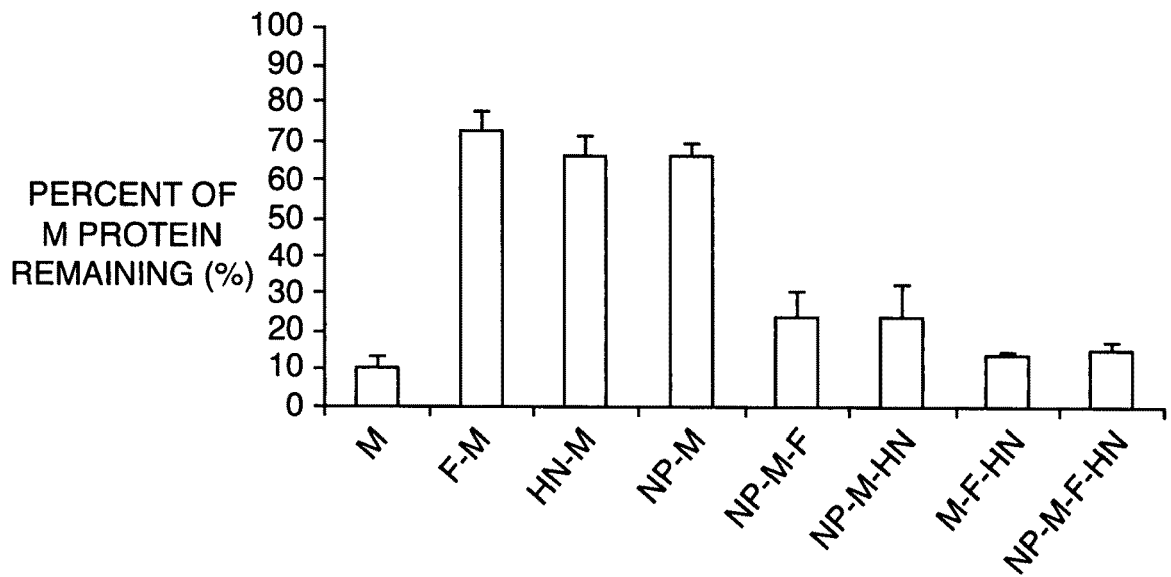
Figure 4E:
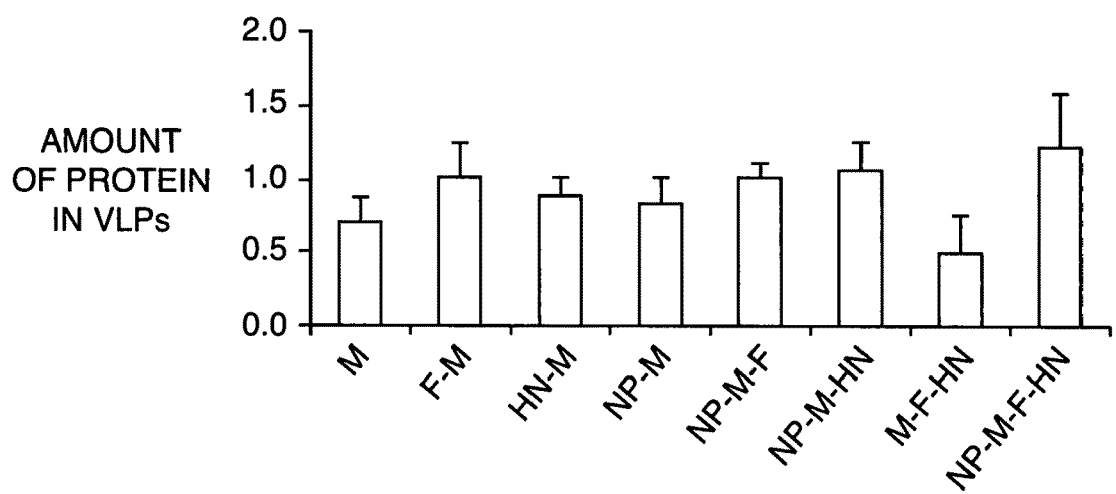
Figure 5A:
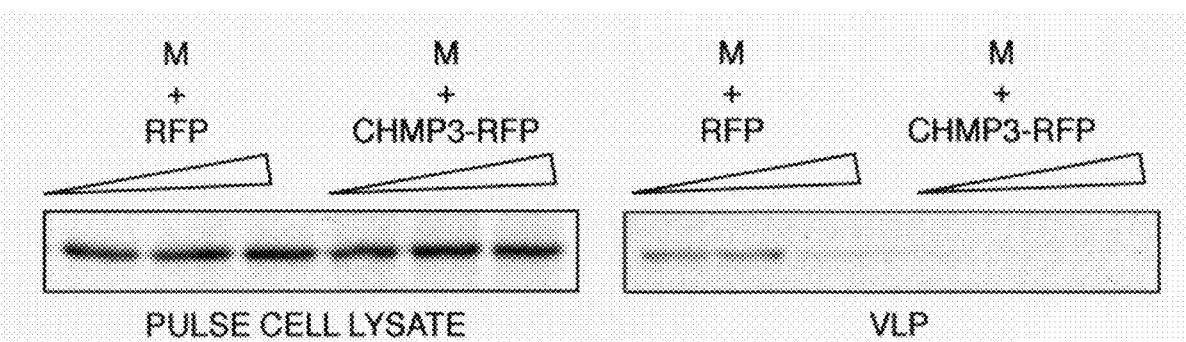
Figure 5B:
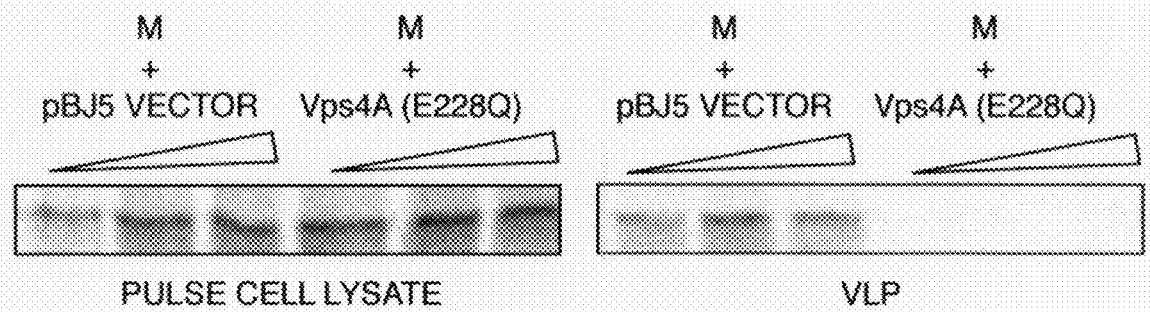
Figure 5C:
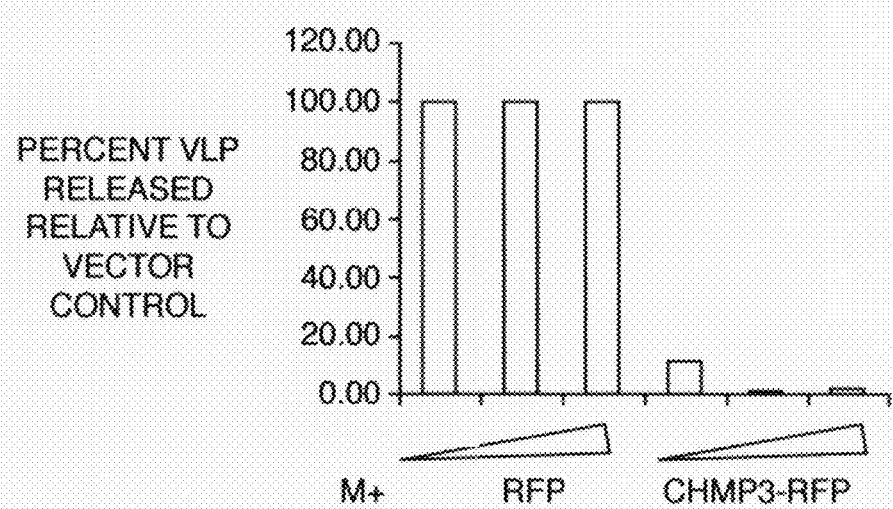
Figure 5D:
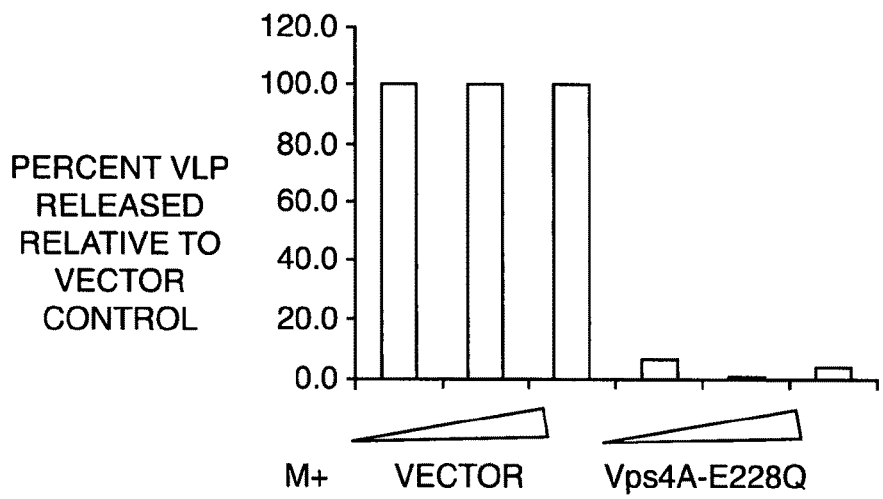
Figure 5E:
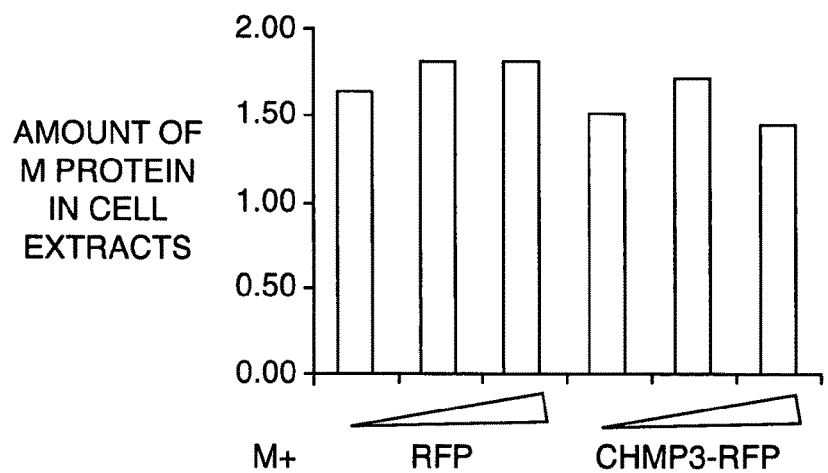
Figure 5F:
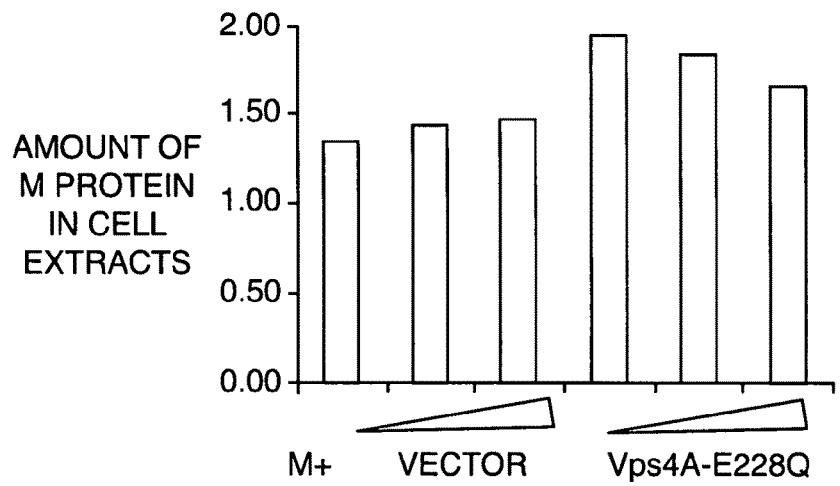
Figure 13A:
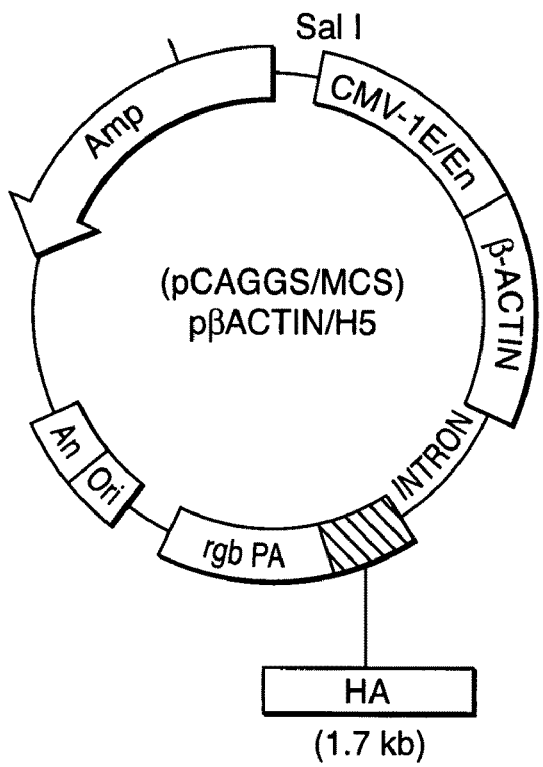
Figure 13B:
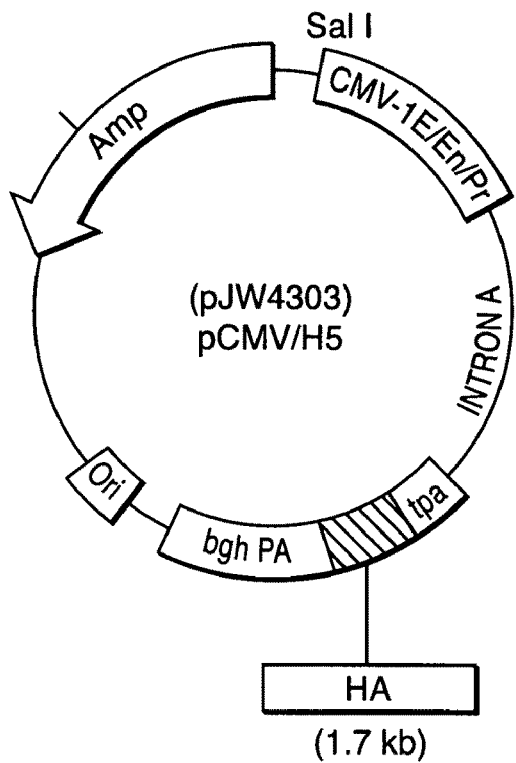
Figure 14A:
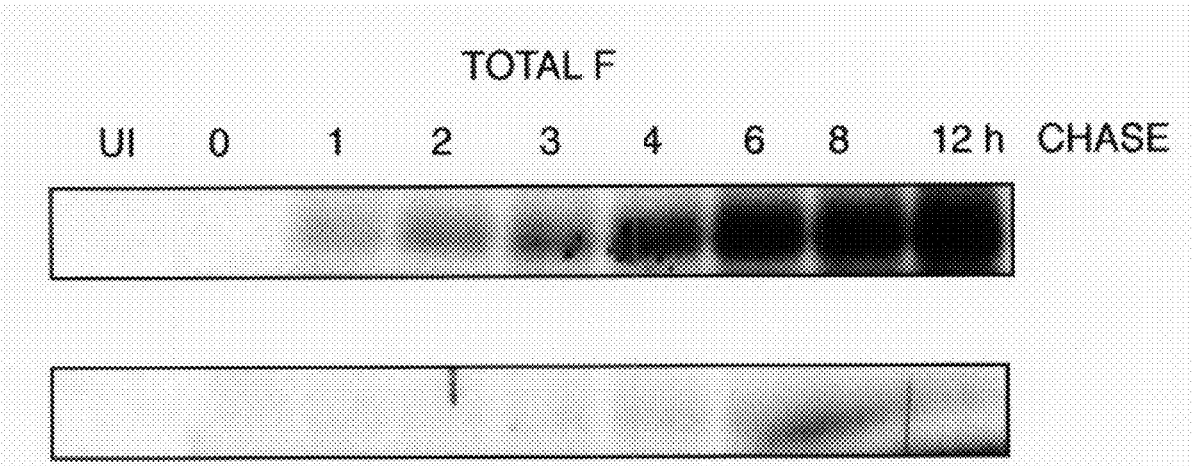
Figure 14B:
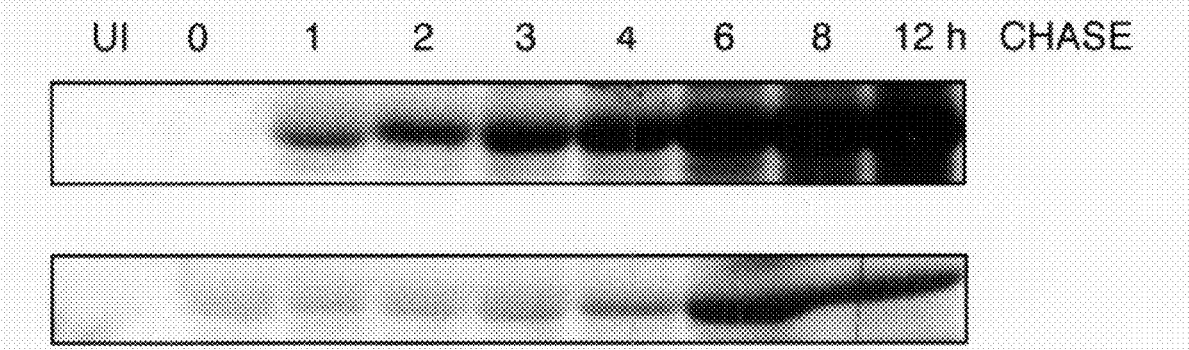
Figure 15A:
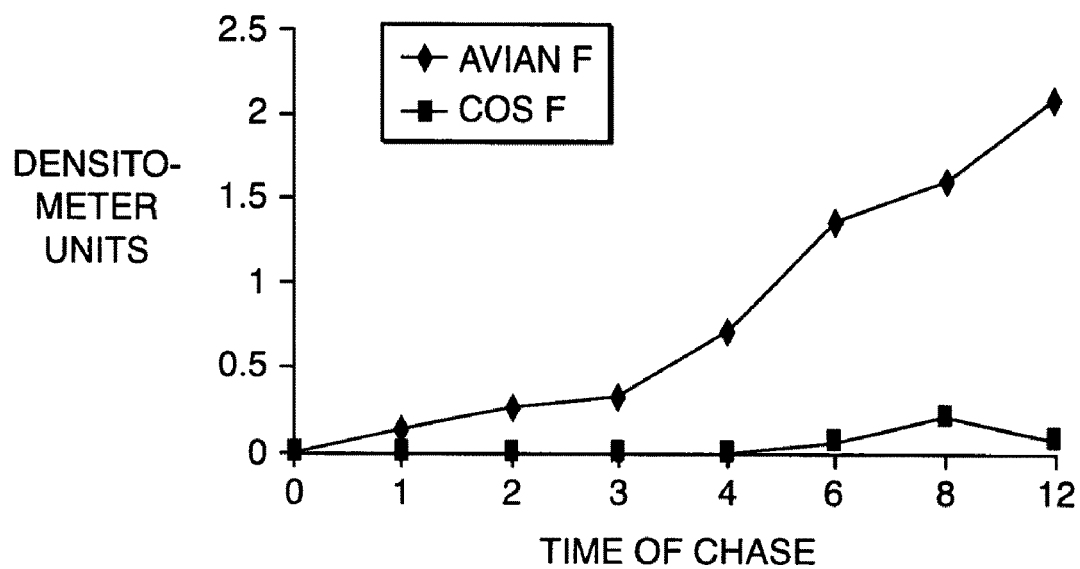
Figure 15B:
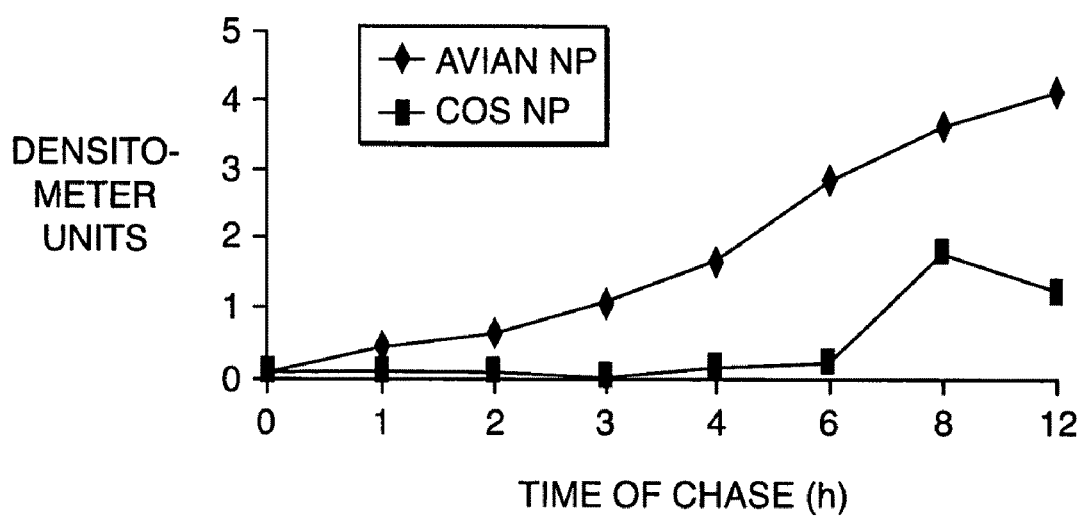
Figure 16A:
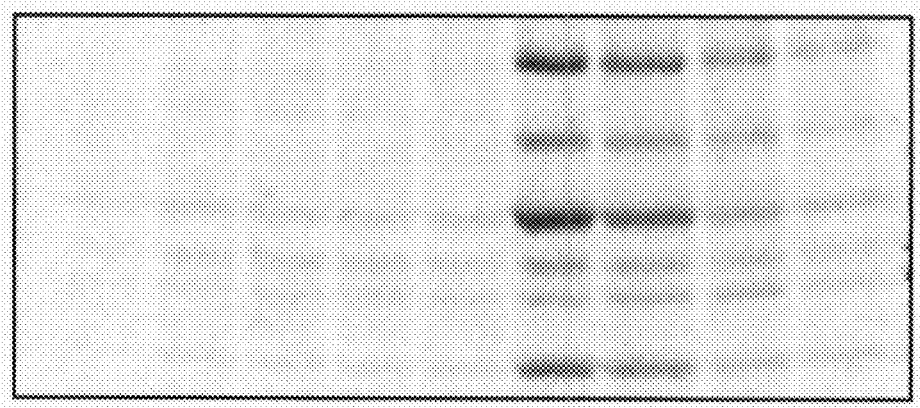
Figure 16B:
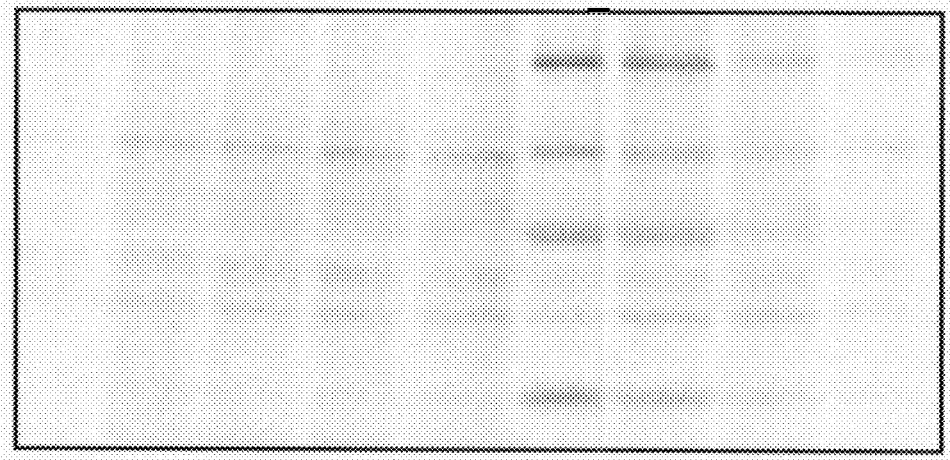

FIG. 4 presents exemplary data showing effects of expressing all combinations of three viral proteins on VLP release. Avian cells, transfected with all possible combinations of three NDV structural protein genes, were labeled in a pulse-chase protocol and particles in the supernatant were concentrated and floated into a sucrose gradient as in FIG. 1. The proteins in the cell extracts were immunoprecipitated with the antibody cocktail.

Panel A show labeled proteins in cell extracts at time of pulse (top) and chase (bottom).

Panel B shows the proteins present in each gradient fraction after immunoprecipitation of each fraction with an antibody cocktail for some of the viral protein combinations. Densities (g/cc) of the fractions are shown at the bottom.

Panel C shows quantification of the amounts of each protein in VLPs.

Panel D shows the efficiency of VLP release based on the percent of pulse labeled M protein remaining in the chase extracts.

Panel E show the relative amounts of M protein in the pulse extracts.

FIG. 5 presents exemplary data showing that dominant-negative mutants of CHMP3 and Vps4-E228Q, blocked release of M protein-containing particles.

Panel A, left, shows pulse labeled extracts of human 293T cells that were simultaneously transfected with pCAGGS-M (1.0 µg) and either pDsRed2-N1 vector (0.1, 0.5 and 1.0 µg) or pDsRed2-N1-CHMP3-RFP (0.1, 0.5 and 1.0 µg). Panel A, right, shows the VLPs released from these cells after an 8 hour chase.

Panel B, left, shows extracts of pulse labeled cells that were simultaneously transfected with pCAGGS-M and either pBJ5 vector or pBJ5-Vps4A-E228Q-Flag. Panel B, right, shows the VLPs released from these cells after an 8 hour chase. Transfected 293T cells in both A and B were labeled in a pulse-chase protocol as described in FIG. 1. Particles from supernatants were concentrated by centrifugation onto a sucrose pad as described in Example 4.

Panels C and D show percent VLPs released from cells transfected with pCAGGS-M and pDsRed2-N1-CHMP3 or pBJ5-Vps4A-E228Q relative to those released from cells transfected with pCAGGS-M and vector only.

Panels E and F show the quantitation of protein expression (pulse label) in the cell extracts. Identical results were obtained in two separate experiments.

FIG. 6 presents a schematic of one embodiment of the viral protein structure of a representative Paramyxovirus.

FIG. 7 presents a schematic of one embodiment of an infectious cycle caused by a representative Paramyxovirus.

FIG. 8 presents an amino acid sequence (SEQ ID NO:6) (Panel A) and a nucleotide sequence (SEQ ID NO:7) (Panel B) encoding a first Newcastle disease virus nucleocapsid protein (AB124608).

FIG. 9 presents an amino acid sequence (SEQ ID NO:8) (Panel A) and a nucleotide sequence (SEQ ID NO:9) (Panel B) encoding a first Newcastle disease virus hemagglutinin-neuraminidase protein (AY288990).

FIG. 10 presents a partial amino acid sequence (SEQ ID NO:10) (Panel A) and a partial nucleotide sequence (SEQ ID NO:11) (Panel B) encoding a first Newcastle disease virus fusion protein (Y18728).

FIG. 11 presents an amino acid sequence (SEQ ID NO:12) (Panel A) and a nucleotide sequence (SEQ ID NO:13) (Panel B) encoding a first Newcastle disease virus matrix protein (AY728363).

FIGS. 12A/B present of a nucleotide sequence (SEQ ID NO:14) for a baculovirus expression vector (DQ003705).

FIG. 13 presents two exemplary plasmids comprising a pCAGGS expression vector.

Panel A: pCAGGS/MCS; Panel B: pJW4303 (U.S. Pat. No. 5,916,879, herein incorporated by reference). It should be noted that the pCAGGS expression vector comprises a hybrid cytomegalovirus (CMV) beta actin promoter sequence.

FIG. 14 presents exemplary autoradiograph data showing viral protein accumulation resulting from a pulse-chase experiment that compares virus release from avian and COS-7 cells. Panel A: F protein. Panel B: NP protein.

FIG. 15 presents exemplary data showing the quantification pulse-chase autoradiography shown in FIG. 14. Panel A: F protein. Panel B: NP protein. Diamonds: Avian cells. Squares: COS-7 cells.

FIG. 16 presents exemplary autoradiograph data from purification of VLPs in sucrose gradients released from avian cells (Panel A) and from COS-7 cells (Panel B). Lanes 1-9 provide banding patterns in sucrose densities of 1.12-1.26, respectively. HN=hemagglutinin-neuraminidase protein. F₀=fusion protein; NP=nucleocapsid protein; M=matrix protein.

Figure 17A:
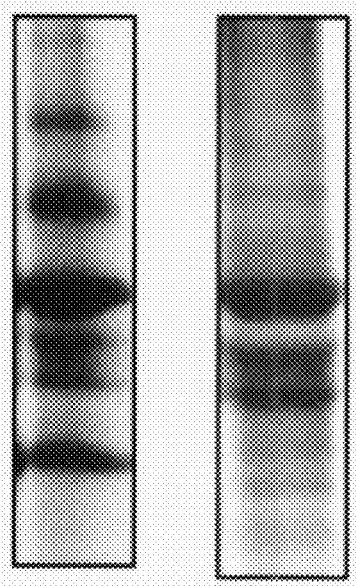
Figure 17B:
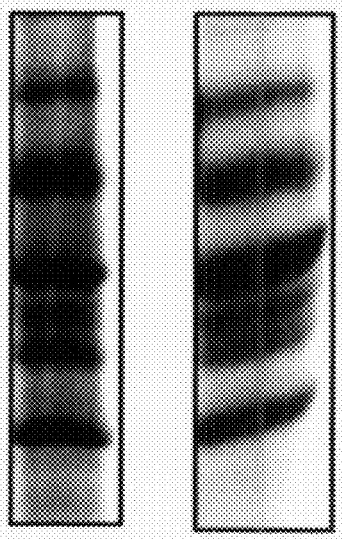

FIG. 17 presents an exemplary autoradiograph showing residual viral proteins in cell extract lysates following a pulse-chase experiment. Panel A: Avian cells. Panel B; COS-7 cells.

Figure 18A:
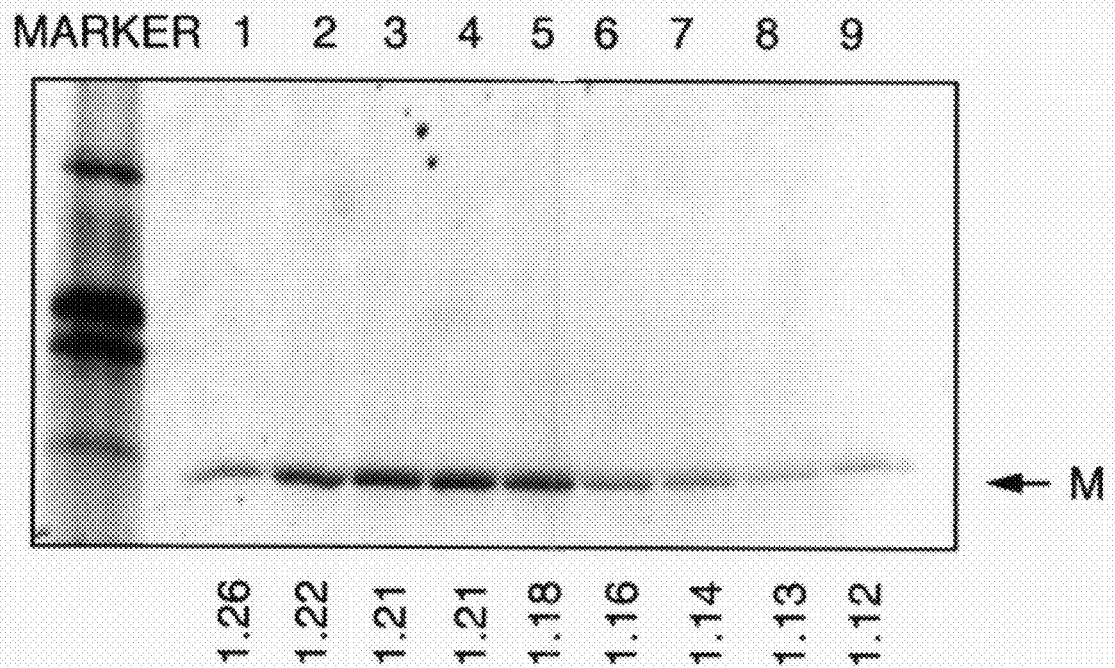
Figure 18B:
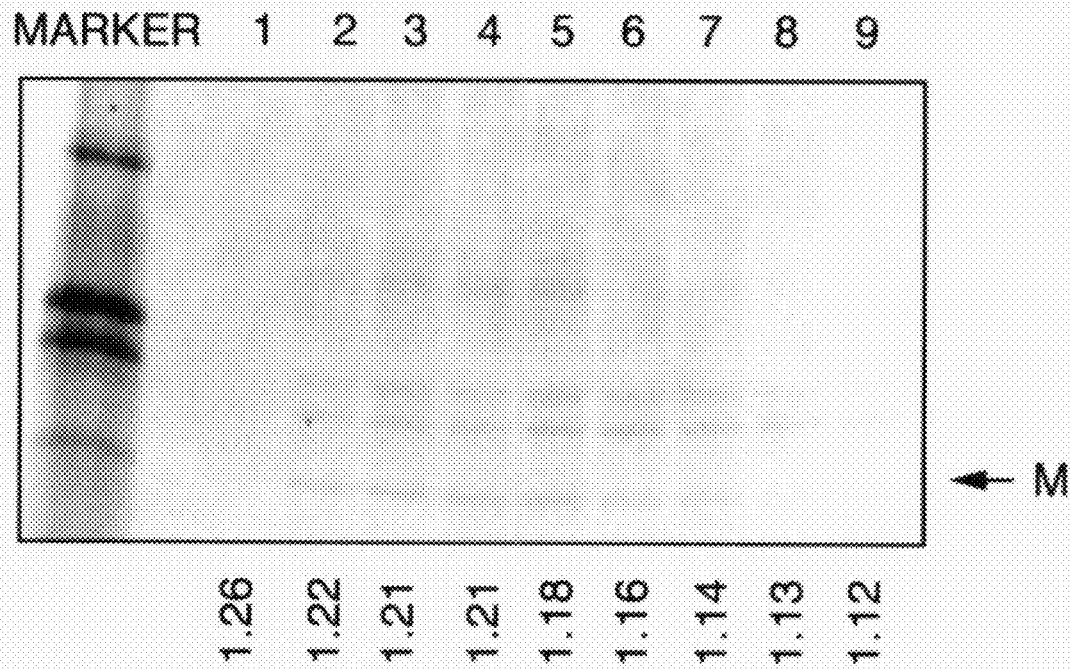

FIG. 18 presents exemplary data demonstrating the improved efficiency of M protein VLP release from avian (Panel A) versus COS-7 primate cells (Panel B) when transfected only by an M protein cDNA. Radioactively labeled M protein (M arrow) is shown in each sucrose gradient density fraction (i.e., Lanes 1-9; 1.12-1.26) is shown.

Figure 19A:
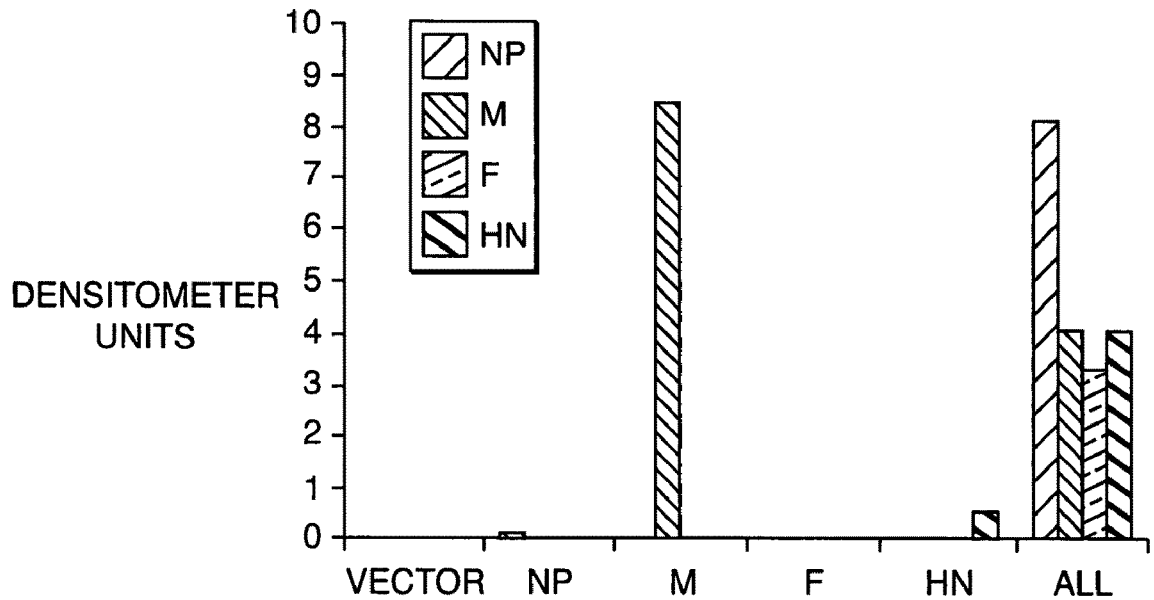
Figure 19B:
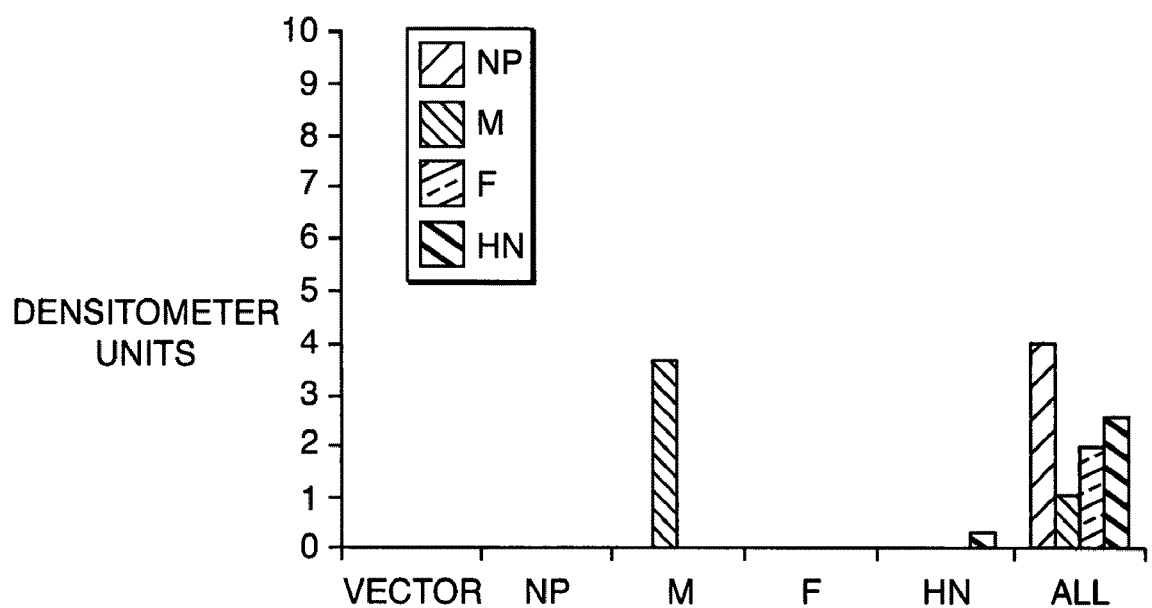

FIG. 19 presents exemplary densitometry data comparing a quantification of VLP particle release from avian (Panel A) and COS-7 primate cells (Panel B) after transfection by either NP, M, F-K115Q, and HN protein cDNAs individually, or transfected using a combination of NP, M, F-K115Q, and HN protein cDNAs, in combination (ALL).

FIG. 20 presents an amino acid sequence (SEQ ID NO:15) (Panel A) and a nucleotide sequence (SEQ ID NO:16) (Panel B) encoding a second Newcastle disease virus hemagglutinin-neuraminidase mRNA (M22110).

FIG. 21 presents an amino acid sequence (SEQ ID NO:17) (Panel A) and a nucleotide sequence (SEQ ID NO:18) (Panel B) encoding a third Newcastle disease virus hemagglutinin-neuraminidase protein (U37193).

FIG. 22 presents an amino acid sequence (SEQ ID NO:19) (Panel A) and a nucleotide sequence (SEQ ID NO:20) (Panel B) encoding a second Newcastle disease virus fusion protein (M21881).

FIG. 23 presents an amino acid sequence (SEQ ID NO:21) for a third Newcastle disease virus B1 fusion protein (AAG36978).

FIG. 24 presents an amino acid sequence (SEQ ID NO:22) (Panel A) and a nucleotide sequence (SEQ ID NO:23) (Panel B) encoding a second Newcastle disease virus nucleocapsid protein. (AF060483).

FIG. 25 presents an amino acid sequence (SEQ ID NO:24) (Panel A) and a nucleotide sequence (SEQ ID NO:25) (Panel B) encoding a second Newcastle disease virus matrix protein (M16622).

FIG. 26 presents one embodiment of an amino acid sequence (SEQ ID NO:26) (Panel A) and a nucleotide sequence (SEQ ID NO:27) (Panel B) encoding a third Newcastle disease virus matrix protein (U25828).

FIGS. 27A-27D present a nucleotide sequence (SEQ ID NO:28) of a Newcastle disease virus B1 complete genome (AF309418).

Figure 28:
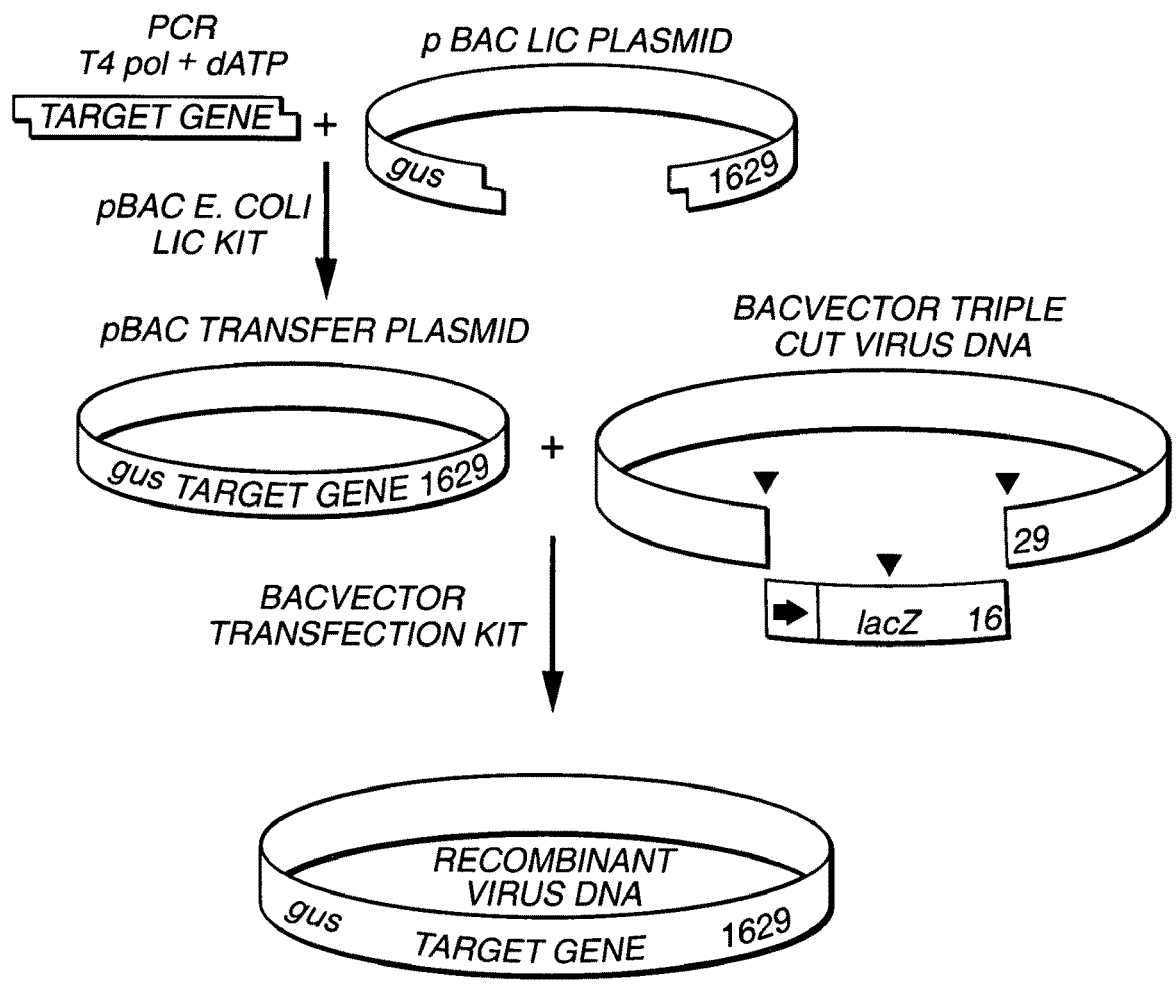

FIG. 28 illustrates one method of constructing baculovirus recombinant DNA.

FIG. 29 (SEQ ID NOS:96-106) illustrates one ligation-independent cloning technique to produce a baculovirus recombinant DNA containing His-tag and S-tag sequence tags.

Figure 30:
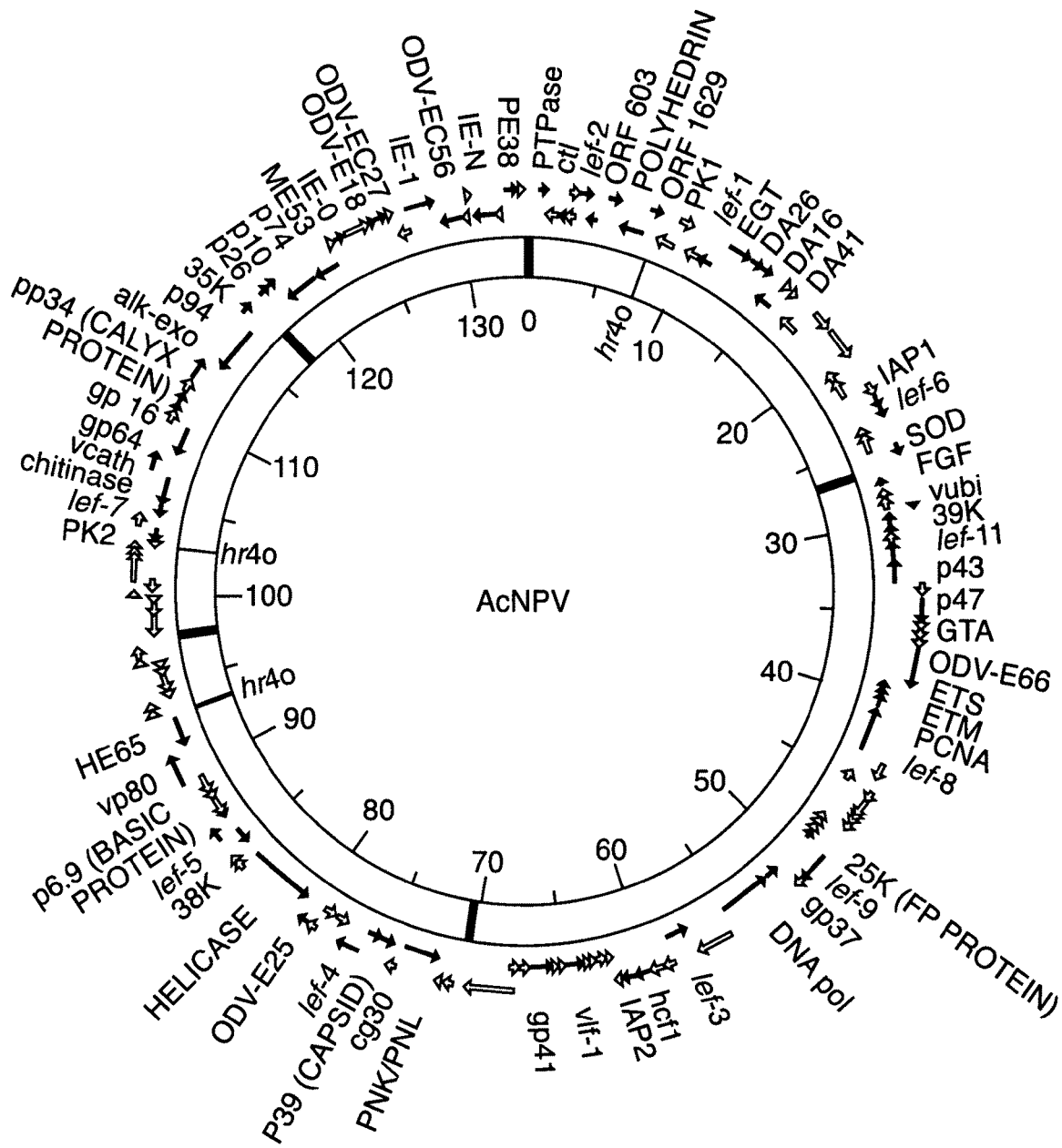

FIG. 30 depicts a circular map of a wild-type AcNPV C6 genome containing 154 putative open reading frames. Genes marked with solid arrows are known and reported in protein sequence databases. hr=AcNPV repetitive homologous region positions.

Figure 31:
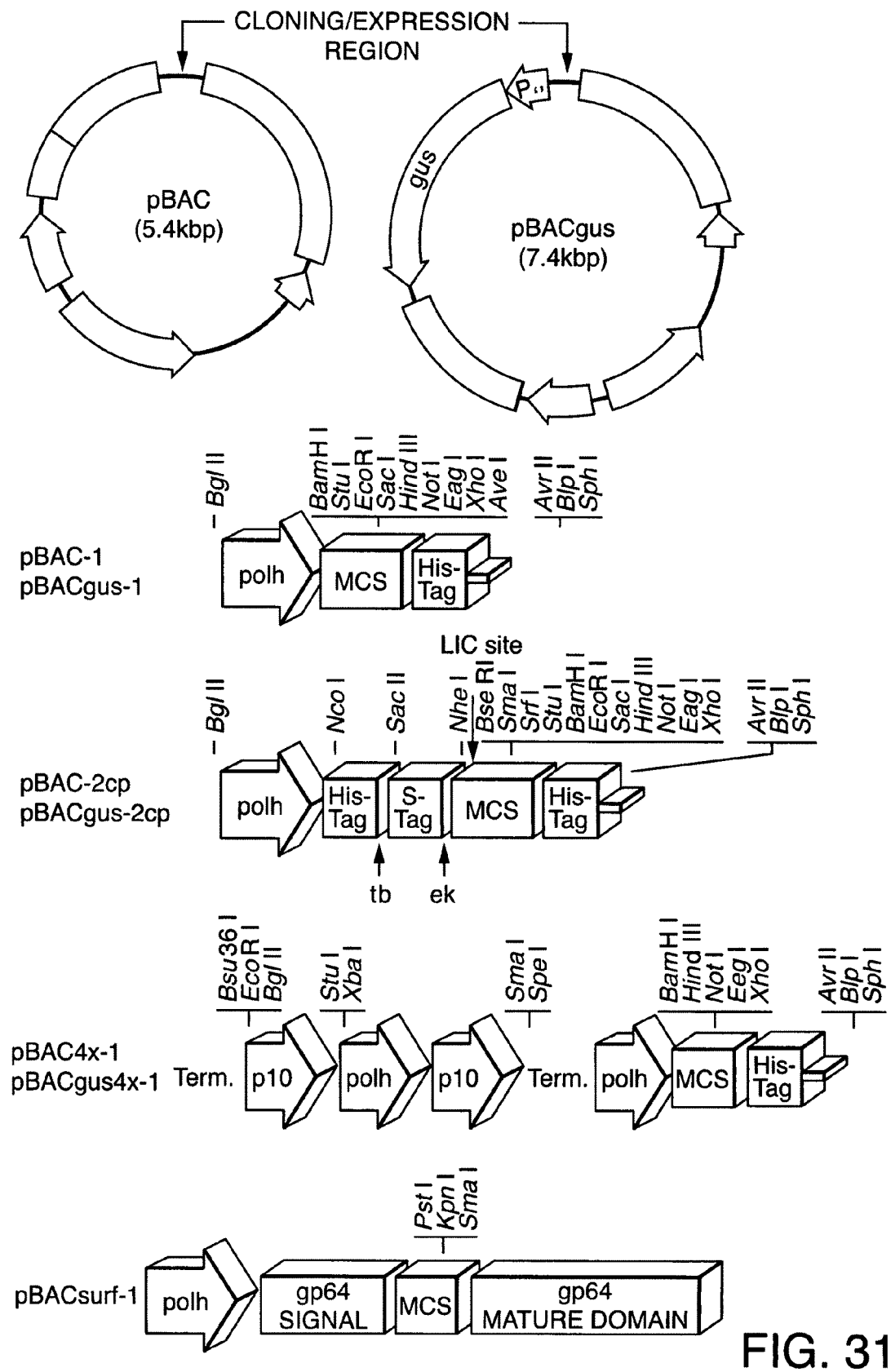

FIG. 31 illustrates seven (7) embodiments of a baculovirus transfer plasmid (pBAC).

FIG. 32 presents one embodiment of an amino acid sequence (SEQ ID NO:29) (Panel A) and a nucleotide sequence (SEQ ID NO:30) (Panel B) encoding a first measles virus hemagglutinin protein (AY249267).

FIG. 33 presents one embodiment of an amino acid sequence (SEQ ID NO:31) (Panel A) and a nucleotide sequence (SEQ ID NO:32) (Panel B) encoding a second measles virus hemagglutinin protein (AY249269).

FIG. 34 presents one embodiment of an amino acid sequence (SEQ ID NO:33) (Panel A) and a nucleotide sequence (SEQ ID NO:34) (Panel B) encoding a third measles virus hemagglutinin protein (DQ011611).

FIG. 35 presents one embodiment of an amino acid sequence (SEQ ID NO:35) (Panel A) and a nucleotide sequence (SEQ ID NO:36) (Panel B) encoding a first measles virus fusion protein (AJ133108).

FIG. 36 presents one embodiment of an amino acid sequence (SEQ ID NO:37) (Panel A) and a nucleotide sequence (SEQ ID NO:38) (Panel B) encoding a second measles virus fusion protein (X05597).

FIG. 37 presents one embodiment of an amino acid sequence (SEQ ID NO:39) (Panel A) and a nucleotide sequence (SEQ ID NO:40) (Panel B) encoding a third measles virus fusion protein (Y17840).

FIG. 38 presents one embodiment of an amino acid sequence (SEQ ID NO:41) (Panel A) and a nucleotide sequence (SEQ ID NO:42) (Panel B) encoding a first measles virus nucleocapsid protein (M89921).

FIG. 39 presents one embodiment of an amino acid sequence (SEQ ID NO:43) (Panel A) and a nucleotide sequence (SEQ ID NO:44) (Panel B) encoding a second measles virus nucleocapsid protein (AF171232).

FIG. 40 presents one embodiment of an amino acid sequence (SEQ ID NO:45) (Panel A) and a nucleotide sequence (SEQ ID NO:46) (Panel B) encoding a third measles virus nucleocapsid protein (X01999).

FIG. 41 presents one embodiment of an amino acid sequence (SEQ ID NO:47) (Panel A) and a nucleotide sequence (SEQ ID NO:48) (Panel B) encoding a first measles virus matrix protein (D12682).

FIG. 42 presents one embodiment of an amino acid sequence (SEQ ID NO:49) (Panel A) and a nucleotide sequence (SEQ ID NO:50) (Panel B) encoding a second measles virus matrix protein (D12683).

FIG. 43 presents one embodiment of an amino acid sequence (SEQ ID NO:51) (Panel A) and a nucleotide sequence (SEQ ID NO:52) (Panel B) encoding a third measles virus matrix protein (AY124779).

FIG. 44 presents one embodiment of an amino acid sequence (SEQ ID NO:53) (Panel A) and a nucleotide sequence (SEQ ID NO:54) (Panel B) encoding a first respiratory syncytial virus G protein (i.e., for example, a glycoprotein G protein) (U92104).

FIG. 45 presents one embodiment of an amino acid sequence (SEQ ID NO:55) (Panel A) and a nucleotide sequence (SEQ ID NO:56) (Panel B) encoding a second respiratory syncytial virus G protein (AY333361).

FIG. 46 presents one embodiment of an amino acid sequence (SEQ ID NO:57) (Panel A) and a nucleotide sequence (SEQ ID NO:58) (Panel B) encoding a third respiratory syncytial virus G protein (AB117522).

FIG. 47 presents one embodiment of an amino acid sequence (SEQ ID NO:59) (Panel A) and a nucleotide sequence (SEQ ID NO:60) (Panel B) encoding a first respiratory syncytial virus fusion protein (AY198177).

FIG. 48 presents one embodiment of an amino acid sequence (SEQ ID NO:61) (Panel A) and a nucleotide sequence (SEQ ID NO:62) (Panel B) encoding a second respiratory syncytial virus fusion protein (Z26524).

FIG. 49 presents one embodiment of an amino acid sequence (SEQ ID NO:63) (Panel A) and a nucleotide sequence (SEQ ID NO:64) (Panel B) encoding a third respiratory syncytial virus fusion protein (D00850).

FIG. 50 presents one embodiment of an amino acid sequence (SEQ ID NO:65) (Panel A) and a nucleotide sequence (SEQ ID NO:66) (Panel B) encoding a first respiratory syncytial virus matrix protein (U02470).

FIG. 51 presents one embodiment of an amino acid sequence (SEQ ID NO:67) (Panel A) and a nucleotide sequence (SEQ ID NO:68) (Panel B) encoding a second respiratory syncytial virus matrix protein (U02510).

FIG. 52 presents one embodiment of an amino acid sequence (SEQ ID NO:69) (Panel A) and a nucleotide sequence (SEQ ID NO:70) (Panel B) encoding a first respiratory syncytial virus nucleocapsid protein (U07233).

FIG. 53 presents one embodiment of an amino acid sequence (SEQ ID NO:71) (Panel A) and a nucleotide sequence (SEQ ID NO:72) (Panel B) encoding a second respiratory syncytial virus nucleocapsid protein (X00001).

FIG. 54 presents one embodiment of an amino acid sequence (SEQ ID NO:73) (Panel A) and a nucleotide sequence (SEQ ID NO:74) (Panel B) encoding a third respiratory syncytial virus nucleocapsid protein (S40504).

FIG. 55 presents one embodiment of an amino acid sequence (SEQ ID NO:75) (Panel A) and a nucleotide sequence (SEQ ID NO:76) (Panel B) encoding a first parainfluenza virus 3 nucleocapsid protein (D10025).

FIG. 56 presents one embodiment of an amino acid sequence (SEQ ID NO:77) (Panel A) and a nucleotide sequence (SEQ ID NO:78) (Panel B) encoding a first parainfluenza virus 3 fusion protein (D00016).

FIG. 57 presents one embodiment of an amino acid sequence (SEQ ID NO:79) (Panel A) and a nucleotide sequence (SEQ ID NO:80) (Panel B) encoding a second parainfluenza virus 3 fusion protein (AF394241).

FIG. 58 presents one embodiment of an amino acid sequence (SEQ ID NO:81) (Panel A) and a nucleotide sequence (SEQ ID NO:82) (Panel B) encoding a first parainfluenza virus 3 matrix protein (D00130).

FIG. 59 presents one embodiment of an amino acid sequence (SEQ ID NO:83) (Panel A) and a nucleotide sequence (SEQ ID NO:84) (Panel B) encoding a first parainfluenza virus 3 hemagglutinin-neuraminidase protein (AB189960).

FIG. 60 presents one embodiment of an amino acid sequence (SEQ ID NO:85) (Panel A) and a nucleotide sequence (SEQ ID NO:86) (Panel B) encoding a second parainfluenza virus 3 hemagglutinin-neuraminidase protein (AB189961).

FIG. 61 presents one embodiment of an amino acid sequence (SEQ ID NO:87) (Panel A) and a nucleotide sequence (SEQ ID NO:88) (Panel B) encoding a third parainfluenza virus 3 hemagglutinin-neuraminidase protein (L25350).

Figure 62:
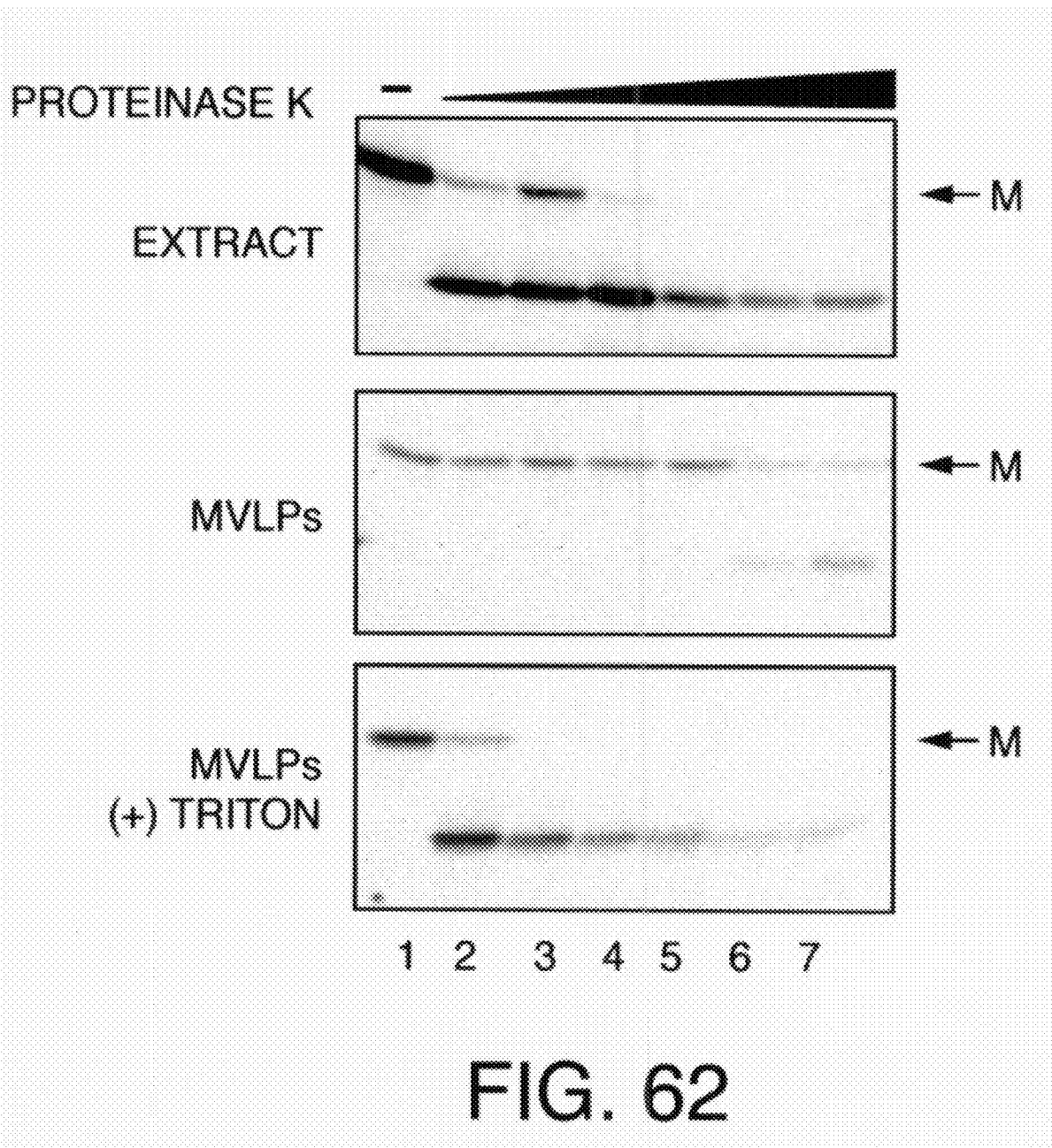

FIG. 62 presents exemplary data showing that M proteins may be encased in membranous particles. Avian cells were transfected with pCAGGS-M and radioactively labeled VLPs were isolated and purified. Extract (upper panel) and VLPs (middle panel) were treated with different concentrations (0.25, 0.5, 1, 5, 10, and 20 µg/ml; lanes 2 to 7 respectively) of Proteinase K for 30 minutes on ice. In parallel, VLPs were incubated in 1% Triton X-100 prior to Proteinase K treatment (bottom panel). After incubation with protease, reactions were stopped by adding 0.1 mM PMSF. M proteins were then immunoprecipitated.

Figure 63:
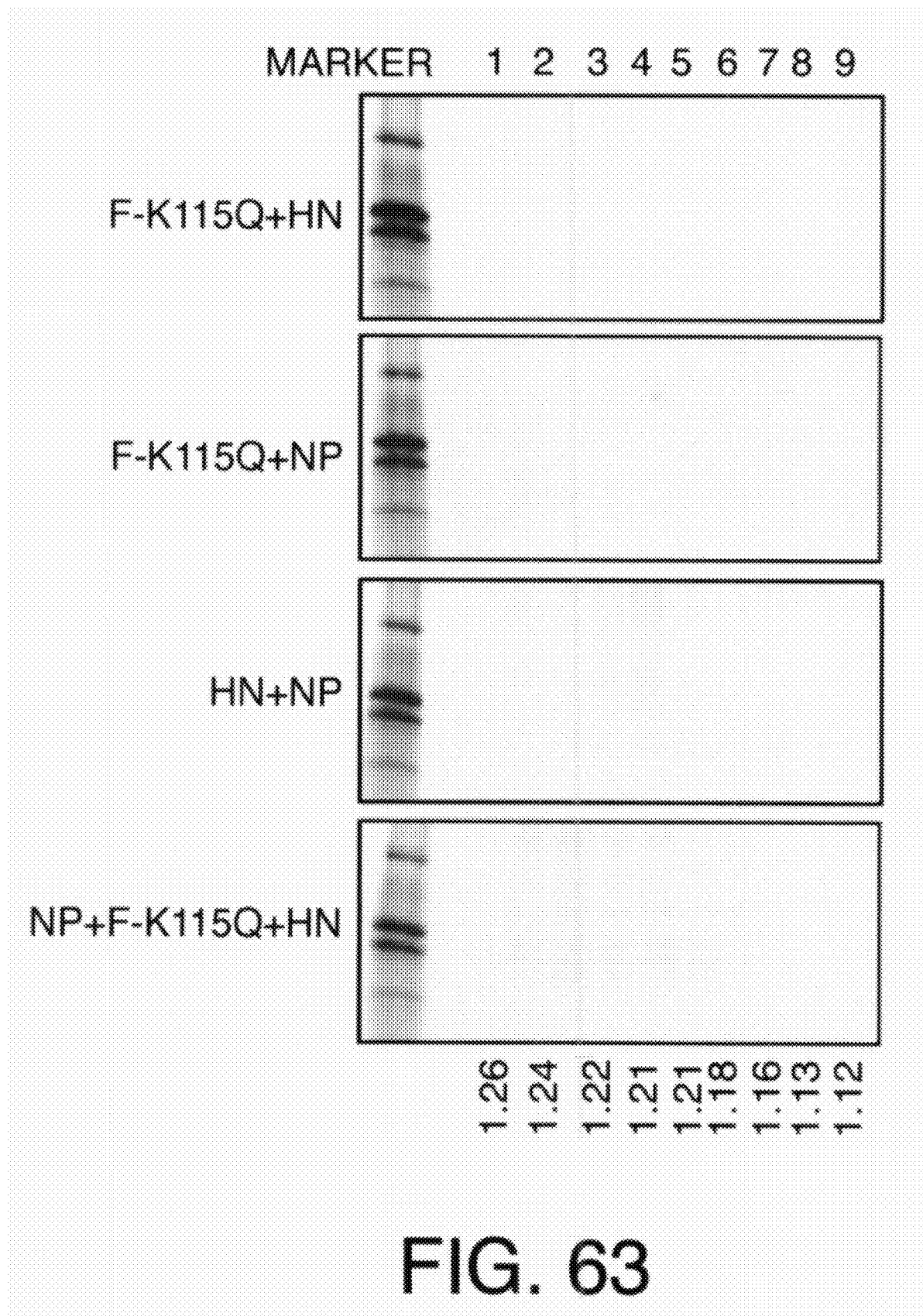

FIG. 63 presents exemplary data showing that M protein is required for VLP release. Avian cells were transfected with all possible combinations of cDNAs in pCAGGS vector encoding NP, F, and HN proteins in the absence of M cDNA (F-K115Q+HN, F-K115Q+NP, HN+NP, NP+F-K115Q+HN). Particles in cell supernatants were then purified. Panels show proteins present in each gradient fraction. Radioactively labeled infected cell extract was used as marker. Densities of fractions are shown at the bottom (g/cc).

Figures 64A, 64B:
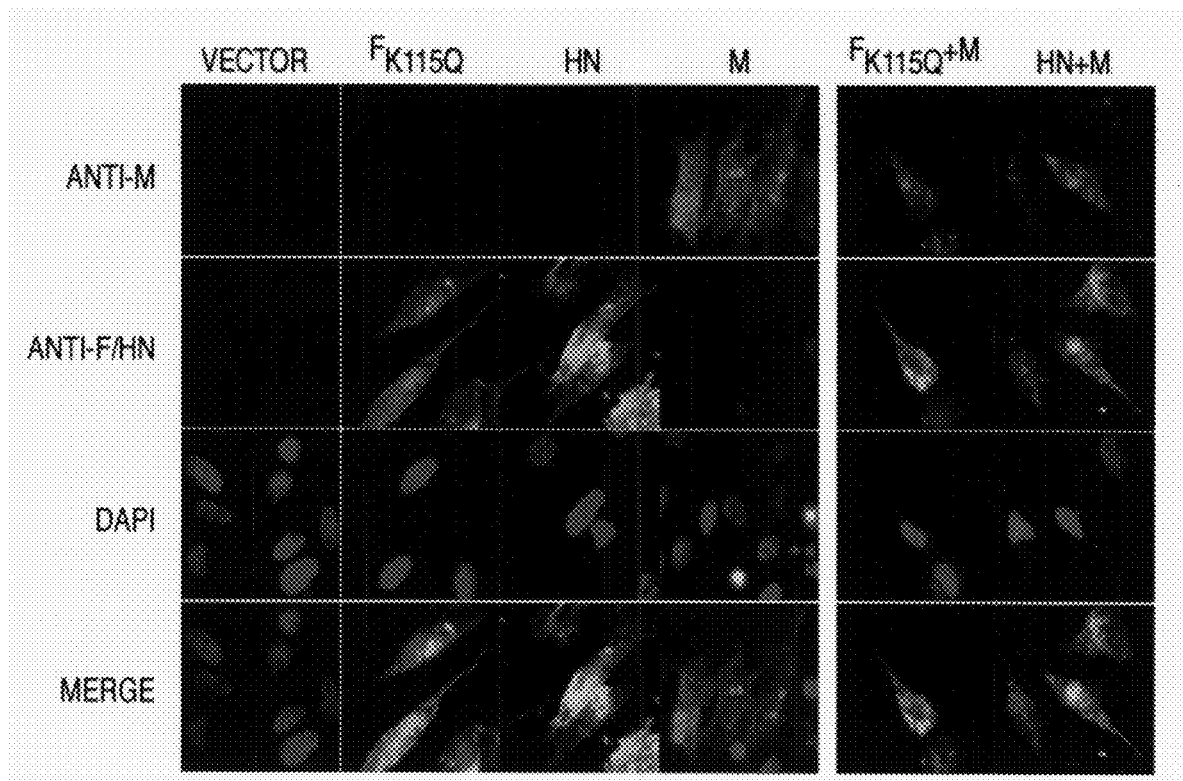
Figures 64C, 64D:
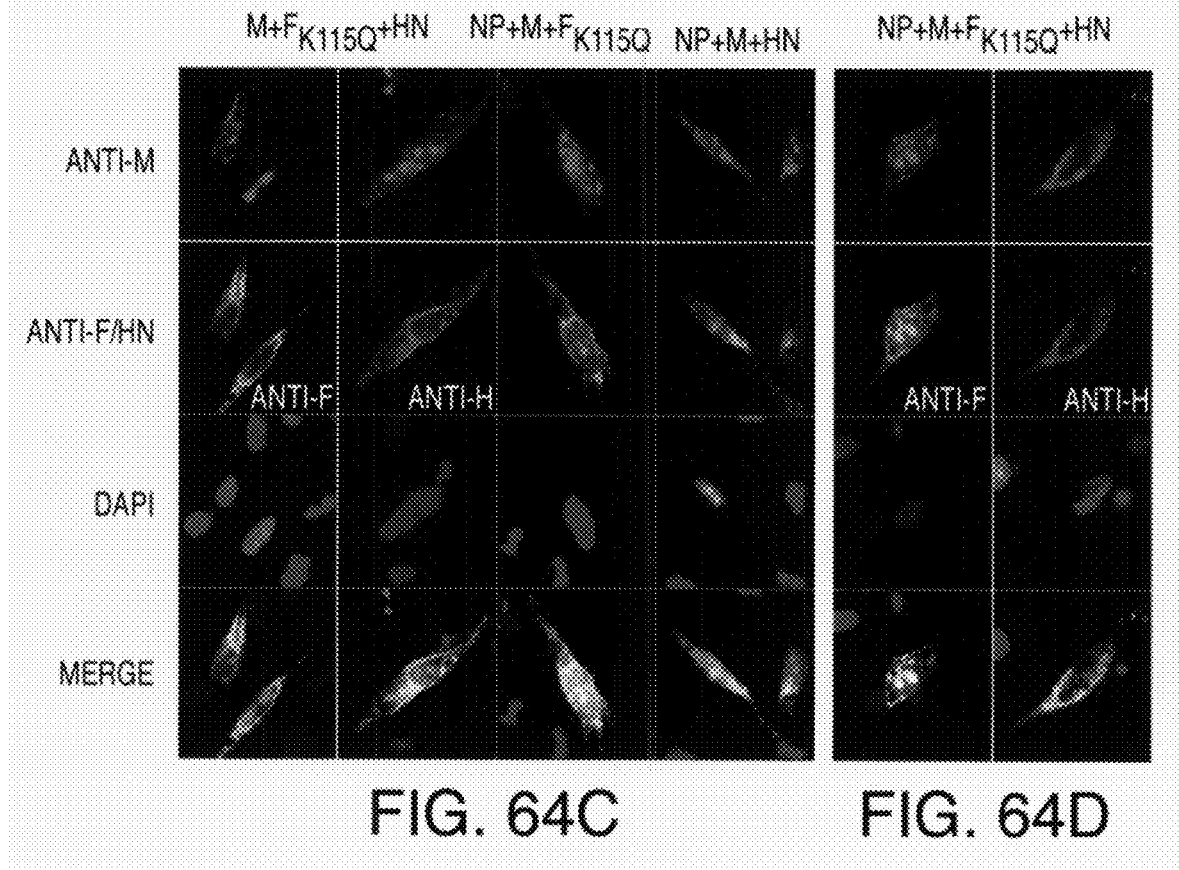

FIG. 64 presents exemplary data showing co-localization of M protein with F and HN proteins. The cell surface localization of NDV F and HN proteins and the cellular localization of M proteins were analyzed by immunofluorescence microscopy. Avian cells were either transfected individually (A) or with F-K115Q+M or HN+M (B), with NP+M+F-K115Q, NP+M+HN or M+F-K115Q+HN (C) and all 4 cDNAs (D). Nuclei were stained with DAPI (blue) 40 h post-transfection. Intact transfected cells were stained with rabbit anti-F protein antibodies or anti-HN protein antibodies as indicated in the panels. Cells were permeabilized with 0.05% Triton X-100 prior to incubation with anti-M protein antibody. Secondary antibodies were anti-rabbit Alexa 488 conjugate (green) and anti-mouse Alexa 568 conjugate (red). Images were merged using Adobe Photoshop.

FIG. 65 presents exemplary data showing co-immunoprecipitation of viral proteins in VLPs. Radioactively labeled VLPs generated from cells expressing NP+M+F-K115Q+HN (A), M+F-K115Q+HN (B), NP+M+F-K115Q (C) and NP+M+HN (D) were lysed in TNE buffer with 1% Triton X-100. Lysed VLPs were then incubated with excess amounts of cocktail of anti-F protein antibodies (anti-HR1, anti-HR2, anti-Ftail, anti-F2-96 and monoclonal anti-F (G5)), anti-HN protein antibodies (mix of monoclonal antibodies), anti-M protein monoclonal antibody or cocktail of NDV-specific antibodies for overnight at 4° C. No antibody as well as pre-immune sera were used as negative controls. Immune complexes were precipitated with prewashed Pansorbin A for at least 2 h at 4° C. with constant mixing. Samples were washed three times in cold TNE with 0.5% Triton X-100. All steps of co-immunoprecipitation were accomplished at 4° C. Proteins were resolved by SDS-PAGE gel electrophoresis. Results show one of three independent experiments, all with identical results.

Figure 66:
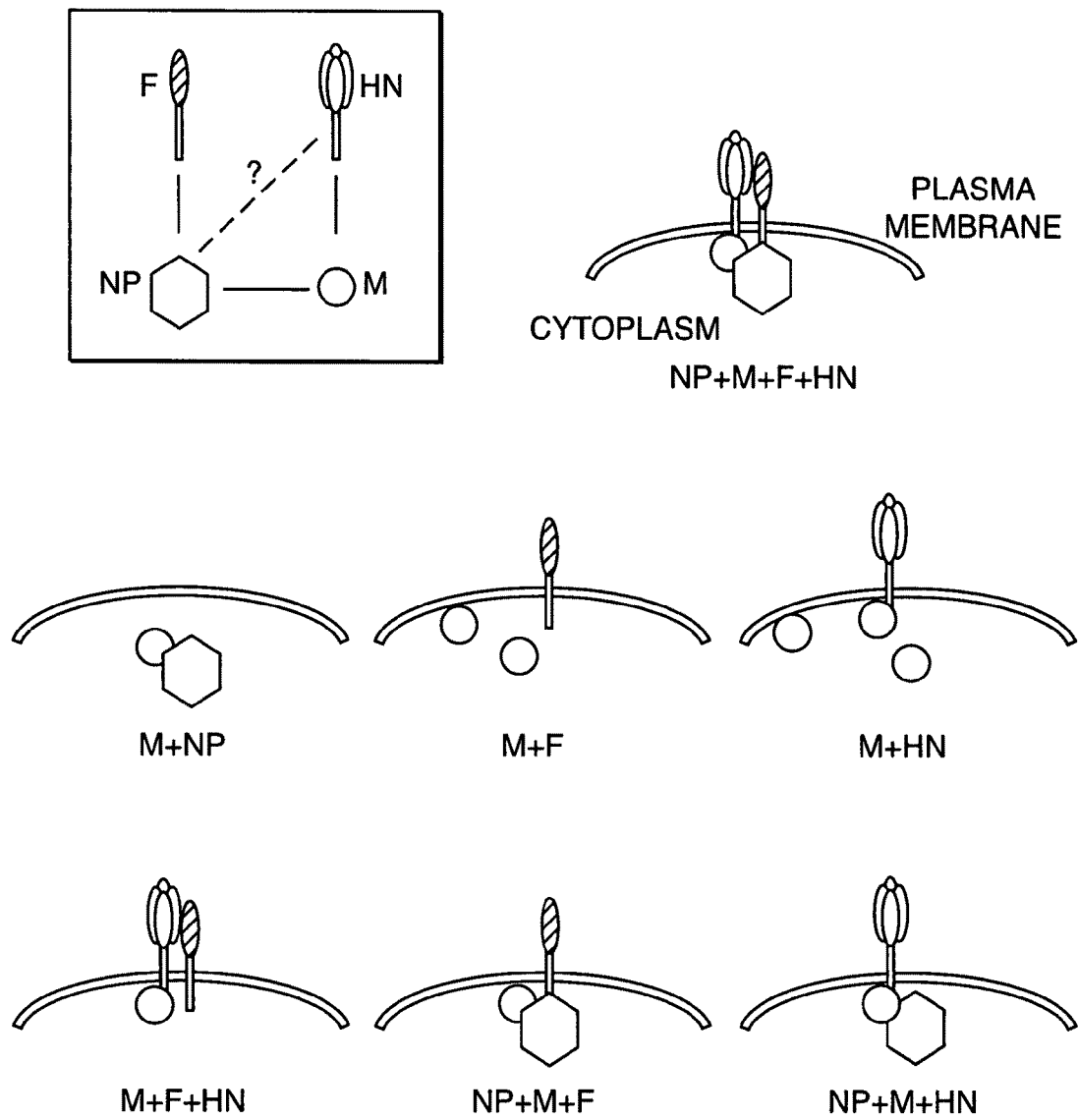

FIG. 66 presents exemplary data showing protein-protein interactions in VLPs. Inset: Various embodiments of viral protein-protein interactions detected by co-immunoprecipitation of proteins in VLPs. Also shown are illustrative potential interactions that may result in assembly of VLPs formed by co-expression of all combinations of NP, F, and HN proteins with M protein.

Figure 67A:
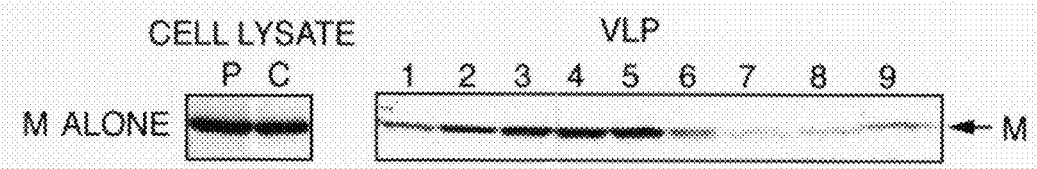
Figure 67B:
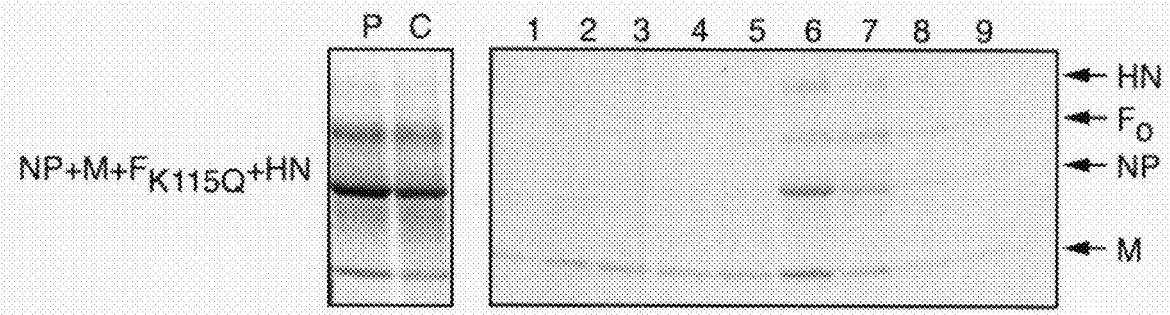
Figure 68A:
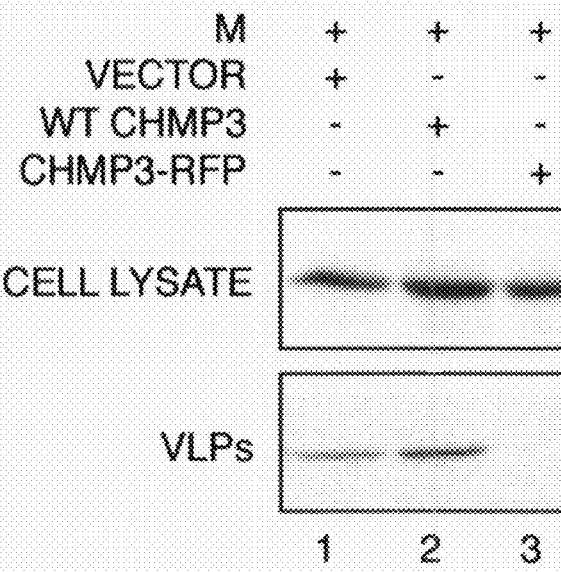
Figure 68B:
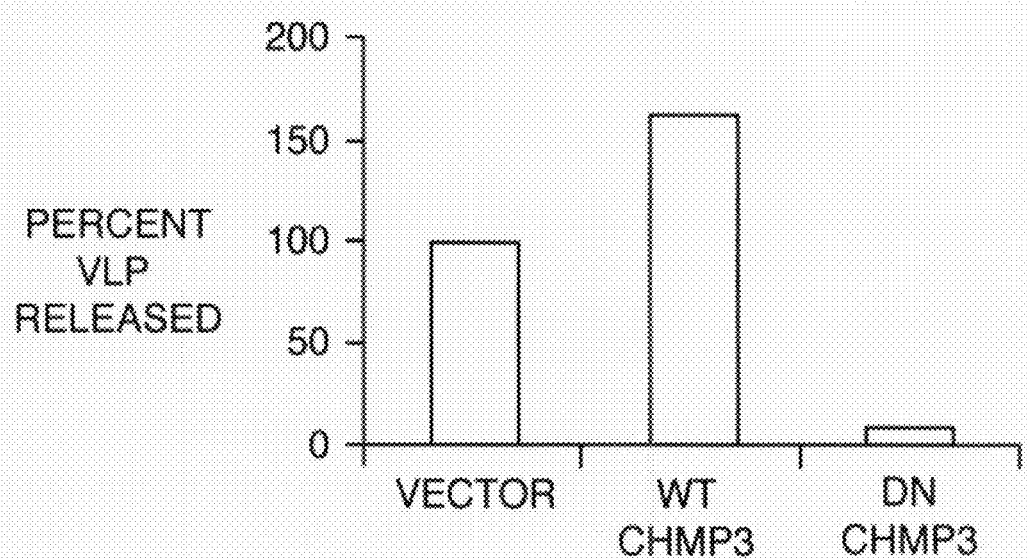
Figure 68C:
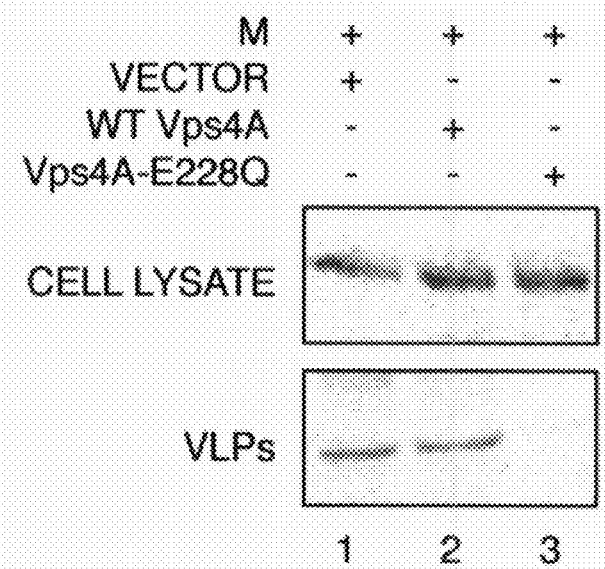
Figure 68D:
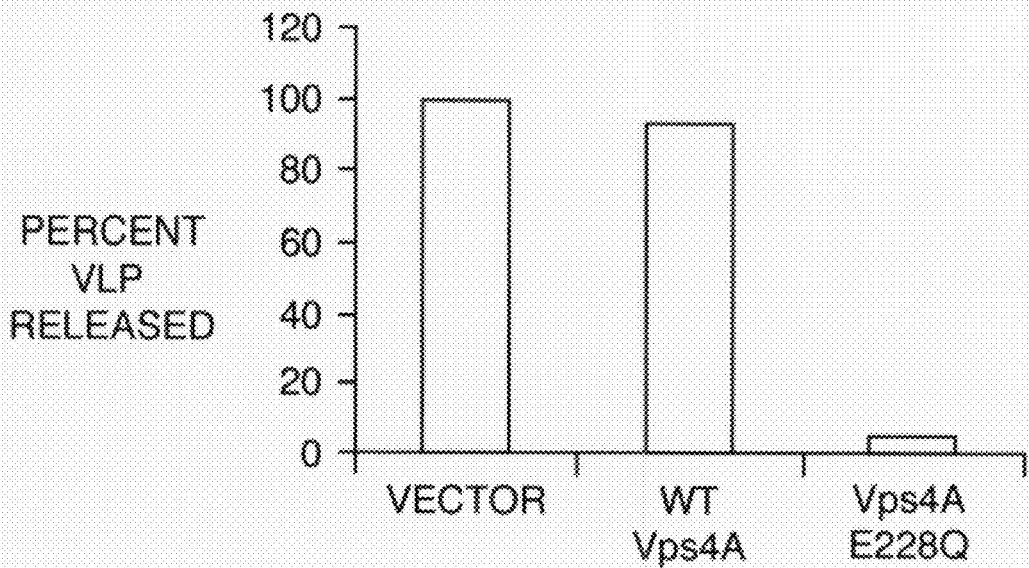
Figures 68E, 68F:
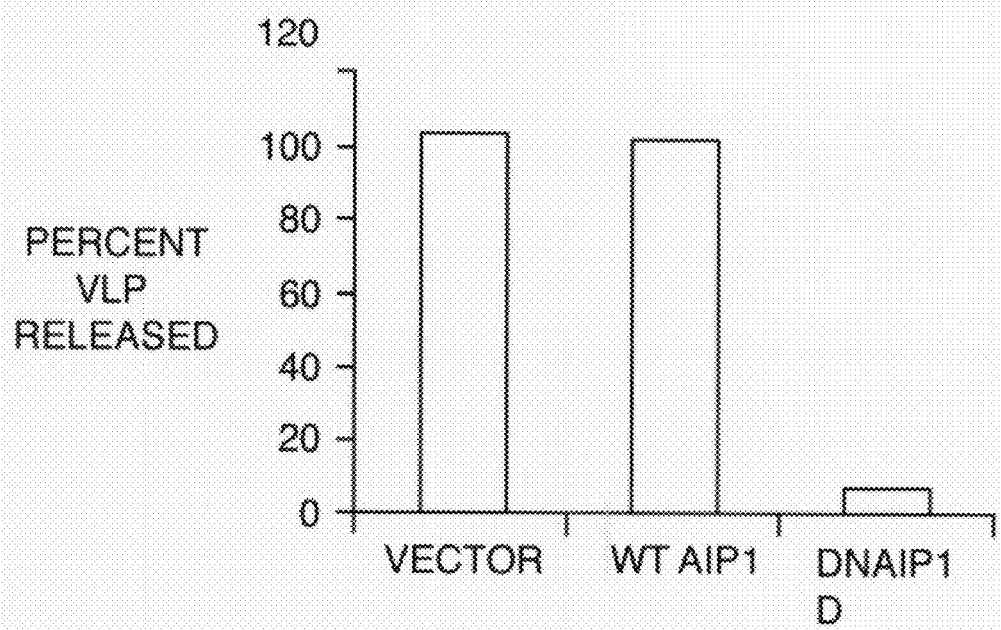
Figure 69A:
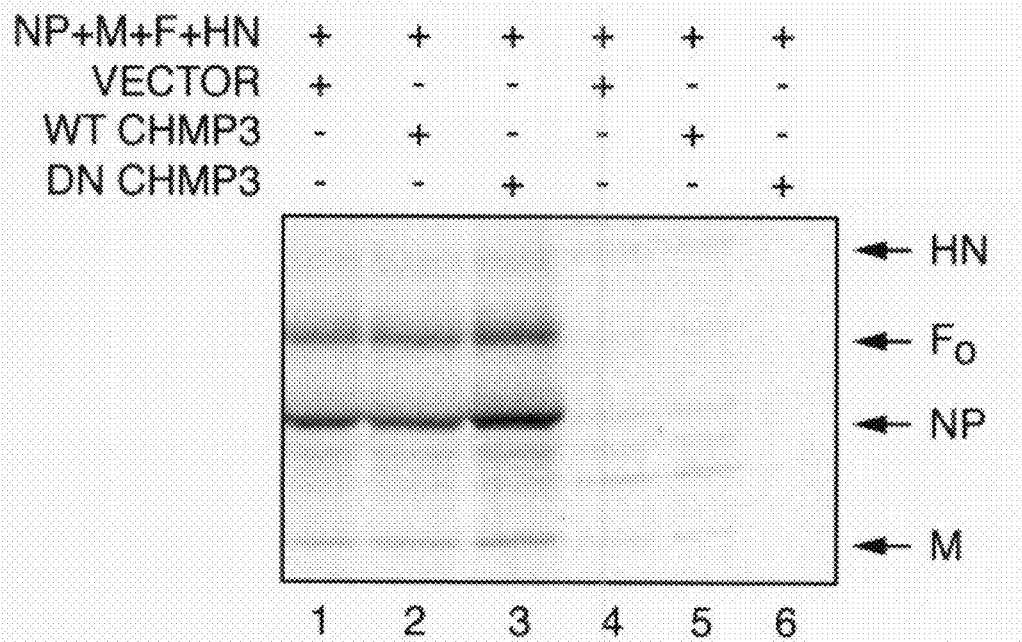
Figure 69B:
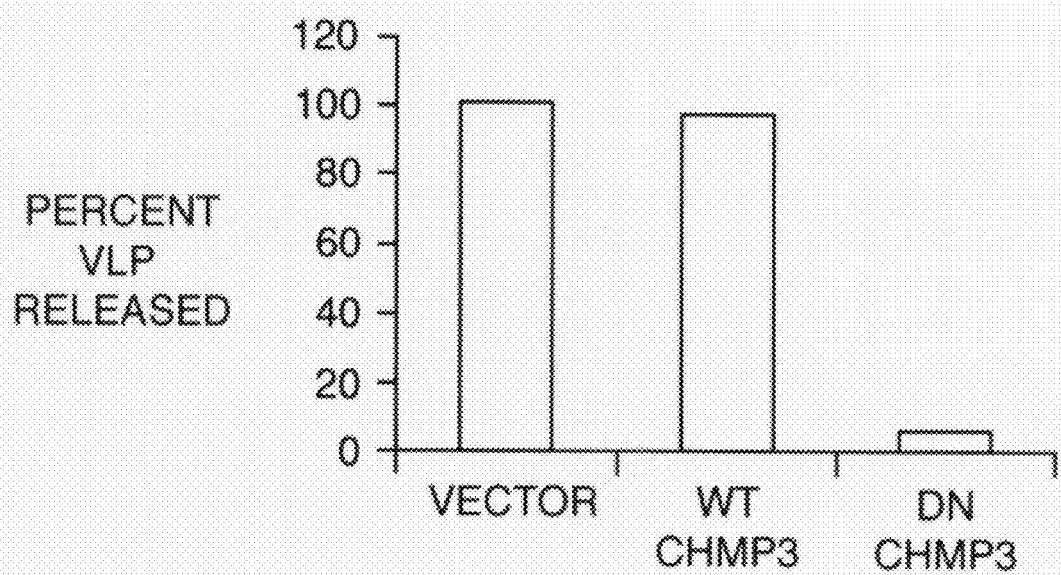
Figure 69C:
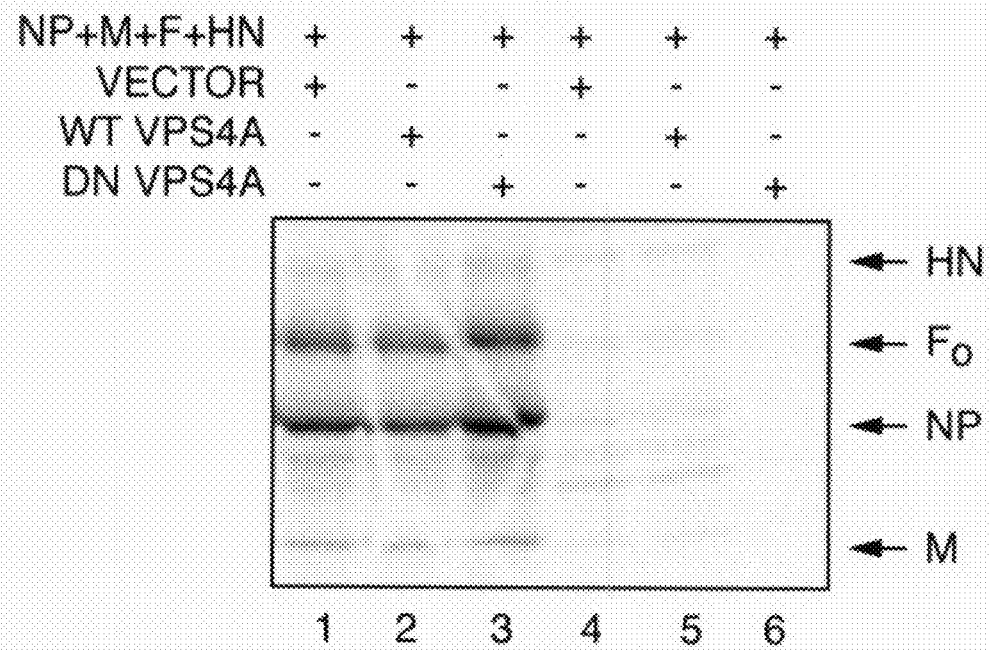
Figure 69D:
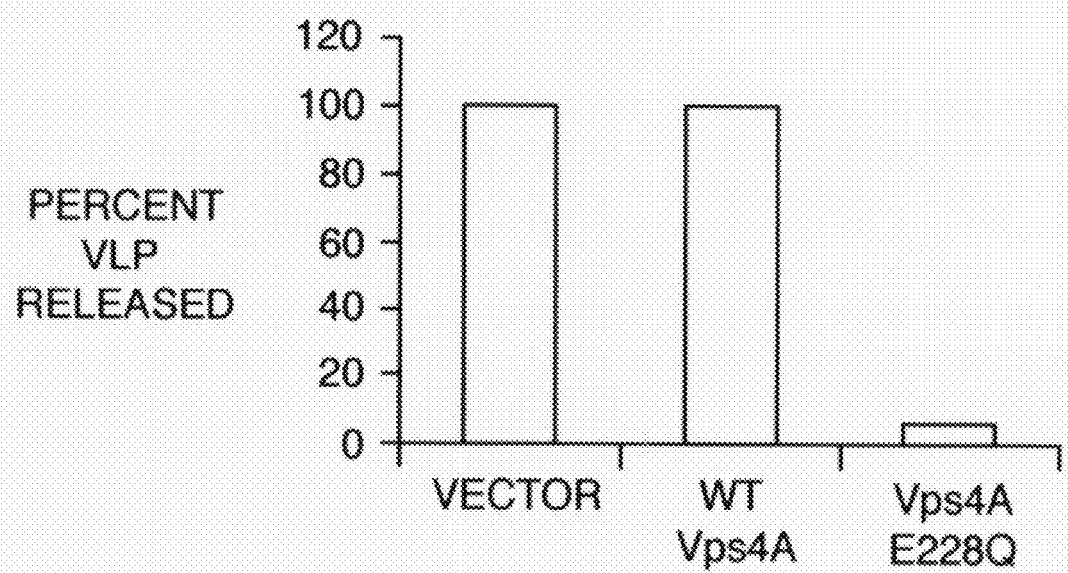
Figure 69E:
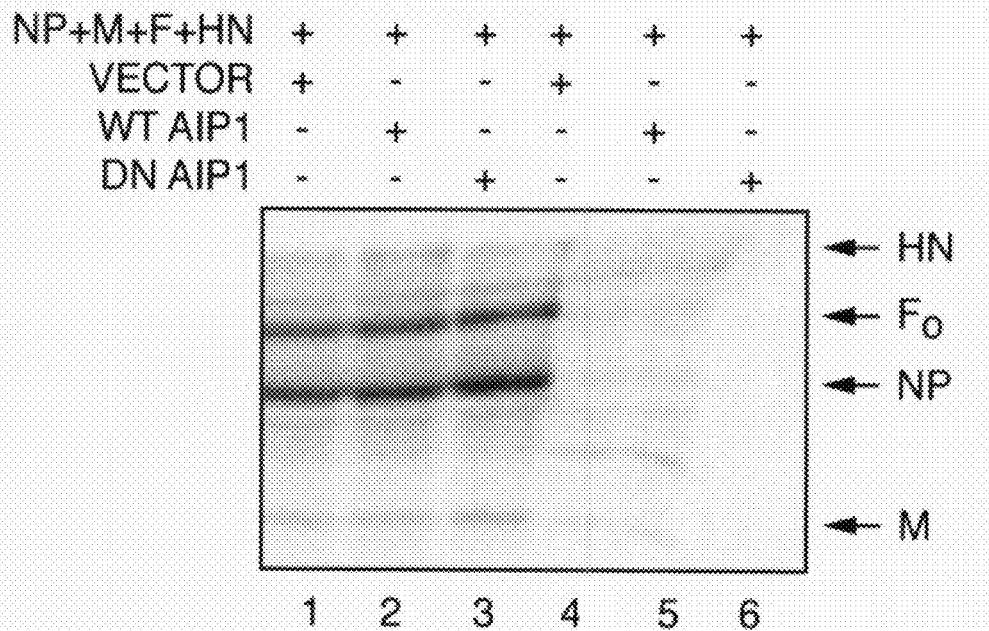
Figure 69F:
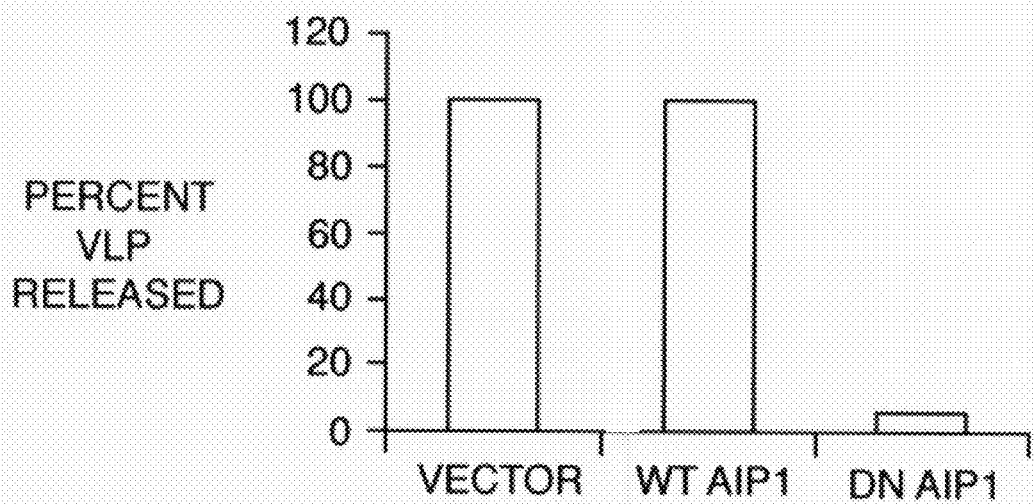
Figure 70A:
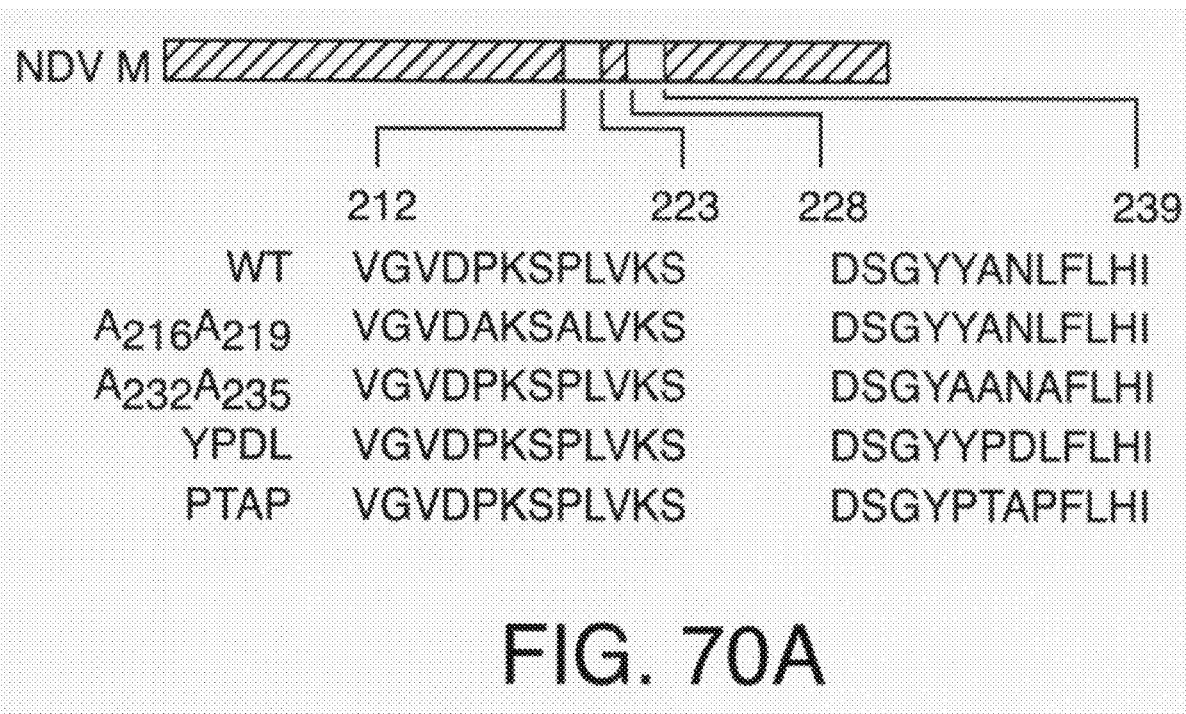
Figure 70B:
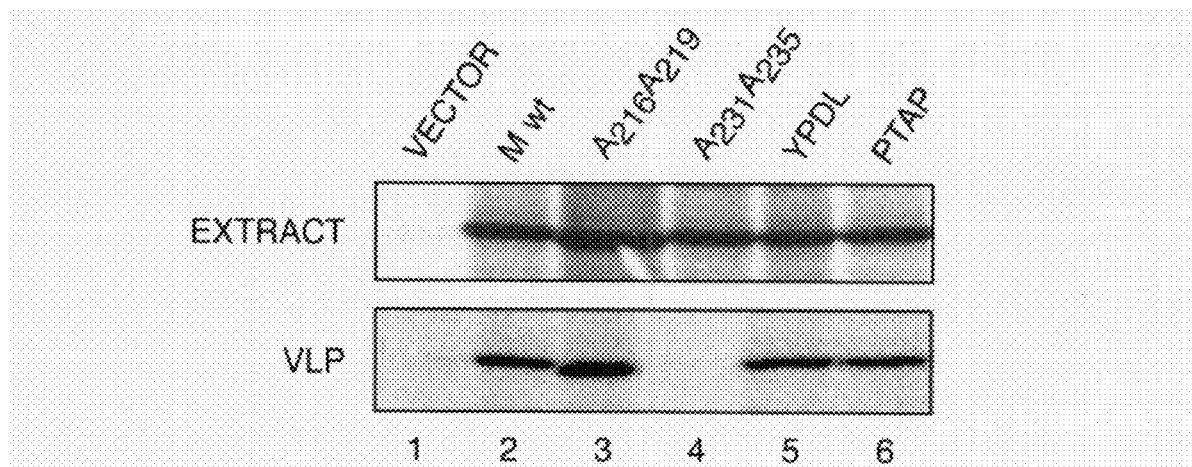
Figure 70C:
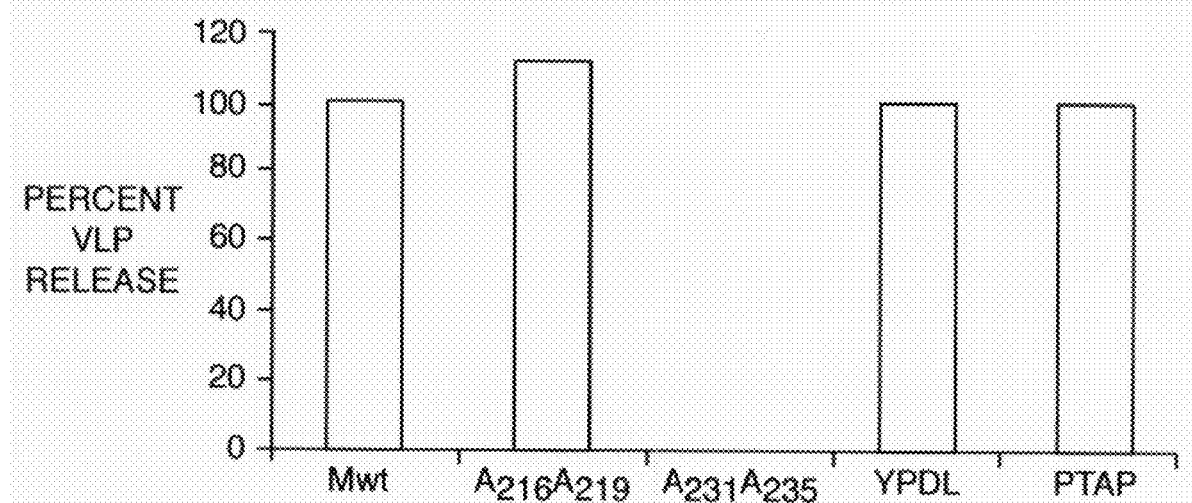
Figure 70D:
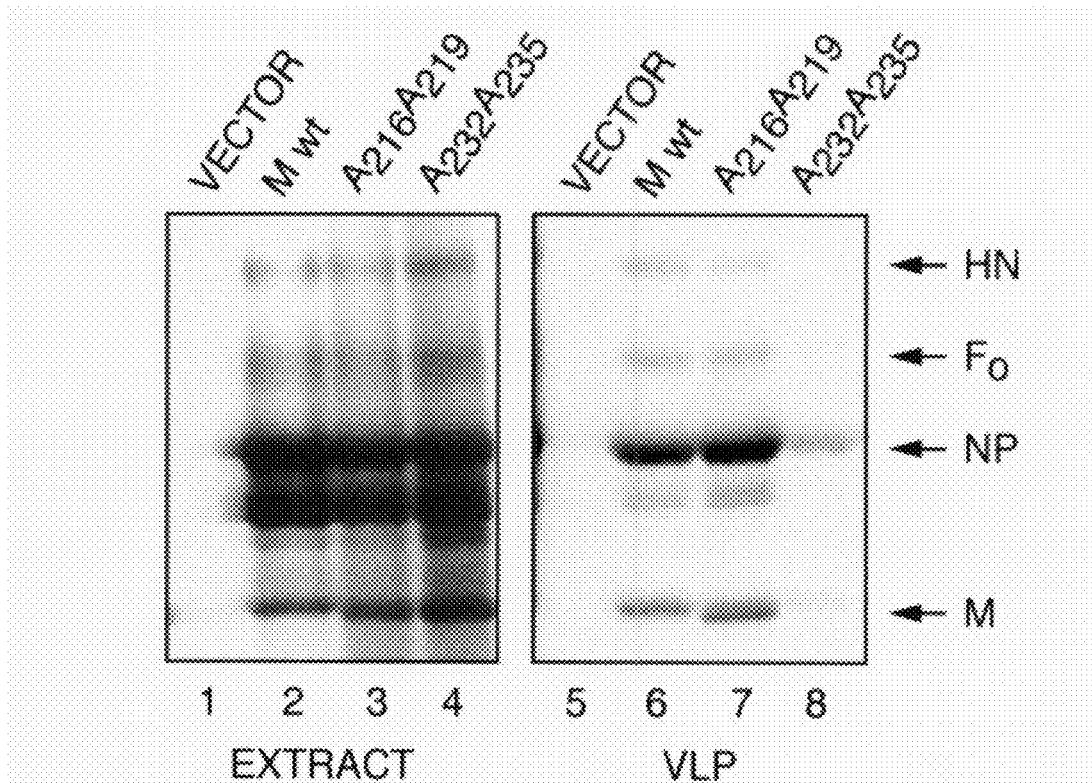
Figure 70E:
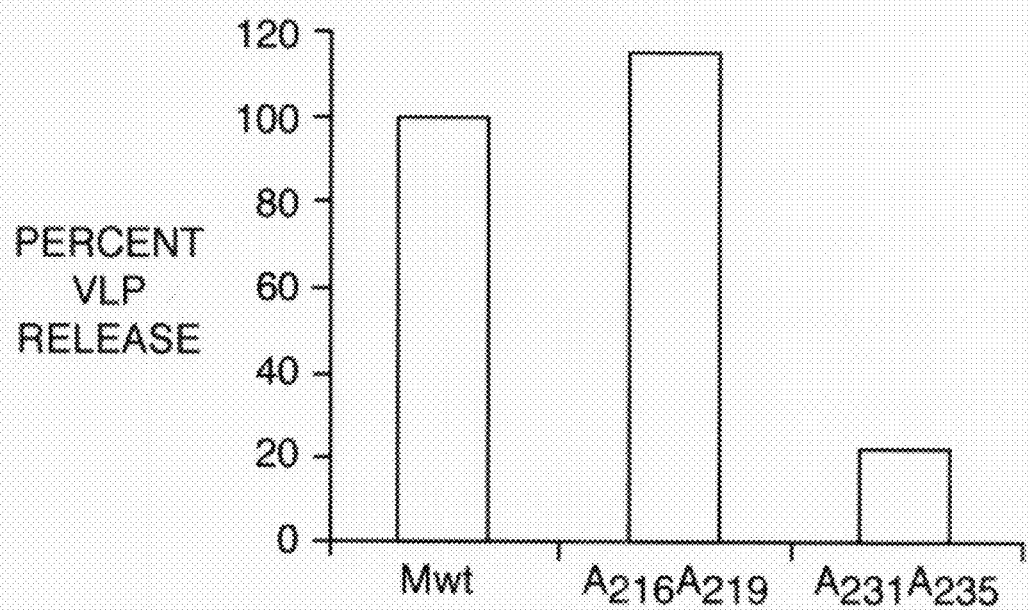

FIG. 67 presents exemplary data showing VLPs released from 293T cells. 293T cells transfected with pCAGGS M (Panel A) or with mixture of pCAGGS-NP, -M, -F-K155Q, and -HN (Panel B), were radioactively labeled with [$^{35}$S] methionine and [$^{35}$S] cysteine for 4 hours (P) and then chased in non-radioactive medium for 8 hours (C). Proteins present in cell lysates were immunoprecipitated with a cocktail of antibodies specific for all viral proteins and the precipitated labeled proteins are shown on the left side of each panel. Particles in cell supernatants were then purified. After flotation into sucrose gradients (right side of each panel), each gradient fraction was immunoprecipitated with the antibody cocktail. The density of each fraction (g/cc) is shown at the bottom.

FIG. 68 presents exemplary data showing the effect of wild type and dominant-negative mutant protein of the VPS pathway M protein VLP release. Panel A shows cell extracts of 293T cells (top) and corresponding released particles (bottom) from cells co-transfected with pCAGGS-M and either pDsRed2-N1 vector (lane 1), pBJ5-WT-CHMP3 (lane 2) or pDsRed2-N1-CHMP3-RFP (lane 3). Panel C shows cell extracts of 293T cells (top) and corresponding released particles (bottom) from cells co-transfected with pCAGGS-M and either pBJ5 vector (lane 1), pBJ5-WT-Vps4A (lane 2) or pBJ5-Vps4A-E228Q (lane 3). Panel E shows extracts of 293T cells (top) and corresponding VLPs (bottom) from cells co-transfected with pCAGGS-M and either pDsRed2-N1 vector (lane 1), pBJ5-AIP1-HA (lane 2) or pDsRed2-N1-AIP1-HA-CHMP3-RFP (lane 3). Extracts are from pulse labeled cells. VLPs are released from pulse labeled cells during an 8-hour nonradioactive chase. Particles were then purified. Proteins were immunoprecipitated using NDV protein-specific antibodies and resolved by SDS-PAGE. Panels B, D and F show quantification of particles released relative to those released from wild type VPS protein controls. Identical results were obtained in two separate experiments.

FIG. 69 presents exemplary data showing the effect of dominant negative mutants of CHMP3, Vps4A and AIP1 on the release of complete VLPs. Panel A shows extracts of 293T cells (lanes 1-3) and corresponding released VLPs (lanes 4-6) from cells co-transfected with NDV cDNAs, encoding NP, M, HN, and F proteins, and either pDsRed2-N1 vector (lanes 1 and 4), pBJ5-WT-CHMP3 (lanes 2 and 5) or pDsRed2-N1-CHMP3-RFP (lanes 3 and 6). Panel C shows extracts of 293T cells (lanes 1-3) and corresponding released VLPS (lanes 4-6) from cells co-transfected with the mixture of four NDV cDNAs and either pBJ5 vector (lanes 1 and 4), pBJ5-WT-Vps4A (lanes 2 and 5) or pBJ5-Vps4A-E228Q (lanes 3 and 6). Panel E shows extracts of 293T cells (lanes 1-3) and corresponding VLPs (lanes 4-6) from cells co-transfected with the mixture of NDV cDNAs and either pDsRed2-N1 vector (lanes 1 and 4), pBJ5-AIP1-HA (lanes 2 and 5) or pDsRed2-N1-AIP1-HA-RFP (lanes 3 and 6). Extracts are from pulse labeled cells. VLPs are released from pulse labeled cells during an 8-hour nonradioactive chase. Particles were then purified. Proteins were immunoprecipitated using NDV protein-specific antibodies and resolved by SDS-PAGE. Panels B, D, and F show quantification of VLPs released relative to vector and to wild type Vps protein controls. Identical results were obtained in two separate experiments.

FIG. 70 presents exemplary data demonstrating the functionality of the L domain in NDV M protein. Panel A shows wild type M protein, mutant M proteins with alanine substitutions at amino acid positions 216 and 219 (M-A216A219) or 232 and 235 (M-A232A235), and YPDL (SEQ ID NO: 119) or PTAP (SEQ ID NO: 4) substitutions at positions 232-235.

Figure 71A:
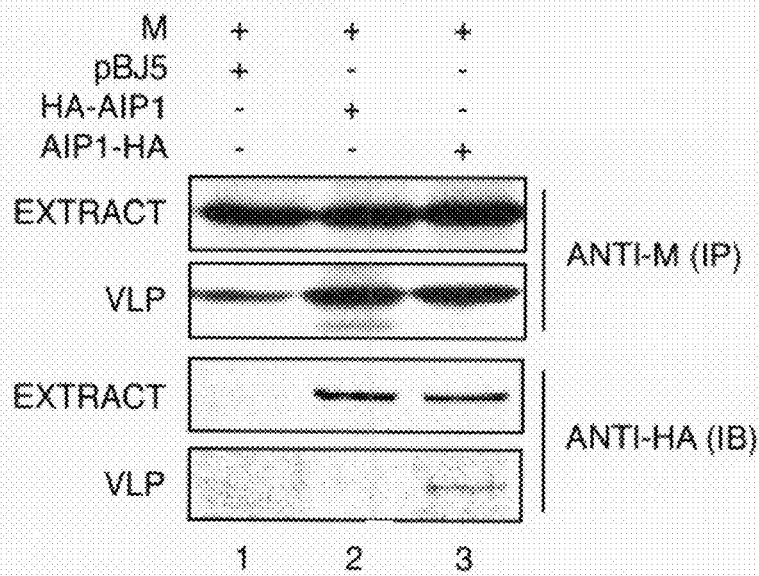
Figure 71B:
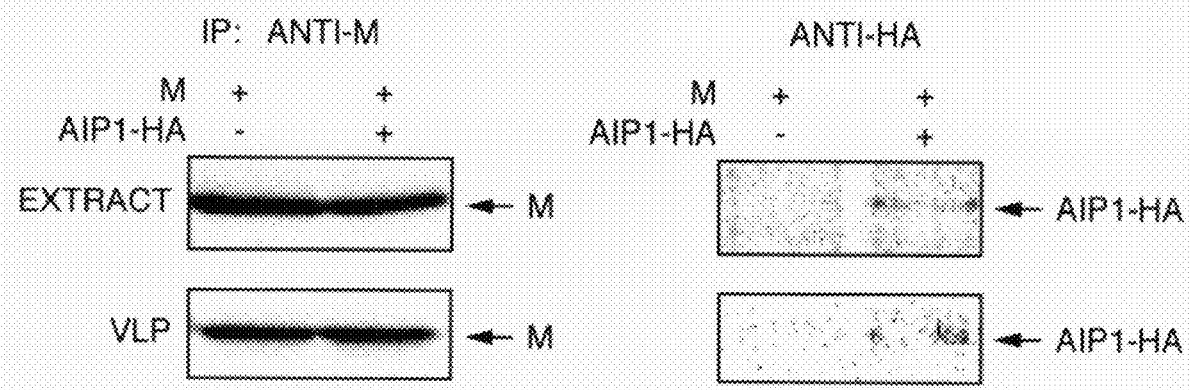

FIG. 71 presents exemplary data showing the incorporation of AIP1 in VLPs. 293T cells were transfected with pCAGGS M and either empty vector, or vector with HA-tagged AIP1. Panel A shows radioactively labeled M protein precipitated from cell extracts (anti-M IP) and VLPs using M protein-specific monoclonal antibody. HA-AIP1 (N-terminally tagged) and AIP1-HA (C-terminally tagged) were detected in extracts and VLPs by immunoblotting using HA antibody conjugated with peroxidase (anti-HA-IB). Panel B shows precipitated radiolabeled M protein and AIP1-HA from cell extracts (top) and VLPs (bottom).

Figure 72:
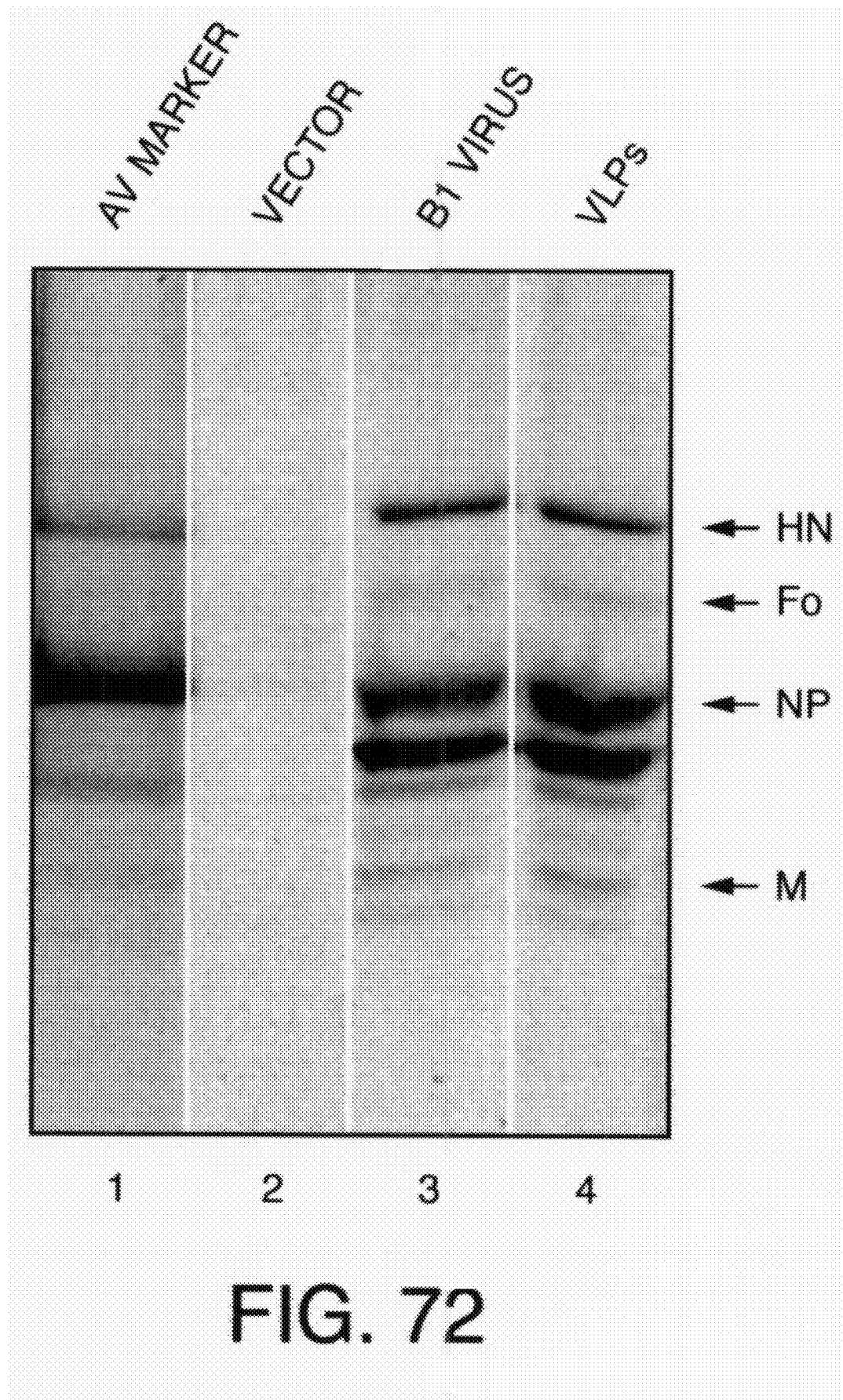

FIG. 72 presents exemplary data comparing the protein content of purified NDV virus and VLPs without prior immunoprecipitation.

Figure 73:
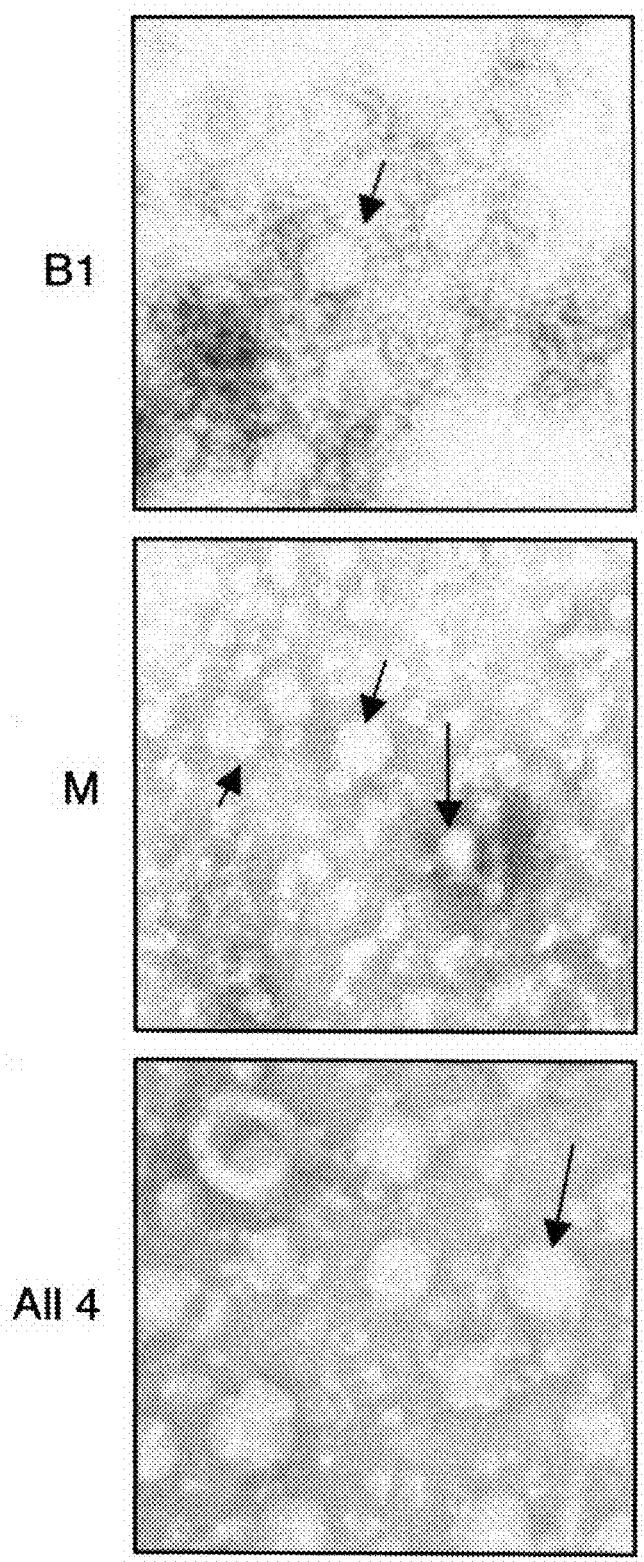

FIG. 73 presents exemplary electron micrographs showing virus (B1) (upper panel), M protein-only VLPs (middle panel) and NP, M, F, and HN VLPs (lower panel).

Figure 74:
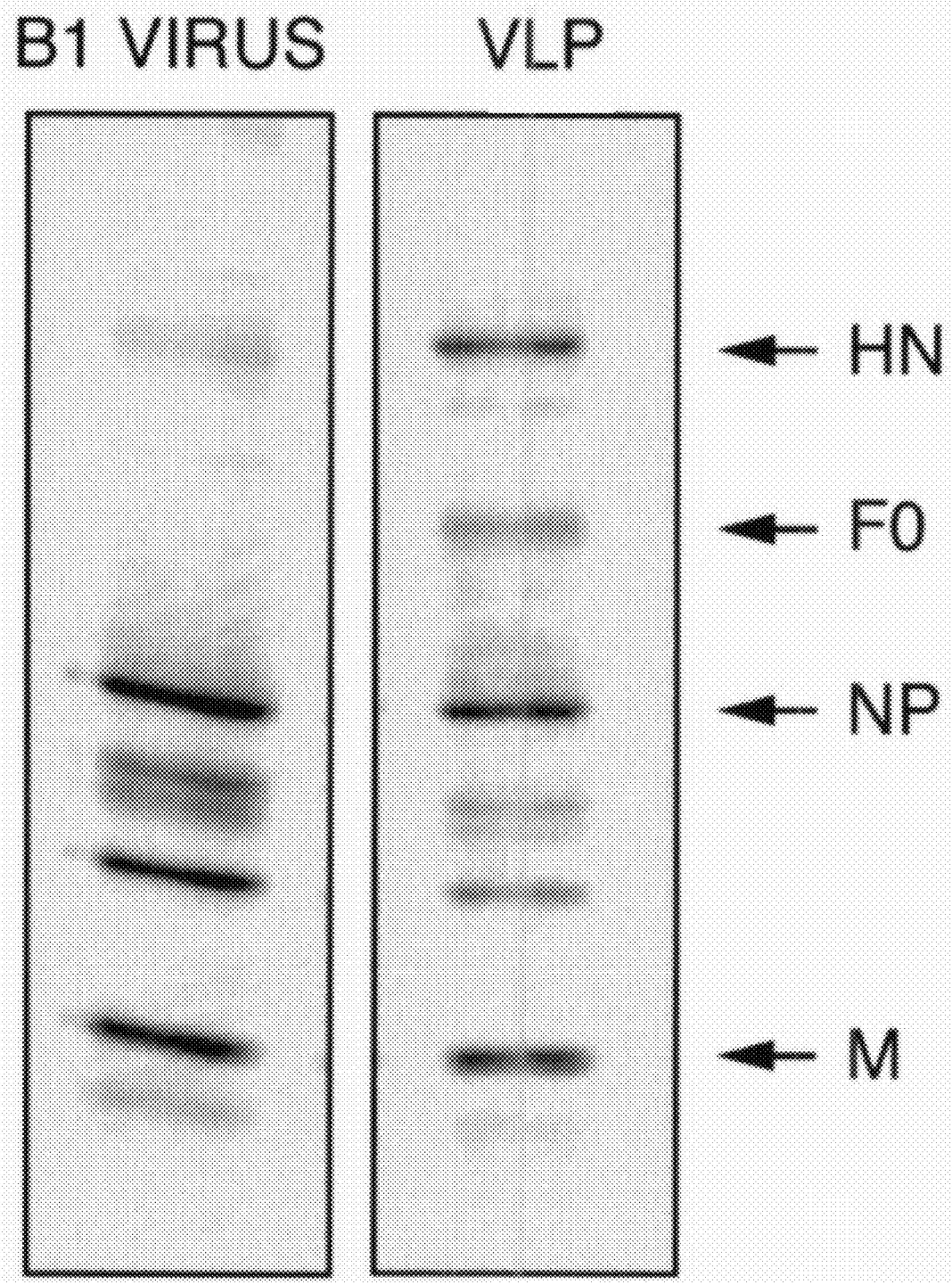

FIG. 74 presents exemplary data showing a silver stain of virus (B1) when grown in eggs as compared to VLPs prepared from a large scale tissue culture.

DETAILED DESCRIPTION OF THE INVENTION

The present invention relates to the field of viral vaccines. In one embodiment, the present invention contemplates a paramyxoviral vaccine effective against diseases such as, but not limited to, Newcastle disease, measles, parainfluenza virus 3, and respiratory syncytial virus. In one embodiment, the present invention contemplates a vaccine comprising Newcastle disease virus-like particles (VLP). In one embodiment, the present invention contemplates a method comprising transfecting avian cells with cDNAs encoding major NDV structural proteins. In another embodiment, a method wherein particles resembling infectious virions are released with nearly 100% efficiency. In one embodiment, the particles are non-infectious and provide a safe and effective NDV vaccine.

Paramyxoviruses have a negative, single-stranded RNA genome which is usually linear. Paramyxovirus morphology comprises a relatively spherical shape having diameters ranging between approximately 150-350 nanometers (nm). Generally, the genomes are packaged with nucleoprotein into ribonucleoprotein cores. Polymerase proteins may also be associated with these ribonucleoprotein cores which play a role in early infection replication and transcription processes. The matrix protein is a prominent feature of paramyxoviruses and lines the inner face of the viral membrane. Transmembrane proteins (i.e., for example, hemaglutinin, fusion or neuraminidase proteins) all form homo-oligomeric complexes (i.e., known in the art as spike proteins) and assist with virus assembly localized at the host cell plasma membrane. Garoff et al., "Virus Maturation By Budding" *Microbiol Mol Biol Rev* 62:1171-1190 (1998).

I. Viral Structure and Assembly

Paramyxoviruses are enveloped and known to assemble their virion components at the plasma membrane of infected cells and subsequently release progeny particles by the process of budding. Newcastle disease virus (NDV), measles, parainfluenza virus 3, and respiratory syncytial virus all belong to Paramyxoviridae, characterized as an enveloped virus with a genomic negative-stranded RNA (i.e., for example, approximately 16 KB) that is packaged with nucleoprotein into a ribonucleoprotein (RNP) core.

The paramyxovirus RNP core also contains the polymerase complex, which is composed of a Phosphoprotein and Large Polymerase. The RNP core is encased in a membrane which contains two transmembrane glycoproteins, the hemagglutinin-neuraminidase (HN) and the fusion (F) proteins, as well as the matrix (M) protein, which is associated with the inner surface of the lipid-containing viral envelope. Lamb et al., "Paramyxoviridae: The Viruses and Their Replication" pp. 1305-1340. In: *Fields Virology, Third Edition*, Vol. 1., Eds: D. M. K. &. P. M. Howley, LippincottWilliams & Wilkins, Philadelphia (2001).

The matrix protein of many enveloped RNA viruses are believed to play a role in virus assembly and budding. Freed, E. O., "The HIV-TSGI01 interface: recent advances in a budding field" *Trends Microbiol.* 11:56-9 (2003); Jasenosky et al., "Filovirus budding" *Virus Res.* 106:1B1-8 (2004); Jayakar et al., "Rhabdovirus assembly and budding" Virus Res. 106:117-32 (2004); Peeples M. E., "Paramyxovirus M proteins: pulling it all together and taking it on the road" pp. 427-456. In: *The Paramyxoviruses*. Ed: D. W. Kingsbury, Plenum, New York, N.Y. (1991); Pornillos et al., "Mechanisms of enveloped RNA virus budding" *Trends Cell Biol.* 12:569-79 (2002); Schmitt et al., "Escaping from the cell: assembly and budding of negative-strand RNA viruses" *Cuff Top Microbiol Immunol* 283:145-96 (2004); and Takimoto et al., "Molecular mechanism of paramyxovirus budding" *Virus Res.* 106:133-45 (2004). However, expression of the retroviral gag precursor protein, in the absence of other viral components, also results in the assembly and release of gag virus-like particles (VLPs) from the plasma membrane. Delchambre et al., "The GAG precursor of simian immunodeficiency virus assembles into virus-like particles" *EMBO J* 8:2653-60 (1989); Demirov et al., "Retrovirus budding" *Virus Res* 106:87-102 (2004); Gheysen et al., "Assembly and release of HIV-1 precursor Pr55gag virus-like particles from recombinant baculovirus-infected insect cells" *Cell* 59:103-12 (1989); and Morita et al., "Retrovirus budding" *Annu Rev Cell Dev Biol.* 20:395-425 (2004). It has been unclear, therefore, which NDV proteins are sufficient and necessary to direct viral particle formation and release.

A. M Proteins

In one embodiment, the present invention contemplates a method comprising an M protein from a paramyxovirus, without any additional glycoproteins, wherein VLPs are created.

M proteins isolated from:

i) Ebola virus (Jasenosky et al., "Filovirus budding" *Virus Res.* 106:1B1-8 (2004); Jasenosky et al., "Ebola virus VP40-induced particle formation and association with the lipid bilayer" *J. Virol.* 75:5205-14 (2001); and Timmins et al., "Vesicular release of Ebola virus matrix protein VP40" *Virology* 283: 1-6 (2001));

ii) vesicular stomatitis virus (Jayakar et al., "Rhabdovirus assembly and budding" *Virus Res.* 106:117-32 (2004); Li et al., "Viral liposomes released from insect cells infected with recombinant baculovirus expressing the matrix protein of vesicular stomatitis virus" *J. Virol.* 67:4415-20 (1993); and Sakaguchi et al., "Double-layered membrane vesicles released from mammalian cells infected with Sendai virus expressing the matrix protein of vesicular stomatitis virus" *Virology* 263:230-43 (1999))

and, iii) influenza virus (Gomez-Puertas et al., "Influenza virus matrix protein is the major driving force in virus budding" *J. Virol.* 74:11538-47 (2000)), when expressed alone, assemble into and are released as VLPs.

Conversely, M protein-deficient rabies virus is known to be severely impaired in virion formation. Mebatsion et al., "Matrix protein of rabies virus is responsible for the assembly and budding of bullet-shaped particles and interacts with the transmembrane spike glycoprotein G" *J. Virol.* 73:242-50 (1999).

Studies in several paramyxovirus systems have also suggested a role for the M protein in virus assembly and budding. Measles virus (MV) and Sendai virus (SV) modified by reverse genetics to lack the M protein genes were impaired in budding. Cathomen et al., "A matrix-less measles virus is infectious and elicits extensive cell fusion: consequences for propagation in the brain" *EMBO J* 17:3899-3908 (1998); and Inoue et al., "A new Sendai virus vector deficient in the matrix gene does not form virus particles and shows extensive cell-to-cell spreading" *J. Virol.* 77:6419-29 (2003), respectively, Moreover, MV containing mutant M protein derived from subacute sclerosing panencephalitis (SSPE) virus was also defective in budding. Patterson et al., "Evidence that the hypermutated M protein of a subacute sclerosing panencephalitis measles virus actively contributes to the chronic progressive CNS disease" *Virology* 291:215-25 (2001).

Recent studies of paramyxovirus assembly have also focused on identifying the viral protein requirements for assembly and budding of VLPs and have demonstrated a role for the M protein. The human parainfluenza virus type 1 (hPIV1) M protein and the SV M protein expressed alone induced budding of VLPs from the plasma membrane. Coronel et al., "Human parainfluenza virus type 1 matrix and nucleoprotein genes transiently expressed in mammalian cells induce the release of virus-like particles containing nucleocapsid-like structures" *J. Virol.* 73:7035-8 (1999); Sakaguchi et al., "Double-layered membrane vesicles released from mammalian cells infected with Sendai virus expressing the matrix protein of vesicular stomatitis virus" *Virology* 263:230-43 (1999); Sugahara et al., "Paramyxovirus Sendai virus-like particle formation by expression of multiple viral proteins and acceleration of its release by C protein" *Virology* 325:1-10 (2004); and Takimoto et al., "Role of matrix and fusion proteins in budding of Sendai virus" *J. Virol.* 75:11384-91 (2001). Expression of M protein was also required for Simian Virus 5 (SV5) VLP formation. Schmitt et al., "Requirements for budding of paramyxovirus simian virus virus-like particles" *J Virol* 76:3952-64 (2002).

However, in contrast to PIY1 and SV, the SV5 M protein was not sufficient for VLP release. Rather, simultaneous expression of SV5 M protein, together with NP and either of the glycoproteins was required. Although existing reports agree upon a role for M protein as a budding organizer in paramyxovirus particle release, there are differences in the protein requirements for assembly and budding of virions. The budding capacities of retrovirus gag protein, Ebola virus M protein, and influenza M1 protein are attributed, in part, to Late Domains (infra). Demirov et al., "Retrovirus budding" *Virus Res* 106:87-102 (2004); Freed, E. O., "Viral late domains" *J. Virol.* 76:4679-87 (2002); Jasenosky et al., "Filovirus budding" *Virus Res.* 106:1B1-8 (2004); Jayakar et al., "Rhabdovirus assembly and budding" *Virus Res.* 106:117-32 (2004); Morita et al., "Retrovirus budding" *Annu Rev Cell Dev Biol.* 20:395-425 (2004); Nayak et al., "Assembly and budding of influenza virus" *Virus Res* 106:147-65 (2004); Pornillos et al., "Mechanisms of enveloped RNA virus budding" *Trends Cell Biol.* 12:569-79 (2002); Schmitt et al., "Escaping from the cell: assembly and budding of negative-strand RNA viruses" *Cuff Top Microbiol Immunol* 283:145-96 (2004); Strack et al., "AIP 1/ALIX is a binding partner for HIV-1 p6 and EIA V p9 functioning in virus budding" *Cell* 114:689-99 (2003); and von Schwedler et al., "The protein network of HIV budding" *Cell* 4:701-13 (2003).

B. Late Domains

Late Domains are short peptide motifs that mediate interactions with a member of the class E proteins, which are involved in the vacuolar protein sorting (VPS) pathway. The Late Domain promotes budding by interacting with components of the cellular machinery responsible for sorting cargo into multivesicular bodies (MVB). The formation of MVB vesicles and the budding of a virus are topologically similar processes. Available evidence suggests that enveloped RNA viruses bud by co-opting the cellular machinery that is normally used to create MVB inside the cell. Carter, C. A., "Tsg101: HIV-1's ticket to ride" *Trends Microbiol.* 10:203-205 (2002); Demirov et al., "Retrovirus budding" *Virus Res* 106:87-102 (2004); Freed, E. O., "The HIV-TSGI01 interface: recent advances in a budding field" *Trends Microbiol.* 11:56-9 (2003); Freed, E. O., "Viral late domains" *J. Virol.* 76:4679-87 (2002); Garrus et al., "Tsg 1-01 and the vacuolar protein sorting pathway are essential for HIV-1 budding" *Cell* 107:55-65 (2001); Morita et al., "Retrovirus budding" *Annu Rev Cell Dev Biol.* 20:395-425 (2004); Pornillos et al., "Mechanisms of enveloped RNA virus budding" *Trends Cell Biol.* 12:569-79 (2002); Pornillos et al., "HN Gag mimics the Tsg101-recruiting activity of the human Hrs protein" *J Cell Biol* 162:425-34 (2003); Strack et al., "AlP 1/ALIX is a binding partner for HIV-1 p6 and EIA V p9 functioning in virus budding" *Cell* 114:689-99 (2003); von Schwedler et al., "The protein network of HIV budding" *Cell* 4:701-13 (2003). Martindale, D., "Budding viral hijackers co-opt the endocytic machinery to make a getaway" *J Biol.* 3:2 (2003); and Simons et al., "The budding mechanisms of enveloped animal viruses" *J. Gen. Virol.* 50:1-21 (1980).

In one embodiment, the present invention contemplates that dominant negative mutant protein component of the VPS pathway may also inhibit particle release. In one embodiment, an YXXL (SEQ ID NO:3) sequence in the NDV M protein has properties of a Late Domain. Although it is not necessary to understand the mechanism of an invention, it is believed that the YXXL (SEQ ID NO: 3) mutation abolishes particle release while substitution of late domains such as YPDL (SEQ ID NO: 119) and/or PTAP (SEQ ID NO: 4) fully restore particle release.

C. Budding

Within the paramyxovirus family, it is known that the VPS pathway is involved in the SV5 budding. It was shown that a dominant-negative mutation VPS4(E228Q) (an ATPase required for recycling protein complexes involved in the VPS pathway) inhibited budding of SV5 virions as well as VLPs. Schmitt et al., "Evidence for a new viral late-domain core sequence, FPIV, necessary for budding of a paranyxovirus" *J. Virol.* 79:2988-97 (2005). Since it is known that VPS4 (E228Q) also inhibits the VPS pathway, one may believe that the VPS pathway is involved in SV5 budding. In addition, a putative Late Domain in SV5 M was identified. However, SV5 M protein is not sufficient for VLP formation and release, complicating the interpretation of this result. Thus, the general rules for assembly and release of paramyxoviruses are not yet clear. Schmitt et al., "Requirements for budding of paramyxovirus simian virus virus-like particles" *J Virol* 76:3952-64 (2002). Open questions include: i) the further definition of paramyxovirus late domains in viral structural proteins, ii) the role or contribution of each viral protein in virus assembly, and iii) the cellular factors involved in the assembly and budding process.

Various embodiments of the present invention answer these questions. In one embodiment, the present invention contemplates a method for producing NDV VLPs from cells transfected with nucleic acids encoding viral structural proteins. In another embodiment, the present invention contemplates transfecting with nucleic acid encoding an NDV M protein that is both necessary and sufficient for release of lipid-containing particles (i.e., for example VLPs). In another embodiment, the present invention contemplates that the most efficient incorporation (i.e., for example, almost 100%) of other viral proteins into VLPs requires the expression of M protein with at least two other NDV proteins. For example, it is known that dominant-negative mutations of CHMP3 and Vps4 proteins (both components of the host VPS system) inhibited release of VLPs. Morita et al., "Retrovirus budding" *Annu Rev Cell Dev Biol.* 20:395-425 (2004); Strack et al., "AlP 1/ALIX is a binding partner for HIV-1 p6 and EIA V p9 functioning in virus budding" *Cell* 114:689-99 (2003); and von Schwedler et al., "The protein network of HIV budding" *Cell* 4:701-13 (2003). It is further contemplated that AIP1 is also incorporated into VLPs thereby playing a role in NDV particle budding.

D. Dominant Negative Mutations

The dominant negative Vps4 protein may block release of SV5 virions or VLPs composed of NP, HN, F, and M proteins, implicating the VPS system in paramyxovirus release. Schmitt et al., "Evidence for a new viral late-domain core sequence, FPIV, necessary for budding of a paramyxovirus" *J. Virol.* 79:2988-2997 (2005). Confirming these results, a dominant negative version of Vps4, Vps4 A-E228Q, blocked NDV VLP release. Martin-Serrano et al., "Role of ESCRT-I in retroviral budding" *J Virol* 77:4794-4804 (2003); Strack et al., "AIP1/ALIX is a binding partner for HIV-1 p6 and EIAV p9 functioning in virus budding" *Cell* 114:689-699 (2003); and von Schwedler et al., "The protein network of HIV budding" *Cell* 114:701-713 (2003)).

Although it is not necessary to understand the mechanism of an invention, it is believed that the results demonstrated herein show that these dominant negative proteins blocked release of particles containing only M protein. For example, a dominant negative version of CHMP3, a subunit of the ESCRT III complex (1), and a dominant negative mutant of AIP1, a protein that binds both ESCT I and III proteins, inhibited NDV VLP release as well as release of particles containing only M protein. This inhibition was not due to over expression of the protein since transfection of the wild type versions of these proteins had little effect on M particle release. These results show that an intact VPS pathway facilitates NDV VLP budding. Furthermore, these results indicate that the VPS pathway is involved in M particle release.

Many studies have demonstrated that L domains in the matrix proteins of viruses mediate their interaction with specific molecules of the VPS pathway. Bieniasz, P. D., "Late budding domains and host proteins in enveloped virus release" *Virology* 344:55-63 (2006); Freed, E. O., "Viral late domains" *J. Virol.* 76:4679-4687 (2002); and Morita et al., "Retrovirus budding" *Annu Rev Cell Dev Biol* 20:395-425 (2004). Three L domain motifs, PTAP (SEQ ID NO: 4), YPXL (SEQ ID NO: 120), and PPXY (SEQ ID NO: 5) (Pornillos et al., "Mechanisms of enveloped RNA virus budding" Trends Cell Biol. 12:569-579 (2002)), have been identified in retroviruses (Puffer et al., "Equine infectious anemia virus utilizes a YXXL (SEQ ID NO: 3) motif within the late assembly domain of the Gag p9 protein" J Virol 71:6541-6546 (1997)), rhabdoviruses and filoviruses (Irie et al., "Budding of PPxY-containing rhabdoviruses is not dependent on host proteins TGS101 and VPS4A" J Virol 78:2657-2665 (2004)). An YRKL (SEQ ID NO: 121) sequence has been identified as a late domain in orthomyxoviruses (Hui et al., "YRKL sequence of influenza virus M1 functions as the L domain motif and interacts with VPS28 and Cdc42" J Virol 80:2291-2308 (2006)).

Binding of the PTAP sequence to TSG101 (tumor susceptibility gene 101) protein, a component of ESCRT I, has been reported. Huang et al., "p6Gag is required for particle production from full-length human immunodeficiency virus type 1 molecular clones expressing protease" *J Virol* 69:6810-6818 (1995). Further, the YPXL (SEQ ID NO: 120) sequence has been shown to interact with AP2 (adaptor protein 2) and AIP1. Chen et al., "Functions of early (AP-2) and late (AIP1/ALIX) endocytic proteins in equine infectious anemia virus budding" *J Biol Chem* (2005); and Strack et al., "AIP1/ALIX is a binding partner for HIV-1 p6 and EIAV p9 functioning in virus budding" *Cell* 114:689-699 (2003), respectively. The YRKL (SEQ ID NO: 121) sequence in the influenza virus M1 protein binds to VSP28, an ESCRT 1 protein that binds tsg101, as well as Cdc42, a member of the Rho family of GTP-binding proteins. The PPXY (SEQ ID NO: 5) motif binds to Nedd4-like (neural precursor cell expressed, developmentally down regulated gene 4) ubiquitin ligases. Vana et al., "Role of Nedd4 and ubiquitination of Rous sarcoma virus Gag in budding of virus-like particles from cells" J Virol 78:13943-13953 (2004); and Xiang et al., "Fine mapping and characterization of the Rous sarcoma virus Pr76gag late assembly domain" J Virol 70:5695-5700 (1996)).

Paramyxovirus M proteins do not have a PTAP (SEQ ID NO: 4), an YPXL (SEQ ID NO: 120), an YRKL (SEQ ID NO: 121), or a PPXY (SEQ ID NO: 5) motif. The sequence FPIV (SEQ ID NO: 1), however, in the SV5 M protein may be a late domain in paramyxoviruses. Mutation of FPIV (SEQ ID NO: 1) inhibited release of particles and addition of this sequence in a retrovirus gag construct stimulated the release of particles. However, since the SV5 M protein is not sufficient for SV5 particle release, FPIV (SEQ ID NO: 1) is not believed to function independently as a late domain in the context of this paramyxovirus M protein. Schmitt et al., "Evidence for a new viral late-domain core sequence, FPIV, necessary for budding of a paramyxovirus" J. Virol. 79:2988-2997 (2005).

Thus, it is not clear how SV5 uses the VPS pathway or how the FPIV (SEQ ID NO: 1) sequence might function as a late domain. Sequence analysis of the NDV M protein shows the presence of this FPIV (SEQ ID NO: 1) motif. In addition, NDV M protein contains a PKSP (SEQ ID NO: 117) and a YANL (SEQ ID NO: 118) sequence, not found in the SV5 M protein. In one embodiment, the present invention contemplates a YANL (SEQ ID NO: 118) motif comprising properties of an L domain. In one embodiment, a YANL (SEQ ID NO: 118) mutation reduces M protein particle release. Although it is not necessary to understand the mechanism of an invention, it is believed that substitution of a YANL (SEQ ID NO: 118) mutation with other known late domains (i.e., for example, PTAP (SEQ ID NO: 4) or YPDL (SEQ ID NO: 119)) particle release may become fully restored.

It is further believed that inhibition of particle release by mutation of the YANL (SEQ ID NO: 118) sequence is not likely due only to effects on protein folding. The data provided herein suggests that the NDV M protein may access the VPS pathway using either type of late domain, an YPDL (SEQ ID NO: 119) or a PTAP (SEQ ID NO: 4) domain and that the FPIV (SEQ ID NO: 1) sequence in the NDV M protein may not function as a late domain independent of the YANL (SEQ ID NO: 118) sequence since the YANL (SEQ ID NO: 118) mutant protein M-A232-A235 has a wild type FPIV (SEQ ID NO: 1) sequence.

YPDL (SEQ ID NO: 119) late domains have been shown to interact with the VPS protein AIP1. In one embodiment, the present invention contemplates that AIP1 protein is found in released particles containing only M protein.

The M protein of Sendai virus has also been shown to be sufficient for release of particles (Sugahara et al., "Paramyxovirus Sendai virus-like particle formation by expression of multiple viral proteins and acceleration of its release by C protein" Virology 325:1-10 (2004); and Takimoto et al., "Role of matrix and fusion proteins in budding of Sendai virus" J. Virol. 75:11384-11391 (2001)). The Sendai virus M protein has an YLDL (SEQ ID NO: 122) sequence, which could serve as a late domain for SV M protein. As noted above, the SV5 M protein is not sufficient for release of neither particles nor does it has an YXXL (SEQ ID NO: 3) motif. Schmitt et al., "Requirements for budding of paramyxovirus simian virus 5 virus-like particles" J Virol 76:3952-3964 (2002). However, the SV5 NP protein has a number of YXXL (SEQ ID NO: 3) motifs including a YPLL (SEQ ID NO: 123) sequence. Alternatively, an SV5 late domain may be present on the SV5 NP rather than the M protein. Indeed, it has been reported that SV5 VLP release is significantly enhanced by the expression of the SV5 NP protein with M protein as well as a glycoprotein. Schmitt et al., "Requirements for budding of paramyxovirus simian virus 5 virus-like particles" J Virol 76:3952-3964 (2002). Consequently, it is clear that differential requirements for the release of particles in different paramyxovirus systems exist and may be due in part to different distributions of the late domains on structural proteins. Nevertheless, the present invention contemplates that the host cell VPS pathway facilitates M protein budding and that the YANL (SEQ ID NO: 118) motif in the NDV M protein has the properties of a late domain.

II. Virus-Like Particle (VLP) Formation and Release

In one embodiment, the present invention contemplates transfecting a host cell with nucleic acid encoding only a paramyxovirus M protein so that the transfected cells express the matrix protein and create paramyxoviral VLPs. In another embodiment, the present invention contemplates co-expression of two or more paramyxovirus glycoproteins including, but not limited to, NP, F-K115Q, and/or HN proteins (together with M protein) under conditions such that paramyxovirus VLP formation and release occurs.

The present invention contemplates conditions for the efficient generation of VLPs of a virulent paramyxoviral strain. In one embodiment, the paramyxoviral strain comprises the group including, but not limited to, Newcastle disease, measles, parainfluenza virus 3, or respiratory syncytial virus. In another embodiment, the VLPs comprise the same major antigens as infectious virus. In another embodiment, the VLPs comprise major antigens having the same ratios as infectious virus. In one embodiment, the major antigens are selected from the group comprising nucleocapsid protein, membrane/matrix protein, hemagglutinin-neuraminidase protein, and fusion protein.

The production of VLPs in accordance with embodiments of the present invention is much simpler and likely more cost effective than currently available live or attenuated virus vaccines. VLPs can be harvested from cell supernatants and purified by the same protocols used to purify virus. VLPs can be engineered to increase the spectrum of immune responses. The VLPs can also be engineered so that the immune response can be distinguished from that induced by an infection.

A. VLP Release Characteristics

In one embodiment, VLPs are released from cells co-expressing the major structural proteins of paramyxoviruses. In one embodiment, NDV VLP particles are released from a chicken fibroblast cell line co-expressing NP, M, F and HN proteins that can be purified and characterized. In one embodiment, an uncleaved version of F protein eliminated any potential effects of cell-to-cell fusion on virus release. In one embodiment, avian cells are used because birds are the natural host of NDV. For example, as detailed in the Examples below, cells (i.e., for example, avian or human) were co-transfected with plasmids encoding NDV viral proteins using concentrations of DNA previously determined to result in expression levels and ratios of proteins comparable to infected cells. Cells were then pulse-labeled with $^{35}$S-methionine and $^{35}$S-cysteine and then chased for 8 hours (a time also resulting in maximal particle release). VLPs in the cell supernatants were isolated and fractionated by sucrose density ultracentrifugation.

In one embodiment, the efficiency of paramyxoviral VLP release from cells expressing at least four viral proteins (85%) was comparable to the efficiency of infectious particle release from paramyxovirus-infected cells (92%). Although it is not necessary to understand the mechanism of an invention, it is believed that this result suggests that four paramyxovirus proteins (i.e., for example, M protein, NP protein, F, protein, or HN protein) may provide an efficient formation of particles. It is further believed that the viral Large Polymerase or Phosphoprotein proteins have little quantitative effect on virus release.

Although it is not necessary to understand the mechanism of an invention, it is believed that paramyxoviral VLPs, which can be isolated on sucrose gradients, have a relatively homogeneous density that is slightly less than the average density of an authentic virus. Although it is not necessary to understand the mechanism of an invention, it is believed that this result is likely due to the absence of the viral genomic RNA in the particles. It is further believed, therefore, that the VLPs are non-infectious.

Although it is not necessary to understand the mechanism of an invention, it is believed that paramyxoviral VLPs are likely folded into conformations virtually identical to an authentic virus and are packaged into particles in a manner identical to paramyxoviral particles. As a result, these particles should be as antigenic as authentic virus. VLPs do not, however, contain the viral genome, since the cells (i.e., for example, avian or human), which are forming and releasing these particles, are not infected with virus. Therefore, VLPs cannot be infectious and cannot cause disease.

B. M Protein Function

In one embodiment, a paramyxovirus M protein is both sufficient and necessary for VLP particle release. In one embodiment, the paramyxovirus is selected from the group including, but not limited to, Newcastle disease virus, measles virus, parainfluenza virus 3, and syncytial respiratory virus. That is to say, expression of the M protein alone resulted in very efficient release of M protein containing paramyxovirus VLP particles. For example, the efficiency of M protein release is comparable to that observed when at least four proteins were co-expressed. Although it is not necessary to understand the mechanism of an invention, it is believed that this result suggests that it is the M protein that directs the budding of paramyxovirus VLPs. Furthermore, VLPs are released when only M protein is present. Consequently, significant VLP particle release will not occur the absence of M protein even if viral protein expression (or co-expression of a combination of viral proteins) is present. For example, cells expressing HN protein, alone, released only trace amounts of a very light density HN protein-containing material into cell supernatants, and it is unlikely that this material reflects a significant component of virus assembly. In one embodiment, the present invention contemplates that no NDV protein, other than M protein, can function independently in the release of lipid containing particles that reflect virus assembly.

Although it is not necessary to understand the mechanism of an invention, it is believed that VLP particles released from cells expressing only M protein have very heterogeneous densities because this budding occurs indiscriminately from different cell membranes or from different plasma membrane domains and, consequently, contain different lipid-to-protein ratios due to variable M protein oligomerization. For example, particles formed from monomer M protein may have a higher lipid to protein ratio than particles formed from M protein in an oligomeric state. It is known that M proteins of other negative stranded RNA viruses can form oligomeric structures. Garoff et al., "Virus maturation by budding" *Microbiol Mol Biol Rev* 62:1171-90 (1998); and Panch et al., "In vivo oligomerization and raft localization of Ebola virus protein VP40 during vesicular budding" *Proc Natl Acad Sci USA* 100:15936-41 (2003).

C. Glycoprotein Function

Formation of infectious paramyxovirus virions is believed to involve the incorporation of both the HN and F glycoproteins. In one embodiment, the present invention contemplates a composition comprising glycoprotein incorporation into a paramyxovirus VLP when M protein is co-expressed with at least two glycoproteins. Single glycoprotein co-expression (i.e., for example HN+M or F+M) resulted in only trace amounts of either HN or F glycoprotein incorporated into VLP particles. Further, when HN and F glycoproteins were co-expressed with M protein, the glycoprotein incorporation levels were comparable to that observed with co-expression of at least four proteins.

Although it is not necessary to understand the mechanism of an invention, it is believed that these results indicate that the M protein binds more efficiently with a complex of HN and F glycoproteins. This possibility is also supported by observations that co-expression of these two glycoproteins with M protein resulted in paramyxovirus VLPs having a more homogenous and decreased density. M protein VLP particles generally have a very heterogeneous density. Co-expression of M protein with either glycoprotein, alone, did not change the general density of M protein containing particles. It is believed that these results indicate that interactions of M protein with an HN-F protein complex affected the protein to lipid ratio of the VLPs or affected the membrane from which the particles were released.

It should be noted that not just any combination of M protein and viral glycoproteins produce paramyxovirus VLPs in good yield as contemplated herein. For example, co-expression of a single glycoprotein and an M protein results in a 40-60% VLP release suppression when compared to VLP release observed after: i) co-expression with all four proteins; ii) expression of an M protein with at least two glycoproteins; and iii) expression of M protein alone. Empirical studies revealed that this release suppression is relieved by co-expression of M protein with NP and another glycoprotein.

Although it is not necessary to understand the mechanism of an invention, it is believed that VLP release suppression by a single glycoprotein+M protein is consistent with observations that NP+M protein VLP release is: i) 70% lower when compared to release from cells expressing at least four proteins; and ii) 80% lower when compared to release from cells expressing only M protein. Although it is not necessary to understand the mechanism of an invention, it is believed that the large amount of NP in the cytoplasm may pull M protein away from the plasma membrane, thereby preventing its association with this membrane and, therefore, budding of particles. Consequently, one hypothesis suggests that co-expression with another glycoprotein may redirect both NP and M protein to a cellular membrane thereby relieving VLP release suppression.

D. Vacuolar Protein Sorting (VPS) System and Multivesicular Buds (MVBs)

Although it is not necessary to understand the mechanism of an invention, it is believed that paramyxovirus M protein-dependent VLP release uses the host vacuolar protein sorting (VPS) system. The VPS system has been reported to mediate budding of other enveloped viruses. Morita et al., "Retrovirus budding" *Annu Rev Cell Dev Biol*. 20:395-425 (2004); and Pornillos et al., "Mechanisms of enveloped RNA virus budding" *Trends Cell Biol*. 12:569-79 (2002).

Budding of retroviruses, filoviruses, and influenza viruses are thought to depend upon the host cell VPS pathway. The VPS pathway also serves to form MVBs. Demirov et al., "Retrovirus budding" *Virus Res* 106:87-102 (2004); Jasenosky et al., "Filovirus budding" *Virus Res*. 106:1B1-8

(2004); Morita et al., "Retrovirus budding" *Annu Rev Cell Dev Biol.* 20:395-425 (2004); Pornillos et al., "Mechanisms of enveloped RNA virus budding" *Trends Cell Biol.* 12:569-79 (2002); Freed, E. O., "Viral late domains" *J. Virol.* 76:4679-87 (2002); and Schmitt et al., "Escaping from the cell: assembly and budding of negative-strand RNA viruses" *Cuff Top Microbiol Immunol* 283:145-96 (2004). MVBs are formed by invagination of endosomal membranes into the endosomallumen thereby creating a vesicle inside a vesicle. Martindale, D., "Budding viral hijackers co-opt the endocytic machinery to make a getaway" *J Biol.* 3:2 (2003). The topology of MVB formation is similar to that of virus budding from plasma membrane.

It has been proposed that viral proteins usurp this host cell machinery to direct virus budding. Demirov et al., "Retrovirus budding" *Virus Res* 106:87-102 (2004); Martindale, D., "Budding viral hijackers co-opt the endocytic machinery to make a getaway" *J Biol.* 3:2 (2003); and Morita et al., "Retrovirus budding" *Annu Rev Cell Dev Biol.* 20:395-425 (2004). Currently, research suggests that the formation of MVBs involves three protein complexes, first characterized in yeast, and are collectively known as the Endosomal Sorting Complexes Required for Transport (i.e., for example, ESCRT I, II, and III). Babst et al., "ESCRT-III: an endosome-associated heterooligomeric protein complex 4 required for MVB sorting" *Dev Cell* 3:271-282 (2002); Jiang et al., "Multivesicular bodies: a mechanism to package lytic and storage functions in one organelle?" *Trends Cell Biol.* 12:362-7 (2002); Katzmann et al., "Ubiquitin-dependent sorting into the multivesicular body pathway requires the function of a conserved endosomal protein sorting complex, ESCRT-I" *Cell* 106:145-55 (2001); and Katzmann et al., "Vps27 recruits ESCRT machinery to endosomes during MVB sorting" *J Cell Biol.* 162:413-23 (2003). In addition, Vps4 protein (i.e., for example, an ATPase) is required for the dissociation of the full ESCRT complex. Raiborg et al., "Protein sorting into multivesicular endosomes" *Cuff Opin Cell Biol* 15:446-55 (2003).

E. VLP Release Inhibition

Studies with a number of virus types, most prominently retroviruses, have shown that cellular proteins involved in the formation of MVBs are recruited by retrovirus gag proteins and other matrix-like proteins by interactions of viral Late Domains with a component of the VPS pathway. Demirov et al., "Retrovirus budding" *Virus Res* 106:87-102 (2004); Morita et al., "Retrovirus budding" *Annu Rev Cell Dev Biol.* 20:395-425 (2004); Pornillos et al., "Mechanisms of enveloped RNA virus budding" *Trends Cell Biol.* 12:569-79 (2002); 44. It has been found that dominant negative mutants of Vps4, CHMP3, and CHMP2 can block retrovirus release. Strack et al., "PIP1/ALIX is a binding partner for HIV-1p6 and EIAV p9 functioning in virus budding" *Cell* 114:689-699 (2003).

Although it is not necessary to understand the mechanism of an invention, it is believed that a dominant-negative mutation of Vps4 or Vps4 A-E228Q is capable of blocking M protein paramyxovirus VLP release. It is further believed that a dominant-negative mutation of CHMP3 (i.e., for example, a subunit of the ESCRT III complex) inhibits M protein paramyxovirus VLP release. These observations indicate not only that the VPS pathway is involved in paramyxoviral budding (i.e., for example, VLP release) but that it is the M protein that directly interacts with the VPS pathway.

It has recently been reported that SV5 VLP and virion release are also inhibited by expression of the dominant negative form of VSP4 implicating the VPS pathway in SV5 assembly and release. Schmitt et al., "Evidence for a new viral late-domain core sequence, FPIV, necessary for budding of a paramyxovirus" *J. Virol.* 79:2988-97 (2005). Furthermore, the sequence FPIV (SEQ ID NO:1) in the SV5 M protein is believed to be a Late Domain. The SV5 M protein, however, is known not to be sufficient for particle release. Schmitt et al., "Requirements for budding of paramyxovirus simian virus virus-like particles" *J Virol* 76:3952-64 (2002). Consequently, it is not clear how SV5 uses the VPS pathway or how this sequence might function as a Late Domain.

In one embodiment, a sequence analysis of an NDV M protein also shows the presence of an FPIV motif (SEQ ID NO:1). In one embodiment, an NDV M protein further comprises a PXXP motif (SEQ ID NO:2) and an YXXL motif (SEQ ID NO:3), sequences not found in the SV5 M protein. Other motifs identified in the art might also be candidate Late Domains for other paramyxovirus M proteins; i.e., domains that could function in budding independent of other viral proteins. Demirov et al., "Retrovirus budding" *Virus Res* 106:87-102 (2004); and Freed, E. O., "Viral late domains" *J. Virol.* 76:4679-87 (2002).

F. Host-Specific VLP Expression

Virus-like particle expression from human 293T cells have been reported in three other paramyxovirus systems (Sendai virus (SV), PIV1, and SV5) at efficiencies ranging between 18% to 70%. Schmitt et al., "Requirements for budding of paramyxovirus simian virus virus-like particles" *J Virol* 76:3952-64 (2002); Sugahara et al., "Paramyxovirus Sendai virus-like particle formation by expression of multiple viral proteins and acceleration of its release by C protein" *Virology* 325:1-10 (2004); and Takimoto et al., "Role of matrix and fusion proteins in budding of Sendai virus" *J. Virol.* 75: 11384-91 (2001).

In one embodiment, the present invention contemplates a method comprising improving the efficiency of paramyxovirus VLP release by using cells from the natural host of the virus. In one embodiment, a paramyxovirus is selected from the group including, but not limited to, Newcastle disease virus, measles virus, parainfluenza virus 3, or respiratory syncytial virus. In one embodiment, a M protein paramyxovirus VLP is released from avian cells with an efficiency of 90%. In another embodiment, M protein paramyxovirus VLP is released from human 293T cells with an efficiency of 50%. Furthermore, the efficiency of release of both M protein VLPs, as well as complete VLPs, from COS cells was significantly lower than release from avian cells; a difference that is not due to a lower expression level of viral proteins in COS cells versus avian cells. Although it is not necessary to understand the mechanism of an invention, it is believed that differences between the efficiencies of paramyxovirus VLP formation may be due to a host cell-specific dependency.

It is known that the protein requirements for VLP formation in other paramyxovirus systems also vary. For example, paramyxovirus systems comprising M proteins of SV, hPIV1 and SV5 are considered involved in directing virus assembly and budding, but there are differences in the role of M protein in actual particle formation. Coronel et al., "Human parainfluenza virus type 1 matrix and nucleoprotein genes transiently expressed in 12 mammalian cells induce the release of virus-like particles containing 13 nucleocapsid-like structures" *J. Virol.* 73:7035-8 (1999); Schmitt et al., "Requirements for budding of paramyxovirus simian virus virus-like particles" *J Virol* 76:3952-64 (2002); Sugahara et al., "Paramyxovirus Sendai virus-like particle formation by expression of multiple viral proteins and acceleration of its release by C protein" *Virology* 325:1-10 (2004); and Takimoto et al., "Role of matrix and fusion proteins in budding of Sendai virus" *J. Virol.* 75: 11384-91 (2001). Similar to NDV M protein, the SV and hPIV1 M proteins were sufficient for particle release, the SV5 M protein, however, was not sufficient. SV5 M protein co-expression with NP and at least one glycoprotein was required for efficient formation and release of SV5 VLPs. Schmitt et al., "Requirements for budding of paramyxovirus simian virus virus-like particles" *J Virol* 76:3952-64 (2002).

In one embodiment, the present invention contemplates that only M protein, and no other paramyxovirus protein, can solely direct VLP particle release. Previous studies do indicate that SV F protein may exhibit an autonomous exocytosis activity demonstrated by the release of vesicles containing the only the F protein. Sugahara et al., "Paramyxovirus Sendai virus-like particle formation by expression of multiple viral proteins and acceleration of its release by C protein" *Virology* 325:1-10 (2004); and Takimoto et al., "Role of matrix and fusion proteins in budding of Sendai virus" *J. Virol.* 75: 11384-91 (2001).

In contrast, cells contemplated by the present invention expressing the NDV F protein, alone, did not release F protein-containing material, and cells expressing HN protein, alone, released only trace amounts of very light density material HN protein containing material into the cell supernatants. These observations are similar to other reports showing that expression of SV5 F or HN glycoproteins, alone, did not result in VLP particle release. Schmitt et al., "Requirements for budding of paramyxovirus simian virus virus-like particles" *J Virol* 76:3952-64 (2002). Although it is not necessary to understand the mechanism of an invention, it is believed that despite observations that SV F and other enveloped negative strand virus glycoproteins have been shown to exhibit budding activity, no Late Domains have been identified in any viral glycoproteins. Schmitt et al., "Escaping from the cell: assembly and budding of negative-strand RNA viruses" *Cuff Top Microbiol Immunol* 283:145-96 (2004).

Embodiments of the present invention comprising co-expression of M protein and NP is also in contrast with those reported in the SV system. For example, simultaneous expression of SV M and NP is known to result in the release of VLPs containing both viral proteins. Sugahara et al., "Paramyxovirus Sendai virus-like particle formation by expression of multiple viral proteins and acceleration of its release by C protein" *Virology* 325:1-10 (2004).

G. Protein-Protein Interactions

The present invention contemplates using NDV as a prototype paramyxovirus in order to clarify the role of each paramyxovirus protein in particle assembly and release. Using this model, certain embodiments integrate a definition of the viral protein requirements for assembly and release of VLPs with a characterization of the protein-protein interactions in VLPs formed with different combinations of viral proteins.

Further, in some embodiments the present invention contemplates a co-localization of M protein with the viral glycoproteins in plasma membranes. Although it is not necessary to understand the mechanism of an invention, it is believed that the data presented herein show that particle assembly involves a network of specific protein-protein interactions and likely correct targeting of proteins to specific cellular domains.

In one embodiment, the present invention contemplates, VLP protein interactions form with all combinations of three and four proteins (i.e., for example, when defined by co-immunoprecipitation). In another embodiment, cell surface HN and F proteins are co-localized with M protein when expressed in different combinations with M and NP proteins. In another embodiment, co-expression of two viral proteins with M protein also significantly increased the co-localization of M protein with either HN or F proteins in the plasma membrane indicating increased interactions with M protein.

To define these protein-protein interactions, VLPs formed with different combinations of three and four proteins were solubilized with nonionic detergent and proteins precipitated with cocktails of monospecific antibodies for M, HN, or F proteins. First, each antibody cocktail precipitated all proteins from VLPs formed with M, HN, F and NP, although the efficiency of precipitation for each protein varied with the antibody specificity. Although it is not necessary to understand the mechanism of an invention, it is believed that these results are consistent with a network of interactions between all four proteins such that precipitation of one resulted in the precipitation of the other three proteins but with efficiencies that varied determined by how directly a protein was linked to the precipitated protein.

Protein-protein interactions were more clearly defined by immunoprecipitation of proteins from VLPs formed with all combinations of three proteins. These results show a specific interaction between HN and M proteins, between NP and M protein, and between F protein and NP. (See, FIG. 66). A direct interaction between F protein and M protein was not directly observed but there is likely a weak interaction between F and HN proteins, since anti-F protein antibodies precipitated HN protein from VLPs containing M, HN, and F proteins. The apparent inability for F and M proteins to interact suggest that incorporation of F protein into these VLPs may be mediated by interactions with an HN protein. Alternatively, an interaction between HN protein and NP may also facilitate incorporation processes.

Thus, when all four proteins are co-expressed, NP and HN protein are incorporated into VLPs by a direct interaction with M protein. (See, FIG. 66). Although it is not necessary to understand the mechanism of an invention, it is believed that F protein is likely incorporated indirectly due to interactions with NP and HN protein. It is further believed that an ordered complex of the four proteins is supported by a co-localization of M protein with F protein and M protein with HN protein in the plasma membrane when all four proteins are co-expressed.

However, when only F is expressed with M protein, F protein was likely not significantly incorporated into VLPs because a direct interaction between these two proteins was not observed. (See, FIG. 66). Supporting this conclusion is the observation that there was no co-localization of F and M proteins in the plasma membrane in these cells.

In spite of direct associations of M with NP, there was little NP protein incorporation into VLPs when NP and M proteins were co-expressed in the pair-wise combination. Previous reports that show that the M protein of Sendai virus is recruited in the cytoplasm by the viral nucleocapsid. Stricker et al., "The Sendai virus matrix protein appears to be recruited in the cytoplasm by the viral nucleocapsid to function in viral assembly and budding" *J Gen Virol* 75 (Pt 5): 1031-1042 (1994). Perhaps NP causes the retargeting of M protein to this compartment. Indeed, co-expression of M protein with NP resulted in a 2.5 fold suppression of M protein containing VLP release, a result also consistent with retention of M protein in cells by NP protein.

Although co-immunoprecipitations of VLP proteins formed with M, HN, and F protein indicated a direct interaction of HN protein with M protein, there were only low levels of incorporation of HN protein into VLPs when HN and M proteins were co-expressed in a pair-wise combination. Furthermore, there was little co-localization of the two proteins in the plasma membrane. Perhaps, in the absence of other proteins, HN and M proteins show minimal co-localization in the same regions of the cell, thereby preventing their association. Alternatively, it is also possible that the conformation of the HN protein transmembrane or cytoplasmic tail may be different in the absence of expression of F protein or NP protein inhibiting association of HN protein with M protein. The 50% reduction of M protein VLPs upon co-expression of HN protein with M protein cannot be presently explained but similar results have been previously reported in Sendai virus system. Sugahara et al., "Paramyxovirus Sendai virus-like particle formation by expression of multiple viral proteins and acceleration of its release by C protein" *Virology* 325:1-10 (2004).

It should be realized that immunoprecipitation is not necessary to produce purified VLPs. In one embodiment, the present invention contemplates a VLP preparation comprising pure viral proteins. Protein compositions were compared between purified NDV whole virus and VLPs that have not undergone immunoprecipitation. The data shows that the VLP preparation does not contain any proteins that are not present in the whole virus preparation. See, FIG. 72. Consequently, the VLPs are as pure as the whole virus.

Although it is not necessary to understand the mechanism of an invention, it is believed that VLPs formed with NP, M and F proteins are likely due to interactions between M and NP and interactions between F and NP. (See, FIG. 66). For example, F protein may relocate NP to the plasma membrane drawing M to specific domains containing F protein. Indeed, data presented herein show that addition of NP increases the co-localization of M protein with F protein in the plasma membrane. It is further believed that VLPs formed with NP, M and HN proteins likely form due to interactions of both HN protein and NP with M protein. Data presented herein, show that expression of NP with HN and M proteins increase the co-localization of M and HN proteins in the plasma membrane. One possible hypothesis suggests that NP-M protein interactions alter the conformation of M thereby facilitating its interaction with HN protein. Indeed, surface HN protein in the presence of NP appears more punctuate along the cell edges.

This network of interactions proposed above could account for the conclusions that the cytoplasmic domains (CT) of the HN and F proteins have redundant functions. Schmitt et al., "Requirements for budding of paramyxovirus simian virus 5 virus-like particles" *J Virol* 76:3952-3964 (2002). For example, the CT domain of the F protein may target NP-M complexes to the plasma membrane by interactions with NP protein while the HN protein CT domain targets these complexes by virtue of direct interactions with M protein.

The interaction of M protein and NP suggested by the data herein is supported by studies using Sendai virus. Stricker et al., "The Sendai virus matrix protein appears to be recruited in the cytoplasm by the viral nucleocapsid to function in viral assembly and budding" *J Gen Virol* 75 (Pt 5):1031-1042 (1994). Further, a possible interaction of HN protein with other viral protein is consistent with numerous studies suggesting an interaction of M protein with viral glycoproteins in paramyxovirus-infected cells or in cells transfected with paramyxovirus cDNAs. Ali et al., "Assembly of Sendai virus: M protein interacts with F and HN proteins and with the cytoplasmic tail and transmembrane domain of F protein" *Virology* 276:289-303 (2000); Ghildyal et al., "Interaction between the respiratory syncytial virus G glycoprotein cytoplasmic domain and the matrix protein" *J Gen Virol* 86:1879-1884 (2005); Henderson et al., "Sorting of the respiratory syncytial virus matrix protein into detergent-resistant structures is dependent on cell-surface expression of the glycoproteins" *Virology* 300:244-254 (2002); Sanderson et al., "Sendai virus assembly: M protein binds to viral glycoproteins in transit through the secretory pathway" *J Virol* 67:651-663 (1993); and Yoshida et al., "Membrane (M) protein of HVJ (Sendai virus)—Its role in virus assembly" *Virology* 71:143-161 (1976). Indeed, it has been reported that the respiratory syncytial virus G protein specifically interacts with M protein. However, there are no previous reports of a direct interaction between F protein and NP. It is possible that interactions between viral proteins vary within paramyxoviruses and the requirements for formation of VLPs may depend upon the distribution of late domains on the viral proteins. The results presented herein are consistent with the proposal that the NDV M protein buds and releases indiscriminately from different cellular membranes in the absence of other viral proteins. Although it is not necessary to understand the mechanism of an invention, it is believed that when both glycoproteins and M proteins are present in the plasma membrane, the M protein-plasma membrane association has an improved stability. It is further believed that NP association with F and M protein may also further stabilize and organize the network of interactions within the assembling particle.

This protein-protein interacting network hypothesis has support from observations comparing electron micrographs of whole virus (B1) with VLPs formed only with M protein, and VLPs formed with NP, M, F, and HN proteins. See, FIG. 73. When all four viral proteins are present, the VLP size and shape is very similar to the whole virus. However, an M protein-only VLP size and shape is more heterogeneous when compare to the whole virus but is still remarkably similar.

In one embodiment, the present invention contemplates a VLP production system for NDV. In one embodiment, the M protein facilitates NDV VLP budding such that NDV VLP budding is virtually non-existent in the absence of M protein. In other embodiments, specific protein-protein interactions occur in VLPs involved in the ordered assembly of particles. In one embodiment, an interaction between M and HN or F and NP directs the targeting of M and NP into assembly sites within the plasma membrane.

III. Paramyxoviral Diseases

The present invention is not limited to NDV, measles, parainfluenza virus 3, and respiratory syncytial paramyxovirus diseases. Many other paramyxoviruses diseases are also within the scope of this invention. For example, both human diseases (See Table 1) and animal diseases (See Table 2) are contemplated.

TABLE 1

Paramyxovirus-Mediated Human Diseases Susceptible To VLP Vaccination

| Virus Type | Disease Type | Current Vaccination |
|---|---|---|
| Parainfluenza (1, 2, 3, and 4) | Acute Respiratory Infection | None |
| Mumps | Childhood Disease | Live Attenuated Virus |
| Measles | Childhood Disease | Live Attenuated Virus |
| Respiratory Syncytial | Serious Respiratory Infection | None |
| Nipah | Emerging Infection Acute Neurological Disease | None |
| Hendra | Emerging Infection Acute Neurological Disease | None |
| Metapneumovirus | Acute Respiratory Infection | None |

TABLE 2

Paramyxovirus-Mediated Animal Diseases Susceptible To VLP Vaccination

| Virus Type | Animal Species |
| --- | --- |
| Canine Distemper | Dogs |
| Rhinderpest | Cattle |
| Pneumoviruses | Birds |

A. Newcastle Disease

Newcastle disease virus (NDV) is an avian pathogen. There are different strains of this virus that have been isolated in many regions of the world. Some strains are avirulent and are used as live attenuated vaccines. Others are virulent and cause severe systemic disease in birds with a high mortality rate. Because of the threat to the poultry industry, the United States government has classified virulent NDV strains as select agents under the Patriots Act.

Most chickens in the United States are vaccinated with an avirulent NDV strain. The current vaccine, however, is not ideal. The vaccine, a live attenuated virus, infects chickens and causes a mild respiratory disease. As a result, vaccinated birds have a lower body weight and lower egg production than unvaccinated birds. For this reason, many other countries do not vaccinate against NDV. Thus, there are periodic outbreaks of the disease in these countries forcing massive bird slaughter to contain the disease. Flocks of vaccinated chickens can also be susceptible to some NDV virulent strains. Consequently, there have been Newcastle disease virus outbreaks in the United States. For example, there was an NDV outbreak in California in 2001-2002.

What is needed is a NDV vaccine that does not have negative productivity consequences and can induce a broader range of protection than currently used vaccines.

In birds, clinical evidence of NDV includes, but is not limited to, the respiratory, neurological and gastrointestinal systems. Clinical signs suggestive of Newcastle disease, are observed mainly in young birds. Common symptoms include, but are not limited to, inability to walk or fly, walking in circles, paralysis, twisted necks, depression, and high frequency of sudden death. In mammals, symptoms of Newcastle disease may include, but are not limited to, acute conjuctivitis.

A significant problem of the currently utilized NDV vaccines is a failure to protect against all NDV strains. Currently, inactivated NDV vaccines (i.e., attenuated) are sometimes used to vaccinate flocks of birds. While eliminating the detrimental effects of a live virus vaccination, these vaccines still have the disadvantage that they do not stimulate a broad spectrum of immune responses. Further, incomplete attenuation results in a percentage of vaccinated birds contracting Newcastle disease. These vaccines are also more expensive than embodiments contemplated by the present invention due to the increased manipulation required for inactivation and the monitoring of the effectiveness of inactivation.

Another problem with currently used vaccines, either live virus or inactivated virus, is that it is difficult to distinguish between birds that have been vaccinated and those that have been infected with a wild virus. The present invention contemplates antigens incorporated into a VLP preparation comprising a sequence tag. In one embodiment, the sequence tag may be detected in vivo, thereby identifying a vaccinated animal.

B. Measles

Measles is believed to be a childhood infection characterized by fever, cough, coryza (i.e., for example, an upper respiratory tract infection or inflammation), and often conjunctivitis followed by a maculopapular rash. It has been observed that the severity of the disease varies with the strain of the virus as well as the health status of the infected children. In most children, recovery is complete. However, there is a low incidence of neurological complications of varying severity. Furthermore, malnourishment or another underlying disease can significantly increase the severity of the disease. In addition, the infection is immunosuppressive resulting in increased susceptibility of the child to other life threatening infections, particularly in a third world setting.

The currently used vaccine is a live, attenuated virus that is effective in generating a protective immune response. However, the age of immunization is problematic. Vaccination too early results in a poor antibody response due to maternal antibody. Increasing the dose to overcome this effect results in immunosuppression and increased susceptibility to other potentially life threatening infections. Vaccination at a later age places the infant at a risk of acquiring the disease prior to immunization but after the maternal antibody level declines. Thus there is a need for a vaccine that will generate an effective immune response in the face of material antibody and, more importantly, a vaccine that will not be immunosuppressive at any dosage. In one embodiment, the present invention contemplates that VLPs are a candidate for such a vaccine.

Certain embodiments of the present invention provide virus-like particles (VLPs) as a safe, broad-spectrum, and effective vaccine to protect mammals from a measles virus. Additionally, these embodiments provide systems and protocols for the large-scale, economical production of a measles VLP vaccine (i.e., for example, to be useful as a vaccine, VLP production must be easy and economical).

The present invention contemplates conditions for the generation of VLPs of a measles virus strain. In another embodiment, the VLPs comprise the same major antigens as infectious virus (but, of course, lack the complete viral genome). In another embodiment, the VLPs comprise major antigens having the same ratios as infectious virus. In one embodiment, the major antigens are selected from the group comprising nucleocapsid protein, membrane/matrix protein, hemagglutinin protein, and fusion protein.

Other embodiments of the present invention provide antigens derived from many different measles strains that may be incorporated into a single VLP preparation. A significant problem of the currently utilized measles vaccines is a failure to protect against all measles strains.

Measles is thought to be a highly contagious viral illness having primary symptoms including, but not limited to, fever, cough, conjunctivitis (i.e., redness and irritation in membranes of the eyes), and spreading rash. The viral infection may be spread by contact with droplets from the nose, mouth, or throat of an infected person. The incubation period is 8 to 12 days before symptoms generally appear.

Immunity to the disease occurs after vaccination or active infection. Currently, vaccination is limited to attenuated live virus that has a significant risk of causing measles in the vaccinated subject. Further some believe that the Measles-Mumps-Rubella vaccine can cause autism. Before widespread immunization, measles was so common during childhood that the majority of the population had been infected by age 20. Measles cases dropped over the last several decades to virtually none in the U.S. and Canada because of widespread immunization, but rates are currently on the rise. Public fear, therefore, results in lower vaccination rates that can cause outbreaks of measles, mumps, and rubella—which can be serious. One advantage of one embodiment of the present invention is that a VLP non-replicating measles vaccine carries no risk of infection. The VLP vaccine is thus expected to generate a much higher compliance rate and subsequently the measles occurrence should drop dramatically.

In one embodiment, measles symptoms include, but are not limited to, sore throat, runny nose, cough, muscle pain, fever, bloodshot eyes, tiny white spots inside the mouth (called Koplik's spots), photophobia (light sensitivity), a rash appearing around the fifth day of the disease and lasting 4-7 days that usually starts on the head and spreads to other areas, progressing downward (the rash may be a maculopapular rash appearing as both macules (flat, discolored areas) and papules (solid, red, elevated areas) that later merge together (confluent)), further the rash may itch.

There is no specific treatment of measles, though some children may require supplementation with Vitamin A. Symptoms may be relieved with bed rest, acetaminophen, and humidified air. The probable outcome is excellent in uncomplicated cases. However, pneumonia or encephalitis are possible complications.

C. Respiratory Syncytial Virus

Respiratory syncytial virus (RSV) is believed to be the single most common cause of hospitalization for respiratory infection of infants and young children worldwide. Re-infection also commonly occurs. RSV attack rates for all infant populations is estimated between 100% and 83% and an estimated 50% of these experience two or more infections during the first two years of life (reviewed in Collins, et al, Respiratory Syncytial Virus, in Fields Virology, Ed. Knipe, D. and Howley, P. Lippincott Williams and Wilkins, 2001). RSV is also increasingly recognized as a serious pathogen for the elderly.

Currently, there is no vaccine available for this pathogen. Early trials with a formalin inactivated virus preparation had the disastrous effect of enhancing the severity of disease upon exposure to the live virus. In addition, protein subunit vaccines had a similar effect in experimental animals. It is speculated that proteins in an abnormal conformation, either induced by formalin treatment or by expression and purification of individual proteins, resulted in a loss of epitopes that stimulated a protective immune response. Animal studies suggested that immunopathology was due to immune cells (reviewed in Collins, et al, Respiratory Syncytial Virus, in Fields Virology, Ed. Knipe, D. and Howley, P. Lippincott Williams and Wilkins, 2001. VLPs formed with RSV proteins will likely incorporate viral proteins in their native conformation. These immunogens have the potential to stimulate a protective immune response and to avoid the adverse effects of unfolded proteins.

Certain embodiments of the present invention provide virus-like particles (VLPs) as a safe, broad-spectrum, and effective vaccine to protect mammals from Respiratory Syncytial Virus (RSV). Additionally, these embodiments provide systems and protocols for the large-scale, economical production of RSV VLP vaccines (i.e., for example, to be useful as a vaccine, VLP production must be easy and economical).

The present invention contemplates conditions for the efficient generation of VLPs of a virulent RSV strain. In another embodiment, the VLPs comprise the same major antigens as infectious virus. In another embodiment, the VLPs comprise major antigens having the same ratios as infectious virus. In one embodiment, the major antigens are selected from the group comprising nucleocapsid protein, membrane/matrix protein, G or attachment protein, and fusion protein.

Other embodiments of the present invention provide antigens derived from many different RSV strains that may be incorporated into a single VLP preparation. A significant problem of the currently utilized RSV vaccines is a failure to protect against all RSV strains.

Respiratory syncytial virus (RSV) is believed to be a very common virus that causes mild cold-like symptoms in adults and older healthy children. RSV may cause serious respiratory infections in young babies, especially those born prematurely, who have heart or lung disease, or who are immunocompromised.

RSV is believed to be the most common respiratory pathogen in infants and young children. Specifically, RSV is believe to infect nearly all infants by the age of two years. Seasonal outbreaks of acute respiratory illness occur each year, on a schedule that is somewhat predictable in each region. The season typically begins in the fall and runs into the spring.

RSV may be spread easily by physical contact including, but not limited to, touching, kissing, and shaking hands with an infected subject. Although it is not necessary to understand the mechanism of an invention, it is believed that RSV transmission is usually by contact with contaminated secretions, which may involve tiny droplets or objects that droplets have touched. RSV can live for half an hour or more on the skin surface. It is also believed that RSV can also live up to five hours on countertops and for several hours on used tissues, consequently, RSV often spreads very rapidly in crowded households and day care centers.

In one embodiment, the present invention contemplates a VLP RSV vaccine that prevents the development of infant and young adult diseases such as, but not limited to, pneumonia, bronchiolitis (inflammation of the small airways of the lungs), and tracheobronchitis (croup). In one embodiment, the present invention contemplates a VLP RSV vaccine that prevents the development of a mild respiratory illness in healthy adults and older children.

The lack of a safe and effective RSV vaccine poses a significant public safety and health risk. For example, it is believed that each year up to 125,000 infants are hospitalized due to severe RSV disease; and about 1-2% of these infants die. Further, infants that are: i) born prematurely; ii) suffering chronic lung disease; iii) immunocompromised; or iv) afflicted with certain forms of heart disease are at increased risk for severe RSV disease. Even adults who are exposed to tobacco smoke, attend daycare, live in crowded conditions, or have school-age siblings are also at higher risk of contracting RSV.

In one embodiment, the present invention contemplates RSV symptoms including, but not limited to, nasal congestion, nasal flaring, cough, rapid breathing (tachypnea), breathing difficulty or labored breathing, shortness of breath, cyanosis (bluish discoloration of skin caused by lack of oxygen), wheezing, fever, or croupy cough (often described as a "seal bark" cough). It should be recognized that symptoms are variable and differ with age. For example, infants less than one year old are most severely affected and often have the most trouble breathing. Conversely, older children usually have only mild, cold-like symptoms. In general, symptoms usually appear 4-6 days after exposure.

Because there is no known treatment for an active RSV infection, those in the art have considered preventative drugs. For example, Synagis® (palivizumab) has been approved for prevention of RSV disease in children younger than 24 months of age who are at high risk for serious RSV disease. Synagis® however, must be prescribed and given as a monthly shot to provide complete protection.

D. Parainfluenza 3 (PIV 3)

PIV3 is believed to be a common cause of respiratory disease (rhinitis, pharyngitis, laryngitis, bronchiolitis, and pneumonia). This virus is the second most common cause of respiratory infection in hospitalized pediatric patients. No vaccines are available for PIV 3. A number of different approaches to vaccination have been considered but none has resulted in a licensed vaccine. (reviewed in Chanock, et al, Parainfluenza Viruses, in Fields Virology, Ed. Knipe, D. and Howley, P. Lippincott Williams and Wilkins, 2001).

Physiologically, PIV 3 usually infects the upper and lower respiratory systems. Currently, five serotypes of Parainfluenza virus are known (1, 2, 3, 4a, and 4b), all of which are associated with causing disease. Children are believed highly susceptible to Parainfluenza and may be responsible for approximately 40 percent to 50 percent of all cases of croup, and 10 percent to 15 percent of bronchiolitis and bronchitis and some pneumonias. In the general population, the incidence of parainfluenza is unknown but suspected to be very high. Illness causing only a runny nose and cold-like symptoms may pass as a simple cold rather than parainfluenza. Risk factors include young age. By school age most children have been exposed to parainfluenza virus. Most adults have antibodies against parainfluenza although they can get repeat infections.

Laryngotracheobronchitis (i.e., for example, croup) is believed to be a common clinical manifestation of parainfluenza virus infection. Parainfluenza viruses are found uncommonly associated with other respiratory tract infections in children such as tracheobronchitis, bronchiolitis, and bronchopneumonia. Occasionally, a mild non-specific illness is seen after parainfluenza virus infection. Parainfluenza viruses produce disease throughout the year, but peak prevalence rates occur during wintertime outbreaks of respiratory tract infections, especially croup, in children throughout the temperate zones of the northern and southern hemispheres. Parainfluenza virus infections are primarily childhood diseases, the highest age-specific attack rates for croup occur in children below the age of 3 years. Serotype 3 infections occur earliest and most frequently, so that 50% of children in the US are infected during the first year of life and almost all by 6 years, as determined by seroepidemiological studies.

Parainfluenza viruses generally enters a host through the inhalation of infected droplet nuclei. Virus multiplication occurs throughout the tracheobronchial tree, inducing the production of mucus. The vocal cords of the larynx become grossly swollen, causing obstruction to the inflow of air, which is manifested by inspiratory stridor. In adults, the virus is usually limited to causing inflammation in the upper parts of the respiratory tract. In infants and young children, the bronchi, bronchioles and lungs are occasionally involved, which may reflect on the small size of the airways and the relative immunological immaturity. Viraemia is neither an essential nor a common phase of infection.

Typically, children may exhibit a croupy cough, inspiratory stridor, hoarse voice or cry and respiratory difficulty on inspiration, and are usually afebrile. About 80% of patients exhibit a cough and runny nose 1 to 3 days before the onset of the cough. Respiratory rhonchi are heard frequently throughout the lung fields. Radiological examination is usually normal. Occasionally the epiglottitis is grossly swollen and reddened. Severe airway obstruction may ensue, necessitating an emergency tracheotomy.

IV. VLP Vaccines

Paramyxovirus VLP vaccines are novel in the art. While virosome vaccines are known, these vaccines require disrupting a purified virus, extracting the genome, and reassembling particles with the viral proteins and lipids to form lipid particles containing viral proteins. This approach is very costly. Also, since the starting material is live virus, there is a danger of contaminating the vaccine with live virus. In addition, the resulting vaccine is likely not a broad-spectrum vaccine. Furthermore, the immune response to this vaccine cannot be distinguished from a virus infection.

Paramyxovirus VLPs are believed to be a highly effective type of subunit vaccine that mimics the overall virus structure without containing genetic material that results in host cell infection. For example, a virus-like particle may completely lack the DNA or RNA genome while maintaining the authentic conformation of viral capsid proteins. Consequently, the VLP is non-infectious. Further, a virus-like particle comprising viral capsid proteins may undergo spontaneous self-assembly similar to authentic viruses. It is known, however, that polyomavirus VLP preparations are among the least developed in the art. Noad et al., "Virus-like particles as immunogens" Trends Microbiol 11:438-444 (2003).

In one embodiment, the present invention contemplates a vaccine comprising a paramyxovirus VLP. In one embodiment, the paramyxovirus is selected from the group including, but not limited to, Newcastle disease, measles, parainfluenza virus 3, or respiratory syncytial virus. In one embodiment, the VLP comprises an M protein. In another embodiment, the VLP further comprises at least two glycoproteins. In one embodiment, the glycoproteins are selected from the group consisting of F protein and HN protein.

A. Newcastle Disease Virus

Certain embodiments of the present invention provide virus-like particles (VLPs) as a safe, broad-spectrum, and effective vaccine to protect poultry from Newcastle disease virus. Additionally, these embodiments provide systems and protocols for the large-scale, economical production of VLPs (i.e., for example, to be useful as a vaccine, VLP production must be easy and economical).

A silver stain comparison of whole virus (B1) grown in eggs are compared to VLPs grown in large scale tissue culture demonstrates that VLPs may be produced in microgram quantities (i.e., sufficient for immunogenicity testing in mice). See, FIG. 74. VLPs have been rapidly purified from large amounts of media to facilitate large scale VLP production techniques. See, Table 3.

TABLE 3

Large Scale VLP Preparations

| Particle | | ng/μl | total volume | Total protein(μg) |
|---|---|---|---|---|
| B1 virus | HN | 23.05 | 1 ml | 23.05 |
| | F | 11.09 | | 11.09 |
| | NP | 100.32 | | 100.09 |
| | M | 75.08 | | 75.08 |
| | | | | 209.54 total |
| VLP prep1 | HN | 177.35 | 1.1 ml | 195.08 |
| | F | 349.56 | | 384.52 |
| | NP | 140.19 | | 154.21 |
| | M | 72.02 | | 79.22 |
| | | | | 813.04 total |
| VLP prep2 | HN | 109.70 | 0.5 ml | 54.85 |
| | F | 85.42 | | 42.71 |
| | NP | 98.24 | | 49.71 |
| | M | 63.50 | | 31.75 |
| | | | | 178.43 total |
| VLP prep 3 | HN | 92.55 | 0.2 ml | 18.4 |
| | F | 53.54 | | 10.70 |
| | NP | 92.13 | | 18.26 |
| | M | 60.89 | | 12.18 |
| | | | | 59.54 total |

Preparation 1 was contaminated with albumin, which co-migrates with F protein. Therefore, the amounts of F in Preparation 1 appear enhanced when compared to NP. This albumin contamination was successfully eliminated in Preparations 2 & 3

Although it is not necessary to understand the mechanism of an invention, it is believed that virus (B1) grown in eggs (as is standard in the art) are deficient in the HN and F glycoproteins (typical of avirulent (AV) virus particles), unlike the presently disclosed VLP production methods in which virus (AV) VLP comprise HN and F glycoproteins. In one embodiment, the present invention contemplates an improved vaccine comprising an NVD VLP comprising HN and F glycoproteins.

NDV subunit protein expression has been reported in the art. For example, electron microscopic examination of negatively stained extracellular fluids (ECF) from *Spodoptera frugiperda* cell cultures infected with a recombinant baculovirus expressing the Newcastle disease virus (NDV) haemagglutinin-neuraminidase (HN) revealed NDV-like envelopes which resembled the envelopes of authentic NDV. Immunogold staining with anti-NDV HN monoclonal antibodies demonstrated HN antigen in spikes on the NDV-like envelopes. The ECF from the recombinant-infected cultures also contained baculovirus particles which resembled standard baculovirus particles except that some showed polar protrusions of the envelope. Unlike the embodiments contemplated in the present invention, it was concluded that NDV HN, in the absence of the matrix protein (i.e., M protein), might be able to initiate and control the production of viral envelopes which are morphologically identical to those of authentic NDV. Nagy et al., "Synthesis of Newcastle disease virus (NDV)-like envelopes in insect cells infected with a recombinant baculovirus expressing the haemagglutinin-neuraminidase of NDV" *J Gen Virol.* 72:753-756 (1991).

In one embodiment, the present invention contemplates a method comprising a commercially usable NDV VLP vaccine. In one embodiment, producing a NDV VLP vaccine is economical and efficient. In another embodiment, immunization with an NDV VLP vaccine stimulates production of a broad spectrum of protective antibodies. In one embodiment, an avian cell line continuously expresses at least four NDV glycoproteins In one embodiment, the present invention contemplates a method producing NDV VLP vaccines in a transient expression system. In one embodiment, the system comprises avian cells transfected with nucleic acid (e.g., in plasmids, expression vectors, etc) encoding at least one NDV viral glycoprotein. In one embodiment, the system comprises an avian cell line with select viral genes as part of the avian cell chromosome, wherein the incorporated viral gene continually releases NDV VLP particles useful for vaccines. In one embodiment, the viral gene comprises a viral glycoprotein. In one embodiment, the viral glycoprotein is selected from the group comprising NP protein, M protein, F-K115Q protein, or HN protein.

In one embodiment, the present invention contemplates a method of generating VLPs comprising antigens for many different NDV strains of NDV. Although it is not necessary to understand the mechanism of an invention, it is believed that an integrated NDV vaccine confers a broader protection range than that generated by current vaccines. In one embodiment, the present invention contemplates an VLP vaccine expression system comprising a first cDNA encoding a first viral protein gene from a first strain; a second cDNA encoding a second viral protein gene from a second strain; and a third cDNA encoding a third viral protein gene from a third strain.

In one embodiment, the first viral protein gene is selected from the group comprising HN protein, F protein, NP protein or M protein. In one embodiment, the first strain is selected from the group comprising strain Hertz, strain AV, or strain B1. In one embodiment, the second viral protein gene is selected from the group comprising HN protein, F protein, NP protein or M protein. In one embodiment, the second strain is selected from the group comprising strain Hertz, strain AV, or strain B1. In one embodiment, the third viral protein gene is selected from the group comprising HN protein, F protein, NP protein or M protein. In one embodiment, the third strain is selected from the group comprising strain Hertz, strain AV, or strain B1. In one embodiment, the present invention contemplates a method for detecting a viral protein gene incorporated into a VLP vaccine comprising contacting the viral protein gene with strain specific antibodies or incorporated sequence tags.

In one embodiment, the present invention contemplates a method comprising a baculovirus expression system producing NDV VLP vaccines. Although it is not necessary to understand the mechanism of an invention, it is believed that baculovirus expression systems are capable the highest levels of expression of a protein of all expression systems available. In one embodiment, a baculovirus expression system produces milligrams of VLP vaccine. In one embodiment, a baculovirus expression vector encodes an NDV VLP vaccine. In one embodiment, an insect cell is transfected with a baculovirus expression system encoding an NDV VLP vaccine. In one embodiment, a baculovirus vector comprises at least four NDV structural proteins. For a VLP to be a realistic vaccine candidate, it needs to be produced in a safe expression system that is amenable to large-scale production. An insect-cell-based protein production system has many advantages for VLP production. The first is that large amounts of recombinant proteins can be produced in high-density cell culture conditions in eukaryotic cells, resulting in high recovery of correctly folded antigen. Second, as the insect cells used for vaccine production can be cultured without mammalian-cell-derived supplements, the risk of culturing opportunistic pathogens is minimized. Third, the baculovirus used for recombinant protein expression has a narrow host range that includes only a few species of *Lepidoptera*, and therefore represents no threat to vaccinated individuals. Fourth, baculovirus is easily inactivated by simple chemical treatment, and is localized mainly in the nucleus and culture media of insect cell preparations, whereas most VLPs are purified from cytoplasmic extracts. Finally, the baculovirus system can be scaled-up for large-scale vaccine production.

B. Measles

In one embodiment, the present invention contemplates a measles vaccine comprising a measles virus like particle, wherein said particle comprises a measles matrix protein. In one embodiment, the vaccine further comprises at least two measles glycoproteins.

The use of VLP vaccines have been proposed for the measles paramyxovirus virus, but only retrovirus HIV VLP production was demonstrated in yeast cells. Morikawa Y., "Virus-like micrograms and process of producing the same" United States Patent Application Publ. No. 20040009193 (2004). This proposed technique is limited to VLP expression in eukaryotic bacterial cells and does not suggest either baculovirus or mammalian cell culture techniques. Further, there is no showing that these eukaryotic VLP vaccines are, in fact, safe and effective. More importantly, Morikawa's VLP measles vaccines relies upon type IV budding as described by Garoff et al., supra. Some embodiments described herein clearly demonstrate that the ribonucleic acid core is not required for paramyxovirus budding; as Garoff et al. teaches.

Another approach suggested as useful for the development of a paramyxovirus measles vaccine involves gene therapy techniques by administering a DNA vaccine. Robinson et al., "Compositions and methods for generating an immune response" United States Patent Application Publ. No. 20040105871 (2004). This technique has been demonstrated by the stable transfection of a host genome with an expression cassette comprising an HIV DNA VLP vaccine. See also, Mazzara et al., "Self assembled, defective, nonself-propagating viral particles" U.S. Pat. No. 5,804,196 (1998) (herein incorporated by reference).

An alternative gene therapy approach suggests incorporating live attenuated measles virus into an expression vector to produce a vaccine, either in vivo or in vitro. VLPs, however, are not contemplated for measles virus vaccines. Herold J., "SARS-coronavirus virus-like particles and methods of use" United States Patent Application Publ. No. 20050002953 (2005).

C. Respiratory Syncytial Virus

In one embodiment, the present invention contemplates a respiratory syncytial virus vaccine comprising a respiratory syncytial virus like particle, wherein said particle comprises a respiratory syncytial virus matrix protein. In one embodiment, the vaccine further comprises at least two respiratory syncytial virus glycoproteins.

VLPs have been disclosed for the production and use of HIV-related vaccines. In passing, it is suggested that many other virus (i.e., respiratory syncytial virus and measles virus) might also be compatible with the disclosed technology. No detail, however, is presented to support these speculations. Barnett et al., Expression of HIV polypeptides and production of virus-like particles" U.S. Pat. No. 6,602,705 (2003).

It has also been suggested that it might be possible to produce respiratory syncytial virus VLP vaccines in a manner identical to Bluetongue VLPs comprising the VP3, VP7, VP2, and VP5 genes. Ermak et al., "Oral immunization with multiple particulate antigen delivery system" U.S. Pat. No. 5,690,938 (1997) (herein incorporated by reference). Aside from this brief mention, Ermak does not provide any technical information regarding paramyxoviruses, and is limited to the Orbivirus genus (Reoviridae family).

In vivo mouse cytotoxic lymphocyte responses (i.e., an immunization response) are hypothesized to occur following exposure to recombinant HIV-1-IIIB gp160 envelope glycoprotein complexed to microspheres and administered as a vaccine. Rock, K. L., "Compositions and methods for inducing cytotoxic T lymphocyte responses by immunization with protein antigens" U.S. Pat. No. 6,328,972 (2001). Rock suggests that VLPs having antigens to either respiratory syncytial virus or measles virus might also stimulate these cytotoxic lymphocytes to generate an immune response. There is, however, no discussion, of any technical details or expectations of success regarding this approach. In fact, Rock does not show any data relevant to VLP vaccines for any antigen.

D. Parainfluenza 3 Virus

In one embodiment, the present invention contemplates a parainfluenza 3 virus vaccine comprising a parainfluenza 3 virus like particle, wherein said particle comprises a parainfluenza 3 virus matrix protein. In one embodiment, the vaccine further comprises at least two parainfluenza 3 glycoproteins.

E. Enhancement of VLP Vaccines

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

In the case of the oral formulations, the manipulation of T-cell subsets employing adjuvants, antigen packaging, or the addition of individual cytokines to various formulation can result in improved oral vaccines with optimized immune responses.

1. Adjuvants

The present invention further contemplates immunization with or without adjuvant. In one embodiment, the present invention contemplates a co-administration of a paramyxovirus VLP vaccine and an adjuvant, wherein the resultant immune response is enhanced. If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant. Another preferred use of adjuvant is the use of Gerbu adjuvant (GMDP; C.C. Biotech Corp.). The invention also contemplates the use of RIBI fowl adjuvant (MPL; RIBI Immunochemical Research, Inc.). Other adjuvants include, but are not limited to, potassium alum, aluminum phosphate, aluminum hydroxide, QS21 (Cambridge Biotech), Titer Max adjuvant (CytRx), or Quil A adjuvant.

2. Cytokines

In one embodiment, the present invention contemplates a co-administration of a paramyxovirus VLP vaccine and a cytokine, wherein the resultant immune response is enhanced. Although it is not necessary to understand the mechanism of an invention, it is believed that cytokines may modulate proliferation, growth, and differentiation of hematopoietic stem cells that ultimately produce vaccine related antibodies. In one embodiment, a cytokine may be selected from the group comprising interleukin-12 (IL-12), granulocyte-macrophage colony-stimulating factor (GM-CSF), interleukin-6 (IL-6), interleukin-18 (IL-18), alpha, beta, or gamma-interferon ($\alpha,\beta,\gamma$-IFN) or chemokines. Especially preferred cytokines include IL-12 and GM-CSF. The cytokines can be used in various combinations to fine-tune the response of an animal's immune system, including both antibody and cytotoxic T lymphocyte responses, to bring out the specific level of response needed to control or eliminate a paramyxovirus infection.

V. VLP Vaccine Expression Systems

In one embodiment, the present invention contemplates methods to produce VLP vaccines economically and at high production rates. In one embodiment, the present invention contemplates a method comprising transfecting a cell culture with a nucleic acid expression vector comprising a paramyxovirus VLP vaccine cassette. In one embodiment, the cell culture comprises avian cells (i.e., for example, ELL-0 cells). In one embodiment, the cell culture comprises a viruses (i.e., for example, baculovirus).

A. Avian Continuous Cell Culture Expression Systems

In one embodiment, the present invention contemplates a method comprising expressing paramyxoviral proteins using an avian cell culture (i.e., for example, ELL-0 cell culture). In one embodiment, the cell culture continuously expresses the proteins. In one embodiment, the paramyxoviral proteins are selected from the group including, but not limited to, Newcastle disease viral protein, measles virus proteins, parainfluenza virus 3, or respiratory syncytial virus proteins. In one embodiment, the paramyxoviral proteins are selected from the group including, but not limited to, matrix (M) proteins, nucleocapsid (NP) proteins, fusion (F) proteins, or hemagglutinin-neuraminidase (NM) proteins (and combinations thereof).

To generate avian cell lines expressing paramyxoviral proteins, it is useful to integrate the viral genes into an avian cell chromosome. The use of retrovirus vectors is a useful approach to accomplish this integration. Avian cells can be infected with a retrovirus containing a paramyxovirus gene and, as part of the retrovirus replication cycle, the retrovirus genome with the paramyxovirus gene will integrate into the cell chromosome. Four avian cell lines will be made: i) avian cells expressing M, NP, F, and HN proteins; ii) avian cells expressing M, NP, and F; iii) avian cells expressing M, NP, and HN proteins; and iv) avian cells expressing M, HN, and F proteins.

The retrovirus vector may be constructed such that the vector is unable to direct the formation of new, progeny retroviruses in the avian cells (i.e., non-replicability). The general approach for such studies is as follows. The paramyxovirus genes are cloned into a vector with the retrovirus ends (LTRs) and the packaging signal. This vector is, however, replication incompetent due to the lack of essential genes for that process (i.e., for example, gag or pol).

The vector DNA is transfected into a packaging cell line (i.e., for example, GP-293), a cell line expressing the retroviral structural proteins; gag, pol, and env. Also transfected with the vector is another DNA encoding the vesicular stomatitis virus (VSV) G protein (i.e., for example, pVSV-G). These cells then replicate retrovirus vectors and package the vector RNAs in an envelope with the env protein as well as the VSV-G protein (called a pseudotype). These cells release particles, which are then purified and used to infect avian cells. The presence of the VSV-G protein allows these particles to initiate infection in the avian cells and expands the host range of the retrovirus.

Following transfection, the vector RNA is converted to DNA, which is then integrated into the avian cell chromosome. Because the avian cells are not expressing gag or pol, the retrovirus infection does not proceed and no progeny virus are released. The transfected avian cells thus continuously express the integrated paramyxoviral genes, but not retrovirus genes.

This protocol will be repeated to sequentially integrate each of the four paramyxovirus proteins. Cell lines will be characterized for expression of the paramyxovirus genes and the release of VLPs from these cell lines will be verified.

Vectors and packaging cell lines (pantropic retrovirus expression system) to accomplish these steps are available from Clontech (BD Biosciences Clontech). In addition, there is available a vector (Q vector) which is engineered so that transcription of the target gene is driven by an internal promoter once the expression cassette is integrated into the avian cell genome. The Q vectors reduce the likelihood that cellular sequences located adjacent to the vector integration site will interfere with the expression of the paramyxovirus genes or that these sequences are abnormally expressed due to proximity with the retroviral LTR.

B. Baculovirus Expression Systems

In one embodiment, the present invention may be practiced using the BacVector® system (Novagen). This system uses the baculovirus *Autographa californica* nuclear polyhedrosis virus (AcNPV) containing inserted genes to express proteins in an insect cell line (i.e., for example, Sf9). See FIG. 30. The present invention is not limited to one method of integrating target genes in to the AcNPV genome. Numerous different transfer plasmids may be used. For example, by co-transfecting cells with AcNPV DNA and the transfer plasmid, viruses can be isolated to have the genes inserted into the virus genome by homologous recombination (i.e., for example, using BacVector® Triple Cut Virus DNA, Novagen). See FIG. 28. In one embodiment, target genes (i.e., for example, NDV, measles, parainfluenza virus 3, or respiratory syncytial viral particle proteins) may be cloned into a pBAC transfer plasmid to produce recombinant baculovirus vectors. In one embodiment, the recombination may comprise a ligation-independent cloning (LIC) technique. See FIG. 29. For example, a LIC transfer plasmid pBAC/pBACgus-2 cp may encode an upstream His-Tag and S-Tag peptide having an enterokinase (ek) cleavage site. The recombination is facilitated by primer sequences comprising: sense strand, 5' to ATG: GACGACGACAAG (SEQ ID NO:89); antisense strand, 5' to TTA: GAGGAGAAGCCCGG (SEQ ID NO:90).

Upon transfection, the BacVector® DNA will not produce virus unless there is a recombination event between the virus DNA and the transfer plasmid; i.e., a recombination that repairs the circular viral DNA required for replication. In one embodiment, the transfer plasmid comprises pBAC4x-1 (Novagen). See FIG. 31. Although it is not necessary to understand the mechanism of an invention, it is believed that pBAC4x-1 is constructed such that up to four (4) genes can be inserted into a single plasmid and, therefore, a single AcNPV. It is also believed that each gene is expressed using either the polh or the p10 promoters; promoters that can result in very high levels of protein expression from 24-72 hours post-infection. The pBAC4x-1 transfer vector was designed for expression of multi-subunit protein complexes and is capable of expressing the NDV M, NP, HN, and F genes either singly or in any combination.

Subsequent to co-transformation using a transfer plasmid and virus DNA, the infected cells (i.e., for example, Sf9) form plaques and express virus particles. These plaques are then isolated, wherein the expressed virus particles are purified and characterized for inserted protein gene expression. In one embodiment, the present invention contemplates an infected cell expressing virus particles comprising NDV, measles, parainfluenza virus 3, or respiratory syncytial protein genes, wherein the cell was transformed with baculovirus transfer plasmid. In one embodiment, the expression is characterized for optimal conditions, and times of expression, to support large-scale VLP preparation.

AcNPV-infected cells are known to produce extremely high quantities of the major very late gene products; polyhedrin (polh) and p10; 40-50% of the total cellular protein consists of these two gene products by the end of the infection cycle. Very late in infection (i.e., occurring after the budding and release phase), in both insects and in tissue culture, a large majority of the cell's transcriptional activity is dedicated to the polh and p10 promoters, which makes them ideal for use to drive the high-level expression of introduced target genes that replace these viral genes. Yields of up to 100 mg target protein per $10^9$ cells can be obtained.

The convenience of baculoviral expression systems has improved by developing viruses having Bsu36 I restriction sites positioned within an essential gene (i.e., for example, ORF 1629) downstream of the AcNPV polyhedrin gene and in the upstream ORF 603. such that digestion releases a fragment containing a sequence necessary for virus growth.

Kitts et al., *BioTechniques* 14:810-817 (1993). When insect cells are co-transfected with an appropriate recombinant transfer plasmid and Bsu36 I-cut virus DNA, the necessary ORF 1629 sequence is supplied by the transfer plasmid through homologous recombination. The vast majority of the progeny viruses derived from these co-transfections contain the repaired virus with the target gene, thus minimizing the need to screen and multiply plaque purify recombinants. Alternatively, other baculoviral expression systems utilize other essential genes. For example, the progenitor BacVector-1000® and BacVector-2000® viruses from which the high efficiency BacVector-1000 and -2000 Triple Cut Virus DNAs® are prepared for cotransfections have the lacZ gene (β-galactosidase) in lieu of AcNPV polyhedrin gene. These lacZ-negative recombinants can be distinguished easily from any residual parental viruses, which are visualized as blue plaques when stained with X-Gal.

LacZ recombinants form clear plaques on staining with X-Gal, since the target gene replaces lacZ when the transfer plasmid recombines with the viral genome. A third Bsu36 I site within the lacZ gene further reduces the likelihood of reforming the parental virus. In practice and under optimal conditions, the commercially available baculovirus transfection technology produces plaques that are approximately >95% recombinant.

The recent elucidation of the complete sequence of the 133,894 bp AcNPV genome has revealed a total of some 154 potential genes. See FIG. 30. A large number of these genes are unnecessary for growth of the virus in tissue culture. These non-essential genes are known to compete with target genes for cellular resources and can be deleterious to the expression of some gene products. It is preferable to use a baculovirus expression system wherein competing non-essential genes have been deleted.

In one embodiment, the present invention contemplates using pBAC transfer plasmids designed for the expression of target proteins (i.e., for example, NDV, measles, parainfluenza virus 3, or respiratory syncytial viral proteins). Several potential pBAC transfer plasmids are shown in FIG. 31. For example, two vector backbones (shown at the top) differ only by the presence of the reporter β-glucuronidase (gus) gene driven by the p6.9 promoter (i.e., for example, the pBACgus series). Because the gus gene and P6.9 are carried with the target gene into the baculovirus genome, recombinants produce β-glucuronidase and can be identified by staining with X-gluc. The corresponding transfer plasmids lacking the gus indicator gene are about 2 kbp smaller in size and may produce higher cloning efficiencies with some large inserts.

Additionally, LIC vectors including, but not limited to, pBAC-2cp and pBACgus-2cp plasmids are ready for annealing with appropriately prepared inserts. See FIG. 31. In practice, a target sequence is generated by PCR using primers extended with defined sequences. See FIG. 29. For example, vector compatible cohesive ends (13 and 14 bp on the N- and C-terminal coding sequences, respectively) are produced by treatment with T4 DNA polymerase in the presence of dATP. The 3'-5' exonuclease activity of the enzyme digests one strand of the duplex until a dT residue is encountered in the complementary strand, whereupon the available dA is added by the polymerase activity. Aslanidis et al., *Nucleic Acids Res.* 18:6069-6074 (1990). The treated insert and pBAC LIC transfer plasmid are briefly annealed, and the mixture transformed into NovaBlue Competent Cells.

The prepared vectors allow fusion of target genes at the most desirable position relative to the enterokinase cleavage site following the His-Tag and S-Tag fusion sequences. Inserts may be placed such that vector-encoded sequences can be completely removed by enterokinase cleavage. See FIG. 29. In addition, the configuration of restriction sites in the multiple cloning region allows direct subcloning of inserts from many pET bacterial vectors into pBAC-1 or -2 series plasmids. The His-Tag sequence may be incorporated into, for example, the pBAC-1 or -2 vectors and encodes a consecutive stretch of 6 histidines. Alternatively, a S-Tag sequence encodes a 15 AA domain of ribonuclease A, which has a strong affinity for the 104 AA S-protein. Richards et al., In: *The Enzymes*, Vol. IV (Boyer, P. D., Ed.), pp. 647-806, Academic Press, New York (1971). This highly specific protein-protein interaction forms the basis for sensitive detection of fusion proteins with S-protein-reporter molecule conjugates. Chemiluminescent detection of S-Tag fusion proteins may be observed using an S-protein HRP conjugate and SuperSignal™ CL-HRP substrate. (S-Tag Rapid Assay Kit, Novagen).

The pBAC4x vectors are designed for coexpression of up to 4 genes in the same cell. These vectors are extremely useful for expression of multisubunit proteins, multiple copies of a gene, multiprotein complexes, and for studies of protein-protein interactions. Weyer et al., *J. Gen. Virol.* 72:2967-2974 (1991); Belyaev et al., *Nucleic Acids Res.* 21:1219-1223 (1993); and Belyaev et al., *Gene* 156:229-233 (1995).

It is known that baculoviral expression technology may be developed into an eukaryotic virus display system. Boublik et al., *Bio/Technology* 13:1079-1084 (1995). By appropriately engineering the AcNPV major surface glycoprotein (i.e., for example, gp64) functional proteins, including glycoproteins, can be expressed on the virus surface. A pBACsurf-1 transfer plasmid may be designed for in-frame insertion of target genes between the gp64 signal sequence and the mature protein coding sequence, under the control of the polh promoter. See FIG. 31. With this system, it is possible to construct and screen virus libraries of complex proteins for desired functional characteristics.

In one embodiment, the present invention contemplates using baculovirus expression technology to infect an Sf9 insect cell culture to express NDV, measles, parainfluenza virus 3, or respiratory syncytial viral proteins. These cells may be adapted for serum or serum-free monolayer, suspension, or fermentation culture, and ready for direct infection, transfection and plaque assay.

Extracts of wild-type AcNPV infected and uninfected Sf9 cells are useful for blocking non-specific binding of antibodies and other reagents to virus and insect cell proteins. The extracts are also useful for running as negative controls on Western blots, ELISA, binding assays, or enzymatic assays in which target proteins are analyzed in cell lysates.

In one embodiment, the present invention contemplates a VLP vaccine comprising proteins from different paramyxovirus strains. In one embodiment, the paramyxovirus strain is selected from the group including, but not limited to, Newcastle disease virus, measles virus, parainfluenza virus 3, or respiratory syncytial virus. In one embodiment, the NDV strain is virulent. In another embodiment, the virulent NDV strain may be selected from the group comprising strain AV and strain Hertz. In one embodiment, the NDV strain is avirulent. In another embodiment, the avirulent strain comprises strain B1.

In one embodiment, the present invention contemplates a composition comprising a cDNA clones encoding at least one paramyxovirus structural protein. In one embodiment, the structural protein comprises an HN glycoprotein. In one embodiment, the paramyxovirus is selected from the group including, but not limited to, Newcastle disease virus, measles virus, parainfluenza virus 3, or respiratory syncytial virus. In one embodiment, the clone is derived from a virulent NDV strain. In another embodiment, the virulent NDV strain may be selected from the group comprising strain AV and strain Hertz. In another embodiment, the clone is derived from an avirulent NDV strain. In one embodiment, the avirulent NDV strain comprises strain B1.

VI. VLP Vaccine Sequence Tags

In another embodiment, the present invention contemplates a paramyxovirus VLP vaccine such as, but not limited to, a Newcastle disease virus VLP vaccine, a measles virus VLP vaccine, a parainfluenza virus 3 VLP vaccine, or a respiratory syncytial virus VLP vaccine, wherein said vaccine comprises a sequence tag. In one embodiment, the vaccine is administered to a host. In one embodiment, the sequence tag is detected.

In one embodiment, the present invention contemplates a vector comprising at least one cDNA encoding a paramyxoviral protein, wherein said cDNA comprises a sequence tag. In one embodiment, the cDNA is transfected into a host cell. In one embodiment, the cDNA is incorporated into a host genome. In another embodiment, the cDNA resides in the host cytoplasm. In one embodiment, the sequence tag is detected.

A. Antibody Tags

The present invention contemplates some embodiments comprising a paramyxoviral glycoprotein expressed with a terminal sequence tag. In one embodiment, the tag comprises FLAG, HA and MYC tags.

In response to the rapidly growing field of proteomics, the use of recombinant proteins has increased greatly in recent years. Recombinant hybrids contain a polypeptide fusion partner, termed affinity tag (i.e., for example, a sequence tag), to facilitate the purification of the target polypeptides. The advantages of using fusion proteins to facilitate purification and detection of recombinant proteins are well-recognized. The present invention is compatible with various affinity sequence tags including, but not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin. Terpe K., "Overview of tag protein fusions: from molecular and biochemical fundamentals to commercial systems" *Appl Microbiol Biotechnol.* 60:523-33 (2003).

FLAG, HA, and MYC are short amino acid sequences for which there are commercially available antibodies (i.e., for example, ELISA kits). In one embodiment, a F protein comprises a terminal FLAG tag. In one embodiment, the terminal comprises the C-terminal. In another embodiment, the terminal comprises the N-terminal. Although it is not necessary to understand the mechanism of an invention, it is believed that F or HN viral proteins comprising a terminal sequence tag (i.e., for example, FLAG or HA) are completely functional. It is further believed that when an F protein (or any other viral protein) comprising a terminal tag is incorporated into a VLP, immunized animals will make antibodies not only to the F protein, but also to the terminal tag (i.e., for example, a FLAG amino acid sequence).

Antibodies specific for sequence tags have affinities for specific protein sequences, known as an epitopes. An epitope has the property that it selectively interacts with molecules and/or materials containing acceptor groups. The present invention is compatible with many epitope sequences reported in the literature including, but not limited to, H is X6 (HHHHHH) (SEQ ID NO:91) (ClonTech), C-myc (-EQKLISEEDL) (SEQ ID NO:92) (Roche-BM), FLAG (DYKDDDDK) (SEQ ID NO:93) (Stratagene), SteptTag (WSHPQFEK) (SEQ ID NO:94) (Sigma-Genosys), and HA Tag (YPYDVPDYA) (SEQ ID NO:95) (Roche-BM).

The FLAG peptide (Asp-Tyr-Lys-Asp-Asp-Asp-Asp-Lys) (SEQ ID NO:93) has been used as an epitope tag in a variety of cell types. For example, the modification of the cytomegalovirus (CMV) promoter containing vector, pCMV5, created two transient expression vectors designed for secretion and intracellular expression of FLAG-fusion proteins in mammalian cells. As a functional test, the bacterial alkaline phosphatase gene was cloned into both vectors, and anti-FLAG monoclonal antibodies were used for detection of FLAG epitope-tagged bacterial alkaline phosphatase in mammalian cells. In addition, secreted bacterial alkaline phosphatase was purified from the extracellular medium by anti-FLAG affinity chromatography. Chubet et al., "Vectors for expression and secretion of FLAG epitope-tagged proteins in mammalian cells" *Biotechniques* 20:136-41 (1996).

The net negatively charged HA-tag sequence (Tyr-Pro-Tyr-Asp-Val-Pro-Asp-Tyr-Ala) (SEQ ID NO:95) from the hemagglutinin influenza virus has proven useful in tagging proteins related to a wide variety of proteomic applications. In one embodiment, embodiment the present invention contemplates an improved HA epitope tag. Although it is not necessary to understand the mechanism of an invention, it is believed that the ability to metabolically label proteins with $^{35}$S-methionine facilitates the analysis of protein synthesis and turnover. However, efficient labeling of proteins in vivo is often limited by a low number of available methionine residues, or by deleterious side-effects associated with protein overexpression. To overcome these limitations, a methionine-rich variant of the widely used HA tag, called HAM, may be useful with ectopically expressed proteins. In one embodiment, the present invention contemplates the development of a series of vectors, and corresponding antisera, for the expression and detection of HAM-tagged VLP viral proteins. These HAM tags improve the sensitivity of $^{35}$S-methionine labeling and permit the analysis of Myc oncoprotein turnover even when HAM-tagged Myc is expressed at levels comparable to that of the endogenous protein. Because of the improved sensitivity provided by the HAM tag, the vectors described herein should be useful for the detection of radiolabeled VLP proteins. Herbst et al., "HAM: a new epitope-tag for in vivo protein labeling" *Mol Biol Rep.* 27:203-8 (2000).

Alternatively, antibodies may be generated to recognize specific sequences within a protein or oligonucleotide. Such antibodies may be polyclonal or monoclonal. For example, specific sequences to a carcinoembryonic antigen may be detectable by antibodies. Barnett et al., "Antibody preparations specifically binding to unique determinants of CEA antigens or fragments thereof and use of the antibody preparations in immunoassays" U.S. Pat. No. 6,013,772 (2000) (herein incorporated by reference). Similarly, antibodies may be raised to specific nucleotide sequences. Tchen et al., "Probe containing a modified nucleic acid recognizable by specific antibodies and use of this probe to detect and characterize a homologous DNA sequence" U.S. Pat. No. 5,098,825 (1992)(herein incorporated by reference).

Numerous immunoassays may be used according to the present invention. The readout systems capable of being employed in these assays are numerous and non-limiting examples of such systems include fluorescent and calorimetric enzyme systems, radioisotopic labeling and detection and chemiluminescent systems. For example, an antibody preparation having a sequence-specific affinity for a sequence-tagged NDV viral protein (preferably a VLP particle protein) is attached to a solid phase (i.e., for example, a microtiter plate or latex beads). This antibody-VLP protein complex is then washed to remove unbound VLP particle proteins. After washing, color or fluorescence is developed by adding a chromogenic or fluorogenic substrate to activate the VLP protein sequence tag. The amount of color or fluorescence developed is proportional to the amount of VLP protein in the sample.

B. Chemical Tags

Sequence tags (i.e., nucleotide and/or protein sequences) also include molecules which will be recognized by the enzymes of the transcription and/or translation process without steric or electrostatic interference. Detection of sequence tags may occur through release of a label. Such labels may include, but are not limited to one or more of any of dyes, radiolabels, binding moieties such as biotin, mass tags, such as metal ions or chemical groups, charge tags, such as polyamines or charged dyes, haptens such as digoxgenin, luminogenic, phosphorescent or fluorogenic moieties, and fluorescent dyes, either alone or in combination with moieties that can suppress or shift emission spectra, such as by fluorescence resonance energy transfer (FRET) or collisional fluorescence energy transfer. Aizenstein et al., "Methods and compositions for detecting target sequences" U.S. Pat. No. 6,913,881 (2005)(herein incorporated by reference).

When TdT or polyA polymerase is employed, an oligonucleotide may contain a 5' end label. The invention is not limited by the nature of the 5' end label; a wide variety of suitable 5' end labels are known to the art and include biotin, fluorescein, tetrachlorofluorescein, hexachlorofluorescein, Cy3 amidite, Cy5 amidite and digoxigenin. A radioisotope label (e.g., a 32P or 35S-labelled nucleotide) may be placed at either the 5' or 3' end of the oligonucleotide or alternatively, distributed throughout the oligonucleotide (i.e., a uniformly labeled oligonucleotide). A biotinylated oligonucleotide may be detected by probing with a streptavidin molecule that is coupled to an indicator (e.g., alkaline phosphatase or a fluorophore) or a hapten such as dioxigenin and may be detected using a specific antibody coupled to a similar indicator. The reactive group may also be a specific configuration or sequence of nucleotides that can bind or otherwise interact with a secondary agent, such as another nucleic acid, and enzyme, or an antibody.

To be useful, sequence tags must possess certain physical and physio-chemical properties. First, a sequence tag must be suitable for incorporation into either a growing peptide chain or oligonucleotide. This may be determined by the presence of chemical groups which will participate in peptide or phosphodiester bond formation. Second, sequence tags should be attachable to a tRNA molecule or a nucleic acid polymerase complex. Third, sequence tags should have one or more physical properties that facilitate detection and possibly isolation of nascent proteins or oligonucleotides. Useful physical properties include a characteristic electromagnetic spectral property such as emission or absorbance, magnetism, electron spin resonance, electrical capacitance, dielectric constant or electrical conductivity.

Useful sequence tags comprise native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent, chromatic or have a distinctive mass. Fluorescent moieties which are useful as sequence tags include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids and more preferably has high quantum yield of fluorescence can be excited in both the UV and visible portion of the spectrum. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired. DiCesare et al., *BioTechniques* 15:152-59 (1993). These sequence tags are detectable at the femtomolar ranges and below.

In addition to fluorescence, properties based on the interaction and response of a sequence tag to electromagnetic fields, radiation, light absorption (i.e., for example, UV, visible and infrared), resonance Raman spectroscopy, electron spin resonance activity, nuclear magnetic resonances, and mass spectrometry. Electromagnetic spectroscopic properties of a sequence tag are preferably not possessed by a naturally occurring compound and, therefore, are readily distinguishable. For example, the amino acid tryptophan absorbs near 290 nm, and has fluorescent emission near 340 nm. Thus, tryptophan analogs with absorption and/or fluorescence properties that are sufficiently different from tryptophan can be used to facilitate their detection in proteins.

For example, many different modified amino acids which can be used as sequence tags are commercially available (Sigma Chemical; St. Louis, Mo.; Molecular Probes; Eugene, Oreg.). One such sequence tag is N-∈-dansyllysine and may created by the misaminoacylation of a dansyl fluorophore to a tRNA molecule. Another such sequence tag is a fluorescent amino acid analog based on the highly fluorescent molecule coumarin. This fluorophore has a much higher fluorescence quantum yield than dansyl chloride and can facilitate detection of much lower levels. Rothschild et al., "Methods for the detection, analysis and isolation of nascent proteins" U.S. Pat. No. 6,875,592 (2005)(herein incorporated by reference).

Sequence tags for a protein can be chemically synthesized from a native amino acid and a molecule with marker properties which cannot normally function as an amino acid. For example a highly fluorescent molecule can be chemically linked to a native amino acid group. The chemical modification can occur on the amino acid side-chain, leaving the carboxyl and amino functionalities free to participate in a polypeptide bond formation. For example, a highly fluorescent dansyl chloride can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

In one embodiment, the present invention contemplates a fluorophore comprising a dipyrromethenboron difluoride (BODIPY) derivative. The core structure of all BODIPY fluorophores is 4,4-difluoro-4-bora-3a,4a-diaza-s-indacene. See U.S. Pat. Nos. 4,774,339; 5,187,288; 5,248,782; 5,274,113; 5,433,896; 5,451,663 (all hereby incorporated by reference). All BODIPY fluorophores have a high extinction coefficient, high fluorescence quantum yield, spectra that are insensitive to solvent polarity and pH, narrow emission bandwidth resulting in a higher peak intensity compared to other dyes such as fluorescein, absence of ionic charge and enhanced photostability compared to fluorescein. The addition of substituents to the basic BODIPY structure which cause additional conjugation can be used to shift the wavelength of excitation or emission to convenient wavelengths compatible with the means of detection.

A variety of BODIPY molecules are commercially available in an amine reactive form which can be used to derivatize aminoacylated tRNAs. One example of a compound from this family which exhibits superior properties for incorporation of a detectable sequence tag into nascent proteins is 4,4-difluoro-5,7-dimethyl-4-bora-3a,4a-diaza-s-indacene (BODIPY-FL). When the sulfonated N-hydroxysuccinimide (NHS) derivative of BODIPY-FL is used to place a sequence tag on an *E. coli* initiator tRNA$^{fmet}$, the labeled protein can be easily detected on polyacrylamide gels after electrophoresis using a standard UV-transilluminator and photographic or CCD imaging system. This can be accomplished by using purified tRNA$^{fmet}$ which is first aminoacylated with methionine and then the α-amino group of methionine is specifically modified using NHS-BODIPY. Varshney et al., "Direct analysis of aminoacylation levels of tRNA in vitro" *J. Biol. Chem.* 266:24712-24718 (1991).

C. Unique Sequence Tags

Serial Analysis of Gene Expression (SAGE) is a technique that allows a rapid, detailed analysis of thousands of transcripts. SAGE is based on two principles. First, a short nucleotide sequence tag (i.e., for example, 9 to 10 base pairs (bps)) contains sufficient information to uniquely identify a transcript, provided it is isolated from a defined position within the transcript. For example, a sequence as short as 9 bp can distinguish 262,144 transcripts given a random nucleotide distribution at the tag site, whereas current estimates suggest that even the human genome encodes only about 80,000 transcripts. Second, concatenation of short sequence tags allows the efficient analysis of transcripts in a serial manner by the sequencing of multiple tags within a single clone. As with serial communication by computers, wherein information is transmitted as a continuous string of data, serial analysis of the sequence tags requires a means to establish the register and boundaries of each tag.

Double-stranded cDNA may then be synthesized from mRNA by means of a biotinylated oligo(dT) primer. The cDNA is then cleaved with a restriction endonuclease (anchoring enzyme) that can be expected to cleave most transcripts at least once. Typically, restriction endonucleases with 4-bp recognition sites are used for this purpose because they cleave every 256 bp on average, whereas most transcripts are considerably larger. The most 3' portion of the cleaved cDNA is then isolated by binding to streptavidin beads. This process provides a unique site on each transcript that corresponds to the restriction site located closest to the polyadenylated [poly (A)] tail. The cDNA is then divided in half and ligated via the anchoring restriction site to one of two linkers containing a type IIS (tagging enzyme). Type IIS restriction endonucleases cleaves at a defined distance up to 20 bp away from their asymmetric recognition sites. The linkers are designed so that cleavage of the ligation products with the tagging enzyme results in release of the linker with a short piece of the cDNA.

For example, a combination of anchoring enzyme and tagging enzyme that would yield a 9-bp tag can be cured. After blunt ends are created, the two pools of released tags are ligated to each other. Ligated tags then serve as templates for polymerase chain reaction (PCR) amplification with primers specific to each linker. This step serves several purposes in addition to allowing amplification of the tag sequences. First, it provides for orientation and punctuation of the tag sequence in a very compact manner. The resulting amplification products contain two tags (one ditag) linked tail to tail, flanked by sites for the anchoring enzyme. In the final sequencing template, this results in 4 bp of punctuation per ditag. Second and most importantly, the analysis of ditags, formed before any amplification steps, provides a means to completely eliminate potential distortions introduced by PCR. Because the probability of any two tags being coupled in the same ditag is small, even for abundant transcripts, repeated ditags potentially produced by biased PCR can be excluded from analysis without substantially altering the final results. Cleavage of the PCR product with the anchoring enzyme allows for the isolation of ditags that can then be concentrated by ligation, cloned, and sequenced.

In addition to providing quantitative information on the abundance of known transcripts, SAGE can be used to identify NDV expressed genes. SAGE can provide both quantitative and qualitative data about gene expression. The combination of different anchoring enzymes with various recognition sites and type IIS enzymes with cleavage sites 5 to 20 bp from their recognition elements lends great flexibility to this strategy.

D. Direct Detection Technology

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA).

The cycling probe reaction (CPR), uses a long chimeric oligonucleotide in which a central portion is made of RNA while the two termini are made of DNA. Duck et al., *BioTech.,* 9:142 (1990). Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may be carried through sample preparation.

Branched DNA (bDNA) involves oligonucleotides with branched structures that allow each individual oligonucleotide to carry 35 to 40 labels (e.g., alkaline phosphatase enzymes). Urdea et al., *Gene* 61:253-264 (1987). While this enhances the signal from a hybridization event, signal from non-specific binding is similarly increased.

VII. In Vivo Vaccination

In one embodiment, the present invention contemplates a paramyxovirus VLP vaccine comprising at least one viral glycoprotein wherein the vaccine is antigenic. In one embodiment, the vaccine stimulates an immune response to diseases including, but not limited to, Newcastle disease, measles, parainfluenza virus 3, or respiratory syncytial virus infection. In one embodiment, the present invention contemplates a method comprising administering a purified antigenic paramyxovirus VLP vaccine to a host (i.e., for example, a mouse or chicken) under conditions that generate an immune response. In one embodiment, the immune response is characterized by measuring the serum glycoprotein antibody levels. In one embodiment, the viral glycoprotein comprises an NDV glycoprotein. In one embodiment, the viral glycoprotein comprises a measles virus glycoprotein. In one embodiment, the viral glycoprotein comprises a respiratory syncytial virus glycoprotein.

In one embodiment, the present invention contemplates a method comprising administering a purified antigenic NVD, measles, parainfluenza virus 3, or respiratory syncytial virus VLP vaccine to a chicken to create a vaccinated chicken. In one embodiment, the method further comprises administering a live virus challenge to the vaccinated chicken. In one embodiment, the method further comprises determining the NDV infection rate to the vaccinated chicken.

EXPERIMENTAL

The following examples are only illustrative of specific embodiments of the present invention and are not intended as limiting.

Example 1

Cell Cultures

This example describes the cell cultures used in the Examples below to construct specific embodiments of the present invention.

A spontaneously transformed fibroblast cell line derived from the East Lansing strain (ELL-O) of chicken embryos (UMNSAH/DF-1) was obtained from the American Type Culture Collection and maintained in Dulbecco's modified Eagle medium (DMEM) supplemented with penicillin-streptomycin and 10% fetal calf serum (FCS).

Human renal epithelial cells expressing the SV 40 T antigen (293T) were also propagated in DMEM supplemented with 10% FCS, penicillin-streptomycin, vitamins, non-essential amino acids, and glutamine. NDV, strain A V, was propagated in embryonated chicken eggs by standard protocols.

Example 2

Plasmids

This example describes the types of plasmids used in the Examples below to construct various embodiments of the present invention.

NDV cDNA sequences encoding NP (i.e., for example, SEQ ID NO:23), M (i.e., for example, SEQ ID NO:27), HN (i.e., for example, SEQ ID NO:18), and uncleaved F (i.e., for example, SEQ ID NO:20 or, alternatively, an F-K115Q) proteins were subcloned into the expression vector pCAGGS to generate pCAGGS-NP, pCAGGS-M, pCAGGS-HN and pCAGGS-F-KI15Q, respectively. Miyazaki et al., "Expression vector system based on the chicken beta-actin promoter directs efficient production of interleukin-5" *Gene* 79:269-77 (1989); and Niwa et al., "Efficient selection for high-expression transfectants with a NDVe1 eukaryotic vector" *Gene* 108:193-9 (1991).

F protein cDNA contains a point mutation in the cleavage site sequence, F-KI15Q, which eliminates the furin recognition site. Li et al., "Effect of cleavage mutants on syncytium formation directed by the wild-type fusion protein of Newcastle disease virus" *J. Virol.* 72:3789-95 (1998).

pBJ5 expression vector containing the gene encoding a Flag-tagged Vps4A with E228Q mutation and pDsRed2-N1 vector (Clontech) containing the gene encoding the CHMP3-RFP fusion protein were previously described. Strack et al., "PIP1/ALIX is a binding partner for HIV-1p6 and EIAV p9 functioning in virus budding" *Cell* 114:689-699 (2003).

Example 3

Transfection, Infection, and Metabolic Labeling

This examples describes the basic techniques used to develop and express various embodiments of the present invention.

Transfections of sub-confluent ELL-O cells and/or 293T cells were accomplished using Lipofectamine (Invitrogen) as recommended by the manufacturer. The following amounts of plasmid DNA were used per 35 mm dish: 1.0 μg pCAGGS-NP, 1.0 μg pCAGGS-M, 0.75 μg pCAGGS-F-KI15Q, and 1.0 μg pCAGGS-HN, either alone or in mixtures. These amounts were previously determined to yield levels of expression similar to cells infected with NDV at a multiplicity of infection of 5.

A total of 3.75 μg of plasmid DNA per 35 mm plate was used in all transfection experiments. When only one, two, or three cDNAs were used, the total amount of transfected DNA was kept constant by adding vector pCAGGS DNA. For each transfection, a mixture of DNA and 5 μl of Lipofectamine in OptiMEM media (Gibco/Invitrogen) was incubated at room temperature for 45 minutes, and added to cells previously washed with OptiMEM. The cells were incubated for 5 hours, the Lipofectamine-DNA complexes were removed, and 2 ml of supplemented DMEM was added.

After 36 hours, the medium was replaced with 0.7 ml DMEM without cysteine and methionine and supplemented with 100 μCi of $^{35}$S-methionine and $^{35}$S-cysteine mixture (NEG-772 EASYTAG™ Express Protein Labeling Mix, $^{35}$S, Perkin Elmer Life Sciences Inc.). After 4 hours of pulse label, one set of transfected plates was lysed, while in another set the medium was replaced with 1.0 ml of supplemented DMEM with 0.1 mM cold methionine (Nutritional Biochemicals Corporation). After 8 hours of chase, the medium was collected and the cells were lysed in 0.5 ml lysis buffer containing Triton-DOC (1% Triton, 1% sodium deoxycholate) and 25 mg N-ethylmaleimide (NEM). Cells were harvested with a cell scraper and homogenized by passing through a 26 gauge needle 10 to 15 times.

Sub-confluent 293T cells were simultaneously transfected with pCAGGS-M and different concentrations of either pBJ5-Vps4-E228Q-Flag or pDsRed2-NI-CHMP3. Corresponding empty vectors were used as control. Cells were incubated for 36 hours and the same pulse-chase protocol was performed as described above.

ELL-O cells were infected at an MOI of 5 pfu for 5 hours, labeled with $^{35}$S-methionine and $^{35}$S-cysteine mixture for 30 min, and chased in nonradioactive medium for 8 hours as described above. Cell supernatant was harvested and virions purified as described below. Cells were lysed and homogenized as described above.

Example 4

VLP Purification and Isolation

Virus and VLP, as well as virions, were purified from cell supernatants in protocols previously reported. Levinson et al., "Radiation studies of avian tumor viruses and Newcastle disease virus" *Virology* 28:533-542 (1966). The cell supernatants were centrifuged at 5000 rpm for 5 min at 4° C., overlaid on top of a block gradient consisting of 3.5 ml 20% and 0.5 ml 65% sucrose solutions in TNE buffer (25 mM Tris-HCl pH 7.4, 150 mM NaCl, 5 mM EDTA), and re-centrifuged at 40,000 rpm for 12 hours at 4° C. using a SW50.1 rotor (Beckman). The sucrose gradient interface (containing concentrated particles) was collected in 0.5 ml, mixed with 2.0 ml of 80% sucrose, and overlaid on top of 1.0 ml 80% sucrose cushion. Additional layers of sucrose (1.0 ml of 50% and 0.5 ml of 10% sucrose) were layered on top of the sample. The gradient was centrifuged at 38,000 rpm for 20 h at 4° C. The gradient was collected from the bottom into one 1 ml fraction and eight 0.5 ml fractions using a polystaltic pump. Densities of each fraction were determined using a refractometer. VLPs derived from expression of all combinations of proteins were prepared in a single experiment, thus enabling direct comparison of results.

The experiments were repeated three times. Immunoprecipitation and polyacrylamide gel electrophoresis. Immunoprecipitation was accomplished by combining one volume of cell lysate or sucrose gradient fraction with two volumes of TNE buffer. Samples were incubated with specific antibodies for 16 hours at 4° C. Antisera used to precipitate NP, F and HN were rabbit polyclonal antibody raised against UV inactivated NDV by standard protocols; anti-HR1 and anti-HR2 McGinnes et al., "Newcastle disease virus HN protein alters the conformation of the F protein at cell surfaces" *J. Virol.* 76:12622-33 (2002); anti-F2-96 and anti-A. McGinnes et al., "Role of carbohydrate processing and calnexin binding in the folding and activity of the HN protein of Newcastle disease virus" *Virus Res* 53:175-85 (1998).

Anti-F2-96 was raised against a glutathione S-transferase (GST) fusion protein that contained the F protein sequences from amino acid 96 to 117. Antiserum used to precipitate M protein was a mouse monoclonal antibody raised against purified M protein. Faeberg et al., "Strain variation and nuclear association of 20 NDV Matrix protein" *J Virol.* 62:586-593 (1988). Immune complexes (ICs) were adsorbed to Protein A (Pansorbin Cells, CALBIOCHEM) for 2 hours at 4° C., pelleted, and then washed three times in immunoprecipitation (IP) wash buffer (phosphate buffer saline (PBS) containing 0.5% 9 Tween-20 and 0.4% sodium dodecyl sulfate (SDS). ICs were resuspended in SDS-polyacrylamide gel electrophoresis sample buffer (125 mM Tris-HCl [pH 6.8], 2% SDS, 10% glycerol, 0.4% Bromphenol blue) with 1 M J3 mercaptoethanol (BME) and boiled.

Proteins were separated in 8% polyacrylamide-SDS gel and detected by autoradiography. Quantification of resulting autoradiographs was accomplished using a Fluor-S™ Multi-Imager (BioRad).

Example 5

High Efficiency VLP Release

Co-expression of NP, M, F and HN proteins resulted in the release of VLPs with a density of 1.19 to 1.16 g/cc (FIG. 1, panel A). Virus particles purified in parallel from NDV, strain AV, infected cells had a density of 1.21 to 1.19 g/cc (FIG. 1, panel B). Although it is not necessary to understand the mechanism of an invention, it is believed that the slightly lighter density of VLPs compared to authentic virus is likely due to the absence of the virion RNA within the VLPs. The efficiencies of VLP and virus release were calculated as the percentage of M protein remaining in the cell extracts after the chase relative to the amount of protein in the pulse. The loss of M protein from cells in the chase portion of the experiment is due to release from cells as VLPs or virions. By this criterion, the efficiency of VLP release was 85%, while the efficiency of NDV release was 92% (FIG. 1, panel C). The results show that release of VLPs is almost as efficient as release of virions.

These results demonstrate that NDV VLPs are efficiently assembled and released from avian cells expressing the four major structural proteins. In one embodiment, M protein is sufficient for VLP release. Minimum protein requirements for VLP formation, were determined by individually assessing the capability of each protein to direct particle release. Cells expressing each of the viral proteins individually were radioactively labeled in a pulse-chase protocol and VLPs were isolated as described above.

Example 6

M Protein Dependent VLP Release

VLPs are released only from cells expressing the M protein. FIG. 2, Panel B. Almost no M protein is detectable in cell extracts after the 8 hour chase. FIG. 2A, right panel. Although it is not necessary to understand the mechanism of an invention, it is believed that this indicates that much of the pulse-labeled protein was released from cells. It is further believed that by comparing the levels of M protein in the pulse labeled extract and the chase extract, the efficiency of release was calculated to be 90%.

In contrast, most of the pulse labeled NP, F and HN proteins remained in extracts after the chase (FIG. 2A). Significant amounts of VLPs were also not detected in the corresponding cell supernatant (FIG. 2, panel B) although there was a trace of very light density material released from HN protein expressing cells. FIG. 2, panel C, shows the quantification of VLPs produced from cells expressing each protein individually. Interestingly, the amount of M protein-containing particles from cells expressing M protein alone was greater than when all four structural proteins were expressed. However, the M protein-only VLPs had a very heterogeneous density, with values ranging from 1.23 to 1.12 g/cc (FIG. 2, panel B). These results reveal that M protein is sufficient for the release of particles.

Example 7

M Protein Dependent VLP Release: Pair Wise Combinations

As shown in Example 6, M protein is required for VLP release. To determine the contribution of NP, F or HN proteins to M protein-driven VLP formation, VLPs from cells expressing all possible combinations of two proteins were isolated and characterized as described above. Cells expressing any combination of proteins without M protein did not release VLPs (FIG. 3; panel C). Furthermore, in the absence of M protein, NP, F and HN proteins expressed in pair wise combinations were retained in cell extracts after the 8 hour chase (FIG. 3A). This finding suggests that M protein is required for particle release. Pair wise expression of NP, F, or HN proteins with M protein resulted in the release of VLPs containing both proteins (FIG. 3, panel B). Intriguingly, however, there was only trace amounts of NP, F or HN proteins and M protein was the predominant protein in the VLPs (FIG. 3, panel B).

The distribution of NP, F, or HN proteins in the gradients was identical to that of M protein (FIG. 3, panel B). In addition, the VLP densities were very heterogeneous and were much like that of M protein-only VLPs. Surprisingly also, the amount of M protein containing VLPs was significantly decreased (by about 2 to 2.5 fold) upon co-expression of M protein with either NP, F, or HN proteins (FIG. 3, panel C). These results suggest that NP, F, or HN proteins can individually suppress M protein-driven VLP release.

Example 8

M Protein Dependent VLP Protein Incorporation

Efficient incorporation of other viral proteins into VLPs requires the expression of M protein and at least two of the other proteins. To examine the effects of expression of three viral proteins on particle release, cells were transfected with all possible combinations of three cDNAs. Again, VLPs were only released from cells expressing M protein. Expression of NP, F, and HN proteins without the M protein did not result in the release of any particles (FIG. 4, panel C). This finding further strengthens our conclusion that the M protein is required for release of VLPs.

In contrast to the expression of a single glycoprotein with the M protein, co-expression of both F and HN glycoproteins with M protein resulted in significantly increased incorporation of both glycoproteins into VLPs (FIG. 4, panels B and C). The F and HN proteins were detected in the same gradient fractions as M protein. Furthermore, the densities of the VLPs were more homogenous compared to those generated from cells expressing M protein alone (compare FIG. 4, panel B and FIG. 2, panel B) or M protein with a single glycoprotein. These results indicate that expression of both F and HN proteins with M protein is necessary for efficient incorporation of either glycoprotein into particles.

Expression of M protein with NP and either F or HN protein resulted in increased incorporation of NP as well as the glycoprotein into VLPs (FIG. 4, panels B and C). The distribution of NP protein-containing particles in the gradient was similar to that of VLPs released from cells expressing all four structural proteins (compare FIG. 1, panel A and FIG. 4, panel B). Importantly, the densities of these particles were more homogenous compared to particles released from cells expressing M alone, and were analogous to the density of the authentic virus or complete VLPs (compare FIG. 4, panel B, and FIG. 1, panel B). Overall, these results indicate that M protein is necessary and sufficient for particle release and that expression of M protein with at least two other proteins is required for efficient incorporation of other proteins into VLPs.

Example 9

VLP Release Inhibition

Host cell VPS pathway is involved in VLP formation and release. Previous studies have implicated the VPS pathway in budding of other enveloped RNA viruses. Demirov et al., "Retrovirus budding" *Virus Res* 106:87-102 (2004); Pornillos et al., "Mechanisms of enveloped RNA virus budding" *Trends Cell Biol.* 12:569-79 (2002); and Morita et al., "Retrovirus budding" *Annu Rev Cell Dev Biol.* 20:395-425 (2004). This pathway might be involved in M protein-driven VLP release because CHMP3 is a subunit of the ESCRT III complex. von Schwedler et al., "The protein network of HIV budding" *Cell* 4:701-13 (2003).

Fusion of CHMP3 with RFP transforms it into a dominant-negative protein which inhibits HIV-1 gag VLP release. Strack et al., "PIP1/ALIX is a binding partner for HIV-1p6 and EIAV p9 functioning in virus budding" *Cell* 114:689-699 (2003). Simultaneous expression of the M protein with CHMP3-RFP resulted in 98.5% inhibition of VLP release (FIG. 5, panels A and C). Expression of another dominant-negative component of the VPS pathway, Vps4A-E228Q with M protein, yielded the same result, with 96.2% inhibition (FIG. 5, panels B and D). Expression of both dominant-negative CHMP3 and Vps4A did not suppress the expression of M protein (FIG. 5, panels E and F). Thus an intact host cell VPS pathway is essential for M protein VLP release.

Example 10

Cell Type Dependent Effects on Virus and VLP Release

This example provides exemplary data showing that VLP release is dependent upon the host cell type. Host cell type affects basic VLP release mechanisms as well as overall VLP release efficiencies.

Basic Release Mechanisms

VLP release from avian cells (ELL-0) was compared with VLP release from primate cells (COS-7 cells). To compare virus particle release from these cells, equal numbers of avian cells and COS-7 cells were infected with NDV at an MOI=5. The cells were radioactively labeled in a pulse and then subjected to a nonradioactive chase. Virions were harvested from the cell supernatant at various times during the chase and the proteins in the virus particles resolved by polyacrylamide gel electrophoresis.

An autoradiograph of the NP and F proteins in virus particles at different times of chase are shown in FIG. 14A and FIG. 14B, respectively (top gel: avian; bottom gel: COS-7). A quantification of the levels of each protein is shown in FIG. 15A and FIG. 15B, respectively. Clearly, the amounts of virus released from avian cells were higher than amounts released from COS-7 cells and the rate of release from avian cells was faster than the rate of release from COS-7 cells. This difference between avian and primate cells was not due to differences in the levels of protein expression in the two cell types. The levels of total viral proteins made during the pulse label were higher in COS-7 cells than avian cells (not shown), a result that suggests that virus entry, replication and translation were at least as efficient in COS-7 as in avian cells.

These data show that the rate of virus particle release is faster in avian cells than primate cells and the amounts of virus released from avian cells are significantly higher than amounts released from primate cells.

Release Efficiencies

To determine if avian cells were also more efficient in the release of VLPs, equal numbers of avian cells and COS-7 cells were transfected with cDNAs encoding the NP, M, HN, and F-K115Q proteins of NDV. Cells were radioactively labeled for four (4) hours (i.e., pulsed) and then subjected to a non-radioactive incubation for eight (8) hours (i.e., chased). VLPs were subsequently isolated from the cell supernatant. VLPs in the supernatants were purified by flotation into sucrose gradients.

Sucrose gradients were generated that contain VLPs released from avian cells and COS-7 cells, respectively. See FIGS. 16A and 16B, respectively. Clearly, the data show that more VLPs were released from avian cells than from COS-7 cells.

Cell lysate extracts from avian cell and COS-7 cells were prepared after the pulse-label and after the nonradioactive chase. See FIGS. 17A and 17B, respectively. Importantly, the HN, F, and M proteins were no longer present in avian cell extracts after the nonradioactive chase. This observation is consistent with a more efficient release from avian cells and/or incorporation into VLPs. Conversely, significant levels of these viral proteins remained in the COS-7 cell extracts. This observation is consistent with viral protein retention in COS-7 cells and a lower release of the viral proteins into particles. Clearly, the data demonstrate that VLP release is more efficient from avian cells than from COS-7 cells.

Example 11

Comparison of Specific Viral Protein-Induced VLP Release

This example demonstrates that VLPs are also more efficiently released from avian cells when transfected with NDV containing only an M protein.

VLP particle release was determined from cells transfected with only M protein cDNA as described above. A sucrose density gradient purification of M protein VLPs were generated from both avian and COS-7 primate cells. See FIG. 18A and FIG. 18B, respectively. Clearly, the amounts of VLP M proteins released from avian cells were significantly higher, and therefore more efficient, than VLP M proteins released from primate cells.

Further, equal numbers of cells were transfected with either NP protein cDNA, M protein cDNA, F-K115Q protein cDNA, or HN protein cDNA alone. Alternatively, the experiment used cells transfected with a vector having all four (4) viral protein cDNAs in combination. VLPs were then prepared as described above. A sucrose gradient purification was generated for each transfection and particle release was determined by densitometry. When the various viral protein cDNAs were transfected individually, only M protein resulted in any VLP viral protein release (i.e., only M protein). When a cell was transfected with all four proteins, VLP viral protein release contained all four proteins. In both cases, released VLPs contained greater amounts of viral proteins in avian cells versus COS-7 cells. See FIG. 19A and FIG. 19B, respectively. Clearly, release efficiency of both M protein VLPs and complete VLPs is better from avian cells than COS-7 cells.

Example 12

Generation of Antibodies to VLP Viral Vaccines

I. Monoclonal Antibodies

Balb/c mice are immunized with multiple I.P. inoculations of a KLH conjugated NDV viral peptide. Splenocytes from immunized animals are then fused with the mouse myeloma AG8 using standard protocols. Wunderlich et al., *J. Immunol. Methods* 147:1-11 (1992). Supernatants from resultant hybridomas are then screened for immunoreactivity to an ovalbumin-coupled NDV viral peptide using standard ELISA protocols known in the art. Hybridomas positive for the expression of immunoreactive MAbs are cloned at least twice by limiting dilution and MAb isotype analysis performed. Purified MAb IgG will be prepared from ascites fluid using protein-A affinity chromatography. After fusion, screening will show a plurality of positive parental signals, from which monoclonal antibody producing clones may be prepared.

Immunoprecipitation/Scintillation Assay for Hybridoma Screening

To develop and screen for monoclonal antibodies which recognize the VLP viral protein in solution rather, than when attached to a solid phase, an assay will be developed in which immunoprecipitation of an $^{35}$S-methionine-labeled in vitro-translated VLP viral protein is measured. A standard amount of in vitro translated VLP viral protein is allowed to form antibody/antigen complexes in a solution which can be optimized for ionic strength, pH, and detergent composition. After the immune complexes are precipitated with Protein G (Omnisorb cells) and washed extensively, bound radioactivity is counted in a liquid scintillation counter; background is subtracted and the efficiency of precipitation calculated. This Immunoprecipitation/Scintillation assay (IPSA) allows for both the rapid identification and characterization of antibodies, and will be used to test a variety of monoclonal VLP viral protein antibodies. The assay is applicable, in general, to monoclonal hybridoma supernatants as well as polyclonal sera to identify antibodies which can be used for immunoprecipitations.

Briefly, approximately $1.5\times10^5$ DPMs of $^{35}$S-methionine-labeled in vitro-translated VLP viral proteins are added to 10 μl of a 10× immunoprecipitation buffer (150 mM NaCl, 10% NP-40, 5% deoxycholic acid, 1% SDS, 500 mM Tris pH 8). To this, 90 μl of monoclonal cell supernatant from the monoclonal fusion of interest is added and allowed to react for 2 hrs at 4° C. After 2 hrs, 40 μl of a 10% solution of Omnisorb cells (Calbiochem) equilibrated in IX immunoprecipitation buffer (RIPA buffer; 150 mM NaCl, 1% NP-40, 0.5% deoxycholic acid, 0.1% SDS, 50 mM Tris pH 8) is added and allowed to react for an additional 2 hrs at 4° C. with rocking. The cells are pelleted by centrifugation for 5 min at 4500 g and 4° C., and washed 3× with 800 μl cold 1× immunoprecipitation buffer. Pellets were quantitatively transferred to scintillation vials and counted in a Beckman LS6000 scintillation counter in the Auto DPM mode. The percentage of VLP viral protein immunoprecipitated may then be calculated.

Characterization of VLP Viral Protein MAbs

To further characterize a best cell line, a competition immunoprecipitation/scintillation assay (Competition IPSA) may be performed. In this variation, a clone producing monoclonal antibodies to a VLP viral protein was added to an approximate 200 fold molar excess of unlabelled competitor peptide at the same time as labeled in vitro translated VLP viral protein. As expected, peptides to the suspected epitope regions will be compared with peptides that are not suspected of representing the epitope regions. A high percentage of competition in assays containing the suspected epitope regions will verify the VLP viral protein monoclonal antibody binding specificity.

II. Antisera

Antisera used to precipitate viral proteins were a cocktail of anti-NDV antibodies. Antiserum used to precipitate NP was rabbit polyclonal antibody raised against UV inactivated NDV by standard protocols. Antisera used to precipitate F protein were raised against glutathione S-transferase (GST) fusion proteins that contained amino acid sequences 130 to 173 (anti-HR1) (McGinnes et al., "Newcastle disease virus HN protein alters the conformation of the F protein at cell surfaces" *J. Virol.* 76:12622-12633 (2002).), 470 to 500 (anti-HR2) (Dolganiuc et al., "Role of the cytoplasmic domain of the Newcastle disease virus fusion protein in association with lipid rafts" *J Virol* 77:12968-12979 (2003)), or 96 to 117 (anti-$F_2$-96). Antiserum used to precipitate HN protein was raised against HN protein sequences from amino acid 96 to 117 (anti-A) (McGinnes et al., "Role of carbohydrate processing and calnexin binding in the folding and activity of the HN protein of Newcastle disease virus" *Virus Res* 53:175-185 (1998)). Antiserum used to precipitate M protein was a mouse monoclonal antibody raised against purified M protein (Faeberg et al., "Strain variation and nuclear association of NDV Matrix protein" *J. Virol.* 62:586-593 (1988)). Antibody used to precipitate HA-tagged proteins was a mouse monoclonal HA antibody conjugated to agarose beads (Sigma). Secondary antibody used for immunoblotting was a peroxidase conjugated mouse monoclonal anti-HA antibody (Sigma).

Example 13

Construction of Recombinant Baculovirus Vectors

This example describes a general methodology from the construction of recombinant baculovirus vectors.

A general scheme for constructing baculovirus recombinants is shown in FIG. 28. As a first step, the target gene (i.e., for example, an NDV particle protein), shown as a PCR-derived DNA, is cloned downstream of a copy of an AcNPV promoter in a suitable plasmid transfer vector (i.e., for example, pBAC4x-1). The transfer vector has upstream and downstream segments of baculovirus DNA flanking the promoter and target gene.

A selected clone of the derived recombinant transfer vector is grown in a bacterial cell culture (i.e., for example, E. coli), avian cell culture (i.e., for example, ELL-O), or a human cell culture (i.e., for example, 293T) and the resulting recombinant plasmid DNA is characterized and purified.

In the second step, the purified recombinant transfer plasmid is co-transfected with linearized virus DNA into insect cells (i.e., for example, Sf9) to construct the recombinant baculovirus. The flanking regions of the transfer vector participate in homologous recombination with the virus DNA sequences during virus replication and introduce the target gene into the baculovirus genome at a specific locus (usually polyhedrin or p10, depending on the transfer plasmid).

Following transfection and plaque purification to remove parental virus, a high titer virus stock is prepared from the appropriate recombinant. Once a high titer virus stock is obtained, it is employed to determine the optimal times for target protein expression (depending on the promoter and the properties of the gene product). After these parameters are established, a large scale culture is prepared and used for protein production.

Example 14

Production of Measles VLP Vaccine

This example presents a protocol that will result in the production of VLP vaccines specific for the measles virus. Vectors: MV cDNA sequences encoding NP (i.e., for example, SEQ ID NO:42), M (i.e., for example, SEQ ID NO:48), HA (i.e., for example, SEQ ID NO:30), and uncleaved F (i.e., for example, SEQ ID NO:36) proteins will be subcloned into the expression vector pCAGGS to generate pCAGGS-NP, pCAGGS-M, pCAGGS-HA and pCAGGS-F-K111G, respectively. The cDNA encoding the MV F protein will be mutated to eliminate the furin recognition site at amino acid 108-112. The mutation will introduce a glycine in place of lysine at amino acid 111, the position analogous to the K115Q mutation in the NDV F protein. Elimination of cleavage of the F protein will inhibit the ability of the F protein to fuse. Absence of cell-cell fusion in the culture will likely increase the yield of VLPs.
Cell lines: Measles virus is released efficiently from human and primate cell lines but not murine cell lines (Vincent, et al Virology 265: 185). Thus Hela cells (human cervical carcinoma cells), 293 cells (human embryonic kidney cells), VERO cells (African green monkey kidney cells) and COS-7 (primate) cells will be used.
Transfection infection and metabolic labeling: Transfections of sub confluent cells will be accomplished using Lipofectamine (Invitrogen) as recommended by the manufacturer. The following amounts of plasmid DNA will be used per 35 mm dish: 1.0 μg pCAGGS-NP, 1.0 μg pCAGGS-M, 0.75 μg pCAGGS-F-K111G, and 1.0 μg pCAGGS-HA. A total of 3.75 μg of plasmid DNA per 35 mm plate will be used in all transfection experiments. When only one, two, or three cDNAs are used, the total amount of transfected DNA will be kept constant by adding vector pCAGGS DNA. For each transfection, a mixture of DNA and 5 μl of Lipofectamine in OptiMEM media (Gibco/Invitrogen) will be incubated at room temperature for 45 minutes, and added to cells previously washed with OptiMEM. The cells will be incubated for 5 hours, the Lipofectamine-DNA complexes removed, and 2 ml of supplemented DMEM added. After 36 hours, the medium will be replaced with 0.7 ml DMEM without cysteine and methionine and supplemented with 100 μCi of $^{35}$S-methionine and $^{35}$S-cysteine mixture (NEG-772 EASYTAG™ Express Protein Labeling Mix, $^{35}$S, Perkin Elmer Life Sciences Inc.). After 4 hours of pulse label, one set of transfected plates will be lysed, while in another set the medium will be replaced with 1.0 ml of supplemented DMEM with 0.1 mM cold methionine (Nutritional Biochemicals Corporation). After 8 hours of chase, the cell supernatant will be collected. In addition, the cells will be sonicated to release cell-associated VLPs. The resulting cell supernatants will be combined. The cells will be lysed in 0.5 ml lysis buffer (10 mM NaCl, 1.5 mM MgCl2, 10 mM Tris-HCl pH7.4) containing Triton-DOC (1% Triton, 1% sodium deoxycholate) and 1.25 mg N-ethylmaleimide (NEM). Cells will be harvested with a cell scraper and homogenized by passing through a 26-gauge needle 10 to 15 times.

To determine if the VPS pathway is involved in VLP budding, sub confluent 293T cells will be simultaneously transfected with pCAGGS-M and different concentrations of either pBJ5-Vps4-E228Q-Flag or pDsRed2-N1-CHMP3. Corresponding empty vectors will be used as control. Cells will be incubated for 36 hours and the same pulse-chase protocol was performed as described above.

To generate virus particles for controls, primate or human cells will be infected at an MOI of 5 pfu for 30 hours and labeled with $^{35}$S-methionine and $^{35}$S-cysteine mixture for 4 hours, and chased in nonradioactive medium for 8 hours as described above. Cell supernatant will be harvested and virions purified as described below. Cells will be lysed and homogenized as described above.
Virus and VLP purification: VLPs as well as virions will be purified from cell supernatants in protocols previously developed for virus purification. The cell supernatants will be clarified by centrifugation at 5000 rpm for 5 min at 4° C., overlaid on top of a step gradient consisting of 3.5 ml 20% and 0.5 ml 65% sucrose solutions in TNE buffer (25 mM Tris-HCl pH 7.4, 150 mM NaCl, 5 mM EDTA), and centrifuged at 40,000 rpm for 12 hours at 4° C. using a SW50.1 rotor (Beckman). The interface (containing concentrated particles) will be collected in 0.5 ml, mixed with 2.0 ml of 80% sucrose, and overlaid on top of 1.0 ml 80% sucrose cushion. Additional layers of sucrose (1.0 ml of 50% and 0.5 ml of 10% sucrose) will be layered on top of the sample. The gradient will be centrifuged at 38,000 rpm for 20 h at 4° C. The gradient will be collected from the bottom into one 1 ml fraction and eight 0.5 ml fractions using a polystaltic pump. Densities of each fraction will be determined using a refractometer. VLPs derived from expression of all combinations of proteins will be prepared in a single experiment, thus enabling direct comparison of results.
Immunoprecipitation and polyacrylamide gel electrophoresis: Immunoprecipitation will be accomplished by combining one volume of cell lysate or sucrose gradient fraction with two volumes of TNE buffer. Samples were incubated with MV specific polyclonal antibodies for 16 hours at 4° C. Antiserum used to precipitate NP, F and HA will be rabbit polyclonal antibody raised against UV inactivated MV by standard protocols. Immune complexes (ICs) will be adsorbed to Protein A (Pansorbin Cells, CALBIOCHEM) for 2 hours at 4° C., pelleted, and then washed three times in immunoprecipitation (IP) wash buffer (phosphate buffer saline (PBS) containing 0.5% Tween-20 and 0.4% sodium dodecyl sulfate (SDS)). ICs will be resuspended in SDS-polyacrylamide gel electrophoresis sample buffer (125 mM Tris-HCl, pH 6.8, 2% SDS, 10% glycerol, 0.4% Bromphenol blue) with 1 M β-mercaptoethanol (BME) and boiled. Proteins will be separated on 8% polyacrylamide-SDS gel and subjected to autoradiography. Quantification of resulting autoradiographs will be accomplished using a Fluor-S™ MultiImager (BioRad).

Example 15

Production of Respiratory Syncytial Virus VLP Vaccine

This example presents a protocol that will result in the production of VLP vaccines specific for the respiratory syncytial virus (RSV).
Vectors: RSV cDNA sequences encoding NP (i.e., for example, SEQ ID NO:70), M (i.e., for example, SEQ ID NO:66 or, alternatively, M2-1), G (i.e., for example, SEQ ID NO:54), and an uncleaved F (i.e., for example, SEQ ID NO:60) protein will be subcloned into the expression vector pCAGGS to generate pCAGGS-NP, pCAGGS-M2-1, pCAGGS-G and pCAGGS-F-R108N/R109N, respectively. The cDNA encoding the RSV F protein will be mutated to eliminate one of the two furin recognition sites at amino acids 106-109 and 131-136, as previously reported (Gonzalez-Reyes, et al, PNAS 98: 9859). Elimination of cleavage will inhibit the ability of the F protein to fuse. The absence of cell-cell fusion will likely increase the release of VLPs. A double mutation, R108N/R109N, eliminates one cleavage and inhibits the fusion activity of the protein (Gonzalez-Reyes, et al, PNAS 98: 9859). Additional RSV proteins not found in other paramyxoviruses are NS1, NS2, M2-2, and SH, but all have been shown to be nonessential for virus assembly (reviewed in Collins, et al, Respiratory Syncytial Virus, in Fields Virology, Ed. Knipe, D. and Howley, P. Lippincott Williams and Wilkins, 2001). G protein is also nonessential for assembly but likely contributes to a protective immune response to the virus.
Cell lines: RSV grows efficiently in a variety of cell lines from human and animal sources. However, HEp-2 cells (a Hela cell variant) are the most efficient in production of virus (reviewed in Collins, et al, Respiratory Syncytial Virus, in Fields Virology, Ed. Knipe, D. and Howley, P. Lippincott Williams and Wilkins, 2001), thus these cells will be used. A549 cells (type II alveolar epithelial lung carcinoma cells), also reported to be permissive for RSV, will be used as well.
Transfection, infection and metabolic labeling: Transfections of sub confluent cells will be accomplished using Lipofectamine (Invitrogen) as recommended by the manufacturer. The following amounts of plasmid DNA will be used per 35 mm dish: 1.0 µg pCAGGS-NP, 1.0 µg pCAGGS-M2-1, 0.75 µg pCAGGS-F-R108N/R109N, and 1.0 µg pCAGGS-G. A total of 3.75 µg of plasmid DNA per 35 mm plate will be used in all transfection experiments. When only one, two, or three cDNAs are used, the total amount of transfected DNA will be kept constant by adding vector pCAGGS DNA. For each transfection, a mixture of DNA and 5 µl of Lipofectamine in OptiMEM media (Gibco/Invitrogen) will be incubated at room temperature for 45 minutes, and added to cells previously washed with OptiMEM. The cells will be incubated for 5 hours, the Lipofectamine-DNA complexes removed, and 2 ml of supplemented DMEM added. After 36 hours, the medium will be replaced with 0.7 ml DMEM without cysteine and methionine and supplemented with 100 µCi of $^{35}$S-methionine and $^{35}$S-cysteine mixture (NEG-772 EASYTAG™ Express Protein Labeling Mix, $^{35}$S, Perkin Elmer Life Sciences Inc.). After 4 hours of pulse label, one set of transfected plates will be lysed, while in another set the medium will be replaced with 1.0 ml of supplemented DMEM with 0.1 mM cold methionine (Nutritional Biochemicals Corporation). After 8 hours of chase, the medium will be collected. In addition, the cells will sonicated to release cell associated VLPs. The resulting cell supernatants will be combined. The cells will be lysed in 0.5 ml lysis buffer (10 mM NaCl, 1.5 mM MgCl$_2$, 10 mM Tris-HCl, pH 7.4) containing Triton-DOC (1% Triton, 1% sodium deoxycholate) and 1.25 mg N-ethylmaleimide (NEM). Cells will be harvested with a cell scraper and homogenized by passing through a 26-gauge needle 10 to 15 times.
To determine if the VPS pathway is involved in VLP budding, sub confluent HEp-2 cells will be simultaneously transfected with pCAGGS-M2-1 and different concentrations of either pBJ5-Vps4-E228Q-Flag or pDsRed2-N1-CHMP3. Corresponding empty vectors will be used as control. Cells will be incubated for 36 hours and the same pulse-chase protocol was performed as described above.
To generate virus particles for controls, cells will be infected at an MOI of 10 pfu for 30 hours and labeled with $^{35}$S-methionine and $^{35}$S-cysteine mixture for 4 hours, and chased in nonradioactive medium for 8 hours as described above. Cell supernatant will be harvested and virions purified as described below. Cells will be lysed and homogenized as described above.
Virus and VLP purification: VLPs as well as virions will be purified from cell supernatants in protocols previously developed for virus purification. The cell supernatants will be clarified by centrifugation at 5000 rpm for 5 min at 4° C., overlaid on top of a step gradient consisting of 3.5 ml 20% and 0.5 ml 65% sucrose solutions in TNE buffer (25 mM Tris-HCl pH 7.4, 150 mM NaCl, 5 mM EDTA), and centrifuged at 40,000 rpm for 12 hours at 4° C. using a SW50.1 rotor (Beckman). The interface (containing concentrated particles) will be collected in 0.5 ml, mixed with 2.0 ml of 80% sucrose, and overlaid on top of 1.0 ml 80% sucrose cushion. Additional layers of sucrose (1.0 ml of 50% and 0.5 ml of 10% sucrose) will be layered on top of the sample. The gradient will be centrifuged at 38,000 rpm for 20 h at 4° C. The gradient will be collected from the bottom into one 1 ml fraction and eight 0.5 ml fractions using a polystaltic pump. Densities of each fraction will be determined using a refractometer. VLPs derived from expression of all combinations of proteins will be prepared in a single experiment, thus enabling direct comparison of results.
Immunoprecipitation and polyacrylamide gel electrophoresis: Immunoprecipitation will be accomplished by combining one volume of cell lysate or sucrose gradient fraction with two volumes of TNE buffer. Samples will be incubated with RSV specific polyclonal antibodies for 16 hours at 4° C. Antiserum to be used is commercially available from several sources. Immune complexes (ICs) will be adsorbed to Protein A (Pansorbin Cells, CALBIOCHEM) for 2 hours at 4° C., pelleted, and then washed three times in immunoprecipitation (IP) wash buffer (phosphate buffer saline (PBS) containing 0.5% Tween-20 and 0.4% sodium dodecyl sulfate (SDS)). ICs will be resuspended in SDS-polyacrylamide gel electrophoresis sample buffer (125 mM Tris-HCl, pH 6.8, 2% SDS, 10% glycerol, 0.4% Bromphenol blue) with 1 M β-mercaptoethanol (BME) and boiled. Proteins will be separated on 8% polyacrylamide-SDS gel and subjected to autoradiography. Quantification of resulting autoradiographs will be accomplished using a Fluor-S™ MultiImager (BioRad).

Example 16

Production of Parainfluenza 3 VLP Vaccine

This example presents a protocol that will result in the production of VLP vaccines specific for the parainfluenza 3 (PIV).
Vectors: PIV3 cDNA sequences encoding NP (i.e., for example, SEQ ID NO:76), M (i.e., for example, SEQ ID NO:80), HN (i.e., for example, SEQ ID NO:84), and an uncleaved F (i.e., for example, SEQ ID NO:78) protein will be subcloned into the expression vector pCAGGS to generate pCAGGS-NP, pCAGGS-M, pCAGGS-HN and pCAGGS-F, respectively. The cDNA encoding the PIV3 F protein will be mutated to eliminate the furin recognition site at amino acid 109. The lysine at amino acid 108 will be changed to glycine. Elimination of cleavage will inhibit the ability of the F protein to fuse. The absence of cell-cell fusion will likely increase the release of VLPs.
Cell lines: PIV 3 grows efficiently in a variety of cell lines from human and primate sources. Thus Hela cells (human cervical carcinoma cells), 293 cells (human embryonic kidney cells), VERO cells (African green monkey kidney cells) and COS-7 (primate) cells will be used. (reviewed in Chanock, et al, Parainfluenza Viruses, in Fields Virology, Ed. Knipe, D. and Howley, P. Lippincott Williams and Wilkins, 2001. LLC-MK2 (rhesus kidney cells) and NCI-H292 (human lung carcinoma) cells will also be used as they have been successfully used to generate virus.
Transfection, infection and metabolic labeling: Transfections of sub confluent cells will be accomplished using Lipofectamine (Invitrogen) as recommended by the manufacturer. The following amounts of plasmid DNA will be used per 35 mm dish: 1.0 μg pCAGGS-NP, 1.0 μg pCAGGS-M, 0.75 μg pCAGGS-F-K108G, and 1.0 μg pCAGGS-HN. A total of 3.75 μg of plasmid DNA per 35 mm plate will be used in all transfection experiments. When only one, two, or three cDNAs are used, the total amount of transfected DNA will be kept constant by adding vector pCAGGS DNA. For each transfection, a mixture of DNA and 5 μl of Lipofectamine in OptiMEM media (Gibco/Invitrogen) will be incubated at room temperature for 45 minutes, and added to cells previously washed with OptiMEM. The cells will be incubated for 5 hours, the Lipofectamine-DNA complexes removed, and 2 ml of supplemented DMEM added. After 36 hours, the medium will be replaced with 0.7 ml DMEM without cysteine and methionine and supplemented with 100 μCi of $^{35}$S-methionine and $^{35}$S-cysteine mixture (NEG-772 EASYTAG™ Express Protein Labeling Mix, $^{35}$S, Perkin Elmer Life Sciences Inc.). After 4 hours of pulse label, one set of transfected plates will be lysed, while in another set the medium will be replaced with 1.0 ml of supplemented DMEM with 0.1 mM cold methionine (Nutritional Biochemicals Corporation). After 8 hours of chase, the cell supernatant will be collected. The cells will be lysed in 0.5 ml lysis buffer (10 mM NaCl, 1.5 mM MgCl2, 10 mM Tris-HCl pH7.4) containing Triton-DOC (1% Triton, 1% sodium deoxycholate) and 1.25 mg N-ethylmaleimide (NEM). Cells will be harvested with a cell scraper and homogenized by passing through a 26-gauge needle 10 to 15 times.

To determine if the VPS pathway is involved in VLP budding, sub confluent HEp-2 cells will be simultaneously transfected with pCAGGS-M and different concentrations of either pBJ5-Vps4-E228Q-Flag or pDsRed2-N1-CHMP3. Corresponding empty vectors will be used as control. Cells will be incubated for 36 hours and the same pulse-chase protocol was performed as described above.

To generate virus particles for controls, cells will be infected at an MOI of 10 pfu for 30 hours and labeled with $^{35}$S-methionine and $^{35}$S-cysteine mixture for 4 hours, and chased in nonradioactive medium for 8 hours as described above. Cell supernatant will be harvested and virions purified as described below. Cells will be lysed and homogenized as described above.

Virus and VLP purification: VLPs as well as virions will be purified from cell supernatants in protocols previously developed for virus purification. The cell supernatants will be clarified by centrifugation at 5000 rpm for 5 min at 4° C., overlaid on top of a step gradient consisting of 3.5 ml 20% and 0.5 ml 65% sucrose solutions in TNE buffer (25 mM Tris-HCl pH 7.4, 150 mM NaCl, 5 mM EDTA), and centrifuged at 40,000 rpm for 12 hours at 4° C. using a SW50.1 rotor (Beckman). The interface (containing concentrated particles) will be collected in 0.5 ml, mixed with 2.0 ml of 80% sucrose, and overlaid on top of 1.0 ml 80% sucrose cushion. Additional layers of sucrose (1.0 ml of 50% and 0.5 ml of 10% sucrose) will be layered on top of the sample. The gradient will be centrifuged at 38,000 rpm for 20 h at 4° C. The gradient will be collected from the bottom into one 1 ml fraction and eight 0.5 ml fractions using a polystaltic pump. Densities of each fraction will be determined using a refractometer. VLPs derived from expression of all combinations of proteins will be prepared in a single experiment, thus enabling direct comparison of results.

Immunoprecipitation and polyacrylamide gel electrophoresis: Immunoprecipitation will be accomplished by combining one volume of cell lysate or sucrose gradient fraction with two volumes of TNE buffer. Samples will be incubated with PIV3 specific polyclonal antibodies for 16 hours at 4° C. Antiserum to be used is commercially available from several sources. Immune complexes (ICs) will be adsorbed to Protein A (Pansorbin Cells, CALBIOCHEM) for 2 hours at 4° C., pelleted, and then washed three times in immunoprecipitation (IP) wash buffer (phosphate buffer saline (PBS) containing 0.5% Tween-20 and 0.4% sodium dodecyl sulfate (SDS)). ICs will be resuspended in SDS-polyacrylamide gel electrophoresis sample buffer (125 mM Tris-HCl, pH 6.8, 2% SDS, 10% glycerol, 0.4% Bromphenol blue) with 1 M β-mercaptoethanol (BME) and boiled. Proteins will be separated on 8% polyacrylamide-SDS gel and subjected to autoradiography. Quantification of resulting autoradiographs will be accomplished using a Fluor-S™ MultiImager (BioRad).

Example 17

Site-Specific Mutagenesis of Late Domains

Mutations in the M protein PKSP (SEQ ID NO: 117) and YANL (SEQ ID NO: 118) sequences at amino acids 216 and 219 and amino acids 232 and 235 were introduced by PCR to yield M-A216A219 and M-A232A235, respectively. Specific sited-directed mutagenic primers were designed to substitute the proline residues at positions 216 and 219 and tyrosine and leucine residues at positions 232 and 235, respectively, with alanine. Additional mutant M genes were constructed by substituting PTAP (SEQ ID NO: 4) or YPDL (SEQ ID NO: 119) sequences for YANL (SEQ ID NO: 118) at amino acid positions 232 to 235.

Example 18

VLP Release from 293T Cells

This example evaluates the effects on particle release of available dominant negative mutant human VPS proteins and whether human renal epithelial cells (293T) could support the release of NDV VLPs.

VLP particles were released from 293T cells expressing M protein alone (top panel) or 293T cells co-expressing NP, M, F-K115Q and HN proteins (bottom panel). FIG. 67, Panel A. Particles released from 293T cells expressing M protein alone were very heterogeneous with respect to density (FIG. 67, panel A, top panel), very similar to particles released from avian cells expressing M protein alone (data not shown). In contrast, VLPs released from 293T cells expressing all 4 major structural proteins were more homogenous in density. These particles were slightly less dense (1.18 g/cc) than the authentic virus (1.2 g/cc; (Lamb et al., In: *Paramyxoviridae: The Viruses and Their Replication*, Third edition ed, vol. 1. LippincottWilliams & Wilkins, Philadelphia (2001))) due to absence of genomic RNA.

These combined results show that M protein VLPs and complete VLPs were released from 293T cells. However, the efficiency of release of particles from 293T cells, as measured by the percentage of pulse labeled M protein remaining in cells after a long nonradioactive chase, was lower than VLP release from avian cells (50% vs. 84%, respectively, data not shown).

Example 19

Dominant Negative VPS Protein Mutants Inhibit Particle Release

This example was designed to determine if inhibition of particle release was due only to over expression of dominant negative VPS proteins.

293T cells were transfected with vector control, wild type CHMP3, wild type Vps4A, wild type AIP1, dominant negative (dn) CHMP3, dn Vps4A, and dn AIP1.

The wild type forms of each VPS protein had little effect on particle release. M protein particle release was inhibited by dn-CHMP3 to about 90%. (FIG. 68, Panels A and B). Vps4A-E228Q inhibited M protein VLP release by about 90% (FIG. 68, Panels C and D), and AIP-1-RFP inhibited particle release by 90% (FIG. 68, Panels E and F). The dominant negative forms of CHMP3, Vps4A, and AIP1, but not the wild type forms, inhibited the release of VLPs containing all four viral proteins. FIG. 69.

These combined results show that the inhibition of VLP release was not due to over expression of the VPS protein, but rather due to specific effect of the dn mutant proteins. These results support the conclusion that an intact VPS pathway facilitates M protein particle release.

Example 20

YANL Sequence Mutations Inhibit VLP Release

This example presents data showing that the L domain of an NDV M protein plays a role in particle budding. For example, the sequence of a NDV M protein has two possible L domain sequences, PKSP (SEQ ID NO: 117) and YANL (SEQ ID NO: 118), which are similar to the classical L domains PTAP (SEQ ID NO: 4) and YPXL (SEQ ID NO: 120), respectively (Freed, E. O., "Mechanisms of enveloped virus release" Virus Res 106:85-86 (2004)). The data below shows that by inducing mutations in these L domain sequences, VLP release may be inhibited.

The proline residues in the PKSP (SEQ ID NO: 117) sequence were substituted with alanine (M-A216A219); and the tyrosine and leucine in the YANL (SEQ ID NO: 118) sequence were substituted with alanine (M-A232A235) (FIG. 70, Panel A). These mutant M proteins were expressed either individually (FIG. 70, Panel B, extracts) or in combination with NP, F-K115Q and HN proteins (FIG. 70, Panel D, extracts). Particles were released from cells expressing the M-$A_{216}A_{219}$ mutant at levels comparable to cells expressing wild type M protein. FIG. 5, Panels B-E.

In contrast, there was a significant reduction of particles released from cells expressing the M-$A_{232}A_{235}$ mutant (FIG. 70, Panel B). Similarly, co-expression M-$A_{232}A_{235}$ mutant protein with NP, F-K115Q and HN proteins resulted in 80% reduction in particles released (FIG. 70, Panel D, compare lanes 6 and 8 and Panel E). Amounts of VLPs released from cells co-expressing the M-$A_{216}A_{219}$ mutant protein with NP, F-K115Q and HN proteins were comparable to wild type levels (FIG. 70, Panel D, lanes 6 and 7).

To determine if the inhibition of particle release by mutation of the YANL (SEQ ID NO: 118) sequence was due to elimination of L domain activity or defects in conformation of the M protein, the YANL (SEQ ID NO: 118) sequence was substituted separately with two known classical L domain sequences, YPDL (SEQ ID NO: 119) and PTAP (SEQ ID NO: 4) (Morita et al., "Retrovirus budding" Annu Rev Cell Dev Biol 20:395-425 (2004); Strack et al., "AIP1/ALIX is a binding partner for HIV-1 p6 and EIAV p9 functioning in virus budding" Cell 114:689-699 (2003)).

Both the YPDL (SEQ ID NO: 119) and PTAP (SEQ ID NO: 4) sequences supported release of the NDV M protein particles. FIG. 70, Panels B & C. The amounts of particles released from NDV M protein containing the substituted YPDL (SEQ ID NO: 119) and PTAP (SEQ ID NO: 4) motif were comparable to wild type levels. These results strongly indicate that the YANL (SEQ ID NO: 118) sequence at position 232 to 235 in the NDV M protein functions as an L domain.

Retrovirus particles, which have a gag protein with an YPXL (SEQ ID NO: 120) L domain, contain AIP1 (Strack et al., "AIP1/ALIX is a binding partner for HIV-1 p6 and EIAV p9 functioning in virus budding" Cell 114:689-699 (2003)) and may represent a polypeptide with an approximate size of 100 kD in the SDS-PAGE gels containing NDV VLP proteins or virion proteins. AIP1 was incorporated into NDV particles and VLPs, thereby co-expressing M protein with an HA-tagged AIP1 at either the N-terminal (HA-AIP1) or the C-terminal (AIP1-HA), or with vector alone. M protein particles were released from both cells expressing M protein with vector and cells expressing M protein and either HA-tagged AIP1. FIG. 71, Panel A. The expression of HA-AIP1 and AIP1-HA were at comparable levels (FIG. 71, panel A, IB extract gel, lanes 2 and 3). However, only AIP1-HA incorporated into VLPs (FIG. 71, panel A, IB VLP gel lane 3). AIP1-HA can also be precipitated from purified disrupted VLPs. FIG. 71, Panel B, right.

These results demonstrated that AIP1 is incorporated into VLPs and suggest that AIP1 may be interacting directly or indirectly with the M protein in particles.

Example 21

Co-Immunoprecipitation

Purified VLPs were incubated in ice cold TNE buffer (25 mM Tris HCl, pH 7.4, 150 mM NaCl, 5 mM EDTA) containing 1% Triton X-100, 2.5 mg/ml N-ethylmaleimide for 15 minutes. Excess primary antibody was added and VLPs were incubated at 4° C. overnight. Pansorbin cells, blocked overnight in TNE buffer containing 1% Triton X-100 and 5 mg bovine serum albumin (BSA) and then prewashed in TNE containing 1% Triton X-100 and 1 mg/ml BSA, were added in excess as determined in preliminary experiments, and incubation was continued at 4° C. with constant mixing for at least 2 h. Immune complexes were collected by centrifugation (10,000 rpm for 30 seconds in a microcentrifuge) and washed three times in ice-cold TNE containing 0.5% Triton X-100. The pelleted complexes were resuspended in gel sample buffer.

Example 22

Protease Protection Assay

Protease digestion of M protein from avian cell extracts and VLPs was accomplished by adding 0.25, 0.5, 1, 5, 10, and 20 μg of proteinase K per ml of sample and incubating for 30 min on ice. In parallel, VLPs were also made 0.5% with respect to Triton X-100 prior to incubation with proteinase K. After digestion, phenylmethylsulfonyl fluoride (PMSF) (0.1 M) was added. For subsequent immunoprecipitation, the reaction mixtures were made 1% with respect to Triton X-100 and 0.5% with respect to sodium deoxycholate.

Example 23

Immunofluorescence Microscopy

Avian cells, grown in 35 mm dish containing glass coverslips, were transfected with different combinations of NDV cDNAs as described above. After 40 hours, nuclei were stained with 5 μg/ml 4',6-Diamidino-2-phenylindole (DAPI) for 30 min at 37° C. Cells were washed twice with ice-cold immunofluorescence (IF) buffer (PBS containing 1% bovine serum albumin, 0.02% sodium azide, and 5 mM $CaCl_2$), fixed with 2% paraformaldehyde, blocked with IF buffer for 2 hours, and incubated for 1 hour at 4° C. in IF buffer containing polyclonal antibodies against HN and F proteins.

Cells were washed twice with ice-cold IF buffer, permeabilized with 0.05% Triton X-100, blocked with IF buffer for at least 2 hours and incubated for 1 hour at 4° C. in IF buffer containing purified ascites fluids containing anti-M protein monoclonal antibody (52-E5). Cells were then washed twice with ice-cold buffer followed by incubation for 1 hour at 4° C. in IF buffer containing fluorescein conjugated goat anti-rabbit IgG (Alexa® 488; Molecular Probes) and rhodamine conjugated goat anti-mouse IgG (Alexa® 568; Molecular Probes) secondary antibodies. Cells were washed with ice-cold IF buffer, mounted onto slides using a mounting medium (Vectashield®, Vector Labs, Inc) for immunofluorescence microscopy. Fluorescence images were acquired using a Nikon fluorescence microscope and Openlab® software and processed using Adobe Photoshop®.

Example 24

Membrane Associated M Protein

This example provides data confirming sucrose gradient data suggesting that M protein may be associated with membranes by incubation with a protease.

VLPs and cell extracts were either left untreated (FIG. 62, lane 1) or treated with different concentrations of Proteinase K (lanes 2 to 7). As expected, the M protein in cell extracts was sensitive to low concentrations of protease (FIG. 62 upper panel). The lower band below the M protein is a protease digestion product indicating that M protein has a protease resistant core. However, M proteins in VLPs were largely protected from protease digestion (FIG. 62, middle panel). In contrast, disruption of the particle membrane with detergent resulted in digestion of the M protein (FIG. 62, lower panel).

Taken together, these results demonstrated that the M protein VLPs are membrane-bound particles.

Example 25

M Protein Mediated VLP Release

This example extends the data relevant to M protein sufficiency for VLP release by studying the release of VLPs in the absence of an M protein gene.

Cells were transfected with all possible combinations of NP, F, and HN cDNAs in the absence of the M gene. Cells expressing any combination of proteins without M protein did not release VLPs. FIG. 63. Furthermore, in the absence of M protein, NP, F and HN proteins (expressed in pair-wise combinations) were retained in cell extracts after the 8 hour chase (FIG. 3; Panel A: lanes 2, 4 and 5, and Panel C).

These results strongly suggest that VLP release is mediated by the M protein.

Example 26

M Protein/Glycoprotein Co-Localization

This example explores further the role played by each protein in VLP assembly. Specifically, the plasma membrane localization of M, F and HN proteins was determined by immunofluorescence.

Transfected cells were incubated with anti-F protein or anti-HN protein antibodies prior to cell permeabilization to limit binding of antibodies to cell surface F or HN proteins. Cells were then permeabilized using 0.05% Triton X-100 and then incubated with M protein specific antibody.

Vector-transfected control cells and as well as cells expressing individually M, F-K115Q or HN proteins, demonstrated that the F-K115Q and HN proteins were diffusely distributed on the surface of the cells (FIG. 64, Panel A). M protein exhibited diffuse cytoplasmic staining as well as punctate structures of various sizes (FIG. 64, Panel A; anti-M image and merged image). Co-expression of either F or HN proteins with M protein, however, had little effect on the distribution of M protein, F protein, or HN protein. Further, little to no co-localization of F or HN glycoproteins with M protein was observed. FIG. 64, Panel B. These findings correlate with the very low incorporation of F or HN proteins into M protein containing VLPs after pair-wise co-expression.

Co-expression of M protein with at least two other proteins slightly changed the distribution of M protein. For example, M protein co-expression with F and HN proteins increased the co-localization of M protein with either F or HN proteins. FIG. 64, Panel C. This result is consistent with an increased incorporation of HN, F, or NP proteins when two proteins are co-expressed with M protein.

When all four proteins were co-expressed, the distribution of M protein was changed to more punctuate structures distributed mostly along the edges of the cells. Further, most of the F or HN protein signal co-localized with the M protein. FIG. 64, Panel D. Although it is not necessary to understand the mechanism of an invention, it is believed that this result is consistent with a more ordered assembly of VLPs when all four proteins are co-expressed.

Altogether, these results suggest that co-localization of viral proteins is detected with expression of three proteins and is most dramatic when NP, M, F and HN proteins are co-expressed. These results also suggest that there are specific protein-protein interactions involved in assembling particles.

Example 27

VLP Viral Protein Interactions

This example provides identification of several specific protein interactions involved in VLP assembly using co-immunoprecipitation techniques.

Radioactively labeled VLPs formed with different combinations of proteins were solubilized in 1% Triton X-100 and the proteins present were precipitated, separately, with cocktails of monospecific antibodies for M, HN or F proteins. Proteins were also precipitated with a mix of antibodies with specificities for all proteins in order to precipitate total VLP proteins (lane 6).

First, each antibody cocktail precipitated all proteins from VLPs formed with M, HN, F and NP, although the efficiency of precipitation for each protein varied with the antibody specificity (FIG. 65, Panel A). Although it is not necessary to understand the mechanism of an invention, it is believed that these results are consistent with a network of interactions between all four proteins such that precipitation of one resulted in the precipitation of the other three proteins.

The results also suggested that proteins indirectly linked to the precipitated protein were less efficiently precipitated than a protein directly linked to a precipitated protein. For example, anti-F protein antibody precipitated NP very efficiently but M protein very inefficiently (lane 3). This observation suggests that there may be a direct link between F protein and NP, but not F protein and M protein.

The protein interactions in VLPs were more clearly defined by precipitation of proteins from VLPs formed with all combinations of three proteins. In VLPs released from cells expressing M, F-K115Q and HN proteins, anti-F protein precipitated only F protein and traces of HN protein (FIG. 65, Panel B, lane 3). This result indicates that the F protein does not directly complex with the M protein.

Anti-HN protein antibody co-precipitated M protein and HN protein (FIG. 65, panel B, lane 4). Likewise, anti-M protein antibody co-precipitated HN protein and M protein (FIG. 65, panel B, lane 5). These results strongly suggest that the M protein interacts with HN protein but not with the F protein.

VLPs were also released containing NP, M and F-K115Q proteins. Anti-F protein antibody co-precipitated NP and F protein, but not M protein. (FIG. 65, panel C, lane 3). Anti-M protein antibody co-precipitated NP and M protein, but not F protein (FIG. 65, panel C, lane 4). These observations indicate that M protein directly interacts with NP and that the F protein interacts with NP and confirm that F and M protein do not interact.

Although it is not necessary to understand the mechanism of an invention, it is believed that anti-M protein antibody does not indirectly precipitate detectable amounts of F protein because an inefficient precipitation of NP protein may decrease the amounts of F protein precipitated to very low levels. Alternatively, NP-NP interactions required to precipitate F protein with anti-M protein antibody may be disrupted by VLP lysis. For example, when VLPs containing NP, M and HN were used, complexes formed with anti-HN protein antibody contained NP and M proteins as well as HN protein (FIG. 65, panel D, lane 3). In addition, anti-M protein antibody precipitated NP and HN proteins (FIG. 65, panel D, lane 4). These observations are consistent with the conclusion that the M protein interacts with both NP and HN proteins. It is further contemplated that, in one embodiment, HN protein and NP protein may interact.

Overall, results of co-immunoprecipitation of proteins in VLPs as well as results of cellular co-localization studies provide a rational basis for the incorporation of viral proteins into VLPs and suggest that specific protein interactions are involved in the assembly of an NDV virus-like particle.

---

We claim:

1. A non-infectious, replication incompetent virus-like particle comprising a Newcastle Disease Virus (NDV) matrix protein, wherein said virus-like particle
   i) lacks NDV RNA, and
   ii) is produced by extracellular release from a cell that expresses a recombinant nucleotide sequence comprising a sequence that encodes said Newcastle Disease Virus (NDV) matrix protein,
   wherein at least 85% of the expressed NDV matrix protein is released from said cell.

2. The virus-like-particle of claim 1, further comprising a viral glycoprotein.

3. The virus-like particle of claim 2, comprising at least two viral glycoproteins.

4. The virus-like particle of claim 1, further comprising one or more NDV proteins selected from the group consisting of nucleocapsid protein, fusion protein, and hemagglutinin-neuraminidase protein.

5. A non-infectious, replication incompetent virus-like particle comprising a Newcastle Disease Virus (NDV) matrix protein, wherein said virus-like particle
   i) lacks NDV RNA, and
   ii) is produced by extracellular release from a cell that expresses a recombinant nucleotide sequence comprising a sequence that encodes said Newcastle Disease Virus (NDV) matrix protein, and
   wherein at least 85% of the expressed NDV matrix protein is released from said cell, and wherein said NDV matrix protein comprises a Late Domain that functions in extracellular release of said virus-like particles from said cell.

6. The virus-like-particle of claim 5, wherein said Late Domain comprises the amino acid sequence PKSP (SEQ ID NO:117).

7. The virus-like-particle of claim 5, wherein said Late Domain comprises the amino acid sequence YANL (SEQ ID NO:118).

8. A non-infectious, replication incompetent virus-like particle comprising a Newcastle Disease Virus (NDV) matrix protein, wherein said virus-like particle is produced by extracellular release from a cell that expresses a recombinant nucleotide sequence comprising a sequence that encodes said Newcastle Disease Virus (NDV) matrix protein, wherein at least 85% of the expressed NDV matrix protein is released from said cell, wherein said NDV matrix protein comprises a Late Domain that functions in extracellular release of said virus-like particles from said cell, and wherein said Late Domain comprises an amino acid sequence selected from the group consisting of YPDL (SEQ ID NO:119) and PTAP (SEQ ID NO:4).

9. The virus-like-particle of claim 1, wherein said cell is an avian cell.

10. The virus-like-particle of claim 1, wherein said cell is an insect cell.

11. The virus-like-particle of claim 1, wherein said virus-like particle is released from said cell at an efficiency of 90%.

12. The virus-like-particle of claim 1, wherein said virus-like particle is released from said cell at an efficiency of approximately 100%.

13. The virus-like-particle of claim 1, wherein said Newcastle Disease Virus (NDV) matrix protein is selected from the group consisting of (a) SEQ ID NO:12, (b) SEQ ID NO:24, (c) SEQ ID NO:26, and (d) a protein comprised in an amino acid sequence encoded by nucleotide sequence SEQ ID NO:28.

14. The virus-like-particle of claim 6, wherein said NDV matrix protein comprises a sequence selected from the group consisting of SEQ ID NO:12 and SEQ ID NO:24.

15. The virus-like particle of claim 7, wherein said NDV matrix protein comprises a sequence selected from the group consisting of SEQ ID NO:12, SEQ ID NO:24, and SEQ ID NO:26.

16. A non-infectious, replication incompetent virus-like particle comprising a Newcastle Disease Virus (NDV) matrix protein, wherein said virus-like particle is produced by extracellular release from a cell that expresses a recombinant nucleotide sequence comprising a sequence that encodes said Newcastle Disease Virus (NDV) matrix protein, wherein least 85% of the expressed NDV matrix protein is released from said cell, wherein said NDV matrix protein comprises a Late Domain that functions in extracellular release of said virus-like particles from said cell, wherein said NDV matrix protein comprises a sequence selected from the group consisting of SEQ ID NO:12, SEQ ID NO:24, and SEQ ID NO:26, except that said amino acid sequence YANL that is at amino acids 232 to 235 of said SEQ ID NO:12, SEQ ID NO:24, and SEQ ID NO:26 is substituted with amino acid sequence PTAP (SEQ ID NO:4).

17. A non-infectious, replication incompetent virus-like particle comprising a Newcastle Disease Virus (NDV) matrix protein, wherein said virus-like particle is produced by extracellular release from a cell that expresses a recombinant nucleotide sequence comprising a sequence that encodes said Newcastle Disease Virus (NDV) matrix protein, wherein at least 85% of the expressed NDV matrix protein is released from said cell, wherein said NDV matrix protein comprises a Late Domain that functions in extracellular release of said virus-like particles from said cell, wherein said NDV matrix protein comprises a sequence selected from the group consisting of SEQ ID NO:12, SEQ ID NO:24, and SEQ ID NO:26, except that said amino acid sequence YANL that is at amino acids 232 to 235 of said SEQ ID NO:12, SEQ ID NO:24, and SEQ ID NO:26 is substituted with amino acid sequence YPDL (SEQ ID NO:119).

18. A non-infectious, replication-incompetent virus-like particle comprising a Newcastle Disease Virus (NDV) matrix protein, wherein said virus-like particle lacks NDV RNA and is produced by extracellular release from a cell that expresses a recombinant nucleotide sequence consisting of a sequence that encodes said Newcastle Disease Virus (NDV) matrix protein.

19. The virus-like-particle of claim 18, wherein said virus-like particle is released from said cell at an efficiency greater than the efficiency of release of a VLP comprising NDV M protein, NDV NP protein, NDV F protein, and NDV HN protein.

20. The virus-like-particle of claim 18, wherein at least 85% of the expressed NDV matrix protein is released from said cell.

21. The virus-like-particle of claim 20, wherein 90% of the expressed NDV matrix protein is released from said cell.

22. The virus-like-particle of claim 20, wherein approximately 100% of the expressed NDV matrix protein is released from said cell.

23. The virus-like-particle of claim 19, further comprising a viral glycoprotein.

24. The virus-like particle of claim 23, comprising at least two viral glycoproteins.

25. The virus-like particle of claim 19, further comprising one or more NDV proteins selected from the group consisting of nucleocapsid protein, fusion protein, and hemagglutinin-neuraminidase protein.

26. A non-infectious, replication-incompetent virus-like particle comprising a Newcastle Disease Virus (NDV) matrix protein, wherein said virus-like particle lacks NDV RNA and is produced by extracellular release from a cell that expresses a recombinant nucleotide sequence consisting of a sequence that encodes said Newcastle Disease Virus (NDV) matrix protein, wherein said NDV matrix protein comprises a Late Domain that functions in extracellular release of said virus-like particles from said cell.

27. The virus-like-particle of claim 26, wherein said Late Domain comprises the amino acid sequence PKSP (SEQ ID NO:117).

28. The virus-like-particle of claim 26, wherein said Late Domain comprises the amino acid sequence YANL (SEQ ID NO:118).

29. A non-infectious, replication-incompetent virus-like particle comprising a Newcastle Disease Virus (NDV) matrix protein, wherein said virus-like particle is produced by extracellular release from a cell that expresses a recombinant nucleotide sequence consisting of a sequence that encodes said Newcastle Disease Virus (NDV) matrix protein, wherein said NDV matrix protein comprises a Late Domain that functions in extracellular release of said virus-like particles from said cell, and wherein said Late Domain comprises an amino acid sequence selected from the group consisting of YPDL (SEQ ID NO:119) and PTAP (SEQ ID NO:4).

30. The virus-like-particle of claim 18, wherein said cell is an avian cell.

31. The virus-like-particle of claim 18, wherein said cell is an insect cell.

32. The virus-like-particle of claim 18, wherein said Newcastle Disease Virus (NDV) matrix protein is selected from the group consisting of (a) SEQ ID NO:12, (b) SEQ ID NO:24, (c) SEQ ID NO:26, and (d) a protein comprised in an amino acid sequence encoded by nucleotide sequence SEQ ID NO:28.

33. The virus-like-particle of claim 27, wherein said NDV matrix protein comprises a sequence selected from the group consisting of SEQ ID NO:12 and SEQ ID NO:24.

34. The virus-like particle of claim 28, wherein said NDV matrix protein comprises a sequence selected from the group consisting of SEQ ID NO:12, SEQ ID NO:24, and SEQ ID NO:26.

35. A non-infectious, replication-incompetent virus-like particle comprising a Newcastle Disease Virus (NDV) matrix protein, wherein said virus-like particle is produced by extracellular release from a cell that expresses a recombinant nucleotide sequence consisting of a sequence that encodes said Newcastle Disease Virus (NDV) matrix protein, wherein said NDV matrix protein comprises a Late Domain that functions in extracellular release of said virus-like particles from said cell, and wherein said Late Domain comprises amino acid sequence PTAP (SEQ ID NO:4).

36. A non-infectious, replication-incompetent virus-like particle comprising a Newcastle Disease Virus (NDV) matrix protein, wherein said virus-like particle is produced by extracellular release from a cell that expresses a recombinant nucleotide sequence consisting of a sequence that encodes said Newcastle Disease Virus (NDV) matrix protein, wherein said NDV matrix protein comprises a Late Domain that functions in extracellular release of said virus-like particles from said cell, and wherein said Late Domain comprises amino acid sequence YPDL (SEQ ID NO:119).

37. A composition comprising the virus-like particle of any one of claims 1-10 and 11-36.

38. A method for producing the virus-like particle of claim 1, 5, 8, 16, 17, 18, 26, 29, 35, or 36, comprising transfecting a cell with one or more expression vector(s) encoding the particle protein(s) under conditions that said cell produces said virus-like particle.

39. A preparation of virus-like particles produced by the method of claim 38.

40. An isolated cell for producing the virus-like particle of claim 1, 5, 8, 16, 17, 18, 26, 29, 35, or 36, said cell being transfected with one or more expression vectors encoding the protein(s) necessary to produce said particle.

41. A method for immunizing a host susceptible to Newcastle disease, comprising
  a) providing
   1) an immunogenic composition comprising a virus-like particle selected from the group consisting of
    i) the virus-like particle of claim 1,
    ii) the virus-like particle of claim 5,
    iii) the virus-like particle of claim 8,
    iv) the virus-like particle of claim 16,
    v) the virus-like particle of claim 17,
    vi) the virus-like particle of claim 18,
    vii) the virus-like particle of claim 26,
    viii) the virus-like particle of claim 29,
    ix) the virus-like particle of claim 35, and
    x) the virus-like particle of claim 36, and
   2) a host susceptible to Newcastle disease, and
  b) administering said immunogenic composition to said host under conditions such that antibodies directed to said virus-like particle are produced.

42. An immunogenic composition comprising a virus-like particle selected from the group consisting of
  a) the virus-like particle of claim 1,
  b) the virus-like particle of claim 5,
  c) the virus-like particle of claim 8,
  d) the virus-like particle of claim 16,
  e) the virus-like particle of claim 17,
  f) the virus-like particle of claim 18,
  g) the virus-like particle of claim 26,
  h) the virus-like particle of claim 29,
  i) the virus-like particle of claim 35, and
  j) the virus-like particle of claim 36.

43. A method for producing a virus-like particle selected from the group consisting of
  i) the virus-like particle of claim 18,
  ii) the virus-like particle of claim 26,
  iii) the virus-like particle of claim 29,
  iv) the virus-like particle of claim 35, and
  v) the virus-like particle of claim 36, comprising transfecting a cell with one or more expression vector(s) encoding the particle protein(s) under conditions that
  a) said cell produces said virus-like particle, and
  b) at least 85% of the expressed NDV matrix protein is released from said cell.

44. The method of claim 43, wherein 90% of the expressed NDV matrix protein is released from said cell.

45. The method of claim 43, wherein approximately 100% of the expressed NDV matrix protein is released from said cell.

* * * * *

SEQUENCE LISTING

```
<160> NUMBER OF SEQ ID NOS: 123

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Phe Pro Ile Val
1

<210> SEQ ID NO 2
<211> LENGTH: 4
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Pro Xaa Xaa Pro
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

Tyr Xaa Xaa Leu
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Pro Thr Ala Pro
1

<210> SEQ ID NO 5
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Pro Pro Xaa Tyr
1

<210> SEQ ID NO 6
<211> LENGTH: 489
<212> TYPE: PRT
<213> ORGANISM: Newcastle disease virus

<400> SEQUENCE: 6

Met Ser Ser Val Phe Asp Glu Tyr Glu Gln Leu Leu Ala Ala Gln Thr
1               5                   10                  15

Arg Pro Asn Gly Thr His Gly Gly Gly Glu Lys Gly Ser Thr Leu Lys
            20                  25                  30

Val Glu Val Pro Val Phe Thr Leu Asn Ser Asp Asp Pro Glu Asp Arg
        35                  40                  45

Trp Asn Phe Ala Val Phe Cys Leu Arg Ile Ala Val Ser Glu Asp Ala
    50                  55                  60

Asn Lys Pro Leu Arg Gln Gly Ala Leu Ile Ser Leu Leu Cys Ser His
65                  70                  75                  80
```

```
Ser Gln Val Met Arg Asn His Val Ala Leu Ala Gly Lys Gln Asn Glu
            85                  90                  95

Ala Thr Leu Ala Val Leu Glu Ile Asp Ser Phe Ala Asp Ser Val Pro
        100                 105                 110

Gln Phe Asn Asn Arg Ser Gly Val Ser Glu Glu Arg Ala Gln Arg Phe
            115                 120                 125

Met Val Ile Ala Gly Ser Leu Pro Arg Ala Cys Ser Asn Gly Thr Pro
130                 135                 140

Phe Val Thr Ala Gly Val Glu Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
        195                 200                 205

Leu His Pro Val Cys Arg Ser Ala Ile Gln Leu Thr Ile Arg His Ser
    210                 215                 220

Leu Ala Val Arg Ile Phe Leu Val Ser Glu Leu Lys Arg Gly Arg Asn
225                 230                 235                 240

Thr Ala Gly Gly Ser Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Thr
        275                 280                 285

Gly Asp Ile Gln Lys Met Lys Gln Leu Met Arg Leu Tyr Arg Met Lys
    290                 295                 300

Gly Glu Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Gly Lys Tyr Gln Phe Ala Arg
            340                 345                 350

Asp Phe Met Ser Thr Ser Phe Trp Arg Leu Gly Val Glu Tyr Ala Gln
        355                 360                 365

Ala Gln Gly Ser Ser Ile Asn Glu Asp Met Ala Ala Glu Leu Lys Leu
    370                 375                 380

Asn Pro Ala Ala Arg Arg Gly Leu Ala Ala Ala Gln Arg Val Ser
385                 390                 395                 400

Glu Glu Ile Gly Asn Met Asp Ile Pro Thr Gln Ala Gly Val Leu
                405                 410                 415

Thr Gly Leu Ser Asp Lys Gly Pro Arg Ala Pro Gln Gly Gly Pro Ser
            420                 425                 430

Arg Ser Gln Gly Gln Pro Asp Ala Gly Asp Gly Glu Thr Gln Phe Leu
        435                 440                 445

Asp Leu Met Arg Ala Val Ala Asn Ser Met Arg Glu Ala Pro Asn Ser
    450                 455                 460

Ala Gln Ser Thr Ile His Pro Glu Pro Leu Pro Thr His Gly Pro Ser
465                 470                 475                 480

Gln Asp Asn Asp Thr Asp Trp Gly Tyr
                485
```

```
<210> SEQ ID NO 7
<211> LENGTH: 1470
<212> TYPE: DNA
<213> ORGANISM: Newcastle disease virus

<400> SEQUENCE: 7
atgtcgtccg tatttgacga atacgagcag ctcctcgctg ctcagacccg ccctaacgga      60
actcatggag ggggagagaa agggagcact ttaaaagttg aggtcccagt atttacccct    120
aacagtgatg atccagagga tagatggaat tttgcggtat tctgtcttcg gattgctgtt    180
agcgaggatg ccaacaaacc actcaggcaa ggtgctctta tatcccctctt atgctcccat    240 tctcaggtga tgagaaacca cgttgccctt gcagggaaac agaatgaggc tacactggct    300
gttcttgaga tcgatagttt tgccgacagt gtgccccagt tcaacaatag agtggagtg     360 tctgaggaaa gagcacagag attcatggta atagcaggat ctctccctcg ggcatgcagc    420
aacggtactc cgttcgtcac agctggggtt gaagatgatg caccagaaga tatcactgac    480
actctggaaa gaatcctatc tatccaggct caggtatggg tcacagtagc aaaggccatg    540
actgcatatg agacagcaga tgagtcggaa acaagaagaa taaataagta tatgcagcaa    600
ggtagagtcc agaagaaata catccttcac cctgtatgca ggagtgcaat tcaactcaca    660
atcagacatt ctctggcagt ccgtattttc ctagttagtg agctcaagag gggccgcaat    720
acagcaggtg ggagctccac atattacaac ttggtcgggg atgtagactc atacatcaga    780
aacaccgggc ttactgcatt tttcctaaca ctcaaatatg gaatcaatac caagacgtca    840
gccctcgcac tcagcagcct cacaggtgat atccaaaaaa tgaaacagct catgcgttta    900
tatcggatga aggtgaaaaa tgcaccatac atgacattgt taggtgacag tgaccagatg    960
agctttgcac cagctgagta tgcacaactt tattcttttg ccatgggcat ggcatcagtc   1020
ttagataagg gaactggcaa ataccaattc gccagagact tcatgagcac atcattctgg   1080
agactcgggg tggagtatgc tcaggctcag ggaagtagca tcaatgaaga tatggctgct   1140
gaattgaaac ttaacccagc agcaaggagg ggcctggcag ctgctgccca acgagtatct   1200
gaggaaattg gcaacatgga tattcctact caacaggccg gggtccttac tgggctcagc   1260
gacaaaggtc cccgagctcc acagggtgga ccgagcaggt cgcaagggca accggacgcc   1320
ggggatgggg agacccaatt cctggatctg atgagagcag tggcaaacag catgcgagaa   1380
gcgccaaatt ctgcacagag caccattcac ccggagcctc tcccaactca tgggccatct   1440
caagacaacg acaccgactg ggggtactga                                     1470

<210> SEQ ID NO 8
<211> LENGTH: 571
<212> TYPE: PRT
<213> ORGANISM: Newcastle disease virus

<400> SEQUENCE: 8

Met Asp Arg Val Val Ser Arg Val Val Leu Glu Asn Glu Glu Arg Glu
1               5                   10                  15

Ala Lys Asn Thr Trp Arg Leu Val Phe Arg Ile Ala Val Leu Ser Leu
            20                  25                  30

Val Val Met Thr Leu Ala Ile Ser Val Ala Thr Leu Val Tyr Ser Met
        35                  40                  45

Glu Ala Ser Thr Pro Gly Asp Leu Ala Gly Ile Ser Thr Val Ile Ser
    50                  55                  60

Lys Ala Glu Asp Lys Val Ile Ser Leu Leu Ser Ser Asn Gln Asp Val
65                  70                  75                  80
```

```
Val Asp Arg Val Tyr Lys Gln Val Ala Leu Glu Ser Pro Leu Ala Leu
            85                  90                  95

Leu Asn Thr Glu Ser Val Ile Met Asn Ala Ile Thr Ser Leu Ser Tyr
        100                 105                 110

Gln Ile Asn Gly Ala Ala Asn Asn Ser Gly Cys Gly Ala Pro Val His
    115                 120                 125

Asp Pro Asp Tyr Val Gly Gly Val Gly Lys Glu Leu Ile Val Asp Asp
130                 135                 140

Thr Ser Asp Val Thr Ser Phe Tyr Pro Ser Ala Tyr Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Ile Glu Glu Glu Asp Tyr Lys Ser Ala Thr Pro Thr Ser Met Val His
            260                 265                 270

Gly Arg Leu Gly Phe Asp Gly Gln Tyr His Glu Lys Asp Leu Asp Val
        275                 280                 285

Thr Ala Leu Phe Lys Asp Trp Val Ala Asn Tyr Pro Gly Val Gly Gly
290                 295                 300

Gly Ser Leu Ile Gly Asp Arg Val Trp Phe Pro Val Tyr Gly Gly Leu
305                 310                 315                 320

Lys Pro Asn Ser Pro Ser Asp Ile Ala Gln Glu Gly Arg Tyr Val Ile
                325                 330                 335

Tyr Lys Arg Tyr Asn Asn Thr Cys Pro Asp Glu Gln Asp Tyr Gln Val
            340                 345                 350

Arg Met Ala Lys Ser Ser Tyr Lys Pro Gly Arg Phe Gly Gly Lys Arg
        355                 360                 365

Val Gln Gln Ala Ile Leu Ser Ile Lys Val Ser Val Ser Leu Gly Glu
370                 375                 380

Asp Pro Val Leu Thr Val Pro Pro Asn Thr Val Thr Leu Met Gly Ala
385                 390                 395                 400

Glu Gly Arg Val Leu Thr Val Gly Thr Ser His Phe Leu Tyr Gln Arg
                405                 410                 415

Gly Ser Ser Tyr Phe Ser Pro Ala Leu Leu Tyr Pro Met Thr Ile His
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Ile Thr Gly Val Tyr Thr Asp Pro Tyr Pro Val Val Phe His Lys
465                 470                 475                 480

Asn His Thr Leu Arg Gly Val Phe Gly Thr Met Leu Asp Asn Glu Gln
                485                 490                 495

Ala Arg Phe Asn Pro Val Ser Ala Val Phe Asp Tyr Thr Ser Arg Ser
            500                 505                 510
```

Arg Ile Thr Arg Val Ser Ser Ser Thr Lys Ala Ala Tyr Thr Thr
            515                 520                 525

Ser Thr Cys Phe Lys Val Val Lys Thr Asn Lys Ile Tyr Cys Leu Ser
        530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570

<210> SEQ ID NO 9
<211> LENGTH: 2120
<212> TYPE: DNA
<213> ORGANISM: Newcastle disease virus

<400> SEQUENCE: 9

| | | | | |
|---|---|---|---|---|
| acgggtagaa | cggtgggaga | ggccacccct | tagtggggaa | ccaagcttct | taacgtccgt | 60 |
| tctaccgcat | taccaatagc | ataccttagt | catggatcgt | gtagttagta | gggttgtact | 120 |
| agagaatgag | gaaagagaag | caaagaacac | atggcgcctg | gttttcgga | tcgcagtctt | 180 |
| atctctagta | gtaatgactt | tagctatctc | tgttgccacc | ctagtataca | gcatggaggc | 240 |
| tagcacaccg | ggcgatctgg | cgggcatatc | gacggtgatc | tctaaggcag | aggataaggt | 300 |
| gatatctcta | ctcagttcaa | atcaagatgt | ggtagatagg | gtatataaac | aggtggccct | 360 |
| tgagtcccca | ctggcattgc | tgaatactga | gtctgtaatt | atgaatgcaa | taacttctct | 420 |
| ctcctatcaa | attaacggag | ccgcaaataa | tagtgggtgt | ggggcacctg | ttcatgaccc | 480 |
| agattacgtt | gggggagtag | gcaaagagct | catagtagat | gacacaagtg | atgtcacatc | 540 |
| attctaccct | tcagcatacc | aagaacacct | gaattttatc | ccggcgccta | ctacaggatc | 600 |
| aggctgcact | cggataccct | cgttcgacat | gagcgctacc | cattattgtt | atactcacaa | 660 |
| tgtaatatta | tctggttgca | gagatcactc | acactcacat | cagtatttag | cactaggtgt | 720 |
| acttcggaca | tctgcaacag | ggagggtatt | cttttctact | ctgcgctcca | tcaatttgga | 780 |
| tgacacccaa | aatcggaagt | cttgcagtgt | gagtgcgact | cctttaggtt | gtgatatgct | 840 |
| gtgctctaaa | gtcacagara | ttgaagagga | ggattataag | tcagctactc | ccacatcaat | 900 |
| ggtgcatgga | aggttaggrt | ttgacggtca | gtatcatgag | aaggactag | acgtcacagc | 960 |
| cttatttaag | gattgggttg | caaattatcc | aggagtggga | ggagggtctc | ttattggcga | 1020 |
| ccgtgtatgg | ttcccagttt | atggagggct | taaacccaat | tcgcctagtg | acattgcaca | 1080 |
| agagggggaga | tatgtaatat | ataagcgcta | taatacaca | tgccccgatg | aacaggatta | 1140 |
| ccaagttcgg | atggctaagt | cttcatataa | gcctggacgg | tttggtggaa | agcgcgtaca | 1200 |
| gcaagccatc | ttatctatca | aagtatcagt | atctttgggc | gaggaccgg | tgctaaccgt | 1260 |
| accccctaat | acagttacac | tcatgggggc | cgaaggcagg | gtcctcacag | tagggacatc | 1320 |
| tcacttcttg | taccaacgag | ggtcttcata | cttctctccc | gccttactat | accctatgac | 1380 |
| aatacacaac | aaaacagcta | ctcttcatag | tccctataca | ttcaatgctt | tcactcggcc | 1440 |
| aggcagtgtc | ccctgccagg | catcagcaag | gtgccccaac | tcatgcatca | ctggagtcta | 1500 |
| tactgatcca | tatcctgtgg | tcttttcataa | gaatcacacc | ctgcgagggg | tattcgggac | 1560 |
| gatgcttgat | aatgaacaag | caaggttcaa | ccctgtatct | gcagtatttg | attacacatc | 1620 |
| tcgcagtcgc | ataacccggg | taagttcgag | cagcaccaag | gcagcataca | cgacatcgac | 1680 |
| atgttttaaa | gttgtcaaga | ccaataaaat | ttattgtctt | agcattgcag | aaatatccaa | 1740 |
| taccctattt | ggggaattca | ggattgtccc | tctactggtt | gagatcctca | aggatgatag | 1800 |

```
ggtttaagag ctaagttcca gccggccggg tcaaccacga ggaagacggg aagatggcgt      1860
tgtgtcacct accctctgca atgccaagga tcaagcggaa taataatact agcccgaatc      1920
tcatgctatc agacagcctt aatcggataa tgctgacacg atcagcttga atcctgtcaa      1980
tagtcactct gtttagaaaa aatatgagag gtggtgggat ataagagaaa acaacttaca      2040
gaagatagca cgggtaggac atggcgggct ccggtcccga agggcagag caccagatta       2100 tcctaccaga gtcacacctg                                                  2120

<210> SEQ ID NO 10
<211> LENGTH: 256
<212> TYPE: PRT
<213> ORGANISM: Newcastle disease virus

<400> SEQUENCE: 10

Met Gly Ser Lys Pro Ser Thr Arg Ile Pro Val Pro Met Met Leu Ile
1               5                   10                  15

Thr Gln Ile Val Leu Ile Leu Ser Cys Ile Cys Leu Thr Ser Ser Leu
            20                  25                  30

Asp Gly Arg Pro Leu Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Val Ser Thr Ser Arg Gly Arg
            100                 105                 110

Arg Gln Lys Arg Phe Ile Gly Ala Ile Ile Gly Ser Val Ala Leu Gly
        115                 120                 125

Val Ala Thr Ser Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Ile
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

<210> SEQ ID NO 11
<211> LENGTH: 993
<212> TYPE: DNA
<213> ORGANISM: Newcastle disease virus

<400> SEQUENCE: 11
tgaggttact tctactaggt tagagaagag gcacaccatt gctaaataca atcctttcaa      60
gaagtaagtt gcgtccctga gactgcgatc cacccacttt cctggatcat cgcaacgcaa     120
```

```
aataatgatc tgtctcgatt gcttgcagtt ggttcacctg tctatctagt tagaaaaaac    180
acgggtagaa gagtctggat cccagctggc acattcaagg tgcagtatgg gctctaaacc    240
ttctaccagg atcccagtac ctatgatgct gatcacccaa attgtgttga tactgagctg    300
tatctgtctg acaagctccc ttgacggcag gcctcttgca gctgcgggga ttgtggtaac    360
aggagataaa gcagtcaata tatacacctc atctcagacg gggtcaatca tagtcaagtt    420
gctcccaaat atgcccaagg ataaagaggc gtgtgcaaaa gccccgttag aagcatacaa    480
cagaacactg accactttac tcacccccct tggtgattcc atccgcagga tacaagggtc    540
tgtgtccaca tcaagaggaa ggagacagaa acgctttata ggtgccatta tcggcagtgt    600
agctcttggg gtcgcaacat cggcacagat aacagcagct gcggccctaa tacaagccaa    660
ccagaatgcc gccaacatcc tccggcttaa ggagagcatt gctgcaacca atgaagctgt    720
gcatgaggtc accgacggat tatcgcaact agcagtggca gttgggaaga tgcagcagtt    780
tgttaatgac caatttaata atacggcgcg agaattggac tgtatcaaaa ttacacaaca    840
agtcggtata gaactcaacc tatacctaac tgagttgact acagtgttcg gccacaaat     900 cacttcccct gccctaactc agctgactat ccaggcactt tataatttag ctggtggcaa    960
catggattac ttgttgacta agttaggcgt agg                                 993

<210> SEQ ID NO 12
<211> LENGTH: 364
<212> TYPE: PRT
<213> ORGANISM: Newcastle disease virus

<400> SEQUENCE: 12

Met Asp Ser Ser Arg Thr Ile Gly Leu Tyr Phe Asp Ser Ala Leu Pro
1               5                   10                  15

Ser Ser Asn Leu Leu Ala Phe Pro Ile Val Leu Gln Asp Thr Gly Asp
                20                  25                  30

Gly Lys Lys Gln Phe Ala Pro Gln Tyr Arg Ile Gln Arg Leu Asp Ser
            35                  40                  45

Trp Thr Asp Ser Lys Glu Asp Ser Val Phe Ile Thr Thr Tyr Gly Phe
        50                  55                  60

Ile Phe Gln Val Gly Asp Glu Glu Ala Thr Val Gly Met Ile Asn Asp
65                  70                  75                  80

Glu Pro Lys Arg Glu Leu Leu Ser Ala Ala Met Leu Cys Leu Gly Ser
                85                  90                  95

Val Pro Asn Val Gly Asp Leu Val Glu Leu Ala Arg Ala Cys Leu Thr
            100                 105                 110

Met Ala Val Thr Cys Lys Lys Ser Ala Thr Asn Thr Glu Arg Met Val
        115                 120                 125

Phe Ser Val Val Gln Ala Pro Gln Val Leu Gln Ser Cys Arg Val Val
    130                 135                 140

Ala Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
                165                 170                 175

Ser Leu Thr Val Val Pro Arg Lys Asp Val Tyr Lys Ile Pro Thr Ala
            180                 185                 190

Ala Leu Lys Val Ser Gly Ser Ser Leu Tyr Asn Leu Ala Leu Asn Val
        195                 200                 205

Thr Ile Asp Val Glu Val Asp Pro Lys Ser Pro Leu Val Lys Ser Leu
    210                 215                 220
```

```
Ser Lys Ser Asp Ser Gly Tyr Tyr Ala Asn Leu Phe Leu His Ile Gly
225                 230                 235                 240

Leu Met Ser Thr Val Asp Lys Lys Gly Lys Lys Val Thr Phe Asp Lys
            245                 250                 255

Leu Glu Lys Lys Ile Arg Arg Leu Asp Leu Ser Val Gly Leu Ser Asp
        260                 265                 270

Val Leu Gly Pro Ser Val Leu Val Lys Ala Arg Gly Ala Arg Thr Lys
    275                 280                 285

Leu Met Ala Pro Phe Phe Ser Ser Ser Gly Thr Ala Cys Tyr Pro Ile
290                 295                 300

Ala Asn Ala Ser Pro Gln Val Ala Lys Ile Leu Trp Ser Gln Thr Ala
305                 310                 315                 320

His Leu Arg Ser Val Lys Val Ile Ile Gln Ala Gly Thr Gln Arg Ala
            325                 330                 335

Val Ala Val Thr Ala Asp His Glu Ala Thr Ser Thr Lys Leu Glu Lys
        340                 345                 350

Gly His Thr His Ser Lys Tyr Asn Pro Phe Lys Lys
        355                 360
```

<210> SEQ ID NO 13
<211> LENGTH: 1095
<212> TYPE: DNA
<213> ORGANISM: Newcastle disease virus

<400> SEQUENCE: 13

```
atggactcat ctaggacaat cggactgtac tttgattctg cccttccttc tagcaacttg      60
ttagcattcc cgatcgtcct acaggacaca ggagatggaa agaagcaatt cgccccgcaa     120
tataggatcc agcgtcttga ctcgtggacc gatagtaaag aagactcagt attcatcaca     180
acctatggat tcatcttcca ggtcggggat gaggaagcca ctgtcggtat gatcaatgat     240
gaacccaagc gcgagttact ttctgctgcg atgctctgtc taggaagtgt cccaaacgtc     300
ggagatctcg ttgagctggc aagggcctgt ctcaccatgg cagtcacatg caagaagagt     360
gcaactaata ctgagaggat ggttttctca gtggtgcagg caccacaagt gctgcagagc     420
tgcagggttg tggcaaataa atattcgtca gtgaatgctg ttaagcacgt gaaggcgcca     480
gagaagatcc ctggaagcgg gaccctagag tacaaggtga actttgtctc cttgaccgtg     540
gtaccgagaa aggatgtcta caagatccca accgcagcat tgaaggtttc tggttcgagt     600
ctgtataatc ttgcgctcaa tgtcaccatt gatgtggagg tggatccgaa gagcccgttg     660
gttaaatcgc tatctaagtc tgacagtggc tattacgcta atctcttctt gcatattgga     720
cttatgtcca ctgtagataa gaaggggaag aaagtgacat tgacaaaatt ggaaagaag      780 ataaggagac ttgatctatc tgtcgggctc agtgacgtgc ttggaccttc cgtgttggtg     840
aaggcaagag gtgcacggac caaattgatg gcacctttct ctccagtag tggaacagcc      900 tgctacccca tagcgaatgc ctctcctcag gtagccaaga tactctggag tcaaaccgcg     960
cacctgcgga gtgtgaaagt catcatccaa gcaggcaccc aacgcgccgt cgcagtgact    1020
gctgaccacg aggctacatc caccaagctg gaaaaggggc atacccattc caaatacaat    1080
cctttcaaga aatag                                                     1095
```

<210> SEQ ID NO 14
<211> LENGTH: 6159
<212> TYPE: DNA
<213> ORGANISM: Baculovirus expression vector pUltraBac-1

```
<400> SEQUENCE: 14
ttctctgtca cagaatgaaa attttttctgt catctcttcg ttattaatgt ttgtaattga      60
ctgaatatca acgcttattt gcagcctgaa tggcgaatgg gacgcgccct gtagcggcgc     120
attaagcgcg gcgggtgtgg tggttacgcg cagcgtgacc gctacacttg ccagcgccct     180
agcgcccgct cctttcgctt tcttcccttc ctttctcgcc acgttcgccg gctttccccg     240
tcaagctcta atcggggggc tccctttagg gttccgattt agtgctttac ggcacctcga     300
ccccaaaaaa cttgattagg gtgatggttc acgtagtggg ccatcgccct gatagacggt     360
ttttcgccct ttgacgttgg agtccacgtt ctttaatagt ggactcttgt tccaaactgg     420
aacaacactc aaccctatct cggtctattc ttttgattta agggatttt gccgatttc     480
ggcctattgg ttaaaaaatg agctgattta acaaaaattt aacgcgaatt ttaacaaaat     540
attaacgttt acaatttcag gtggcacttt tcggggaaat gtgcgcggaa cccctatttg     600
tttattttc taaatacatt caaatatgta tccgctcatg agacaataac cctgataaat     660
gcttcaataa tattgaaaaa ggaagagtat gagtattcaa catttccgtg tcgcccttat     720
tcccttttt gcggcatttt gccttcctgt ttttgctcac ccagaaacgc tggtgaaagt     780
aaaagatgct gaagatcagt tgggtgcacg agtgggttac atcgaactgg atctcaacag     840
cggtaagatc cttgagagtt ttcgccccga agaacgtttt ccaatgatga gcacttttaa     900
agttctgcta tgtggcgcgg tattatcccg tattgacgcc gggcaagagc aactcggtcg     960
ccgcatacac tattctcaga atgacttggt tgagtactca ccagtcacag aaaagcatct    1020
tacggatggc atgacagtaa gagaattatg cagtgctgcc ataaccatga gtgataacac    1080
tgcggccaac ttacttctga caacgatcgg aggaccgaag gagctaaccg cttttttgca    1140
caacatgggg gatcatgtaa ctcgccttga tcgttgggaa ccggagctga atgaagccat    1200
accaaacgac gagcgtgaca ccacgatgcc tgtagcaatg gcaacaacgt tgcgcaaact    1260
attaactggc gaactactta ctctagcttc ccggcaacaa ttaatagact ggatggaggc    1320
ggataaagtt gcaggaccac ttctgcgctc ggcccttccg gctggctggt ttattgctga    1380
taaatctgga gccggtgagc gtgggtctcg cggtatcatt gcagcactgg ggccagatgg    1440
taagccctcc cgtatcgtag ttatctacac gacggggagt caggcaacta tggatgaacg    1500
aaatagacag atcgctgaga taggtgcctc actgattaag cattggtaac tgtcagacca    1560
agtttactca tatatacttt agattgattt aaaacttcat ttttaattta aaaggatcta    1620
ggtgaagatc ctttttgata atctcatgac caaaatccct taacgtgagt tttcgttcca    1680
ctgagcgtca gaccccgtag aaaagatcaa aggatcttct tgagatcctt ttttttctgcg    1740
cgtaatctgc tgcttgcaaa caaaaaaacc accgctacca gcggtggttt gtttgccgga    1800
tcaagagcta ccaactcttt ttccgaaggt aactggcttc agcagagcgc agataccaaa    1860
tactgtcctt ctagtgtagc cgtagttagg ccaccacttc aagaactctg tagcaccgcc    1920
tacatacctc gctctgctaa tcctgttacc agtggctgct gccagtggcg ataagtcgtg    1980
tcttaccggg ttggactcaa gacgatagtt accggataag cgcagcggt cgggctgaac    2040
ggggggttcg tgcacacagc ccagcttgga gcgaacgacc tacaccgaac tgagatacct    2100
acagcgtgag cattgagaaa gcgccacgct tcccgaaggg agaaaggcgg acaggtatcc    2160
ggtaagcggc agggtcggaa caggagagcg cacgagggag cttccagggg gaaacgcctg    2220
gtatctttat agtcctgtcg ggtttcgcca cctctgactt gagcgtcgat ttttgtgatg    2280
ctcgtcaggg gggcggagcc tatggaaaaa cgccagcaac gcggcctttt tacggttcct    2340
```

```
ggccttttgc tggccttttg ctcacatgtt ctttcctgcg ttatcccctg attctgtgga    2400
taaccgtatt accgcctttg agtgagctga taccgctcgc cgcagccgaa cgaccgagcg    2460
cagcgagtca gtgagcgagg aagcggaaga gcgcctgatg cggtattttc tccttacgca    2520
tctgtgcggt atttcacacc gcagaccagc cgcgtaacct ggcaaaatcg gttacggttg    2580
agtaataaat ggatgccctg cgtaagcggg tgtgggcgga caataaagtc ttaaactgaa    2640
caaaatagat ctaaactatg acaataaagt cttaaactag acagaatagt tgtaaactga    2700
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact ttgtatagag agccactgcg gatcgtcac cgtaatctgc    3000 ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acctgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcagggccg agcctacatg tgcgaatgat    3360
gcccatactt gagccaccta actttgttt agggcgactg ccctgctgcg taacatcgtt    3420
gctgctgcgt aacatcgttg ctgctccata acatcaaaca tcgacccacg gcgtaacgcg    3480
cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg ccctggcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcct acgtacccgt agtggctatg gcagggcttg ccgccccgac    4020
gttggctgcg agccctgggc cttcacccga acttgggggt tggggtgggg aaaggaaga    4080 aacgcgggcg tattggtccc aatggggtct cggtggggta tcgacagagt gccagccctg    4140
ggaccgaacc ccgcgtttat gaacaaacga cccaacaccc gtgcgtttta ttctgtcttt    4200
ttattgccgt catagcgcgg gttccttccg gtattgtctc cttccgtgtt tcagttagcc    4260
tcccccatct cccggtaccg catgctatgc atcggccgct ttacttgtac agctcgtcca    4320
tgccgagagt gatcccggcg gcggtcacga actccagcag gaccatgtga tcgcgcttct    4380
cgttggggtc tttgctcagg gcggactggg tgctcaggta gtggttgtcg ggcagcagca    4440
cggggccgtc gccgatgggg gtgttctgct ggtagtggtc ggcgagctgc acgctgccgt    4500
cctcgatgtt gtggcggatc ttgaagttca ccttgatgcc gttcttctgc ttgtcggcca    4560
tgatatagac gttgtggctg ttgtagttgt actccagctt gtgccccagg atgttgccgt    4620
cctccttgaa gtcgatgccc ttcagctcga tgcggttcac cagggtgtcg ccctcgaact    4680
tcacctcggc gcgggtcttg tagttgccgt cgtccttgaa gaagatggtg cgctcctgga    4740
```

-continued

```
cgtagccttc gggcatggcg gacttgaaga agtcgtgctg cttcatgtgg tcggggtagc    4800
ggctgaagca ctgcacgccg taggtcaggg tggtcacgag ggtgggccag ggcacgggca    4860
gcttgccggt ggtgcagatg aacttcaggg tcagcttgcc gtaggtggca tcgccctcgc    4920
cctcgccgga cacgctgaac ttgtggccgt ttacgtcgcc gtccagctcg accaggatgg    4980
gcaccacccc ggtgaacagc tcctcgccct tgctcaccat ggctcgagat cccgggcgtt    5040
taaattgtgt aatttatgta gctgtaattt ttaccttatt aatattttt acgctttgca    5100
ttcgacgact gaactcccaa atatatgttt aactcgtctt ggtcgtttga attttttgttg   5160
ctgtgttttcc taatattttc catccactta aatatgttat tgtaatcctc aatgttgaac   5220
ttgcaattgg acacggcata gttttccata gtcgtgtaaa acatggtatt ggctgcattg    5280
taatacatcc gactgagcgg gtacggatct atgtgtttga gcagcctgtt caaaaactct    5340
gcatcgtcgc aaaacggaat ttggtacccg ggcgtatact ccggaatatt aatagatcat    5400
ggagataatt aaaatgataa ccatctcgca aataaataag tattttactg ttttcgtaac    5460
agttttgtaa taaaaaaacc tataaatatt ccggattatt cataccgtcc caccatcggg    5520
cgccatggat cccggtccga agcgcgcgga attcaaaggc ctacgtcgac gagctcacta    5580
gtcgcggccg ctttcgaatc tagagcctgc agtctcgaca agcttgtcga aagtactag    5640
aggatcataa tcagccatac cacatttgta gaggttttac ttgctttaaa aaacctccca    5700
cacctccccc tgaacctgaa acataaaatg aatgcaattg ttgttgttaa cttgtttatt    5760
gcagcttata atggttacaa ataaagcaat agcatcacaa atttcacaaa taaagcattt    5820
ttttcactgc attctagttg tggtttgtcc aaactcatca atgtatctta tcatgtctgg    5880
atctgatcac tgcttgagcc taggagatcc gaaccagata agtgaaatct agttccaaac    5940
tattttgtca tttttaattt tcgtattagc ttacgacgct acaccagtt cccatctatt     6000
ttgtcactct tccctaaata atccttaaaa actccattc caccccctccc agttcccaac    6060
tattttgtcc gcccacagcg gggcatttt cttcctgtta tgttttaat caaacatcct     6120
gccaactcca tgtgacaaac cgtcatcttc ggctacttt                           6159
```

<210> SEQ ID NO 15
<211> LENGTH: 570
<212> TYPE: PRT
<213> ORGANISM: Newcastle disease virus

<400> SEQUENCE: 15

```
Met Asn Arg Ala Val Cys Gln Val Ala Leu Glu Asn Asp Glu Arg Glu
 1               5                  10                  15

Ala Lys Asn Thr Trp Arg Leu Val Phe Arg Ile Ala Ile Leu Leu Leu
             20                  25                  30

Thr Val Met Thr Leu Ala Ile Ser Ala Ala Ala Leu Ala Tyr Ser Met
         35                  40                  45

Glu Ala Ser Thr Pro Gly Asp Leu Val Ser Ile Pro Thr Ala Ile Ser
     50                  55                  60

Arg Ala Glu Gly Lys Ile Thr Ser Ala Leu Gly Ser Asn Gln Asp Val
 65                  70                  75                  80

Val Asp Arg Ile Tyr Lys Gln Val Ala Leu Glu Ser Pro Leu Ala Leu
                 85                  90                  95

Leu Asn Thr Glu Ser Ile Ile Met Asn Ala Ile Thr Ser Leu Ser Tyr
            100                 105                 110

Gln Ile Asn Gly Ala Ala Asn Asn Ser Gly Cys Gly Ala Pro Val His
        115                 120                 125
```

-continued

```
Asp Pro Asp Tyr Ile Gly Gly Ile Gly Lys Glu Leu Ile Val Asp Asp
    130                 135                 140
Thr Ser Asp Val Thr Ser Phe Tyr Pro Ser Ala Phe Gln Glu His Leu
145                 150                 155                 160
Asn Phe Ile Pro Ala Pro Thr Thr Gly Ser Gly Cys Thr Arg Ile Pro
                165                 170                 175
Ser Phe Asp Met Ser Ala Thr His Cys Tyr Thr His Asn Val Ile Phe
                180                 185                 190
Ser Gly Cys Arg His His Ser His Ser His Gln Tyr Leu Ala Leu Gly
            195                 200                 205
Val Leu Arg Thr Ser Ala Thr Gly Arg Val Phe Ser Thr Leu Arg
    210                 215                 220
Ser Ile Asn Leu Asp Asp Thr Gln Asn Arg Lys Ser Cys Ser Val Ser
225                 230                 235                 240
Ala Thr Pro Leu Gly Cys Asp Met Leu Cys Ser Lys Val Thr Glu Thr
                245                 250                 255
Glu Glu Gln Asp Tyr Asn Ser Val Ile Pro Thr Ser Met Val His Gly
                260                 265                 270
Arg Leu Gly Phe Asp Gly Gln Tyr His Glu Lys Asp Leu Asp Val Thr
            275                 280                 285
Thr Leu Phe Gly Asp Trp Val Ala Asn Tyr Pro Gly Val Gly Gly Gly
    290                 295                 300
Ser Phe Ile Asp Asn Arg Val Trp Phe Pro Val Tyr Gly Gly Leu Lys
305                 310                 315                 320
Pro Ser Ser Pro Ser Asp Thr Gly Gln Glu Gly Arg Tyr Val Ile Tyr
                325                 330                 335
Lys Arg Tyr Asn Asp Thr Cys Pro Asp Glu Gln Asp Tyr Gln Ile Arg
                340                 345                 350
Met Ala Lys Ser Ser Tyr Lys Pro Gly Arg Phe Gly Gly Lys Arg Val
            355                 360                 365
Gln Gln Ala Ile Leu Ser Ile Lys Val Ser Thr Ser Leu Gly Glu Asp
    370                 375                 380
Pro Val Leu Thr Ile Pro Pro Asn Thr Val Thr Leu Met Gly Ala Glu
385                 390                 395                 400
Gly Arg Val Leu Thr Val Gly Thr Ser His Phe Leu Tyr Gln Arg Gly
                405                 410                 415
Ser Ser Tyr Phe Ser Pro Ala Leu Leu Tyr Pro Met Thr Val Asn Asn
                420                 425                 430
Asn Thr Ala Thr Leu His Ser Pro Tyr Thr Phe Asn Ala Phe Thr Arg
            435                 440                 445
Pro Gly Ser Val Pro Cys Gln Ala Ser Ala Arg Cys Pro Asn Ser Cys
    450                 455                 460
Val Thr Gly Val Tyr Thr Asp Pro Tyr Pro Leu Val Phe His Arg Asn
465                 470                 475                 480
His Thr Leu Arg Gly Val Phe Gly Thr Met Leu Asp Asp Glu Gln Ala
                485                 490                 495
Arg Leu Asn Leu Val Ser Ala Val Phe Asp Asn Ile Ser Arg Ser Arg
            500                 505                 510
Ile Thr Arg Val Ser Ser Arg Thr Lys Ala Ala Tyr Thr Thr Ser
    515                 520                 525
Thr Cys Phe Lys Val Val Lys Thr Asn Lys Thr Tyr Cys Leu Ser Ile
    530                 535                 540
Ala Glu Ile Ser Asn Thr Leu Phe Gly Glu Phe Arg Ile Val Pro Leu
545                 550                 555                 560
```

Leu Val Glu Ile Leu Lys Asp Asp Gly Val
           565                   570

<210> SEQ ID NO 16
<211> LENGTH: 1993
<212> TYPE: DNA
<213> ORGANISM: Newcastle disease virus

<400> SEQUENCE: 16

```
acgggtagaa cggtcggaga ggccacccct caatcgggag tcggacctca caacttccat      60
tctgccgcat caccagtagc ggtcttcagt catgaaccgc gcagtttgcc aagttgcgct     120
agagaatgat gaaagggaag cgaagaatac atggcgcttg gtattccgga tcgcaatctt     180
acttttaaca gtaatgacct tagccatctc tgcagccgcc ctggcatata gtatggaggc     240
tagcacacct ggcgaccttg taagcatacc aactgcgatc tctagggcag agggaaagat     300
tacatctgca ctcggttcca atcaggatgt agtagatagg atatacaagc aggtggctct     360
tgaatctccg ttggcattgc taaacaccga atctataatt atgaatgcaa taacatccct     420
ctcttatcaa atcaatggag ctgcaaataa cagcgggtgt gggcacctg ttcatgaccc      480
agattacatc gggggatag gtaaagaact tattgtggat gatactagtg atgtcacatc      540
attctatccc tctgcgttcc aagaacacct gaattttatc ccgcacccca ctacaggatc      600
aggttgcact cggataccct cattcgacat gagtgctacc cactgttata ctcacaatgt      660
gatattttct ggttgcagac accattcaca ctcacatcag tatttagcac tgggtgtgct     720
tcggacatct gcaacaggga gggtattctt ttctaccctg cgttccatca atttggatga     780
cacccaaaat cggaagtctt gcagtgtgag tgcaactccc ttaggttgtg atatgctgtg     840
ctctaaagtc acagagactg aggaacagga ttataattca gttatcccca catcgatggt     900
acatggaagg ttagggtttg acggccaata ccatgagaag gacctagacg tcacaacatt     960
atttgggac tgggtggcaa attacccagg agtgggaggt gggtcttta ttgacaaccg     1020
cgtatggttc ccagtctacg gagggctaaa acccagttcg cctagtgaca ctggacaaga    1080
agggagatat gtaatatata gcgatacaa tgacacatgc ccagatgagc aagattacca    1140
gattcggatg gctaagtctt cgtataagcc tgggcggttt ggtggaaagc gtgtacagca    1200
ggccatctta tctatcaagg tgtcaacatc cttgggtgag acccggtgc tgactatacc     1260
gcccaacaca gtcacactca tggggccga aggcagagtt ctcacagtag gacatctca     1320
tttcttgtac cagcgagggt catcatattt ctctcctgct ttattatacc ctatgacagt    1380
caacaacaac acagccactc ttcatagtcc ttatacattc aatgctttca ctcggccagg    1440
tagtgtccct tgccaggctt cagcaagatg ccctaactca tgtgtcactg ggtctatac     1500
tgatccatat cccttagtct tccataggaa ccacaccttg cgaggggtat tcgggacaat    1560
gcttgatgat gaacaagcaa gactcaacct tgtatctgca gtatttgata acatatcccg    1620
cagtcgcata acccgggtaa gttcaagcag aaccaaggca gcatacacga catcaacgtg    1680
ttttaaagtt gtcaagacca ataaaaccta ttgcctcagc attgcagaaa tatccaatac    1740
cctctttggg gaattcagga tcgtcccttt actagttgag attctcaagg atgatggggt    1800
ttagaaagcc aggtctagcc ggttgagcca actgtgagag ggttggaaag atgacattgt    1860
gtcacctatc ttttgtagcg ccaagaatca aactgaatac cggccacgag ctcgaatcct    1920
ccgctgccag tcggtcataa tcactagtgc taatgtgatt agtctgaatc ttgtcgatag    1980
tcacttgatt aag                                                      1993
```

```
<210> SEQ ID NO 17
<211> LENGTH: 577
<212> TYPE: PRT
<213> ORGANISM: Newcastle disease virus

<400> SEQUENCE: 17

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380
```

```
Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
            405                 410                 415

Gly Ser Ser Tyr Phe Ser Pro Ala Leu Leu Tyr Pro Met Thr Val Ser
        420                 425                 430

Asn Lys Thr Ala Thr Leu His Ser Pro Tyr Thr Phe Asn Ala Phe Thr
    435                 440                 445

Arg Pro Gly Ser Ile Pro Cys Gln Ala Ser Ala Arg Cys Pro Asn Ser
450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ile Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly

<210> SEQ ID NO 18
<211> LENGTH: 1734
<212> TYPE: DNA
<213> ORGANISM: Newcastle disease virus

<400> SEQUENCE: 18
atggaccgcg ccgttagcca agttgcgtta gagaatgatg aaagagaggc aaaaaataca      60
tggcgcttga tattccggat tgcaatctta ttcttaacag tagtgacctt ggctatatct     120
gtagcctccc ttttatatag catgggggct agcacaccta gcgatcttgt aggcataccg     180
actaggattt ccagggcaga agaaaagatt acatctacac ttggttccaa tcaagatgta     240
gtagatagga tatataagca agtggcccct gagtctccat ggcattgtt aaatactgag      300
accacaatta tgaacgcaat aacatctctc tcttatcaga ttaatggagc tgcaaacaac     360
agcgggtggg gggcacctat tcatgaccca gattatatag gggggatagg caaagaactc     420
attgtagatg atgctagtga tgtcacatca ttctatccct ctgcatttca agaacatctg     480
aatttttatcc cggcgcctac tacaggatca ggttgcactc gaataccctc atttgacatg     540
agtgctaccc attactgcta cacccataat gtaatattgt ctggatgcag agatcactca     600
cactcacatc agtatttagc acttggtgtg ctccggacat ctgcaacagg gagggtattc     660
tttttctactc tgcgttccat caacctggac gacacccaaa atcggaagtc ttgcagtgtg     720
agtgcaactc ccctgggttg tgatatgctg tgctcgaaag ccacggagac agaggaagaa     780
gattataact cagctgtccc tacgcggatg gtacatggga ggttagggtt cgacggccaa     840
tatcacgaaa aggacctaga tgtcacaaca ttattcgggg actgggtggc caactaccca     900
ggagtagggg gtggatcttt tattgacagc cgcgtatggt tctcagtcta cggagggtta     960
aaacccaata cacccagtga cactgtacag gaagggaaat atgtgatata caagcgatac    1020
```

```
aatgacacat gcccagatga gcaagactac cagattcgaa tggccaagtc ttcgtataag    1080
cctggacggt ttggtgggaa acgcatacag caggctatct tatctatcaa agtgtcaaca    1140
tccttaggcg aagacccggt actgactgta ccgcccaaca cagtcacact catgggggcc    1200
gaaggcagaa ttctcacagt agggacatcc catttcttgt atcagcgagg gtcatcatac    1260
ttctctcccg cgttattata tcctatgaca gtcagcaaca aaacagccac tcttcatagt    1320
ccttatacat tcaatgcctt cactcggcca ggtagtatcc cttgccaggc ttcagcaaga    1380
tgccccaact cgtgtgttac tggagtctat acagatccat atcccctaat cttctataga    1440
aaccacacct tgcgaggggt attcgggaca atgcttgatg gtgaacaagc aagacttaac    1500
cctgcgtctg cagtattcga tagcacatcc cgcagtcgca taactcgagt gagttcaagc    1560
agcatcaaag cagcatacac aacatcaact tgttttaaag tggtcaagac caataagacc    1620
tattgtctca gcattgctga aatatctaat actctcttcg gagaattcag aatcgtcccg    1680
ttactagttg agatcctcaa agatgacggg gttagagaag ccaggtctgg ctag           1734
```

<210> SEQ ID NO 19
<211> LENGTH: 553
<212> TYPE: PRT
<213> ORGANISM: Newcastle disease virus

<400> SEQUENCE: 19

```
Met Gly Pro Arg Ser Ser Thr Arg Ile Pro Ile Pro Leu Met Leu Thr
1               5                   10                  15

Ile Arg Ile Ala Leu Ala Leu Ser Cys Val His Leu Ala Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

Arg Gln Lys Arg Phe Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Thr Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255
```

-continued

```
Asn Asn Gln Leu Ser Ser Leu Ile Gly Ser Gly Leu Ile Thr Gly Asn
        260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
        290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Leu Asp Thr Ser
                325                 330                 335

Tyr Cys Ile Glu Thr Asp Leu Asp Leu Tyr Cys Thr Arg Ile Val Thr
        340                 345                 350

Phe Pro Met Ser Pro Gly Ile Tyr Ser Cys Leu Asn Gly Asn Thr Ser
        355                 360                 365

Ala Cys Met Tyr Ser Lys Thr Glu Gly Ala Leu Thr Thr Pro Tyr Met
        370                 375                 380

Thr Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
        420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
        450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Ala Leu Thr Ala Ile Ser Leu
        500                 505                 510

Val Cys Gly Ile Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
        530                 535                 540

Gly Gln Met Arg Ala Thr Thr Lys Met
545                 550
```

<210> SEQ ID NO 20
<211> LENGTH: 1759
<212> TYPE: DNA
<213> ORGANISM: Newcastle disease virus

<400> SEQUENCE: 20

| | | | |
|---|---|---|---|
| acgggtagaa gagtttggat cccggttggc gcattcaagg cgcaagatgg gccccagatc | 60 |
| ttctaccagg atcccaatac ctctgatgtt gaccatccgg atcgcgctgg cactgagttg | 120 |
| tgtccatctg gcaagttctc ttgatggcag gcctcttgca gctgcaggga tcgtggtaac | 180 |
| aggggataaa gcagtcaaca tatacacctc atcccagaca gggtcaatca tagtcaagtt | 240 |
| actcccaaat atgcccaagg ataagaggc gtgtgcaaaa gccccgttgg aggcatacaa | 300 |
| caggacactg actactttgc tcaccccccct tggtgattct atccgcagga tacaagagtc | 360 |
| tgtgactaca tccggaggaa ggagacagaa acgctttata ggtgctatta tcggcagtgt | 420 |
| agctcttggg gttgcaacag ctgcacagat aacagcagcc tcggccctga tacaagccaa | 480 |

```
tcagaatgct gccaacatcc tccggcttaa ggagagcatt actgcaacca atgaagctgt    540
acatgaggtc actgacggat tatcacaact agcagtggca gttgggaaga tgcagcagtt    600
tgttaatgac cagtttaata acacagctca ggaattggac tgtataaaaa ttacacagca    660
ggttggtgta gaactcaacc tgtacctaac tgaattgact acagtattcg gccacaaat     720 aacttcccct gccttaactc agctgactat ccaggcgctt tacaacctag ctggtggtaa    780
tatggattac ttgttgacta agttaggtgt agggaacaac caactcagct cattaattgg    840
tagcggcttg atcaccggca accctattct gtacgactca cagactcaac tcttgggtat    900
acaggtaact ttaccctcag tcggaaacct aaataatatg cgtgccacct acctggagac    960
cttgtctgta agcacaacca agggatttgc ctcagcactc gtcccaaaag tggtgacaca   1020
ggtcggttct gtgatagaag aacttgacac ttcatactgt atagagaccg atttggattt   1080
gtattgtaca agaatagtga cattccctat gtctcctggt atttattcct gtttgaacgg   1140
caatacatcg gcttgcatgt attcaaagac tgaaggcgca cttactacgc catacatgac   1200
tctcaaaggc tcagttattg ccaattgcaa gatgacaaca tgcagatgtg cagaccccccc  1260 gggtatcata tcgcaaaatt atggagaagc tgtgtctcta atagataggc actcatgcaa   1320
tgtcttatcc ttggacggga taactttgag gctcagtggg gaatttgatg caacttatca   1380
aaagaatatc tcaatactag attctcaagt aatagtgaca ggcaatctcg atatctcaac   1440
tgagcttggg aatgtcaaca actcgataag taatgctttg gataagttag aggaaagcaa   1500 cagcaaaacta gacaaagtca atgtcaaact gaccagcaca tctgctctca ttacctatat   1560
cgctttaact gccatatctc ttgtttgcgg tatacttagt ctggttctag catgctacct   1620
aatgtacaag caaaaggcgc aacaaaagac cttgttatgg cttgggaata ataccctggg    1680
tcagatgaga gccactacaa aaatgtgaat gcagatgaga ggcggaggta tccccaatag   1740
caatttgtgt gcaaattct                                                 1759
```

<210> SEQ ID NO 21
<211> LENGTH: 553
<212> TYPE: PRT
<213> ORGANISM: Newcastle disease virus

<400> SEQUENCE: 21

```
Met Gly Ser Arg Pro Phe Thr Lys Asn Pro Ala Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Phe Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Leu Ile Gln Ala
    130                 135                 140
```

```
Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
            165                 170                 175

Val Ala Val Gly Lys Met Gln Gln Phe Val Asn Asp Gln Phe Asn Lys
        180                 185                 190

Thr Ala Gln Glu Leu Asp Cys Ile Lys Ile Ala Gln Gln Val Gly Val
    195                 200                 205

Glu Leu Asn Leu Tyr Leu Thr Glu Leu Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Leu Asp Thr Ser
                325                 330                 335

Tyr Cys Ile Glu Thr Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
        370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

<210> SEQ ID NO 22

<211> LENGTH: 489
<212> TYPE: PRT
<213> ORGANISM: Newcastle disease virus

<400> SEQUENCE: 22

```
Met Ser Ser Val Phe Asp Glu Tyr Glu Gln Leu Leu Ala Ala Gln Thr
1               5                   10                  15

Arg Pro Asn Gly Ala His Gly Gly Glu Lys Gly Ser Thr Leu Lys
            20                  25                  30

Val Asp Val Pro Val Phe Thr Leu Asn Ser Asp Pro Glu Asp Arg
        35                  40                  45

Trp Ser Phe Val Val Phe Cys Leu Arg Ile Ala Val Ser Glu Asp Ala
    50                  55                  60

Asn Lys Pro Leu Arg Gln Gly Ala Leu Ile Ser Leu Leu Cys Ser His
65                  70                  75                  80

Ser Gln Val Met Arg Asn His Val Ala Leu Ala Gly Lys Gln Asn Glu
                85                  90                  95

Ala Thr Leu Ala Val Leu Glu Ile Asp Gly Phe Ala Asn Gly Thr Pro
            100                 105                 110

Gln Phe Asn Asn Arg Ser Gly Val Ser Glu Glu Arg Ala Gln Arg Phe
        115                 120                 125

Ala Met Ile Ala Gly Ser Leu Pro Arg Ala Cys Ser Asn Gly Thr Pro
130                 135                 140

Phe Val Thr Ala Gly Ala Glu Asp Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
        195                 200                 205

Leu Tyr Pro Val Cys Arg Ser Thr Ile Gln Leu Thr Ile Arg Gln Ser
210                 215                 220

Leu Ala Val Arg Ile Phe Leu Val Ser Glu Leu Lys Arg Gly Arg Asn
225                 230                 235                 240

Thr Ala Gly Gly Thr Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Ser
        275                 280                 285

Gly Asp Ile Gln Lys Met Lys Gln Leu Met Arg Leu Tyr Arg Met Lys
290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Gly Lys Tyr Gln Phe Ala Lys
            340                 345                 350

Asp Phe Met Ser Thr Ser Phe Trp Arg Leu Gly Val Glu Tyr Ala Gln
        355                 360                 365

Ala Gln Gly Ser Ser Ile Asn Glu Asp Met Ala Ala Glu Leu Lys Leu
    370                 375                 380

Thr Pro Ala Ala Arg Arg Gly Leu Ala Ala Ala Gln Arg Val Ser
385                 390                 395                 400
```

```
Glu Val Thr Ser Ser Ile Asp Met Pro Thr Gln Val Gly Val Leu
            405                 410                 415

Thr Gly Leu Ser Glu Gly Gly Ser Gln Ala Leu Gln Gly Gly Ser Asn
        420                 425                 430

Arg Ser Gln Gly Gln Pro Glu Ala Gly Asp Gly Glu Thr Gln Phe Leu
            435                 440                 445

Asp Leu Met Arg Ala Val Ala Asn Ser Met Arg Glu Ala Pro Asn Ser
    450                 455                 460

Ala Gln Gly Thr Pro Gln Ser Gly Pro Pro Thr Pro Gly Pro Ser
465                 470                 475                 480

Gln Asp Asn Asp Thr Asp Trp Gly Tyr
            485

<210> SEQ ID NO 23
<211> LENGTH: 1535
<212> TYPE: DNA
<213> ORGANISM: Newcastle disease virus

<400> SEQUENCE: 23
gccaaaatgt cttccgtatt cgacgagtac gaacagctcc tcgcggctca gactcgcccc      60
aatggagctc atggaggggg ggagaaaggg agtaccttaa agtagacgt cccggtattc     120
actcttaaca gtgatgaccc agaagatagg tggagctttg tggtattctg cctccggatt     180
gctgttagcg aagatgccaa caaaccactc aggcaaggtg ctctcatatc tcttttatgc     240
tcccactcac aggtaatgag gaaccatgtt gcccttgcag ggaaacagaa tgaagccaca     300
ttggccgtgc ttgagattga tggctttgcc aacggcacgc cccagttcaa caataggagt     360
ggagtgtctg aagagagagc acagagattt gcgatgatag caggatctct ccctcgggca     420
tgcagcaacg gcaccccgtt cgtcacagcc ggggctgaag atgatgcacc agaagacatc     480
accgatacc tggagaggat cctctctatc caggctcaag tatgggtcac agtagcaaaa     540
gccatgactg cgtatgagac tgcagatgag tcggaaacaa ggcgaatcaa taagtatatg     600
cagcaaggca gggtccaaaa gaaatacatc ctctaccccg tatgcaggag cacaatccaa     660
ctcacgatca gacagtctct tgcagtccgc atctttttgg ttagcgagct caagagaggc     720
cgcaacacgg caggtggtac ctctacttat tataacctag taggggacgt agactctat      780
atcaggaata ccgggcttac tgcattcttc ttgacactca gtacggaat caacaccaag     840
acatcagccc ttgcacttag tagcctctca ggcgacatcc agaagatgaa gcagctcatg     900
cgtttgtatc ggatgaaagg agataatgcg ccgtacatga cattacttgg tgatagtgac     960
cagatgagct ttgcgcctgc cgagtatgca caactttact cctttgccat gggtatggca    1020
tcagtcctag ataaaggtac tgggaaatac caatttgcca aggactttat gagcacatca    1080
ttctggagac ttggagtaga gtacgctcag gctcagggaa gtagcattaa cgaggatatg    1140
gctgccgagc taaagctaac cccggcagca aggagggggcc tggcagctgc tgcccaacga    1200
gtctccgagg tgaccagcag catagacatg cctactcaac aagtcggagt cctcactggg    1260
cttagcgagg ggggatccca agccctacaa ggcggatcga atagatcgca agggcaacca    1320
gaagccgggg atggggagac ccaattcctg gatctgatga gagcggtagc aaatagcatg    1380
agggaggcgc caaactctgc acagggcact ccccaatcgg ggcctccccc aactcctggg    1440
ccatcccaag ataacgacac cgactggggg tattgattga caaacccag cctgcttcta    1500
caagaacatc ccaatgctct cacccgtagt cgacc                                1535
```

<210> SEQ ID NO 24
<211> LENGTH: 364
<212> TYPE: PRT
<213> ORGANISM: Newcastle disease virus

<400> SEQUENCE: 24

Met Asp Ser Ser Arg Thr Ile Gly Leu Tyr Phe Asp Ser Ala Leu Pro
1               5                   10                  15

Ser Ser Asn Leu Leu Ala Phe Pro Ile Val Leu Gln Asp Ile Gly Asp
            20                  25                  30

Gly Lys Lys Gln Ile Ala Pro Gln Tyr Arg Ile Gln Arg Leu Asp Ser
        35                  40                  45

Trp Thr Asp Ser Lys Glu Asp Ser Val Phe Ile Thr Thr Tyr Gly Phe
    50                  55                  60

Ile Phe Gln Val Gly Asn Glu Glu Val Thr Val Gly Met Ile Ser Asp
65                  70                  75                  80

Asn Pro Lys His Glu Leu Leu Ser Ala Ala Met Leu Cys Leu Gly Ser
                85                  90                  95

Val Pro Asn Val Gly Asp Leu Val Glu Leu Ala Arg Ala Cys Leu Thr
            100                 105                 110

Met Val Val Thr Cys Lys Lys Ser Ala Thr Asp Thr Glu Arg Met Val
        115                 120                 125

Phe Ser Val Val Gln Ala Pro Gln Val Leu Gln Ser Cys Arg Val Val
130                 135                 140

Ala Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
                165                 170                 175

Ser Leu Thr Val Val Pro Arg Lys Asp Val Tyr Lys Ile Pro Thr Ala
            180                 185                 190

Ala Leu Lys Val Ser Gly Ser Ser Leu Tyr Asn Leu Ala Leu Asn Val
        195                 200                 205

Thr Ile Asp Val Glu Val Asp Pro Lys Ser Pro Leu Val Lys Ser Leu
210                 215                 220

Ser Lys Ser Asp Ser Gly Tyr Tyr Ala Asn Leu Phe Leu His Ile Gly
225                 230                 235                 240

Leu Met Ser Thr Val Asp Lys Lys Gly Lys Lys Val Thr Phe Asp Lys
                245                 250                 255

Leu Glu Arg Lys Ile Arg Arg Leu Asp Leu Ser Val Gly Leu Ser Asp
            260                 265                 270

Val Leu Gly Pro Ser Val Leu Val Lys Ala Arg Gly Ala Arg Thr Arg
        275                 280                 285

Leu Leu Ala Pro Phe Phe Ser Ser Gly Thr Ala Cys Tyr Pro Ile
290                 295                 300

Ser Asn Ala Ser Pro Gln Val Ala Lys Ile Leu Trp Ser Gln Thr Ala
305                 310                 315                 320

Arg Leu Arg Ser Val Lys Val Ile Ile Gln Ala Gly Thr Gln Arg Ala
                325                 330                 335

Val Ala Val Thr Ala Asp His Glu Val Thr Ser Thr Lys Ile Glu Lys
            340                 345                 350

Arg His Thr Ile Ala Lys Tyr Asn Pro Phe Lys Lys
        355                 360

<210> SEQ ID NO 25
<211> LENGTH: 1210
<212> TYPE: DNA

<213> ORGANISM: Newcastle disease virus

<400> SEQUENCE: 25

```
acgggtagaa tcggagtgcc ctgattgtgc caagatggac tcatctagga caatagggct      60
atactttgat tctgcccttc cttctagcaa cctgttagca ttcccgatcg tcctacaaga     120
cataggagat gggaagaagc aaatcgcccc gcaatatagg atccagcgtc ttgactcgtg     180
gacagacagt aaagaagact cggtattcat caccacctat ggattcatct tccaggttgg     240
gaatgaagaa gtcactgtcg gcatgatcag cgataatccc aagcacgagt tactttcagc     300
tgcgatgctc tgcctaggaa gtgtcccgaa tgtcggagat cttgttgagt tggcaagggc     360
ctgcctcact atggtggtaa catgcaagaa gagtgcaact gatactgaga gaatggtctt     420
ctcggtagta caggcgcccc aggtgctgca aagctgtagg gtcgtggcaa acaaatactc     480
gtcagtgaat gcagttaagc acgtgaaagc accagagaag atccctggga gcggaaccct     540
agagtacaag gtgaattttg tctctttgac tgtggtgcca aggaaggatg tctacaaaat     600
cccaaccgca gcattgaagg tatctggctc gagcctgtac aatcttgcgc tcaatgtcac     660
tattgatgtg gaggtagacc caaagagccc gttagtcaaa tctctttcaa agtccgacag     720
tggatactat gctaatcttt tcttacatat cggacttatg tccactgtag ataagaaggg     780
aaagaaagtg acatttgaca agctggagag gaagataaga agactcgatt tatctgtcgg     840
gctcagtgat gtgctcggac cttccgtgct tgtgaaggcg agaggtgcac ggactaggct     900
gctggcacct tcttctcta gcagtgggac agcctgctat cctatatcaa atgcctctcc     960
tcaggtagct aagatactct ggagtcaaac tgcgcgcctg cggagtgtaa aagtcattat    1020
tcaagcgggc acccaacgcg ctgtcgcggt gaccgctgac cacgaggtca cctctactaa    1080
gatagaaaag aggcatacca ttgctaaata caatcctttt aagaaataag ctgcatctct    1140
gagactgcaa tccgcccgct ttcccgaatc atcacgacgc ttaataatgg atctgtcctg    1200
attactcaca                                                            1210
```

<210> SEQ ID NO 26
<211> LENGTH: 364
<212> TYPE: PRT
<213> ORGANISM: Newcastle disease virus

<400> SEQUENCE: 26

```
Met Asp Ser Ser Arg Thr Ile Gly Leu Tyr Phe Asp Ser Ala His Ser
1               5                   10                  15

Ser Ser Asn Leu Leu Ala Phe Pro Ile Val Leu Gln Asp Thr Gly Asp
            20                  25                  30

Gly Lys Lys Gln Ile Ala Pro Gln Tyr Arg Ile Gln Arg Leu Asp Ser
        35                  40                  45

Trp Thr Asp Ser Lys Glu Asp Ser Val Phe Ile Thr Thr Tyr Gly Phe
    50                  55                  60

Ile Phe Gln Val Gly Asn Glu Glu Ala Thr Val Gly Met Ile Asp Asp
65                  70                  75                  80

Lys Pro Lys Arg Glu Leu Leu Ser Ala Ala Met Leu Cys Leu Gly Ser
                85                  90                  95

Val Pro Asn Thr Gly Asp Leu Val Glu Leu Thr Arg Ala Cys Leu Thr
            100                 105                 110

Met Met Val Thr Cys Lys Lys Ser Ala Thr Asn Thr Glu Arg Met Val
        115                 120                 125

Phe Ser Val Val Gln Ala Pro Gln Val Leu Gln Ser Cys Arg Val Val
    130                 135                 140
```

Pro Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
            165                 170                 175

Ser Leu Thr Val Val Pro Lys Lys Asp Val Tyr Lys Ile Pro Ala Ala
            180                 185                 190

Val Leu Lys Ile Ser Gly Ser Ser Leu Tyr Asn Leu Ala Leu Asn Val
        195                 200                 205

Thr Ile Asn Val Glu Val Asp Pro Arg Ser Pro Leu Val Lys Ser Leu
    210                 215                 220

Ser Lys Ser Asp Ser Gly Tyr Tyr Ala Asn Leu Phe Leu His Ile Gly
225                 230                 235                 240

Leu Met Thr Thr Val Asp Arg Lys Gly Lys Val Thr Phe Asp Lys
                245                 250                 255

Leu Glu Lys Lys Ile Arg Ser Leu Asp Leu Ser Val Gly Leu Ser Asp
            260                 265                 270

Val Leu Gly Pro Ser Val Leu Val Lys Ala Arg Gly Ala Arg Thr Lys
        275                 280                 285

Leu Leu Ala Pro Phe Phe Ser Ser Ser Gly Thr Ala Cys Tyr Pro Ile
    290                 295                 300

Ala Asn Ala Ser Pro Gln Val Ala Lys Ile Leu Trp Ser Gln Thr Ala
305                 310                 315                 320

Cys Leu Arg Ser Val Lys Ile Ile Gln Ala Gly Thr Gln Arg Ala
                325                 330                 335

Val Ala Val Thr Ala Asp His Glu Val Thr Ser Thr Lys Leu Glu Lys
            340                 345                 350

Gly His Thr Leu Ala Lys Tyr Asn Pro Phe Lys Lys
        355                 360

<210> SEQ ID NO 27
<211> LENGTH: 1223
<212> TYPE: DNA
<213> ORGANISM: Newcastle disease virus

<400> SEQUENCE: 27
tgtgccaaga tggactcatc taggacaatt gggctgtact ttgattctgc ccattcttct      60
agcaacctgt tagcatttcc gatcgtccta caagacacag gagatgggaa gaagcaaatc     120
gccccgcaat ataggatcca gcgccttgac tcgtggactg atagtaagga agactcagta     180
ttcatcacca cctatggatt catctttcaa gttgggaatg aggaagccac tgtcggcatg     240
atcgatgata aacccaagcg cgagttactt tccgctgcga tgctctgcct aggaagcgtc     300
ccaaataccg agaccttgt tgagctgaca agggcctgtc tcactatgat ggtcacatgc     360
aagaagagtg caactaatac tgagagaatg gtttttctcag tagtgcaggc accccaagtg     420
ctgcaaagct gtagggttgt gccaaacaaa tactcatcag tgaatgcagt caagcacgtg     480
aaagcgccag agaagatccc cgggagtgga accctagaat acaaggtgaa ctttgtctcc     540
ttgactgtgg taccgaagaa ggatgtctac aagatcccag ctgcagtatt gaagatttct     600
ggctcgagtc tgtacaatct tgcgctcaat gtcactatta atgtggaggt agacccgagg     660 agtccttttgg ttaaatctct gtctaagtct gacagcggat actatgctaa cctcttcttg     720
catattggac ttatgaccac cgtagatagg aaggggaaga agtgacatt tgacaagctg     780 gaaaagaaaa taaggagcct tgatctatct gtcgggctca gtgatgtgct cgggccttcc     840
gtgttggtaa aagcaagagg tgcacggact aagcttttgg cacctttctt ctctagcagt     900

```
gggacagcct gctatcccat agcaaatgct tctcctcagg tggccaagat actctggagc    960
caaaccgcgt gcctgcggag cgttaaaatc attatccaag caggtaccca acgcgctgtc   1020
gcagtgaccg ctgaccacga ggttacctct actaagctgg agaaggggca cacccttgcc   1080
aaatacaatc cttttaagaa ataagctgcg tctctgagat tgcgctccgc ccactcaccc   1140
agatcatcat gacacaaaaa actaatctgt cttgattatt tacagttagt ttacctgtcc   1200
atcaagttag aaaaaacacg ggt                                            1223

<210> SEQ ID NO 28
<211> LENGTH: 15186
<212> TYPE: DNA
<213> ORGANISM: Newcastle disease virus B1

<400> SEQUENCE: 28
accaaacaga gaatcggtga gttacgataa aaggcgaagg agcaattgaa gtcgcacggg     60
tagaaggtgt gaatctcgag tgcgagcccg aagcacaaac tcgaggaagc cttctgccaa    120
catgtcttcc gtattcgacg agtacgaaca gctcctcgcg gctcagactc gccccaatgg    180
agctcatgga ggggggggaga aagggagtac cttaaaagta gacgtcccgg tattcactct    240
taacagtgat gacccagaag ataggtggag cttttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct tgccaacgca cacgccccag ttcaacaata ggagtggagt    480
gtctgaagag agagcacaga gatttgcgat gatagcagga tctctccctc gggcatgcag    540
caacggcacc ccgttcgtca cagccggggc tgaagatgat gcaccagaag acatcaccga    600
taccctggag aggatcctct ctatccaggc tcaagtatgg gtcacagtag caaaagccat    660
gactgcgtat gagactgcag atgagtcgga acaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctagtaggg gacgtagact catatatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga ataccaattg tgccaaggac tttatgagca catcattctg   1200
gagacttgga gtagagtacg ctcaggctca gggaagtagc attaacgagg atatggctgc   1260
cgagctaaag ctaaccccgg cagcaaggag gggcctggca gctgctgccc aacgagtctc   1320
cgaggtgacc agcagcatag acatgcctac tcaacaagtc ggagtcctca ctgggcttag   1380
cgagggggga tcccaagccc tacaaggcgc atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct ccccaactc ctgggccatc    1560
ccaagataac gacaccgact gggggtattg attgacaaaa cccagcctgc ttctacaaga   1620
acatcccaat gctctcaccc gtagtcgacc cctcgatttg cggctctata tgaccacacc   1680
ctcaaacaaa catcccccct ctttcctccct ccccctgctg tacaactccg cacgccctag   1740
gcaacagagg cacaatgcgg ctcactaaca atcaaaacag agccgaggga attagaaaaa   1800
```

```
agtacgggta gaagagggat attcagagat cagggcaagt ctcccgagtc tctgctctct    1860
cctctacctg atagaccagg acaaacatgg ccacctttac agatgcagag atcgacgagc    1920
tatttgagac aagtggaact gtcattgaca acataattac agcccagggt aaaccagcag    1980
agactgttgg aaggagtgca atcccacaag gcaagaccaa ggtgctgagc gcagcatggg    2040
agaagcatgg gagcatccag ccaccggcca gtcaagacaa ccccgatcga caggacagat    2100
ctgacaaaca accatccaca cccgagcaaa cgaccccgca tgacagcccg ccggccacat    2160
ccgctgacca gccccccacc caggccacag acgaagccgt cgacacacag ctcaggaccg    2220
gagcaagcaa ctctctgctg ttgatgcttg acaagctcag caataaatcg tccaatgcta    2280
aaaagggccc atggtcgagc ccccaagagg ggaatcacca acgtccgact caacagcagg    2340
ggagtcaacc cagtcgcgga aacagtcagg aaagaccgca gaaccaagtc aaggccgccc    2400
ctggaaacca gggcacagac gtgaacacag catatcatgg acaatgggag gagtcacaac    2460
tatcagctgg tgcaacccct catggtctcc gatcaaagca gagccaaaac aatacccctg    2520
tttctgcgga tcatttccac ccacctgtag actttgtgca agcgatgatg tctattatgg    2580 agggatttc ccaaagagta agtaaggttg cctatcaggt agatcttgtt tttaaacaga    2640
catcctccat ccctatgatg gggtccgaaa tccaacagct gaaaacattt gttgcagtca    2700
tggaagccaa cttgggaatg atgaagattt tggatcccgg ttgtgccaac atttcatctt    2760
tgagtgatct acgggcagtt gcccgatctc acccggtttt agtttcaggc cctggagacc    2820
catctcccta tgtgatacaa ggaggcgaaa tggcacttaa taaactttcg caaccagtgc    2880
cacatccatc tgaattgatt aaacccgcca ctgcatgcgg gcctgatata ggagtggaga    2940
gggacactgt ccgtgcattg atcatgtcac gcccaatgca cccgagttct tcagccaagc    3000
tcctaagcaa gttagatgca gccgggtcga tcgaggaaat caggaaaatc aagcgccttg    3060
ctctaaatgg ctaattacta ctgccacacg tagcgggtcc ctgtccactc ggcatcacac    3120
ggaatctgca ccgagttccc ccccgcagac ccaaggtcca actctccaag cggcaatcct    3180
ctctcgcttc ctcagcccca ctgaatgatc gcgcaaccgc aattaatcta gctacattaa    3240
ggattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caagacacag gagatgggaa gaagcaaatc gccccgcaat ataggatcca    3420
gcgccttgac ttgtggactg atagtaagga agactcagta ttcatcacca cctatggatt    3480
catctttcaa gttgggaatg aagaagccac tgtcggcatt atcgatgata aacccaagcg    3540
cgagttactt tccgctgcga tgctctgcct aggaagcgtc ccaaataccg agaccttat    3600 tgagctggca agggcctgtc tcactatgat ggtcacatgc aagaagagtg caactaatac    3660
tgagagaatg gtttctcag tagtgcaggc accccaagtg ctgcaaagct gtagggttgt    3720
ggcaaacaaa tactcatcag tgaatgcagt caagcacgtg aaagcgccag agaagatccc    3780
cgggagtgga accctagaat acaaggtgaa ctttgtctcc ttgactgtgg taccgaagaa    3840
ggatgtctac aagatcccag ctgcagtatt gaagatttct ggctcgagtc tgtacaatct    3900
tgcgctcaat gtcactatta atgtggaggt agacccgagg agtcctttgg ttaaatctct    3960
gtctaagtct gacagcggat actatgctaa cctcttcttg catattggac ttatgaccac    4020
cgtagatagg aaggggaaga aagtgacatt tgacaagctg gaaaagaaaa taaggagcct    4080
tgatctatct gtcgggctca gtgatgtgct cgggccttcc gtgttggtaa aagcaagagg    4140
tgcacggact aagcttttgg caccttttctt ctctagcagt gggacagcct gctatcccat    4200
```

```
agcaaatgct tctcctcagg tggccaagat actctggagt caaaccgcgt gcctgcggag   4260
cgttaaaatc attatccaag caggtaccca acgcgctgtc gcagtgaccg ctgaccacga   4320
ggttacctct actaagctgg agaaggggca caccccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtcc atcaagttag aaaaaacacg   4500
ggtagaagac tctggatccc ggttggcgcc ctccaggtgc aggatgggct ccagaccttt   4560
taccaagaac ccagcaccta tgatgctgac tatccgggtc gcgctggtat tgagttgcat   4620
ctgtccggca aactccattg atggcaggcc ttttgcagct gcaggaattg tggttacagg   4680
agacaaagca gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca ccccccttgg tgactctatc cgtaggatac aagagtctgt   4860
gactacatct ggagggggga dacaggggcg cctataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cccaactagc agtggcagtt gggaagatgc agcagtttgt   5100
taatgaccaa tttaataaaa cagctcagga attagactgc ataaaattg cacagcaagt   5160 tggtgtagag ctcaacctgt acctaaccga attgactaca gtattcggac cacaaatcac   5220
ttcacctgcc ttaaacaagc tgactattca ggcactttac aatctagctg gtgggaatat   5280
ggattactta ttgactaagt taggtatagg gaacaatcaa ctcagctcat taatcggtag   5340
cggcttaatc accggtaacc ctattctata cgactcacag actcaactct gggtataca   5400 ggtaactcta ccttcagtcg ggaacctaaa taatatgcgt gccacctact tggaaacctt   5460
atccgtaagc acaaccaggg gatttgcctc ggcacttgtc ccaaaagtgg tgacacaggt   5520
cggttctgtg atagaagaac ttgacacctc atactgtata gaaactgact tagatttata   5580
ttgtacaaga atagtaacgt tccctatgtc ccctggtatt tactcctgct tgagcggcaa   5640
tacatcggcc tgtatgtact caaagaccga aggcgcactt actacaccat atatgactat   5700
caaaggctca gtcatcgcta actgcaagat gacaacatgt agatgtgtaa acccccggg   5760 tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac cagcacatct gctctcatta cctatatcgt   6060
tttgactatc atatctcttg tttttggtat acttagcctg attctagcat gctacctaat   6120
gtacaagcaa aaggcgcaac aaaagacctt attatggctt gggaataata ccctagatca   6180
gatgagagcc actacaaaaa tgtgaacaca gatgaggaac gaaggtttcc ctaatagtaa   6240
tttgtgtgaa agttctggta gtctgtcagt tcggagagtt aagaaaaaac taccggttgt   6300
agatgaccaa aggacgatat acgggtagaa cggtaagaga ggccgcccct caattgcgag   6360
ccagacttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
```

-continued

```
tccagggcag aagaaaagat tacatctaca cttggttcca atcaagatgt agtagatagg    6660
atatataagc aagtggccct tgagtctcca ttggcattgt taaatactga gaccacaatt    6720
atgaacgcaa taacatctct ctcttatcag attaatggag ctgcaaacaa cagcgggtgg    6780
ggggcaccta ttcatgaccc agattatata gggggggatag gcaaagaact cattgtagat   6840
gatgctagtg atgtcacatc attctatccc tctgcatttc aagaacatct gaattttatc    6900
ccggcgccta ctacaggatc aggttgcact cgaataccct catttgacat gagtgctacc    6960
cattactgct acacccataa tgtaatattg tctggatgca gagatcactc acactcatat    7020
cagtatttag cacttggtgt gctccggaca tctgcaacag ggagggtatt cttttctact    7080
ctgcgttcca tcaacctgga cgacacccaa aatcggaagt cttgcagtgt gagtgcaact    7140
cccctgggtt gtgatatgct gtgctcgaaa gccacggaga cagaggaaga agattataac    7200
tcagctgtcc ctacgcggat ggtacatggg aggttagggt tcgacggcca atatcacgaa    7260
aaggacctag atgtcacaac attattcggg gactgggtgg ccaactaccc aggagtaggg    7320
ggtggatctt ttattgacag ccgcgtatgg ttctcagtct acggagggtt aaaacccaat    7380
tcacccagtg acactgtaca ggaagggaaa tatgtgatat acaagcgata caatgacaca    7440
tgcccagatg agcaagacta ccagattcga atggccaagt cttcgtataa gcctggacgg    7500
tttggtggga aacgcataca gcaggctatc ttatctatca aagtgtcaac atccttaggc    7560
gaagacccgg tactgactgt accgcccaac acagtcacac tcatgggggc cgaaggcaga    7620
attctcacag tagggacatc ccatttcttg tatcagcgag ggtcatcata cttctctccc    7680
gcgttattat atcctatgac agtcagcaac aaaacagcca ctcttcatag tccttataca    7740
ttcaatgcct tcactcggcc aggtagtatc ccttgccagg cttcagcaag atgccccaac    7800
tcgtgtgtta ctggagtcta tacagatcca tatcccctaa tcttctatag aaaccacacc    7860
ttgcgagggg tattcgggac aatgcttgat ggtgaacaag caagacttaa ccctgcgtct    7920
gcagtattcg atagcacatc ccgcagtcgc ataactcgag tgagttcaag cagcatcaaa    7980
gcagcataca caacatcaac ttgttttaaa gtggtcaaga ccaataagac ctattgtctc    8040
agcattgctg aaatatctaa tactctcttc ggagaattca gaatcgtccc gttactagtt    8100
gagatcctca aagatgacgg ggttagagaa gccaggtctg gctagttgag tcaactatga    8160
aagagttgga aagatggcat tgtatcacct atcttctgcg acatcaagaa tcaaaccgaa    8220
tgccggcgcg tgctcgaatt ccatgtcgcc agttgaccac aatcagccag tgctcatgcg    8280
atcagattaa gccttgtcaa tagtctcttg attaagaaaa aatgtaagtg gcaatgagat    8340
acaaggcaaa acagctcatg gtaaataata cgggtaggac atggcgagct ccggtcctga    8400
aagggcagag catcagatta tcctaccaga gtcacacctg tcttcaccat tggtcaagca    8460
caaactactc tattattgga aattaactgg gctaccgctt cctgatgaat gtgacttcga    8520
ccacctcatt ctcagccgac aatggaaaaa aatacttgaa tcggcctctc ctgatactga    8580
gagaatgata aaactcggaa gggcagtaca ccaaactctt aaccacaatt ccagaataac    8640
cggagtactc caccccaggt gtttagaaga actggctaat attgaggtcc ctgattcaac    8700
caacaaattt cggaagattg agaagaagat ccaaattcac aacacgagat atggagaact    8760
gttcacaagg ctgtgtacgc atatagagaa gaaactgctg gggtcatctt ggtctaacaa    8820
tgtcccccgg tcagaggagt tcagcagcat tcgtacggat ccggcattct ggtttcactc    8880
aaaatggtcc acagccaagt ttgcatggct ccatataaaa cagatccaga ggcatctgat    8940
tgtggcagct aggacaaggt ctgcggccaa caaattggtg atgctaaccc ataaggtagg    9000
```

```
ccaagtctttt gtcactcctg aacttgttgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
gggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgcctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacggat acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atacgaccct gtcactaacc tgagcatgtt   9780
cctaaaagac aaggcaatcg cacacccaa cgataattgg cttgcctcgt ttaggcggaa   9840
ccttctctcc gaagaccaga agaaacatgt aaaggaagcg acttcgacta accgcctctt   9900
gatagagttt ttagagtcaa atgattttga tccatataaa gagatggaat atctgacgac   9960
ccttgagtac cttagagatg acaatgtggc agtatcatac tcgctcaaag agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacga tcaaattgtt cgctcatgcc atcaatcagt tgatgggcct  10380
acctcatttc ttcgagtgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag atgactctcc  10680
ggagatggtg ttgacacagt tgcatcaagc cagtgataat ttcttcaagg aattaatcca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa acaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag acatctcctt tgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggacta ctgagtccta acattatgac taatatcctt actaggccgc tgggaatgg   11280
agattggggc agtctgtgca acgacccata ctctttcaat tttgagactg ttgcaagccc  11340
aaatattgtt cttaagaaac atacgcaaag agtcctattt gaaacttgtt caaatccctt  11400
```

```
attgtctgga gtgcacacag aggataatga ggcagaagag aaggcattgg ctgaattctt   11460
gcttaatcaa gaggtgattc atccccgcgt tgcgcatgcc atcatggagg caagctctgt   11520
aggtaggaga aagcaaattc aagggcttgt tgacacaaca aacactgtaa ttaagattgc   11580
gcttactagg aggccattag gcatcaagag gctgatgcgg atagtcaatt attctagcat   11640
gcatgcaatg ctgtttagag acgatgtttt ttcctctagt agatccaacc accccttagt   11700
ctcttctaat atgtgttctc tgacactggc agactatgca cggaatagaa gctggtcacc   11760
tttgacggga ggcaggaaaa tactgggtgt atctaatcct gatacgatag aactcgtaga   11820
gggtgagatt cttagtgtaa gcggagggtg tacaagatgt gacagcggag atgaacaatt   11880
tacttggttc catcttccaa gcaatataga attgaccgat gacaccagca agaatcctcc   11940
gatgagggta ccatatctcg ggtcaaagac acaggagagg agagctgcct cacttgcgaa   12000
aatagctcat atgtcgccac atgtgaaggc tgccctaagg gcatcatccg tgttgatctg   12060
ggcttatggg gataatgaag taaattggac tgctgctctc acgattgcaa aatctcggtg   12120
taatgtaaac ttagagtatc ttcggttact gtcccctttta cccacggctg ggaatcttca   12180
acatagacta gatgatggta taactcagat gacattcacc cctgcatctc tctacaggtg   12240
tcaccttaca ttcacatatc caatgattct caaaggctgt tcactgaaga aggagtcaaa   12300
gaggggaatg tggtttacca acagagtcat gctcttgggt ttatctctaa tcgaatcgat   12360
ctttccaatg acaacaacca gaacatatga tgagatcaca ctgcacctac atagtaaatt   12420
tagttgctgt atcagggaag cacctgttgc ggttcctttc gagctacttg gggtggcacc   12480
ggaactgagg acagtgacct caaataagtt tatgtatgat cctagccctg tatcggaggg   12540
agactttgcg agacttgact tagctatctt caagagttat gagcttaatc tggagtcata   12600
tcccacgata gagctaatga acattcttttc aatatccagc gggaagttga ttggccagtc   12660
tgtggtttct tatgatgaag atacctccat aaagaatgat gccataatag tgtatgacaa   12720
tacccgaaat tggatcagtg aagctcagaa ttcagatgtg gtccgcctat ttgaatatgc   12780
agcacttgaa gtgctcctcc accgttctta ccaactctat tacctgagag taagaggcct   12840
agacaatatt gtcttatata tgggtgattt atacaagaat atgccaggaa ttctactttc   12900
caacattgca gctacaatat ctcatcctgt cattcattca aggttacatg cagtgggcct   12960
ggtcaaccat gacggatcac accaacttgc agatacggat tttatcgaaa tgtctgcaaa   13020
actgttagta tcttgcaccc gacgtgtgat ctccggctta tattcaggaa ataagtatga   13080
tctgctgttc ccatctgtct tagatgataa cctgaatgag aagatgcttc agctgatatc   13140
ccggttatgc tgtctgtaca cggtactctt tgctacaaca agagaaatcc cgaaaataag   13200
aggcttaact gcagaagaga aatgttcaat actcactgag tatttactgt cggatgctgt   13260
gaaaccatta cttagccccg atcaagtgag ctctatcatg tctcctaaca taattacatt   13320
cccagctaat ctgtactaca tgtctcggaa gagcctcaat ttgatcaggg aaagggagga   13380
cagggatact atcctggcgt tgttgttccc ccaagagcca ttattagagt tcccttctgt   13440
gcaagatatt ggtgctcgag tgaaagatcc attcacccga caacctgcgg catttttgca   13500
agagttagat ttgagtgctc cagcaaggta tgacgcattc acacttagtc agattcatcc   13560
tgaactcaca tctccaaatc cggaggaaga ctacttagta cgatacttgt tcagagggat   13620
agggactgca tcttcctctt ggtataaggc atcccatctc cttttctgtac ccgaggtaag   13680 atgtgcaaga cacgggaact cccttatactt ggctgaagga agcggagcca tcatgagtct   13740
tcttgaactg catgtaccac atgaaactat ctattacaat acgctctttt caaatgagat   13800
```

```
gaaccccccg caacgacatt tcgggccgac cccaactcag ttttttgaatt cggttgttta     13860 taggaatcta caggcggagg taacatgcaa ggatggattt gtccaagagt tccgtccatt     13920
atggagagaa atacagagg aaagtgacct gacctcagat aaagcagtgg ggtatattac      13980
atctgcagta ccctacagat ctgtatcatt gctgcattgt gacattgaaa ttcctccagg     14040
gtccaatcaa agcttactag atcaactagc tatcaattta tctctgattg ccatgcattc     14100
tgtaagggag ggcggggtag taatcatcaa agtgttgtat gcaatgggat actactttca     14160
tctactcatg aacttgtttg ctccgtgttc cacaaaagga tatattctct ctaatggtta     14220
tgcatgtcga ggggatatgg agtgttacct ggtatttgtc atgggttacc tgggcgggcc     14280
tacatttgta catgaggtgg tgaggatggc aaaaactctg gtgcagcggc acggtacgct     14340
cttgtctaaa tcagatgaga tcacactgac caggttattc acctcacagc ggcagcgtgt     14400
gacagacatc ctatccagtc ctttaccaag attaataaag tacttgagga agaatattga     14460
cactgcgctg attgaagccg ggggacagcc cgtccgtcca ttttgtgcgg aaagtttggt     14520
gagcacgcta gcgaacataa ctcagataac ccagattatc gctagtcaca ttgacacagt     14580
catccggtct gtgatatata tggaagctga gggtgatctc gctgacacag tatttctatt     14640 tacccccttac aatctctcta ctgacgggaa aaagaggaca tcacttaaac agtgcacgag     14700
acagatccta gaggttacaa tactaggtct tagagtcgaa atctcaata aaataggcga      14760 tataatcagc ctagtgctta aaggcatgat ctccatggag gaccttatcc cactaaggac     14820
atacttgaag catagtacct gccctaaata tttgaaggct gtcctaggta ttaccaaact     14880
caaagaaatg tttacagaca cttctgtact gtacttgact cgtgctcaac aaaaattcta     14940
catgaaaact ataggcaatg cagtcaaagg atattacagt aactgtgact cctaacgaaa     15000
atcacatatt aataggctcc ttttttggcc aattgtattc ttgttgattt aattatatta     15060
tgttagaaaa aagttgaact ctgactcctt aggactcgaa ttcgaactca ataaatgtc      15120 tttaaaaaag gttgcgcaca attattcttg agtgtagtct cgtcattcac caaatctttg     15180
tttggt                                                                15186

<210> SEQ ID NO 29
<211> LENGTH: 617
<212> TYPE: PRT
<213> ORGANISM: Measles virus

<400> SEQUENCE: 29

```
Arg Glu Tyr Asp Phe Arg Asp Leu Thr Trp Cys Ile Asn Pro Pro Glu
    130                 135                 140
Arg Ile Lys Leu Asp Tyr Asp Gln Tyr Cys Ala Asp Val Ala Ala Glu
145                 150                 155                 160
Glu Leu Met Asn Ala Leu Val Asn Ser Thr Leu Leu Glu Ala Arg Ala
                165                 170                 175
Thr Asn Gln Phe Leu Ala Val Ser Lys Gly Asn Cys Ser Gly Pro Thr
            180                 185                 190
Thr Ile Arg Gly Gln Phe Ser Asn Met Ser Leu Ser Leu Leu Asp Leu
        195                 200                 205
Tyr Leu Ser Arg Gly Tyr Asn Val Ser Ser Ile Val Thr Met Thr Ser
    210                 215                 220
Gln Gly Met Tyr Gly Gly Thr Tyr Leu Val Glu Lys Pro Asn Leu Ser
225                 230                 235                 240
Ser Lys Gly Ser Glu Leu Ser Gln Leu Ser Met His Arg Val Phe Glu
                245                 250                 255
Val Gly Val Ile Arg Asn Pro Gly Leu Gly Ala Pro Val Phe His Met
            260                 265                 270
Thr Asn Tyr Phe Glu Gln Pro Val Ser Asn Asp Phe Ser Asn Cys Met
        275                 280                 285
Val Ala Leu Gly Glu Leu Lys Phe Ala Ala Leu Cys His Arg Glu Asp
    290                 295                 300
Ala Ile Thr Ile Pro Tyr Gln Gly Ser Gly Lys Gly Val Ser Phe Gln
305                 310                 315                 320
Leu Val Lys Leu Gly Val Trp Lys Ser Pro Thr Asp Met Gln Ser Trp
                325                 330                 335
Val Pro Leu Ser Thr Asp Asp Pro Val Ile Asp Arg Leu Tyr Leu Ser
            340                 345                 350
Ser His Arg Gly Val Ile Ala Asp Asn Gln Ala Lys Trp Ala Val Pro
        355                 360                 365
Thr Thr Arg Thr Asp Asp Lys Leu Arg Met Glu Thr Cys Phe Gln Gln
    370                 375                 380
Ala Cys Lys Gly Lys Ile Gln Ala Leu Cys Glu Asn Pro Glu Trp Ala
385                 390                 395                 400
Pro Leu Lys Asp Asn Arg Ile Pro Ser Tyr Gly Val Leu Ser Val Asn
                405                 410                 415
Leu Ser Leu Thr Val Glu Leu Lys Ile Lys Ile Ala Ser Gly Phe Gly
            420                 425                 430
Pro Leu Ile Thr His Gly Ser Gly Met Asp Leu Tyr Lys Ser Asn His
        435                 440                 445
Asn Asn Val Tyr Trp Leu Thr Ile Pro Pro Met Lys Asn Leu Ala Leu
    450                 455                 460
Gly Val Ile Asn Thr Leu Glu Trp Val Pro Arg Phe Lys Val Ser Pro
465                 470                 475                 480
Asn Leu Phe Thr Val Pro Ile Lys Glu Ala Gly Glu Asp Cys His Ala
                485                 490                 495
Pro Thr Tyr Leu Pro Ala Glu Val Asp Gly Asp Val Lys Leu Ser Ser
            500                 505                 510
Asn Leu Val Ile Leu Pro Gly Gln Asp Leu Gln Tyr Val Leu Ala Thr
        515                 520                 525
Tyr Asp Thr Ser Arg Val Glu His Ala Val Val Tyr Tyr Val Tyr Ser
    530                 535                 540
Pro Ser Arg Ser Phe Ser Tyr Phe Tyr Pro Phe Arg Leu Pro Ile Lys
```

```
                545                 550                 555                 560
Gly Phe Pro Ile Glu Leu Gln Val Glu Cys Phe Thr Trp Asp Gln Lys
                    565                 570                 575
Leu Trp Cys Arg His Phe Cys Val Leu Ala Asp Ser Glu Ser Gly Gly
                580                 585                 590
His Ile Thr His Ser Gly Met Val Gly Met Gly Val Ser Cys Thr Val
            595                 600                 605
Thr Arg Glu Asp Gly Thr Asn Arg Arg
        610                 615

<210> SEQ ID NO 30
<211> LENGTH: 1854
<212> TYPE: DNA
<213> ORGANISM: Measles virus

<400> SEQUENCE: 30
atgtcaccac aacgagaccg gataaatgcc ttctacaaag acaaccccca tcctaaggga      60
agtaggatag ttattaacag agaacatctt atgattgata gaccttatgt tttgctggct     120
gttctgttcg tcatgtttct gagcttgatc gggctgctag ccattgcagg cattagactg     180
catcgggcag ccatctacac cgcagagatc cataaaagcc tcagcaccaa tctagatgta     240
actaactcaa tcgagcatca ggtcaaggac gtgctgacac cactcttcaa gatcattggt     300
gatgaagtgg gcctgaggac acctcagaga ttcactgatc tagtgaaatt catctctgac     360
aagattaaat tccttaatcc ggataggag tacgacttca gagatctcac ttggtgtatc     420
aacccgccag agagaatcaa attggattat gaccaatact gtgcagatgt ggctgctgaa     480
gaactcatga atgcattggt gaactcaact ctactggaag ccaggcaac caatcagttc     540 ctagctgtct caaagggaaa ctgctcaggg cccactacaa tcagaggtca attctcaaac     600
atgtcgctgt ccctgttgga cttgtattta agtcgaggtt acaatgtgtc atctatagtc     660
actatgacat cccagggaat gtacgggga acttacctag tggaaaagcc taatctgagc     720
agcaaaggtt cggagttgtc acaactgagc atgcaccgag tgtttgaagt aggtgttatc     780
agaaatccgg gtttgggggc tccggtgttc catatgacaa actattttga gcaaccagtc     840
agtaatgatt tcagcaactg catggtggct ttaggagagc tcaaattcgc agccctttgt     900
cacagggagg atgctatcac aattccctat caggatcag ggaaaggtgt cagcttccag     960
ctcgtcaagc taggtgtctg gaaatcccca accgacatgc aatcctgggt cccctatca    1020 acggatgatc cagtgataga caggctttac ctctcatctc acagaggcgt tatcgctgac    1080
aatcaagcaa atgggctgt cccgacaaca cggacagatg acaagttgcg aatggagaca    1140
tgcttccagc aggcgtgtaa gggtaaaatc caagcactct gcgagaatcc cgagtgggca    1200
ccattgaagg ataacaggat tccttcatac ggggtcttgt ctgttaatct gagtctgaca    1260
gttgagctta aaatcaaaat tgcttcagga ttcgggccat tgatcacaca cggttcaggg    1320
atggacctgt acaaatccaa ccacaacaat gtgtattggc tgactatccc gccaatgaag    1380
aacctagcct taggtgtaat caacacattg gagtgggtac cgagattcaa ggttagtccc    1440
aacctcttca ctgttccaat caaggaagca ggcgaggact gccatgcccc aacatacctg    1500
cctgcggagg tggatggtga tgtcaaactc agttccaatc tggtgattct acctggtcaa    1560
gacctccaat atgtttggc aacctacgat acttccagag ttgagcatgc tgtggtttat    1620
tacgtttaca gcccaagccg ctcatttttc tactttatc cttttaggtt gcctataaag    1680
gggttcccca tcgaattaca ggtggaatgc ttcacttggg accaaaaact ctggtgccgt    1740
```

```
cacttctgtg tgcttgcgga ctcagaatct ggtggacata tcactcactc tgggatggtg    1800
ggcatgggag ttagctgtac agtcactcga gaagatggaa ccaaccgcag atag          1854
```

<210> SEQ ID NO 31
<211> LENGTH: 617
<212> TYPE: PRT
<213> ORGANISM: Measles virus

<400> SEQUENCE: 31

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Le

```
Thr Thr Arg Thr Asp Asp Lys Leu Arg Met Glu Thr Cys Phe Gln Gln
    370                 375                 380
Ala Cys Lys Gly Lys Ile Gln Ala Leu Cys Glu Asn Pro Glu Trp Ala
385                 390                 395                 400
Pro Leu Lys Asp Asn Arg Ile Pro Ser Tyr Gly Val Leu Ser Val Asn
                405                 410                 415
Leu Ser Leu Thr Val Glu Leu Lys Ile Lys Ile Ala Ser Gly Phe Gly
            420                 425                 430
Pro Leu Ile Thr His Gly Ser Gly Met Asp Leu Tyr Lys Ser Asn His
        435                 440                 445
Asn Asn Val Tyr Trp Leu Thr Ile Pro Pro Met Lys Asn Leu Ala Leu
    450                 455                 460
Gly Val Ile Asn Thr Leu Glu Trp Val Pro Arg Leu Lys Val Ser Pro
465                 470                 475                 480
Asn Leu Phe Thr Val Pro Ile Lys Glu Ala Gly Glu Asp Cys His Ala
                485                 490                 495
Pro Thr Tyr Leu Pro Ala Glu Val Asp Gly Asp Val Lys Leu Ser Ser
            500                 505                 510
Asn Leu Val Ile Leu Pro Gly Gln Asp Leu Gln Tyr Val Leu Ala Thr
        515                 520                 525
Tyr Asp Thr Ser Arg Val Glu His Ala Val Val Tyr Tyr Val Tyr Ser
    530                 535                 540
Pro Ser Arg Ser Phe Ser Tyr Phe Tyr Pro Phe Arg Leu Pro Ile Lys
545                 550                 555                 560
Gly Val Pro Ile Glu Leu Gln Val Glu Cys Phe Thr Trp Asp Gln Lys
                565                 570                 575
Leu Trp Cys Arg His Phe Cys Val Leu Ala Asp Ser Glu Thr Gly Gly
            580                 585                 590
His Ile Thr His Ser Gly Met Val Gly Met Gly Val Ser Cys Thr Val
        595                 600                 605
Thr Arg Glu Asp Gly Thr Asn Arg Arg
    610                 615

<210> SEQ ID NO 32
<211> LENGTH: 1854
<212> TYPE: DNA
<213> ORGANISM: Measles virus

<400> SEQUENCE: 32
atgtcaccac aacgagaccg ataaatgcc  ttctacaaag acaaccccca tcctaaggga      60
agtaggatag ttattaatag agaacatctt atgattgata gaccttatgt tttgctggct     120
gttctattcg tcatgtttct gagcttgatc gggctgctag ccattgcagg cattagactg     180
catcgggcag ctatctacac cgcagagatc cataaaagcc tcagcaccaa tctagatgta     240
actaactcaa tcgagcatca ggtcaaggac gtgctgacac cactcttcaa gatcatcggt     300
gatgaagtgg gcctgaggac acctcagaga ttcactgacc tagtgaaatt catctctgac     360
aagattaaat tccttaatcc ggatagggag tacgacttca gagatctcac ttggtgtatc     420
aacccgccag agagaatcaa attggattat gaccaatact gtgcagatgt ggctgctgaa     480
gaactcatga atgcattggt gaactcaact ctactgagg ccagggcaac caatcagttc     540
ttagctgtct caagggaaa ctgctcaggg cccactacaa tcagaggtca attctcaaac     600
atgtcgctgt ccctgttgga cttgtattta agtcgaggtt acaatgtgtc atctatagtc     660
actatgacat cccagggaat gtacggggga acttacctag tggaaaagcc taatctgagc     720
```

```
agcaaagggt cagagttgtc acaactgagc atgcaccggg tgtttgaggt aggtgttatc

-continued

```
Thr Asn Gln Phe Leu Ala Val Ser Lys Gly Asn Cys Ser Gly Pro Thr
            180                 185                 190
Thr Ile Arg Gly Gln Phe Ser Asn Met Ser Leu Ser Leu Leu Asp Leu
        195                 200                 205
Tyr Leu Ser Arg Gly Tyr Asn Val Ser Ser Ile Val Thr Met Thr Ser
    210                 215                 220
Gln Gly Met Tyr Gly Gly Thr Tyr Leu Val Glu Lys Pro Asn Leu Asn
225                 230                 235                 240
Ser Lys Gly Ser Glu Leu Ser Gln Leu Ser Met Tyr Arg Val Phe Glu
                245                 250                 255
Val Gly Val Ile Arg Asn Pro Gly Leu Gly Ala Pro Val Phe His Met
            260                 265                 270
Thr Asn Tyr Phe Glu Gln Pro Ile Ser Lys Asp Leu Ser Asn Cys Met
        275                 280                 285
Val Ala Leu Gly Glu Leu Lys Leu Ala Ala Leu Cys His Gly Gly Asp
    290                 295                 300
Ser Ile Thr Ile Pro Tyr Gln Gly Ser Gly Lys Gly Val Ser Phe Gln
305                 310                 315                 320
Leu Val Lys Leu Gly Val Trp Lys Ser Pro Thr Asp Met Gln Ser Trp
                325                 330                 335
Val Pro Leu Ser Thr Asp Asp Pro Val Ile Asp Arg Leu Tyr Leu Ser
            340                 345                 350
Ser His Arg Gly Val Ile Thr Asp Asn Gln Ala Asn Trp Ala Val Pro
        355                 360                 365
Thr Thr Arg Thr Asp Asp Lys Leu Arg Met Glu Thr Cys Phe Gln Gln
    370                 375                 380
Ala Cys Lys Gly Lys Ile Gln Ala Leu Cys Glu Asn Pro Glu Trp Ala
385                 390                 395                 400
Pro Leu Lys Asp Ser Arg Ile Pro Ser Tyr Gly Val Leu Ser Val Asp
                405                 410                 415
Leu Ser Leu Ala Ala Glu Pro Lys Ile Lys Ile Ala Ser Gly Phe Gly
            420                 425                 430
Pro Leu Ile Thr His Gly Ser Gly Met Asp Leu Tyr Lys Ser Asn His
        435                 440                 445
Asn Asn Val Tyr Trp Leu Thr Ile Pro Pro Met Lys Asn Leu Ala Leu
    450                 455                 460
Gly Val Ile Asn Thr Leu Glu Trp Ile Pro Arg Leu Lys Val Ser Pro
465                 470                 475                 480
Asn Leu Phe Thr Val Pro Ile Lys Glu Ala Gly Glu Asn Cys His Ala
                485                 490                 495
Pro Thr Tyr Leu Pro Ala Glu Val Asp Gly Asp Val Lys Leu Ser Ser
            500                 505                 510
Asn Leu Val Ile Leu Pro Gly Gln Asp Leu Gln Tyr Val Leu Ala Thr
        515                 520                 525
Tyr Asp Thr Ser Arg Val Glu His Ala Val Val Tyr Tyr Val Tyr Ser
    530                 535                 540
Pro Ser Arg Ser Phe Ser Tyr Phe Tyr Pro Phe Arg Leu Pro Ile Lys
545                 550                 555                 560
Gly Thr Pro Ile Glu Leu Gln Val Glu Cys Phe Thr Trp Asp Gln Arg
                565                 570                 575
Leu Trp Cys Arg His Phe Cys Val Leu Ala Asp Ser Glu Ser Gly Gly
            580                 585                 590
His Ile Thr His Ser Gly Met Val Gly Met Gly Val Ser Cys Thr Val
        595                 600                 605
```

Asn Arg Glu Asp Glu Ala Asn Arg Arg
    610                 615

<210> SEQ ID NO 34
<211> LENGTH: 1854
<212> TYPE: DNA
<213> ORGANISM: Measles virus

<400> SEQUENCE: 34

| | | |
|---|---|---|
| atgtcactgc aacgagaccg ataaatgcc ttctacaaag ataaccctca ttccaaagga | 60 |
| agtaggatag ttattaacag agaacatctc atgattgata gaccttatgt tttgctggct | 120 |
| gttctgttcg tcatgtttct gagcttgatc gggttgctgg ccattgcagg cattaggctt | 180 |
| catcgggcag ctatctacac tgcagagatc cataaaagcc tcagcaccaa tctagatgta | 240 |
| actaactcaa tcgagcatca ggtcaaggat gtgctgacac cgctcttcaa aatcatcggt | 300 |
| gatgaagtgg gcctgagaac acctcagaga ttcactgacc tagtgaaatt catctctgac | 360 |
| aagatcaaat tccttaatcc ggatagggag tatgacttca gagatctcac ttggtgtatc | 420 |
| aacccgccag agagaatcaa attgaattat gatcaatact gtgcagatgt ggctgctgaa | 480 |
| gagctcatga atgcattagt gaactcaact ctactggaga ccagaacaac caatcagttc | 540 |
| ctagctgtct caaagggaaa ctgctcaggg cccactacca tcagaggtca attctcaaac | 600 |
| atgtcgctgt ctctgttaga cttatattta agtcgaggtt acaatgtgtc atctatagtc | 660 |
| actatgacgt cccagggaat gtatgggga acttacctag ttgaaaagcc caatctgaac | 720 |
| agcaaaggat cagaattatc acaactgagc atgtaccgag tgtttgaagt aggtgttata | 780 |
| agaaatccag gctggggggc tccggtgttc catatgacaa actattttga acaaccaatc | 840 |
| agcaaggatc tcagcaactg catggtagct ttggggagc tcaaactcgc agccctttgt | 900 |
| cacggggag attccatcac aattccctat cagggatcag ggaaaggtgt cagcttccaa | 960 |
| ctcgtcaagc taggtgtctg gaaatcccca accgacatgc aatcctgggt cccctatca | 1020 |
| acggatgacc cagtgataga caggctctac ctctcatctc acagaggtgt catcactgac | 1080 |
| aatcaagcaa attgggctgt tccgacaaca cgaacagatg ataagttgcg gatggagaca | 1140 |
| tgcttccagc aggcgtgcaa gggcaaaatc caagcactct gtgaaaatcc cgagtgggca | 1200 |
| ccgttgaagg acagcaggat tccttcatac ggggtcttgt ctgtcgacct gagtctggca | 1260 |
| gctgagccca aaatcaaaat tgcttcggga ttcggtccat tgatcactca cggttcaggg | 1320 |
| atggacctat acaaatccaa ccacaacaat gtgtattggc tgactatccc gccaatgaag | 1380 |
| aacttagcct taggtgtaat caacacattg gagtggatac cgagactcaa ggttagtccc | 1440 |
| aacctcttca ctgtcccaat taaggaagct ggcgagaact gccatgcccc aacataccta | 1500 |
| cctgcggagg tggatggtga tgtcaaactc agttccaatc tggtgatttt acctggtcaa | 1560 |
| gatctccaat atgttttggc aacctacgat acttccagag ttgaacatgc tgtgttttat | 1620 |
| tacgtttaca gcccaagccg ctcattctct tactttatc cctttaggtt acctataaag | 1680 |
| gggacccca tcgaattaca agtggaatgc ttcacatggg accaaagact ctggtgccgt | 1740 |
| cacttctgtg tgcttgctga ctcggaatct ggtggacata tcacccactc tgggatggtg | 1800 |
| ggcatgggag tcagctgcac agtcaaccgg aagacgaag ccaatcgcag atag | 1854 |

<210> SEQ ID NO 35
<211> LENGTH: 550
<212> TYPE: PRT
<213> ORGANISM: Measles virus

```
<400> SEQUENCE: 35

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Asn Leu Ser Lys
            20                  25                  30

Ile Gly Val Val Gly Ile Gly Ser Ala Ser Tyr Lys Val Met Thr Arg
            35                  40                  45

Ser Ser His Gln Ser Leu Val Ile Lys Leu Met Pro Asn Ile Thr Leu
50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Phe Gln Ser Val Ala Ser Ser Arg Arg His Lys Arg
            100                 105                 110

Phe Ala Gly Val Val Leu Ala Gly Ala Ala Leu Gly Val Ala Thr Ala
            115                 120                 125

Ala Gln Ile Thr Ala Gly Ile Ala Leu His Gln Ser Met Leu Asn Ser
130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
            195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
            275                 280                 285

Ser Glu Ile Lys Gly Val Ile Val His Arg Leu Glu Gly Val Ser Tyr
290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
            355                 360                 365

Thr Leu Val Ser Gly Ser Phe Gly Asn Arg Phe Ile Leu Ser Gln Gly
370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415
```

```
Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445

Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550

<210> SEQ ID NO 36
<211> LENGTH: 2383
<212> TYPE: DNA
<213> ORGANISM: Measles virus

<400> SEQUENCE: 36
cttagggtca aggaacatac acacccaaca gaacccagac cccgacccac ggcgccgcgc      60
ccccaacccc cgacaaccag agggagcccc caaccaatcc cgccggctcc ctcggtgccc     120
acagacaggc acaccaaccc ccgaacaggc ccagtgccca gccatcgaca atctaagacg     180
ggggggcccc ccccaaaaaa agcccccagg ggccgacagc cagcaccgcg cggaagccca     240
cccaccccac acacgaccac gacaaccaaa ccagaatcca gaccaccctg ggccgccagc     300
tcccagactc ggccatcacc ccgcagaaag gaaagggcac aacccgcgca ccccagcccc     360
gatccggcgg gcagccaccc aacccgaacc ggcacccaag agcgatcccc gaaggacccc     420
cgagccgcaa aggacatcag tatcccacag cctctccaag tcccctggtc tcttcctctt     480
ctcgaaggga ccaaaagatc aatccaccac atccgacgac actcaactcc ccacccctaa     540
aggagacacc gggagtcctg gaatcaagac tcatccaatg tccatcatgg gtctcaaggt     600
gaacgtctct gccatattca tggcagtact gttaactctc caaacaccca ccggtcaaat     660
ccattggggc aatctctcta agataggggt ggtaggaata ggaagtgcaa gctacaaagt     720
tatgactcgt tccagccatc aatcattagt cataaaatta atgcccaata taactctcct     780
caataactgc acgagggtag agattgcaga atacaggaga ctactgagaa cagttttgga     840
accaattaga gatgcactta atgcaatgac ccagaatata agaccgtttc agagtgtagc     900
ttcaagtagg agacacaaga gatttgcggg agtagtcctg gcaggtgcgg ccctaggcgt     960
tgccacagct gctcagataa cagccggcat tgcacttcac cagtccatgc tgaactctca    1020
agccatcgac aatctgagag caagtctgga aactactaat caggcaattg aggcaatcag    1080
acaagcaggg caggagatga tattggctgt tcagggtgtc caagactaca tcaataatga    1140
gctgataccg tctatgaacc aactatcttg tgatttaatc ggccagaagc tcgggctcaa    1200
attgctcaga tactatacag aaatcctgtc attatttggc cctagcttac gggaccccat    1260
atctgcggag atatctatcc aggctttgag ctatgcgctc ggaggagata tcaataaggt    1320
gttagaaaag ctcggatata gcggaggtga tttactgggc atcttagaga gcagaggaat    1380
```

```
aaaggcccgg ataactcacg tcgacacaga gtcctacttc attgtcctca gtatagctta    1440
tccgacgctg tccgagatca aggggtgat tgtccaccgg ctcgagggg tctcgtacaa     1500 cataggctct caagagtggt atacgactgt gcccaagtat gttgcaaccc aagggtacct    1560
tatctcgaat tttgatgagt catcgtgtac ttttatgcca gaggggactg tgtgcagcca    1620
aaatgccttg tacccgatga gtcctctgct ccaagaatgc ctccgggggt ccaccaagtc    1680
ctgtgctcgt acactcgtat ctgggtcttt tgggaaccgg tttattttgt cacaagggaa    1740
cctaatagcc aattgtgcat cgatcctttg caagtgttac acaacaggaa cgatcattaa    1800
tcaagaccct gacaagatcc taacatacat tgctgcagat cactgcccgg tagtcgaagt    1860
gaacggcgtg accatccaag tcgggagcag gaggtatcca gacgctgtgt acttgcacag    1920
aattgacctc ggtcctccca tatcattgga gaggttggac gtaggacaa atctgggaa     1980 tgcaattgct aagttggagg atgccaaaga attgttggag tcatcggacc agatattgag    2040
gagtatgaaa ggtttgtcga gcactagcat agtctacatc ctgattgcag tgtgtcttgg    2100
agggttgata gggatccccg ctttaatatg ttgctgcagg gggcgttgta acaaaaaggg    2160
agaacaagtt ggtatgtcaa gaccaggcct aaagcctgat cttacaggaa catcaaaatc    2220
ctatgtaagg tcgctctgat cctctacaac tcttggaaca caaatgtccc acaagtctcc    2280
tcttcgtcat caagcaacca ccgcatccag catcaagccc acctgaaatt atctccggct    2340 tcccttggc cgaacaatat cggcagttaa ttaaaactta ggg                       2383
```

```
<210> SEQ ID NO 37
<211> LENGTH: 553
<212> TYPE: PRT
<213> ORGANISM: Measles virus

<400> SEQUENCE: 37

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
```

```
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
            245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
            325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
            405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
            485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550

<210> SEQ ID NO 38
<211> LENGTH: 2384
<212> TYPE: DNA
<213> ORGANISM: Measles virus

<400> SEQUENCE: 38
tcgagggcca aggaacatac acacccaaca gaacccagac cccggcccac ggcgccgcgc      60
ccccaacccc cgacaaccag agggagcccc caaccaatcc gccggctccc ccggtgccca     120
```

| | |
|---|---|
| caggcaggga caccaacccc cgaacagacc cagcacccaa ccatcgacaa tccaagacgg | 180 |
| gggggccccc ccaaaaaaaa ggccccccagg ggccgacagc cagcaccgcg aggaagccca | 240 |
| cccaccccac acacgaccac ggcaaccaaa ccagaaccca gaccaccctg ggtcaccagc | 300 |
| tccagacctc ggtcatcacc ccgcagaaag gaaaggcaca acccgcgacc ccagccccga | 360 |
| tccggcgggg agccacccaa cccgaaccag cacccaagag cgatccccga aggaccccg | 420 |
| aaccgcaaag gacatcagta tcccacagcc tctccaagtc ccccggtctc ctcctcttct | 480 |
| cgaagggacc aaaagatcaa tccaccacca cacacccgac gacactcaac tccccacccc | 540 |
| taaaggagac accgggaatc ccagaatcaa gactcatcca atgtccatca tgggtctcaa | 600 |
| ggtgaacgtc tctgccatat tcatggcagt actgttaact ctccaaacac ccaccggtca | 660 |
| aatccattgg ggcaatctct ctaagatagg ggtggtagga ataggaagtg caagctacaa | 720 |
| agttatgact cgttccagcc atcaatcatt agtcataaaa ttaatgccca atataactct | 780 |
| cctcaataac tgcacgaggg tagagattgc agaatacagg agactactga gaacagtttt | 840 |
| ggaaccaatt agagatgcac ttaatgcaat gacccagaat ataagaccgg ttcagagtgt | 900 |
| agcttcaagt aggagacaca agagatttgc gggagtagtc ctggcaggtg cggccctagg | 960 |
| cgttgccaca gctgctcaga taacagccgg cattgcactt caccagtcca tgctgaactc | 1020 |
| tcaagccatc gacaatctga gagcgagcct ggaaactact aatcaggcaa ttgaggcaat | 1080 |
| cagacaagca gggcaggaga tgatattggc tgttcagggt gtccaagact acatcaataa | 1140 |
| tgagctgata ccgtctatga accaactatc ttgtgattta atcggccaga agctcgggct | 1200 |
| caaattgctc agatactata cagaaatcct gtcattattt ggccccagct acgggaccc | 1260 |
| catatctgcg gagatatcta tccaggcttt gagctatgcg cttggaggag acatcaataa | 1320 |
| ggtgttagaa aagctcggat acagtggagg tgatttactg ggcatcttag agagcagagg | 1380 |
| aataaaggcc cggataactc acgtcgacac agagtcctac ttcattgtcc tcagtatagc | 1440 |
| ctatccgacg ctgtccgaga ttaagggggt gattgtccac cggctagagg gggtctcgta | 1500 |
| caacataggc tctcaagagt ggtataccac tgtgcccaag tatgttgcaa cccaagggta | 1560 |
| ccttatctcg aattttgatg agtcatcgtg tactttcatg ccagagggga ctgtgtgcag | 1620 |
| ccaaaatgcc ttgtacccga tgagtcctct gctccaagaa tgcctccggg ggtccaccaa | 1680 |
| gtcctgtgct cgtacactcg tatccgggtc ttttgggaac cggttcattt tatcacaagg | 1740 |
| gaacctaata gccaattgtg catcaatcct ttgcaagtgt tacacaacag gaacgatcat | 1800 |
| taatcaagac cctgacaaga tcctaacata cattgctgcc gatcactgcc cggtagtcga | 1860 |
| ggtgaacggc gtgaccatcc aagtcgggag caggaggtat ccagacgctg tgtacttgca | 1920 |
| cagaattgac ctcggtcctc ccatatcatt ggagaggttg gacgtaggga caaatctggg | 1980 |
| gaatgcaatt gctaagttgg aggatgccaa ggaattgttg gagtcatcgg accagatatt | 2040 |
| gaggagtatg aaaggtttat cgagcactag catagtctac atcctgattg cagtgtgtct | 2100 |
| tggagggttg atagggatcc ccgctttaat atgttgctgc aggggcgtt gtaacaaaaa | 2160 |
| gggagaacaa gttggtatgt caagaccagg cctaaagcct gatcttacgg gaacatcaaa | 2220 |
| atcctatgta aggtcgctct gatcctctac aactcttgaa acacaaatgt tcccacaagt | 2280 |
| ctcctcttcg tcatcaagca accaccgcac ccagcatcaa gcccacctga accagctaaa | 2340 |
| ttatctccgg cttccctctg gccgaacaat atcggtagtt aatt | 2384 |

<210> SEQ ID NO 39
<211> LENGTH: 553
<212> TYPE: PRT

-continued

<213> ORGANISM: Measles virus

<400> SEQUENCE: 39

Met Ser Ile Met Gly Leu Lys Val Asn Val Ser Ala Ile Phe Met Ala
1               5                   10                  15

Val Leu Leu Thr Leu Gln Thr Pro Ala Gly Gln Ile His Tr

```
                      405                 410                 415
Tyr Ile Ala Ala Asp Arg Cys Pro Val Val Glu Val Asn Gly Val Thr
                420                 425                 430

Ile Gln Val Gly Ser Arg Arg Tyr Pro Asp Ala Val Tyr Leu His Arg
            435                 440                 445

Ile Asp Leu Gly Pro Pro Ile Ser Leu Glu Arg Leu Asp Val Gly Thr
        450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Thr Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550

<210> SEQ ID NO 40
<211> LENGTH: 1662
<212> TYPE: DNA
<213> ORGANISM: Measles virus

<400> SEQUENCE: 40
atgtccatca tgggtctcaa ggtgaacgtc tctgccatat tcatggcagt actgttaact      60
ctccaaacac ccgccggtca aatccattgg ggcaatctct ctaagatagg ggtagtagga     120
ataggaagtg caagctacaa agttatgact cgttccagcc atcaatcatt agtcataaaa     180
ttaattccca atataactct cctcaataac tgcacgaagg tagagattgc agagtacagg     240
agactactaa gaacagtttt ggaaccaatt agagatgcac ttaatgcaat gacccagaac     300
ataaggccgg ttcagagcgt agcttcaagt atgagacaca gagatttgc gggagtagtc     360 ctggcaggtg cggccctagg cgttgccaca gctgctcaga taacagccgg cattgcactt     420
caccggtcca tgctgaactc tcaagccatc gacaatctga gagcgagcct ggaaactact     480
aatcaggcaa ttgaggcaat cagacaagca gggcaggaga tgatcttggc tgttcagggg     540
gtccaagact acatcaataa tgagctgata ccatctatga accagctatc ttgtgattta     600
atcgggcaga agctcgggct caaattgctc agatactata cagaaatcct gtcattattt     660
ggccccagcc tacgagaccc catatctgcg gagatatcta tccaggcctt gagctatgca     720
cttggaggag atatcaataa ggtgttagaa aagctcggat acagtggagg cgatttactg     780
ggcatcttag agagcagagg aataaaggct cggataactc acgtcgacac agagtcctac     840
ttcattgtcc tcagtatagc ctatccgaca ctgtccgaga ttaaggggt gattgtccat     900 cggctagagg gggtctcgta caacataggc tctcaagagt ggtataccac tgtgcccaag     960
tatgttgcaa cccaagggta ccttatctcg aattttgatg agtcatcgtg taccttcatg    1020
ccagagggga ctgtgtgcag ccaaaatgcc ttgtacccga tgagtcctct gctccaagaa    1080
tgcctccggg gtccaccaa gtcctgtgct cgtacactcg tatccgggtc ttttgggaac    1140
cggttcattt tatcacaagg gaacctaata gccaattgtg catcaattct ttgcaagtgt    1200
tacacaacag gaacgatcat taatcaagac cctgacaaga ttctaacata catcgctgcc    1260
gatcgctgcc cggtagtcga ggtaaacggc gtgaccatcc aagtcgggag caggaggtat    1320
```

-continued

```
ccagacgctg tgtatttgca cagaattgac ctcggtcctc ccatatcatt ggagaggttg    1380
gacgtaggga caaatctggg gaatgcaatt gccaaattgg aggatgccaa ggaattgttg    1440
gagtcatcgg accagatatt gaggagtatg aaaggtttat cgagcactag catagtctac    1500
atcctgattg cagtgtgtct tggagggctg atagggatcc ccactttaat atgttgctgc    1560 aggggggcgtt gtaacaaaaa gggagaacaa gttggtatgt caagaccagg cctaaagcct    1620
gatcttacag gaacatcaaa atcatatgta aggtcgctct ga                       1662
```

<210> SEQ ID NO 41
<211> LENGTH: 525
<212> TYPE: PRT
<213> ORGANISM: Measles virus

<400> SEQUENCE: 41

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ser Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320
```

```
Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Arg Ile Ser Arg Ala Val Gly Pro Arg Gln Ser Gln
                405                 410                 415

Val Ser Phe Leu His Gly Asp Gln Asn Glu Asn Glu Leu Pro Arg Trp
            420                 425                 430

Gly Gly Lys Glu Asp Met Arg Val Lys Gln Ser Arg Gly Glu Ala Arg
        435                 440                 445

Glu Ser Tyr Arg Glu Thr Arg Pro Ser Arg Ala Ser Asp Ala Arg Ala
    450                 455                 460

Thr His Pro Pro Thr Asp Thr Pro Leu Asp Ile Asp Thr Ala Ser Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Arg Val Tyr Asn Asp Arg Asp Leu Leu Asp
        515                 520                 525
```

<210> SEQ ID NO 42
<211> LENGTH: 1685
<212> TYPE: DNA
<213> ORGANISM: Measles virus

<400> SEQUENCE: 42

```
aggattcaag atcctattat cagggacaag agcaggatta gggatatccg agatggccac     60
acttctaagg agcttagcat tgttcaaaag aaacaaggac aaaccaccca ttacatcagg    120
atccggtgga gccatcagag gaatcaaaca cattattata gtaccaatcc cgggagattc    180
ctcaattacc actcgatcta gacttctgga ccggttggtc aggttaattg gaaacccgga    240
tgtgagcggg cccaaactaa caggggcact aataggtata ttatccttat ttgtggagtc    300
tccaggtcaa ttgattcaga ggatcaccga tgaccctgac gttagcataa ggctgttaga    360
ggttgtccag agtgaccagt cacaatctgg ccttaccttc gcatcaagag gtaccaacat    420
ggaggatgag gcggaccaat atttttcaca tgatgatcca agtagtagtg atcaatccag    480
gttcggatgg ttcgagaaca aggaaatctc agatattgaa gtgcaagacc ctgagggatt    540
caacatgatt ctgggtacca tcctagctca aatttgggtc ttgctcgcaa aggcggttac    600
ggccccagac acggcagctg attcggagct aagaaggtgg ataaagtaca cccaacaaag    660
aagggtagtt ggtgaattta gattggagag aaaatggttg gatgtggtga ggaacaggat    720
tgccgaggac ctctccttac gccgattcat ggtcgctcta atcctggata tcaagagaac    780
acccgggaac aaacccagga ttgctgaaat gatatgtgac attgatacat atatcgtaga    840
ggcaggatta gccagtttta tcctgactat taagtttggg atagaaacta tgtatcctgc    900
tcttggactg catgaatttg ctggtgagtt atccacactt gagtccttga tgaatcttta    960
```

-continued

```
ccagcaaatg ggggaaactg caccatacat ggtaatcctg agaaactca

```
                245                 250                 255
Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Arg Ile Ser Arg Ala Val Gly Pro Arg Gln Ala Gln
                405                 410                 415

Val Ser Phe Leu His Gly Asp Gln Ser Glu Asn Glu Leu Pro Gly Leu
            420                 425                 430

Gly Gly Lys Glu Asp Lys Arg Val Lys Gln Ser Arg Gly Glu Ala Arg
        435                 440                 445

Glu Ser Tyr Arg Glu Thr Gly His Ser Arg Ala Asn Asp Ala Arg Ala
    450                 455                 460

Ala Asp Leu Pro Thr Gly Thr Pro Leu Asp Ile Asp Thr Ala Ser Glu
465                 470                 475                 480

Phe Ser Gln Asp Pro Gln Asp Ser Arg Arg Ser Ala Asp Ala Leu Leu
                485                 490                 495

Arg Leu Gln Ala Met Ala Gly Ile Pro Glu Glu Gln Gly Ser Asp Met
            500                 505                 510

Asp Thr Pro Arg Val Tyr Asn Asp Arg Asp Leu Leu Asp
        515                 520                 525
```

<210> SEQ ID NO 44
<211> LENGTH: 1578
<212> TYPE: DNA
<213> ORGANISM: Measles virus

<400> SEQUENCE: 44

```
atggccacgc tattaaggag cttagcattg ttcaaaagaa acaaggacaa accacccatt      60
acatcaggat ccggtggggc catcagaggg atcaaacaca ttattatagt accaatccct     120
ggagactcct caattaccac tcgatccaga cttctggacc ggttggtcag gctaattgga     180
aacccggatg tgagtgggcc taaattaaca ggggcactaa taggtatatt gtccttattt     240
gtggagtctc caggtcaatt gattcagaga atcaccgatg accctgacgt tagcataagg     300
ctgttagagg ttgtccagag cgaccagtca caatctggcc ttacctttgc atcaagaggt     360
accaacatgg aggatgaggc ggaccaatac tttttacatg atgattcaag tagcggtgat     420
caattcaggt ccggatggtt cgagaacaag gaaatctcag atattgaagt gcaggaccct     480
gagggattca acatgattct gggtaccatc ctagctcaaa tttgggtctt gctcgcaaag     540
gcggttacgg ccccagacac ggcagctgat tcggagctaa gaaggtggat aaaatacacc     600
```

-continued

```
caacaaagaa gggtagtcgg tgaattcaga ttggagagaa aatggttgga tgtagtgagg      660
aacaggattg ccgaggacct ctccttacgc cggttcatgg tcgctctaat cctggatatc      720
aagagaacac ccgggaacaa acccaggatt gctgaaatga tatgtgacat tgacacatat      780
atcgtggagg caggattagc cagttttatc cttactatta agtttgggat agaaaccatg      840
tatcctgctc ttggactgca tgaatttgct ggtgagttat caacacttga gtccttgatg      900
aacctttatc agcaaatggg ggaaactgca ccctacatgg tcattctgga gaactcaatt      960
cagaacaagt tcagtgcagg atcatacccT ctgctctgga gctatgccat gggagtagga     1020
gtggaactcg aaaactccat gggaggtttg aactttggcc gatcttactt tgatccagca     1080
tattttagat taggacaaga gatggtcagg aggtcagctg ggaaggtcag ttccacattg     1140
gcatctgaac tcggtatcac ggccgaggat gcaaggcttg tttcagagat tgcaatgcat     1200
actactgagg acaggatcag tagagcggtt ggacccaggc aagcccaagt gtcatttcta     1260
cacggtgatc aaagtgagaa tgagctaccg ggattgggag gtaaggaaga taagagagtc     1320
aaacagagtc gaggagaagc cagggagagc tatagagaaa ctgggcacag cagagcaaat     1380
gatgcgagag ctgctgacct tccaaccggc acaccctag acattgacac tgcatcggag     1440
ttcagccaag acccacagga cagtcgaagg tcagctgacg ccctgctcag gctgcaagcc     1500
atggcaggga tcccggaaga acaaggctca gacatggaca cccctagagt gtacaatgac     1560
agagatcttc tagactag                                                    1578
```

<210> SEQ ID NO 45
<211> LENGTH: 523
<212> TYPE: PRT
<213> ORGANISM: Measles virus

<400> SEQUENCE: 45

```
Met Ala Thr Leu Leu Arg Ser Leu Ala Leu Phe Lys Arg Asn Lys Asp
 1               5                  10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
```

| | | | | | | | | | | | | |
|---|---|---|---|---|---|---|---|---|---|---|---|---|
| | | 195 | | | | 200 | | | | 205 | | |
| Phe | Arg | Leu | Glu | Arg | Lys | Trp | Leu | Asp | Val | Val | Arg | Asn | Ile | Ile | Ala |
| 210 | | | | | 215 | | | | | 220 | | |

Phe Arg Leu Glu Arg Lys Trp Leu Asp Val Val Arg Asn Ile Ile Ala
210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
            245                 250                 255

Ile Asp Thr Tyr Ile Val Glu Ala Gly Leu Ala Ser Phe Ile Leu Thr
                260                 265                 270

Ile Lys Phe Gly Ile Glu Thr Met Tyr Pro Ala Leu Gly Leu His Glu
            275                 280                 285

Phe Ala Gly Glu Leu Ser Thr Leu Glu Ser Leu Met Asn Leu Tyr Gln
290                 295                 300

Gln Met Gly Lys Pro Ala Pro Tyr Met Val Asn Leu Glu Asn Ser Ile
305                 310                 315                 320

Gln Asn Lys Phe Ser Ala Gly Ser Tyr Pro Leu Leu Trp Ser Tyr Ala
            325                 330                 335

Met Gly Val Gly Val Glu Leu Glu Asn Ser Met Gly Gly Leu Asn Phe
                340                 345                 350

Gly Arg Ser Tyr Phe Asp Pro Ala Tyr Phe Arg Leu Gly Gln Glu Met
            355                 360                 365

Val Arg Arg Ser Ala Gly Lys Val Ser Ser Thr Leu Ala Ser Glu Leu
370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
            405                 410                 415

Val Ser Phe Leu Gln Gly Asp Gln Ser Glu Asn Glu Leu Pro Arg Leu
                420                 425                 430

Gly Gly Lys Glu Asp Arg Arg Val Lys Gln Ser Arg Gly Glu Ala Arg
            435                 440                 445

Glu Ser Tyr Arg Glu Thr Gly Pro Ser Arg Ala Ser Asp Ala Arg Ala
450                 455                 460

Ala His Leu Pro Thr Gly Thr Pro Leu Asp Ile Asp Thr Ala Ser Glu
465                 470                 475                 480

Ser Ser Gln Asp Pro Gln Asp Ser Arg Arg Ser Ala Glu Pro Leu Leu
            485                 490                 495

Ser Cys Lys Pro Trp Gln Glu Ser Arg Lys Asn Lys Ala Gln Thr Arg
            500                 505                 510

Thr Pro Leu Gln Cys Thr Met Thr Glu Ile Phe
            515                 520

<210> SEQ ID NO 46
<211> LENGTH: 1631
<212> TYPE: DNA
<213> ORGANISM: Measles virus

<400> SEQUENCE: 46

```
atggccacac ttttaaggag cttagcattg ttcaaaagaa acaaggacaa accacccatt     60
acatcaggat ccggtggagc catcagagga atcaaacaca ttattatagt accaatccct    120
ggagattcct caattaccac tcgatccaga cttctggacc ggttggtcag gttaattgga    180
aacccggatg tgagcgggcc caaactaaca ggggcactaa taggtatatt atccttattt    240
gtggagtctc caggtcaatt gattcagagg atcaccgatg accctgacgt tagcataagg    300
```

```
ctgttagagg ttgtccagag tgaccagtca caatctggcc ttaccttcgc atcaagaggt      360
accaacatgg aggatgaggc ggaccaatac ttttcacatg atgatccaat tagtagtgat      420
caatccaggt tcggatggtt cgagaacaag gaaatctcag atattgaagt gcaagaccct      480
gagggattca acatgattct gggtaccatc ctagcccaaa tttgggtctt gctcgcaaag      540
gcggttacgg ccccagacac ggcagctgat tcggagctaa aaggtggat aaagtacacc       600 caacaaagaa gggtagttgg tgaatttaga ttggagagaa atggttgga tgtggtgagg       660 aacattattg ccgaggacct ctccttacgc cgattcatgg tcgctctaat cctggatatc      720
aagagaacac ccggaaacaa acccaggatt gctgaaatga tatgtgacat tgatacatat      780
atcgtagagg caggattagc cagttttatc ctgactatta agtttgggat agaaactatg      840
tatcctgctc ttggactgca tgaatttgct ggtgagttat ccacacttga gtccttgatg      900
aacctttacc agcaaatggg gaaacctgca ccctacatgg taaacctgga gaactcaatt      960
cagaacaagt tcagtgcagg atcatacccct ctgctctgga gctatgccat gggagtagga     1020
gtggaacttg aaaactccat gggaggtttg aactttggcc gatcttactt tgatccagca     1080
tattttagat tagggcaaga gatggtaagg aggtcagctg gaaaggtcag ttccacatta     1140
gcatctgaac tcggtatcac tgccgaggat gcaaggcttg tttcagagat tgcaatgcat     1200
actactgagg acaagatcag tagagcggtt ggacccagac aagcccaagt atcatttcta     1260
cagggtgatc aaagtgagaa tgagctaccg cgattggggg gcaaggaaga taggagggtc     1320
aaacagagtc gaggagaagc cagggagagc tacagaaaa ccgggcccag cagagcaagt      1380
gatgcgagag ctgcccatct tccaaccggc acacccctag acattgacac tgcatcggag    1440
tccagccaag atccgcagga cagtcgaagg tcagctgagc ccctgcttag ctgcaagcca    1500
tggcaggaat ctcggaagaa caaggctcag acacggacac ccctacagtg tacaatgaca    1560
gaaatcttct agactaggtg cgagaggccg agggccagaa caacatccgc ctaccctcca    1620
tcattgttat a                                                         1631
```

<210> SEQ ID NO 47
<211> LENGTH: 300
<212> TYPE: PRT
<213> ORGANISM: Measles virus

<400> SEQUENCE: 47

```
Met His Met Phe Pro Leu Gly Val Val Glu Asp Ser Asp Pro Pro Gly
1               5                   10                  15

Pro Pro Ile Gly Arg Ala Ser Gly Ser Pro Pro Gly Ala Gly Arg
            20                  25                  30

Ser Thr Ala Lys Pro Glu Glu Leu Leu Lys Glu Ala Thr Glu Ala Asn
        35                  40                  45

Ile Val Val Arg Arg Thr Ala Gly Leu Asn Glu Lys Leu Ala Phe His
    50                  55                  60

Asn Asn Thr Pro Pro Thr Leu Pro Thr Pro Arg Arg Lys Ala Pro Thr
65                  70                  75                  80

Thr Gly Ser Val Leu Asn Ala Asn Gln Ala Cys Asn Ala Val Asn Leu
                85                  90                  95

Ala Pro Leu Asp Thr Pro Gln Arg Phe Arg Val Val Tyr Met Ser Ile
            100                 105                 110

Thr Arg Pro Leu Asp Asn Gly Tyr Tyr Thr Val Pro Arg Arg Met Leu
        115                 120                 125

Glu Phe Arg Ser Val Asn Ala Val Ala Phe Asn Leu Leu Val Thr Leu
    130                 135                 140
```

```
Arg Ile Asp Lys Ala Ile Gly Pro Gly Lys Ile Ile Asp Asn Ala Glu
145                 150                 155                 160

Gln Leu Pro Glu Ala Thr Phe Met Val His Ile Gly Asp Phe Arg Arg
                165                 170                 175

Lys Lys Ser Glu Val Tyr Ser Ala Asp Tyr Cys Lys Met Lys Ile Glu
            180                 185                 190

Lys Met Gly Leu Val Phe Ala Leu Gly Gly Ile Gly Gly Thr Ser Leu
        195                 200                 205

His Thr Arg Ser Thr Gly Lys Met Ser Lys Thr Leu His Ala Gln Leu
    210                 215                 220

Gly Phe Lys Lys Thr Ser Cys Tyr Pro Pro Met Asp Ile Asn Glu Asp
225                 230                 235                 240

Leu Asn Arg Leu Leu Trp Arg Ser Arg Cys Lys Ile Val Arg Ile Gln
                245                 250                 255

Ala Val Leu Gln Pro Ser Val Pro Gln Glu Leu Arg Ile Tyr Asp Asp
            260                 265                 270

Val Ile Ile Asn Asp Asp Gln Gly Val Phe Lys Val Leu Gln Thr Val
        275                 280                 285

Val Pro Ser Asn Ala Arg Lys Arg Pro Pro Ser Gln
    290                 295                 300

<210> SEQ ID NO 48
<211> LENGTH: 1454
<212> TYPE: DNA
<213> ORGANISM: Measles virus

<400> SEQUENCE: 48
aggagcaaag tgattgcctc ccaagctcca caacgacaga gatccacgac ctcgacaagt      60
cggcatggga catcaagggg tcgatcgctc cgacacaacc caccacccac agtgatggca     120
ggctggtgcc ccaggccaga gccacagatc ctggtctagg cgacaggaag gcgaacgcc     180
ccatgcacat gtttccgctg ggggtcgttg aggacagcga ccccccaggg cctccaatcg     240
ggcgagcatc cggtccccg ccccaggcg ctggcagatc cacagcaaaa cccgaagaac     300
tcctcaaaga ggccaccgag ccaacatag tcgtcagacg cacagcaggg ctcaacgaaa     360
aactggcgtt ccacaacaat accccaccaa ctctccccac accccggaga aaggccccaa     420
caacagggag cgtcctcaac gcaaaccaag cgtgcaatgc ggtcaatctg caccgctgg     480
acaccccgca gaggttccgt gttgtctaca tgagcatcac ccgtcccttg acaacgggt     540
actacaccgt tcccagaaga atgctggaat tcaggtcggt caatgcagtg gccttcaacc     600
tgctggtgac ccttagaatt gacaaggcga ttgggccctgg aagatcatc gacaatgcag     660
agcaacttcc tgaggcaaca ttcatggtcc acatcgggga cttcaggaga aagaagagcg     720
aagtctactc tgccgactat tgcaagatga aaatcgaaaa gatgggcctg gttttgcac     780
ttggtgggat agggggcacc agtcttcaca ctagaagcac aggcaaatg agcaagactc     840
tccatgcaca actcgggttc aagaagacct catgttaccc accaatggat atcaatgaag     900
acctcaatcg actactctgg aggagcagat gcaagatagt aagaatccag gcagttctgc     960
agccatcagt tccccaagaa ctccgcattt acgacgacgt gatcataaat gatgaccaag    1020
gagtattcaa agttctgcag accgtggtgc ccagcaatgc cgaaaacga ccccctcac    1080
aatgacagcc aaaaggcccg acaaaaaaa cccccccga aaactccac ggaccaagcg    1140
agaggccagc cagcagctga cggcaagcgc gaacaccagg cggccccagc acagaacagc    1200
cccgacacaa ggccaccacc agccagccca atctgcatcc tcctcgtggg accccggagg    1260
```

```
accaaccccc aaagttgccc ccgacccaaa ccaccaaccg catccccacc acccctggga    1320
aagaaacccc cagcaactgg aaggcccctt ccccccctccc tcaacacaag aaccccacaa   1380
ccgaaccgca caagcgaccg aggtgaccca accgcaggca cccgactccc tagatagatc    1440
ctctcccccc gggc                                                      1454

<210> SEQ ID NO 49
<211> LENGTH: 295
<212> TYPE: PRT
<213> ORGANISM: Measles virus

<400> SEQUENCE: 49

Met His Met Phe Pro Leu Gly Val Val Glu Asp Ser Asp Pro Pro Gly
1               5                   10                  15

Pro Pro Ile Gly Arg Ala Ser Gly Ser Pro Pro Gly Ala Gly Arg
            20                  25                  30

Ser Thr Ala Lys Pro Glu Glu Leu Leu Lys Glu Ala Thr Glu Ala Asn
        35                  40                  45

Ile Val Val Arg Arg Thr Ala Gly Leu Asn Glu Lys Leu Ala Phe His
    50                  55                  60

Asn Asn Thr Pro Pro Thr Leu Pro Thr Pro Arg Arg Lys Ala Pro Thr
65                  70                  75                  80

Thr Gly Ser Val Leu Asn Ala Asn Gln Ala Cys Asn Ala Val Asn Leu
                85                  90                  95

Ala Pro Leu Asp Thr Pro Gln Arg Phe Arg Val Val Tyr Met Ser Ile
            100                 105                 110

Thr Arg Pro Leu Asp Asn Gly Tyr Tyr Thr Val Pro Arg Arg Met Leu
        115                 120                 125

Glu Phe Arg Ser Val Asn Ala Val Ala Phe Asn Leu Leu Val Thr Leu
    130                 135                 140

Arg Ile Asp Lys Ala Ile Gly Pro Gly Lys Ile Ile Asp Asn Ala Glu
145                 150                 155                 160

Gln Leu Pro Glu Ala Thr Phe Met Val His Ile Gly Asp Phe Arg Arg
                165                 170                 175

Lys Lys Ser Glu Val Tyr Ser Ala Asp Tyr Cys Lys Met Lys Ile Glu
            180                 185                 190

Lys Met Gly Leu Val Phe Ala Leu Gly Gly Ile Gly Thr Ser Leu
        195                 200                 205

His Thr Arg Ser Thr Gly Lys Met Ser Lys Leu His Ala Gln Leu
    210                 215                 220

Gly Phe Lys Lys Thr Ser Cys Tyr Pro Pro Met Asp Ile Asn Glu Asp
225                 230                 235                 240

Leu Asn Arg Leu Leu Trp Arg Ser Arg Cys Lys Ile Val Arg Ile Gln
                245                 250                 255

Ala Val Leu Gln Pro Ser Val Pro Gln Glu Leu Arg Ile Tyr Asp Asp
            260                 265                 270

Val Ile Ile Asn Asp Asp Gln Gly Val Phe Lys Val Leu Gln Thr Val
        275                 280                 285

Val Pro Ser Asn Ala Arg Lys
    290                 295

<210> SEQ ID NO 50
<211> LENGTH: 1454
<212> TYPE: DNA
<213> ORGANISM: Measles virus
```

-continued

<400> SEQUENCE: 50

```
aggagcaaag tgattgcctc ccaagctcca caacgacaga gatccacgac ctcgacaagt      60
cggcatggga catcaagggg tcgatcgctc cgacacaacc caccacccac agtgatggca     120
ggctggtgcc ccaggccaga gccacagatc ctggtctagg cgacaggaag ggcgaacgcc     180
ccatgcacat gtttccgctg gggtcgttg aggacagcga ccccccaggg cctccaatcg      240
ggcgagcatc cgggtccccg cccccaggcg ctggcagatc cacagcaaaa cccgaagaac     300
tcctcaaaga ggccaccgag gccaacatag tcgtcagacg cacagcaggg ctcaacgaaa     360
aactggcgtt ccacaacaat accccaccaa ctctccccac accccggaga aaggccccaa     420
caacagggag cgtcctcaac gcaaaccaag cgtgcaatgc ggtcaatctg gcaccgctgg     480
acaccccgca gaggttccgt gttgtctaca tgagcatcac ccgtcccttg gacaacgggt     540
actacaccgt tcccagaaga atgctggaat tcaggtcggt caatgcagtg gccttcaacc     600
tgctggtgac ccttagaatt gacaaggcga ttggccctgg gaagatcatc gacaatgcag     660
agcaacttcc tgaggcaaca tttatggtcc acatcgggga cttcaggaga aagaagagtg     720
aagtctactc tgccgattat tgcaagatga aaatcgaaaa gatgggcctg gtttttgcac     780
ttggtgggat agggggcacc agtcttcaca ctagaagcac aggcaaaatg agcaagactc     840
tccatgcaca actcgggttc aagaagacct catgttaccc accaatggat atcaatgaag     900
acctcaatcg attactctgg aggagcagat gcaagatagt aagaatccag gcagttctgc     960
agccatcagt tccccaagaa ctccgcattt acgacgacgt gatcataaat gatgaccaag    1020
gagtattcaa agttctgcag accgtggtgc ccagcaatgc ccgaaaatga ccccccctcac   1080
aatgacaacc aaaaggcccg gacaaaaaaa cccccccga aaaactccac ggaccaagcg     1140
agaggccagc cagcagctga cggcaagcgc gaacaccagg cggccccagc acagaacagc    1200
cccgacacaa ggccaccacc agccagccca atctgcatcc tcctcgtggg accccggagg    1260
accaaccccc aaagttgccc ccgacccaaa ccaccaaccg catccccacc acccccggga    1320
aagaaacccc cagcaactgg aaggcccctt ccccccctccc tcaacacaag aaccccacaa   1380
ccgaaccgca caagcgaccg aggtgaccca accgcaggca cccgactccc tagatagatc    1440
ctctcccccc gggc                                                     1454
```

<210> SEQ ID NO 51
<211> LENGTH: 335
<212> TYPE: PRT
<213> ORGANISM: Measles virus

<400> SEQUENCE: 51

```
Met Thr Glu Ile Tyr Asp Phe Asp Lys Ser Ala Trp Asp Ile Lys Gly
1               5                   10                  15

Ser Ile Ala Pro Ile Gln Pro Thr Thr Tyr Ser Asp Gly Arg Leu Val
            20                  25                  30

Pro Gln Val Arg Val Ile Asp Pro Gly Leu Gly Asp Arg Lys Asp Glu
        35                  40                  45

Cys Phe Met Tyr Met Phe Leu Leu Gly Val Val Glu Asp Ser Asp Ser
    50                  55                  60

Leu Gly Pro Pro Ile Gly Arg Ala Phe Gly Ser Leu Pro Leu Gly Val
65                  70                  75                  80

Gly Arg Ser Thr Ala Lys Pro Glu Lys Leu Leu Lys Glu Ala Thr Glu
                85                  90                  95

Leu Asp Ile Val Val Arg Arg Thr Ala Gly Leu Asn Glu Lys Leu Val
            100                 105                 110
```

```
Phe Tyr Asn Asn Thr Pro Leu Thr Leu Leu Thr Pro Trp Arg Lys Val
        115                 120                 125

Leu Thr Thr Gly Ser Val Phe Asn Ala Asn Gln Val Cys Asn Ala Val
    130                 135                 140

Asn Leu Ile Pro Leu Asp Thr Pro Gln Arg Phe Arg Val Val Tyr Met
145                 150                 155                 160
Ser Ile Thr Arg Leu Ser Asp Asn Gly Tyr Tyr Thr Val Pro Arg Arg
                165                 170                 175
Ile Leu Glu Phe Arg Ser Val Asn Ala Val Ala Phe Asn Leu Leu Val
            180                 185                 190
Thr Leu Arg Ile Asp Lys Ala Ile Gly Pro Gly Lys Ile Ile Asp Asn
        195                 200                 205
Thr Glu Gln Leu Pro Glu Ala Thr Phe Met Val His Ile Gly Asn Phe
    210                 215                 220
Met Arg Asn Lys Ser Glu Val Tyr Ser Ala Asp Tyr Cys Lys Met Lys
225                 230                 235                 240
Ile Glu Lys Met Gly Leu Val Phe Ala Leu Gly Gly Ile Gly Gly Thr
                245                 250                 255
Ser Leu His Ile Arg Ser Thr Gly Lys Met Ser Lys Thr Leu His Ala
            260                 265                 270
Gln Leu Gly Phe Lys Lys Thr Leu Cys Tyr Pro Leu Ile Asp Ile Asn
        275                 280                 285
Glu Asp Leu Asn Arg Leu Leu Trp Arg Ser Arg Cys Lys Ile Val Arg
    290                 295                 300
Ile Gln Ala Val Leu Gln Pro Ser Val Pro Gln Glu Phe Arg Ile Tyr
305                 310                 315                 320
Asp Asp Val Ile Ile Asn Asp Asp Gln Gly Leu Phe Lys Val Leu
                325                 330                 335

<210> SEQ ID NO 52
<211> LENGTH: 1008
<212> TYPE: DNA
<213> ORGANISM: Measles virus

<400> SEQUENCE: 52
atgacagaga tctacgactt cgacaagtcg gcatgggaca tcaaagggtc gatcgctccg     60
atacaaccca ccacctacag tgatggcagg ctggtgcccc aggtcagagt catagatcct    120
ggtctaggcg acaggaagga tgaatgcttt atgtacatgt ttctgctggg ggttgttgag    180
gacagcgatt ccctagggcc tccaatcggg cgagcatttg ggtccctgcc cttaggtgtt    240
ggcagatcca cagcaaagcc cgaaaaactc ctcaaagagg ccactgagct tgacatagtt    300
gttagacgta cagcagggct caatgaaaaa ctggtgttct acaacaacac ccccactaact   360 ctcctcacac cttggagaaa ggtcctaaca acagggagtg tcttcaacgc aaaccaagtg    420
tgcaatgcgg ttaatctgat accgctcgat accccgcaga ggttccgtgt tgtttatatg    480
agcatcaccc gtctttcgga taacgggtat tacaccgttc ctagaagaat actggaattc    540
agatcggtca atgcagtggc cttcaacctg ctggtgaccc ttaggattga caaggcgata    600
ggccctggga agatcatcga caatacagag caacttcctg aggcaacatt tatggtccac    660
atcgggaact tcatgagaaa taagagtgaa gtctactctg ccgattattg caaaatgaaa    720
atcgaaaaga tgggcctggt ttttgcactt ggtgggatag ggggcaccag tcttcacatt    780
agaagcacag gcaaaatgag caagactctc catgcacaac tcgggttcaa gaagacctta    840
tgttacccgc tgatagatat caatgaagac cttaatcgat tactctggag gagcagatgc    900
```

```
aagatagtaa gaatccaggc agttttgcag ccatcagttc ctcaagaatt ccgcatttac    960
gacgacgtga tcataaatga tgaccaagga ctattcaaag ttctgtag               1008
```

<210> SEQ ID NO 53
<211> LENGTH: 257
<212> TYPE: PRT
<213> ORGANISM: Bovine respiratory syncytial virus

<400> SEQUENCE: 53

```
Met Ser Asn His Thr His Gln Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Thr Thr Leu Ala Met
        35                  40                  45

Ile Thr Leu Thr Ser Leu Val Ile Thr Ala Ile Ile Tyr Ile Ser Val
    50                  55                  60

Gly Asn Ala Lys Ala Lys Pro Thr Phe Lys Pro Thr Ile Gln Gln Thr
65                  70                  75                  80

Gln Gln Pro Gln Asn His Thr Ser Pro Leu Phe Thr Glu His Asn His
                85                  90                  95

Lys Ser Thr His Thr Ser Ile Gln Ser Thr Thr Leu Ser Gln Pro Leu
            100                 105                 110

Asn Ile Asp Thr Thr Arg Gly Thr Thr Tyr Ser His Ser Thr Asp Glu
        115                 120                 125

Thr Gln Asn Arg Lys Asn Lys Ser Gln Ser Thr Leu Pro Ala Asn Arg
    130                 135                 140

Gln Pro Pro Ile Asn Pro Ser Gly Ser Asn Pro Pro Glu Asn His Gln
145                 150                 155                 160

Asp His Asn Asn Ser Gln Thr Leu Pro Tyr Val Pro Cys Ser Thr Cys
                165                 170                 175

Lys Gly Asn Leu Ala Cys Ser Ser Leu Cys Gln Ile Gly Leu Glu Arg
            180                 185                 190

Ala Pro Ser Arg Ala Pro Thr Ile Thr Leu Lys Arg Ala Ser Lys Pro
        195                 200                 205

Lys Thr Thr Lys Lys Pro Thr Lys Thr Thr His His Arg Thr Ser
    210                 215                 220

Pro Glu Ala Lys Leu Gln Pro Lys Asn Asn Thr Ala Ala Pro Gln Gln
225                 230                 235                 240

Gly Ile Leu Ser Ser Pro Glu His His Thr Asp Gln Ser Thr Thr Gln
                245                 250                 255

Ile
```

<210> SEQ ID NO 54
<211> LENGTH: 774
<212> TYPE: DNA
<213> ORGANISM: Bovine respiratory syncytial virus

<400> SEQUENCE: 54

```
atgtccaacc ataccatca acttaaattc aagacattaa agagggcttg gaaagcctca     60
aaatacttca tagtaggatt atcatgttta taagttca atttaaaatc ccttgtccaa    120
acggctttga ccaccttagc tatgataacc ttgacatcac tcgtcataac agccattatt    180
tacattagtg tgggaaatgc taagccaag cccacattca aaccaaccat ccaacaaaca    240
caacagcccc aaaaccatac ctcacctctt ttcacagagc acaaccacaa atcaactcac    300
```

-continued

```
acatcaatcc aaagcaccac actatcccaa ccactaaaca tagacaccac tagaggaact   360
acatacagtc actcaaccga tgaaacccaa aatagaaaaa acaaaagcca atccactcta   420
cctgccaaca gacaaccacc aatcaaccca tcgggaagca accccctga aaaccaccaa    480 gaccacaaca actcccaaac actcccctat gtgccttgca gtacatgtaa aggcaatctt   540
gcttgctcat cactctgcca aatcgggctg gagagagcac caagcagagc ccccacaatc   600
accctaaaaa gggcgtcaaa acccaaaacc accaaaaaac caaccaagac aacaacccac   660
cacagaacta gccctgaagc caaactgcaa cccaaaaaca cacggcagc tccacaacaa    720 ggcatcctct cttcaccaga gcaccacaca gatcaatcaa ctacacagat ctaa         774
```

<210> SEQ ID NO 55
<211> LENGTH: 295
<212> TYPE: PRT
<213> ORGANISM: Human respiratory syncytial virus

<400> SEQUENCE: 55

```
Met Ser Lys Asn Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Pro Thr Thr Val Thr Val Gln Thr Ile Lys
65                  70                  75                  80

Asn His Thr Glu Lys Asn Ile Thr Thr Tyr Leu Thr His Val Ser Pro
                85                  90                  95

Glu Arg Val Ser Pro Ser Lys Gln Pro Thr Thr Thr Leu Pro Ile His
            100                 105                 110

Thr Asn Ser Ala Thr Ile Ser Pro Asn Thr Lys Ser Glu Thr His His
        115                 120                 125

Thr Thr Ala Gln Thr Lys Gly Ile Ile Thr Thr Pro Thr Gln Thr Asn
    130                 135                 140

Lys Pro Ser Thr Lys Pro Arg Pro Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Leu Ala Lys Thr Leu Lys
    210                 215                 220

Lys Glu Asn Thr Thr Asn Pro Thr Lys Lys Pro Thr Leu Lys Thr Thr
225                 230                 235                 240

Glu Arg Asp Thr Ser Thr Pro Gln Ser Thr Val Leu Asp Thr Thr Thr
                245                 250                 255

Ser Lys His Thr Ile Gln Gln Gln Ser Leu His Ser Thr Thr Pro Glu
            260                 265                 270

Asn Thr Pro Asn Ser Thr Gln Ile Pro Thr Ala Ser Glu Pro Ser Thr
        275                 280                 285

Ser Asn Ser Thr Gln Lys Ile
```

290                 295

<210> SEQ ID NO 56
<211> LENGTH: 921
<212> TYPE: DNA
<213> ORGANISM: Human respiratory syncytial virus

<400> SEQUENCE: 56

| | | |
|---|---|---|
| ggggcaaatg caaccatgtc caaaaacaag aatcaacgca ctgccaggac tctagaaaag | 60 |
| acctgggata tcttaatca tctaattgtg atatcctctt gtttatacag attaaattta | 120 |
| aaatctatag cacaaatagc actatcagtt ttggcaatga atctcaac ctctctcata | 180 |
| attgcagcca taatattcat catctctgcc aatcacaaag ttacaccaac aacggtcaca | 240 |
| gttcaaacaa taaaaaacca cactgaaaaa aacatcacca cttaccttac tcatgtctca | 300 |
| ccagaaaggg ttagcccatc caaacaaccc acaaccacac taccaatcca cacaaactca | 360 |
| gccacaatat cacctaatac aaaatcagaa acacaccata acacagcaca aaccaaaggc | 420 |
| ataatcacca ctccaacaca gaccaacaag ccaagcacaa aaccacgtcc aaaaaatcca | 480 |
| ccaaaaaaac caaagatga ttaccatttt gaagtgttca cttcgttcc ctgtagtata | 540 |
| tgtggcaaca accaactttg caaatccatc tgcaaaacaa taccaagcaa caaaccaaag | 600 |
| aaaaaaccaa ccatcaaacc cacaaacaaa ccaaccacca aaccacaaa caaagagac | 660 |
| ccaaaaacac tagccaaaac gctgaaaaaa gaaaacacca caacccaac aaaaaaacca | 720 |
| accctcaaga ccacagaaag agacaccagc actccacaat ccaccgtgct cgacacaacc | 780 |
| acatcaaaac acacaatcca acagcaatcc ctccactcaa ccaccccga aaacacaccc | 840 |
| aactccacac aaatacccac agcatccgag ccctccacat caaattccac ccaaaaaatc | 900 |
| tagtcacatg cttagttatt c | 921 |

<210> SEQ ID NO 57
<211> LENGTH: 315
<212> TYPE: PRT
<213> ORGANISM: Human respiratory syncytial virus

<400> SEQUENCE: 57

Met Ser Lys Asn Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Lys
                20                  25                  30

Leu Asn Leu Lys Ser Ile Ala Gln Ile Ala Leu Ser Val Leu Ala Met
            35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Ser Pro
                85                  90                  95

Glu Arg Val Ser Pro Ser Lys Gln Pro Thr Thr Thr Pro Pro Ile His
            100                 105                 110

Thr Asn Ser Ala Thr Ile Ser Pro Asn Thr Lys Ser Glu Thr His His
        115                 120                 125

Thr Thr Ala Gln Thr Lys Gly Arg Thr Thr Thr Pro Thr Gln Asn Asn
    130                 135                 140

Lys Pro Ser Thr Lys Pro Arg Pro Lys Asn Pro Pro Lys Lys Pro Lys
145                 150                 155                 160

```
Asp Asp Tyr His Phe Glu Val Phe Asn Phe Val Pro Cys Ser Ile Cys
            165                 170                 175

Gly Asn Asn Gln Leu Cys Lys Ser Ile Cys Lys Thr Ile Pro Ser Asn
                180                 185                 190

Lys Pro Lys Lys Lys Pro Thr Ile Lys Pro Thr Asn Lys Pro Pro Thr
                195                 200                 205

Lys Thr Thr Asn Lys Arg Asp Pro Lys Thr Leu Ala Lys Thr Leu Lys
            210                 215                 220

Lys Glu Thr Thr Ile Asn Pro Thr Lys Lys Pro Thr Pro Lys Thr Thr
225                 230                 235                 240

Glu Gly Asp Thr Ser Thr Ser Gln Ser Thr Val Leu Asp Thr Thr Thr
                245                 250                 255

Ser Lys His Thr Glu Arg Asp Thr Ser Thr Ser Gln Ser Thr Val Leu
            260                 265                 270

Asp Thr Thr Thr Ser Lys His Thr Ile Gln Gln Gln Ser Leu Tyr Ser
                275                 280                 285

Thr Thr Pro Glu Asn Thr Pro Asn Ser Thr Gln Thr Pro Thr Ala Ser
    290                 295                 300

Glu Pro Ser Thr Ser Asn Ser Thr Gln Lys Leu
305                 310                 315
```

<210> SEQ ID NO 58
<211> LENGTH: 981
<212> TYPE: DNA
<213> ORGANISM: Human respiratory syncytial virus

<400> SEQUENCE: 58

```
ggggcaaatg caaccatgtc caaaaacaag aatcaacgca ctgccaggac tctagaaaag     60
acctgggata ctcttaatca tctaattgta atatcctctt gtttatacaa attaaattta    120
aaatctatag cacaaatagc actatcagtt ttggcaatga taatctcaac ctctctcata    180
attgcagcca taatattcat catctctgcc aatcacaaag ttacactaac aactgtcaca    240
gttcaaacaa taaaaaacca cactgagaaa acatcacca cttaccttac tcaagtctca    300
ccagaaaggg ttagcccatc caaacaaccc acaaccacac caccaatcca cacaaactca    360
gccacaatat cacctaatac aaaatcagaa acacaccata acagcacaa accaaaggc     420
agaaccacca ctccaacaca gaacaacaag ccaagcacaa aaccacgtcc aaaaaatcca    480
ccaaaaaaac caaagatga ttaccatttt gaagtattca acttcgttcc ctgtagtata    540
tgtggcaaca atcaactctg caatccatt tgcaaaacaa taccaagcaa taaaccaaag    600
aaaaaaccaa ccataaaacc cacaaacaaa ccacccacca aaaccacaaa caaagagac    660
ccaaaaactc tagccaaaac actgaaaaaa gaaactacca tcaacccaac aaaaaaacca    720
acccccaaga ccacagaagg agacaccagc acctcacagt ccactgtgct cgacacaacc    780
acatcaaagc acagaaaag agacaccagc acctcacaat ccactgtgct cgacacaacc    840
acatcaaaac acacaatcca acagcaatcc ctctactcaa ccaccctga aaacacaccc    900
aactccacac aaacacccac agcatccgag ccctccacat caaattccac ccaaaaactc    960
tagtcatatg cttagttatt c                                              981
```

<210> SEQ ID NO 59
<211> LENGTH: 574
<212> TYPE: PRT
<213> ORGANISM: Human respiratory syncytial virus

<400> SEQUENCE: 59

-continued

```
Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Ala Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu His Leu Lys Asn Tyr Ile Asp Lys Gln Phe Leu Pro Ile Val Asn
        195                 200                 205

Lys Gln Ser Cys Ser Ile Ser Asn Ile Ala Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Met Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430
```

```
Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Ser
            565                 570

<210> SEQ ID NO 60
<211> LENGTH: 1899
<212> TYPE: DNA
<213> ORGANISM: Human respiratory syncytial virus

<400> SEQUENCE: 60
cgcgcaaata acaatggagt tgccaatcct caaaacaaat gctattacca caatccttgc      60
tgcagtcaca ctctgtttcg cttccagtca aacatcact gaagaatttt atcaatcaac      120
atgcagtgca gttagcaaag ctatcttag tgctctaaga actggttggt atactagtgt      180
tataactata gaattaagta atattaaaga aaataagtgt aatggaacag acgccaaggc      240
aaaattgata aaacaagaat tagataaata taaaaatgct gtaacagaat tgcagttgct      300
catgcaaagt actccagcag ccaacaatcg agccagaaga gaactaccaa ggttatgaa      360 ttatacactc aacaatacca aaaacaccaa tgtaacatta agcaagaaaa ggaaaagaag      420
atttcttggt tttttgttag tgttggatc tgcaatcgcc agtggcattg ccgtatccaa      480
ggtcctacac ctagaagggg aagtgaacaa atcaaaagt gctctactat ccacaaacaa      540
ggctgtagtc agcttatcaa atggagtcag tgtttaacc agcaaagtgt acatctcaa      600 aaactatata gataaacagt tcttaccat tgtgaacaag caaagctgca gcatatcaaa      660
cattgcgact gtgatagagt ccaacaaaa gaacaacaga ctactagaga ttaccaggga      720
atttagtgtt aatgcaggcg taactacacc tgtaagtact tatatgttaa ctaatagtga      780
attattatca ttaatcaatg atatgcctat aacaaatgat cagaaaagt taatgtccaa      840 caatgtccaa atagttagac agcaaagtta ctctatcatg tccataataa ggaggaagt      900 cttagcatat gtagtacaat taccactata tggtgtaatg gatacacctt gttggaaact      960
gcacacatcc cctctatgta aaccaacac aaaggaaggg tccaacatct gcttaacaag      1020
aaccgacaga ggatggtact gtgacaatgc aggatcagta tcttctctcc cacaagctga     1080
aacatgtaaa gttcaatcga atcgggtatt ttgtgacaca atgaacagtt aacattacc      1140 aagtgaggta atctctgca acattgacat attcaacccc aaatatgatt gtaaaattat      1200
gacttcaaaa acagatgtaa gcagctccgt tatcacatct ctaggagcca ttgtgtcatg      1260
ctatggcaaa actaaatgta cagcatccaa taaaaatcgt gggatcataa agacattttc      1320
```

```
taacgggtgt gattatgtat caaataaggg ggtggatact gtgtctgtag gtaatacatt   1380
atattatgta ataagcaag aaggcaaaag tctctatgta aaaggtgaac caataataaa    1440
tttctatgac ccattagtgt tcccctctga tgaatttgat gcatcaatat ctcaagtcaa   1500
tgagaagatt aaccagagtc tagcatttat tcgtaaatca gatgaattat tacataatgt   1560
aaatgctggt aaatccacca ttaatatcat gataactact ataattatag tgattatagt   1620
aatattgtta tcattaattg cagttggact gcttctatac tgcaaggcca gaagcacacc   1680
agtcacacta agtaaggatc aactgagtgg tataaataat attgcattta gtagctgaat   1740
aaaaatagca cttaatcata ttcttacaat ggttcactat ctgaccatag ataacccatc   1800
tatcattgga ttttcttaaa atttgaactt catcacaact ttcatctata aaccatctca   1860
cttacactat ttaagtagat tcctagttta tagttatat                         1899

<210> SEQ ID NO 61
<211> LENGTH: 574
<212> TYPE: PRT
<213> ORGANISM: Human respiratory syncytial virus

<400> SEQUENCE: 61

Met Glu Leu Pro Ile Leu Lys Ala Asn Ala Ile Thr Th

```
                    275                 280                 285
Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 62
<211> LENGTH: 1864
<212> TYPE: DNA
<213> ORGANISM: Human respiratory syncytial virus

<400> SEQUENCE: 62
taacaatgga gttgccaatc ctcaaagcaa atgcaattac cacaatcctc gctgcagtca      60
cattttgctt tgcttctagt caaaacatca ctgaagaatt ttatcaatca acatgcagtg     120
cagttagcaa aggctatctt agtgctctaa gaactggttg gtatactagt gttataacta     180
tagaattaag taatatcaag gaaaataagt gtaatggaac agatgctaag gtaaaattga     240
tgaaacaaga attagataaa tataaaaatg ctgtaacaga attgcagttg ctcatgcaaa     300
gcacaccagc agcaaacaat cgagccagaa gagaactacc aaggtttatg aattatacac     360
tcaacaatac caaaaaaacc aatgtaacat taagcaagaa aaggaaaaga agatttcttg     420
gttttttgtt aggtgttgga tctgcaatcg ccagtggcat tgctgtatct aaggtcctgc     480
```

-continued

```
acttagaagg agaagtgaac aagatcaaaa gtgctctact atccacaaac aaggccgtag    540
tcagcttatc aaatggagtt agtgtcttaa ccagcaaagt gttagacctc aaaaactata    600
tagataaaca attgttacct attgtgaata agcaaagctg cagaatatca aatatagaaa    660
ctgtgataga gttccaacaa agaacaaca gactactaga gattaccagg gaatttagtg    720
ttaatgcagg tgtaactaca cctgtaagca cttacatgtt aactaatagt gaattattgt    780
cattaatcaa tgtatatgcct ataacaaatg atcagaaaaa gttaatgtcc aacaatgttc    840
aaatagttag acagcaaagt tactctatca tgtccataat aaaagaggaa gtcttagcat    900
atgtagtaca attccacta tatggtgtga tagatacacc ttgttggaaa ttacacacat    960
cccctctatg tacaaccaac acaaaagaag ggtcaaacat ctgtttaaca agaactgaca   1020
gaggatggta ctgtgacaat gcaggatcag tatctttctt cccacaagct gaaacatgta   1080
aagttcaatc gaatcgagta ttttgtgaca caatgaacag tttaacatta ccaagtgaag   1140
taaatctctg caatgttgac atattcaatc ccaaatatga ttgtaaaatt atgacttcaa   1200
aaacagatgt aagcagctcc gttatcacat ctctaggagc cattgtgtca tgctatggca   1260
aaactaaatg tacagcatcc aataaaaatc gtggaatcat aaagacattt tctaacgggt   1320
gtgattatgt atcaaataaa ggggtggaca ctgtgtctgt aggtaacaca ttatattatg   1380
taaataagca agaaggcaaa agtctctatg taaaaggtga accaataata aatttctatg   1440
acccattagt attcccctct gatgaatttg atgcatcaat atctcaagtc aatgagaaga   1500
ttaaccagag tttagcattt attcgtaaat ccgatgaatt attacataat gtaaatgctg   1560
gtaaatcaac cacaaatatc atgataacta ctataattat agtgattata gtaatattgt   1620
tatcattaat tgctgttgga ctgctcctat actgtaaggc cagaagcaca ccagtcacac   1680
taagcaagga tcaactgagt ggtataaata atattgcatt tagtaactga ataaaaatag   1740
cacctaatca tgttcttaca atggtttact atctgctcat agacaaccca tctatcattg   1800
gattttctta aaatctgaac ttcatcgaaa ctcttatcta taaaccatct cacttacact   1860
attt                                                                 1864
```

<210> SEQ ID NO 63
<211> LENGTH: 538
<212> TYPE: PRT
<213> ORGANISM: Turkey rhinotracheitis virus

<400> SEQUENCE: 63

Met Asp Val Arg Ile Cys Leu Leu Phe Leu Ile Ser Asn Pro Ser
1               5                   10                  15

Ser Cys Ile Gln Glu Thr Tyr Asn Glu Glu Ser Cys Ser Thr Val Thr
            20                  25                  30

Arg Gly Tyr Lys Ser Val Leu Arg Thr Gly Trp Tyr Thr Asn Val Phe
        35                  40                  45

Asn Leu Glu Ile Gly Asn Val Glu Asn Ile Thr Cys Asn Asp Gly Pro
    50                  55                  60

Ser Leu Ile Asp Thr Glu Leu Val Leu Thr Lys Asn Ala Leu Arg Glu
65                  70                  75                  80

Leu Lys Thr Val Ser Ala Asp Gln Val Ala Lys Glu Ser Arg Leu Ser
                85                  90                  95

Ser Pro Arg Arg Arg Arg Phe Val Leu Gly Ala Ile Ala Leu Gly Val
            100                 105                 110

Ala Thr Ala Ala Ala Val Thr Ala Gly Val Ala Leu Ala Lys Thr Ile
        115                 120                 125

```
Arg Leu Glu Gly Glu Val Lys Ala Ile Lys Asn Ala Leu Arg Asn Thr
    130                 135                 140

Asn Glu Ala Val Ser Thr Leu Gly Asn Gly Val Arg Val Leu Ala Thr
145                 150                 155                 160

Ala Val Asn Asp Leu Lys Glu Phe Ile Ser Lys Lys Leu Thr Pro Ala
                165                 170                 175

Ile Asn Gln Asn Lys Cys Asn Ile Ala Asp Ile Lys Met Ala Ile Ser
                180                 185                 190

Phe Gly Gln Asn Asn Arg Arg Phe Leu Asn Val Val Arg Gln Phe Ser
            195                 200                 205

Asp Ser Ala Gly Ile Thr Ser Ala Val Ser Leu Asp Leu Met Thr Asp
    210                 215                 220

Asp Glu Leu Val Arg Ala Ile Asn Arg Met Pro Thr Ser Ser Gly Gln
225                 230                 235                 240

Ile Ser Leu Met Leu Asn Asn Arg Ala Met Val Arg Arg Lys Gly Phe
                245                 250                 255

Gly Ile Leu Ile Gly Val Tyr Asp Gly Thr Val Val Tyr Met Val Gln
                260                 265                 270

Leu Pro Ile Phe Gly Val Ile Glu Thr Pro Cys Trp Arg Val Val Ala
            275                 280                 285

Ala Pro Leu Cys Arg Lys Glu Lys Gly Asn Tyr Ala Cys Ile Leu Arg
    290                 295                 300

Glu Asp Gln Gly Trp Tyr Cys Thr Asn Ala Gly Ser Thr Ala Tyr Tyr
305                 310                 315                 320

Pro Asn Lys Asp Asp Cys Glu Val Arg Asp Asp Tyr Val Phe Cys Asp
                325                 330                 335

Thr Ala Ala Gly Ile Asn Val Ala Leu Glu Val Glu Gln Cys Asn Tyr
                340                 345                 350

Asn Ile Ser Thr Ser Lys Tyr Pro Cys Lys Val Ser Thr Gly Arg His
            355                 360                 365

Pro Val Ser Met Val Ala Leu Thr Pro Leu Gly Gly Leu Val Ser Cys
    370                 375                 380

Tyr Glu Ser Val Ser Cys Ser Ile Gly Ser Asn Lys Val Gly Ile Ile
385                 390                 395                 400

Lys Gln Leu Gly Lys Gly Cys Thr His Ile Pro Asn Asn Glu Ala Asp
                405                 410                 415

Thr Ile Thr Ile Asp Asn Thr Val Tyr Gln Leu Ser Lys Val Val Gly
                420                 425                 430

Glu Gln Arg Thr Ile Lys Gly Ala Pro Val Val Asn Asn Phe Asn Pro
            435                 440                 445

Ile Leu Phe Pro Glu Asp Gln Phe Asn Val Ala Leu Asp Gln Val Phe
    450                 455                 460

Glu Ser Ile Asp Arg Ser Gln Asp Leu Ile Asp Lys Ser Asn Asp Leu
465                 470                 475                 480

Leu Gly Ala Asp Ala Lys Ser Lys Ala Gly Ile Ala Ile Ala Ile Val
                485                 490                 495

Val Leu Val Ile Leu Gly Ile Phe Phe Leu Leu Ala Val Ile Tyr Tyr
                500                 505                 510

Cys Ser Arg Val Arg Lys Thr Lys Pro Lys His Asp Tyr Pro Ala Thr
            515                 520                 525

Thr Gly His Ser Ser Met Ala Tyr Val Ser
    530                 535

<210> SEQ ID NO 64
```

```
<211> LENGTH: 1636
<212> TYPE: DNA
<213> ORGANISM: Turkey rhinotracheitis virus

<400> SEQUENCE: 64
gggacaagta ggatggatgt aagaatctgt ctcctattgt tccttatatc taatcctagt      60
agctgcatac aagaaacata caatgaagaa tcctgcagta ctgtaactag aggttataag     120
agtgtgttaa ggacagggtg gtatacgaat gtatttaacc tcgaaatagg gaatgttgag     180
aacatcactt gcaatgatgg acccagccta attgacactg agttagtact cacaaagaat     240
gctttgaggg agctcaaaac agtgtcagct gatcaagtgg ctaaggaaag cagactatcc     300
tcacccagga gacgtagatt tgtactgggt gcaatagcac ttggtgttgc gacagctgct     360
gccgtaacag ctggtgtagc acttgcaaag acaattgat tagagggaga ggtgaaggca      420
attaagaatg ccctccggaa cacaaatgag gcagtatcca cattagggaa tggtgtgagg     480
gtactagcaa ctgcagtcaa tgacctcaaa gaatttataa gtaaaaaatt gactcctgct     540
attaaccaga acaaatgcaa tatagcagat ataaagatgg caattagttt tggccaaaat     600
aacagaaggt tcctgaatgt ggtgaggcaa ttctctgata gtgcaggtat cacatcagct     660
gtgtctcttg atttaatgac agatgatgaa cttgttagag caattaacag aatgccaact     720
tcatcaggac agattagttt gatgttgaac aatcgtgcca tggttagaag gaaggggttt     780
ggtatattga ttggtgttta tgatggaacg gtcgtttata tggtacaact gcccatattc     840
ggcgtgattg agacaccttg ttggagggtg gtggcagcac cactctgtag gaaagagaaa     900
ggcaattatg cttgtatact gagagaagat caagggtggt actgtacaaa tgctggctct     960
acagcttatt atcctaataa agatgattgt gaggtaaggg atgattatgt attttgtgac    1020
acagcagctg gcattaatgt ggccctagaa gttgaacagt gcaactataa catatcgact    1080
tctaaatacc catgcaaagt cagcacaggt agacaccctg tcagtatggt agccttaacc    1140
cccctagggg gtctagtgtc ttgttatgag agtgtaagtt gctccatagg tagcaataaa    1200
gtagggataa taaaacagct aggcaaaggg tgcacccaca ttcccaacaa cgaagctgac    1260
acgataacca ttgataacac tgtgtaccaa ttgagcaagg ttgtaggcga acagaggacc    1320
ataaaaggag ctccagttgt gaacaatttt aacccaatat tattccctga ggatcagttc    1380
aatgttgcac ttgaccaagt atttgagagt atagatagat ctcaggactt aatagataag    1440
tctaacgact tgctaggtgc agatgccaag agcaaggctg gaattgctat agcaatagta    1500
gtgctagtca ttctaggaat cttctttta cttgcagtga tatattactg ttccagagtc    1560
cggaagacca aaccaaagca tgattacccg gccacgacag gtcatagcag catggcttat    1620
gtcagttaag ttattt                                                    1636

<210> SEQ ID NO 65
<211> LENGTH: 256
<212> TYPE: PRT
<213> ORGANISM: Ovine respiratory syncytial virus

<400> SEQUENCE: 65

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Ile Ser Ala Asp Leu Leu
        35                  40                  45

Ile Lys Glu Leu Ile Asn Val Asn Ile Leu Val Arg Gln Ile Ser Thr
```

```
                    50                  55                  60
Leu Lys Gly Pro Ser Leu Lys Ile Met Ile Asn Ser Arg Ser Ala Val
 65                  70                  75                  80

Leu Ala Gln Met Pro Asn Lys Phe Thr Ile Ser Ala Asn Val Ser Leu
                 85                  90                  95

Asp Glu Arg Ser Lys Leu Ala Tyr Asp Ile Thr Thr Pro Cys Glu Ile
            100                 105                 110

Lys Ala Cys Ser Leu Thr Cys Leu Lys Val Lys Asn Met Leu Thr Thr
            115                 120                 125

Val Lys Asp Leu Thr Met Lys Thr Phe Asn Pro Thr His Glu Ile Ile
        130                 135                 140

Ala Leu Cys Glu Phe Glu Asn Ile Met Thr Ser Lys Lys Val Val Ile
145                 150                 155                 160

Pro Thr Phe Leu Arg Ser Ile Asn Val Lys Ala Lys Asp Leu Asp Ser
                165                 170                 175

Leu Glu Asn Ile Ala Thr Thr Glu Phe Lys Asn Ala Ile Thr Asn Ala
            180                 185                 190

Lys Ile Ile Pro Tyr Ala Gly Leu Val Leu Val Ile Thr Val Thr Asp
            195                 200                 205

Asn Lys Gly Ala Phe Lys Tyr Ile Lys Pro Gln Ser Gln Phe Ile Val
        210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ser Ile Lys Pro Ile Glu Asp
                245                 250                 255

<210> SEQ ID NO 66
<211> LENGTH: 948
<212> TYPE: DNA
<213> ORGANISM: Ovine respiratory syncytial virus

<400> SEQUENCE: 66
ggggcaaata tggagacata cgtgaacaaa ctccatgaag ggtcaacata cacagctgct      60
gtccaataca atgttctaga aaaggatgat gatcctgcat ctctcacgat atgggttcct     120
atgtttcaat catccatttc tgctgactta ctcataaagg agttaatcaa tgtgaacata     180
ttagtacgac aaatttctac tctgaaaggc ccatcattaa aaattatgat aaactctaga     240
agtgctgtac tagctcaaat gcccaacaag tttactataa gtgcaaatgt gtcattggat     300
gaacggagca agttggcata tgacataacc accccttgtg agatcaaagc ttgcagtttg     360
acatgcttaa aagtaaaaaa tatgctcact actgtaaaag atcttactat gaaaacattc     420
aatcccactc atgaaatcat tgcactgtgt gaatttgaaa atattatgac gtctaagaaa     480
gttgtaatac caactttttt aaggtctatt aatgtgaagg caaaggattt agattcactg     540
gaaaacatag ctacaacaga gtttaaaaat gccatcacta tgctaaaat tatacccttac     600 gctgggttag tgttagtcat taccgtaact gacaacaaag gagcatttaa gtatatcaag     660
ccacaaagcc aatttatagt tgatcttggt gcatatcttg aaaagagag catatattat     720 gtaactacaa attggaaaca cacagccact agattctcca tcaaacctat agaagattaa     780
atcctaaaca aattatcttg ccaaaataga acactctatt aagaacctac aaaacaccat     840
tgaaatcaaa tcctattgat actccattga acatcactgt cacacattcc caatctggtc     900
aattcacttg atcatctatt ctgttaatta tacctctatt agataaat                  948

<210> SEQ ID NO 67
```

```
<211> LENGTH: 186
<212> TYPE: PRT
<213> ORGANISM: Ovine respiratory syncytial virus

<400> SEQUENCE: 67

Met Ser Arg Arg Asn Pro Cys Lys Tyr Glu Ile Arg Gly His Cys Leu
1               5                   10                  15

Asn Gly Lys Lys Cys His Phe Ser His Asn Tyr Phe Glu Trp Pro Pro
            20                  25                  30

His Ala Leu Leu Val Arg Gln Asn Phe Met Leu Asn Lys Ile Leu Lys
        35                  40                  45

Ser Met Asp Arg Ser Asn Asp Thr Leu Ser Glu Ile Ser Gly Ala Ala
    50                  55                  60

Glu Leu Asp Arg Thr Glu Glu Tyr Ala Leu Gly Val Ile Gly Val Leu
65                  70                  75                  80

Glu Ser Tyr Leu Gly Ser Val Asn Asn Ile Thr Lys Gln Ser Ala Cys
                85                  90                  95

Val Ala Met Ser Lys Leu Leu Gly Glu Ile Asn Ser Asp Asp Ile Lys
            100                 105                 110

Gly Leu Arg Asn Lys Glu Leu Pro Thr Ser Pro Lys Ile Arg Ile Tyr
        115                 120                 125

Asn Thr Val Ile Ser Tyr Ile Asp Ser Asn Lys Arg Asn Pro Lys Gln
    130                 135                 140

Thr Ile His Leu Leu Lys Arg Leu Pro Ala Asp Val Leu Lys Lys Thr
145                 150                 155                 160

Ile Lys Asn Thr Ile Asp Ile His Asn Glu Ile Asn Val Asn Asn Pro
                165                 170                 175

Ser Asp Ile Gly Val Asn Glu Gln Asn Glu
            180                 185

<210> SEQ ID NO 68
<211> LENGTH: 964
<212> TYPE: DNA
<213> ORGANISM: Ovine respiratory syncytial virus

<400> SEQUENCE: 68
ggggcaaata tgtcacgaag aaatccctgc aaatatgaga tcaggggaca ttgcttaaat      60
ggcaaaaaat gccatttcag ccataattac tttgaatggc ctccacatgc tttattagtg     120
aggcaaaatt ttatgttaaa caagatatta agtctatgg ataggagcaa tgatactctg      180
tcagagataa gtggagctgc agaattagat agaacagagg aatatgcatt aggtgtgata     240
ggagttttag aaagttactt gggctctgtt aataacataa caaaacaatc agcttgtgtt     300
gctatgagta attattaggg tgagattaat agtgatgaca tcaaaggatt aagaaacaaa     360
gaattgccaa cttcacctaa gataagaata tataacacag ttatatcata tattgatagc     420
aacaagagaa acccaaaaca aactatacat ttacttaaaa gattgcctgc agatgtgctt     480
aagaagacca tcaagaatac aatagatatt cacaatgaaa taaatgttaa taatccaagt     540
gacataggtg ttaatgaaca aaatgaataa ttccaatatc attattttcc cagagaaata     600
tccttgtagt atatcttctt tgttaatcag agatgagaat aatgttattg tattaaatca     660
tcagaatatt tttgactgct cacagtctca acatccatgt gatatgtatc ctcaaaatca     720
tatacttgac tataccctatt ggacatcaca ggaattgatt gacgatgtac taaagattct     780
tcacctttct agcatcccca taaataggta tgtggtctat gtcttagtgc tgtagtatgt     840
aaatcattta actttcaatc attatctata tatttctcct tgtagccgga aatacaccag     900
```

```
aggacaaaat ggactcactc attcatgaaa actcaaccaa tgtatactta acagatagtt    960
attt                                                                 964
```

<210> SEQ ID NO 69
<211> LENGTH: 391
<212> TYPE: PRT
<213> ORGANISM: Ovine respiratory syncytial virus

<400> SEQUENCE: 69

```
Met Ala Leu Ser Lys Val Lys Leu Asn Asp Thr Phe Asn Lys Asp Gln
1               5                   10                  15

Leu Leu Ser Thr Ser Lys Tyr Thr Ile Gln Arg Ser Thr Gly Asp Asn
            20                  25                  30

Ile Asp Ile Pro Asn Tyr Asp Val Gln Lys His Leu Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Leu
65                  70                  75                  80

Lys Ile Leu Lys Asp Ala Gly Tyr Gln Val Lys Ala Asn Gly Val Asp
                85                  90                  95

Val Ile Thr His Arg Gln Asp Val Asn Gly Lys Glu Met Lys Phe Glu
            100                 105                 110

Val Leu Thr Leu Val Ser Leu Thr Ser Glu Val Gln Val Asn Ile Glu
        115                 120                 125

Val Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Val
145                 150                 155                 160

Leu Cys Ile Ala Ala Leu Val Ile Ala Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Ile Glu Arg Tyr Lys Gly Leu Ile Pro Lys Asp Val Ala Asn Ser
        195                 200                 205

Phe Tyr Glu Val Phe Glu Lys Tyr Pro His Tyr Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365
```

Asp Leu Thr Thr Glu Glu Leu Glu Ala Ile Lys Asn Gln Leu Asn Pro
    370                 375                 380

Lys Asp Asn Asp Val Glu Leu
385                 390

<210> SEQ ID NO 70
<211> LENGTH: 1197
<212> TYPE: DNA
<213> ORGANISM: Ovine respiratory syncytial virus

<400> SEQUENCE: 70

```
ggggcaaata caaaaatggc tctcagcaag gttaaactga atgacacctt caacaaagat      60
caattgctat caactagcaa atataccatc aacgtagca ctggagataa tattgacata     120
cctaattatg atgtacaaaa gcatctcaat aaattgtgtg gtatgctgct aataacagaa     180
gatgctaatc acaaatttac aggattaata ggtatgttat atgccatgtc tcgattggga     240
agggaagata ccctcaaaat actcaaggat gcaggttacc aagtaaaggc caatggagtt     300
gatgtaatta cacatcgaca agatgtaaat ggaaagaaa tgaaatttga agtgctaaca     360
ctagtcagct aacatcaga agttcaagtt aacattgagg tagaatcaag gaatcttac     420
aaaaagatgc taaagagat gggagaggta gctccagaat acagacatga ttctcctgat     480
tgtggtatga tagtgctatg tattgctgct ttggttatag caaattagc agcaggggat     540
agatcaggcc tcaccgcagt catcagaaga gccaacaatg tgcttaagaa tgaaatagag     600
cgatacaagg gacttatacc aaaggatgta gccaacagct tctatgaagt atttgaaaag     660
tatcctcatt atatagacgt atttgtacat tttggaattg ctcagtcctc aacaagagga     720
ggtagtaggg tagaggggat ctttgcaggg ttattcatga atgcgtatgg agcaggtcaa     780
gtaatgttaa gatggggtgt attagccaaa tcagtcaaga atatcatgct tggtcatgcc     840
agtgtgcaag ctgaaatgga acaagttgta gaagtctatg aatatgcaca aaaattagga     900
ggagaagcag gtttctacca catattaaac aacccaaaag catcattatt gtcccttaca     960
cagtttccta acttctccag tgtagtccta ggtaatgctg ctggtttggg aataatgggt    1020
gagtatagag gtacacctag gaatcaggat ttatatgatg ctgccaaagc atatgcagaa    1080
caactgaaag agaatggagt catcaattac agtgtattag atctaactac agaggaatta    1140
gaggcaatca agaaccagct aaatcccaag gataatgatg tggaactgtg agttaat      1197
```

<210> SEQ ID NO 71
<211> LENGTH: 467
<212> TYPE: PRT
<213> ORGANISM: Human respiratory syncytial virus

<400> SEQUENCE: 71

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
                20                  25                  30

Ile Asp Thr Pro Asn Tyr Asp Val Gln Lys His Ile Asn Lys Leu Cys
            35                  40                  45

Gly Met Leu Leu Ile Thr Glu Asp Ala Asn His Lys Phe Thr Gly Leu
        50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
            115                 120                 125

Ile Glu Ser Arg Lys Ser Tyr Lys Lys Met Leu Lys Glu Met Gly Glu
            130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
                180                 185                 190

Glu Met Lys Arg Tyr Lys Gly Leu Leu Pro Lys Asp Ile Ala Asn Ser
            195                 200                 205

Phe Tyr Glu Val Phe Glu Lys His Pro His Phe Ile Asp Val Phe Val
            210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
            275                 280                 285

Glu Tyr Ala Gln Lys Leu Gly Gly Glu Ala Gly Phe Tyr His Ile Leu
            290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
            355                 360                 365

Asp Leu Thr Ala Glu Glu Leu Thr Leu Lys Thr Thr Lys Lys Asp Pro
            370                 375                 380

Lys Pro Gln Thr Thr Lys Ser Lys Glu Val Pro Thr Thr Lys Pro Thr
385                 390                 395                 400

Glu Glu Pro Thr Ile Asn Thr Thr Lys Thr Asn Ile Ile Thr Thr Leu
                405                 410                 415

Leu Thr Ser Asn Thr Thr Gly Asn Pro Glu Leu Thr Ser Gln Met Glu
            420                 425                 430

Thr Phe His Ser Thr Ser Ser Glu Gly Asn Pro Ser Pro Ser Gln Val
            435                 440                 445

Ser Thr Thr Ser Glu Tyr Pro Ser Gln Pro Ser Ser Pro Pro Asn Thr
            450                 455                 460

Pro Arg Gln
465

<210> SEQ ID NO 72
<211> LENGTH: 1421
<212> TYPE: DNA
<213> ORGANISM: Human respiratory syncytial virus

<400> SEQUENCE: 72

```
caaatacaaa gatggctctt agcaaagtca agttgaatga tacactcaac aaagatcaac     60
ttctgtcatc cagcaaatac accatccaac ggagcacagg agatagtatt gatactccta    120
attatgatgt gcagaaacac atcaataagt tatgtggcat gttattaatc acagaagatg    180
ctaatcataa attcactggg ttaataggta tgttatatgc gatgtctagg ttaggaagag    240
aagacaccat aaaaatactc agagatgcgg gatatcatgt aaaagcaaat ggagtagatg    300
taacaacaca tcgtcaagac attaatggaa agaaatgaa atttgaagtg ttaacattgg    360
caagcttaac aactgaaatt caatcaaca ttgagataga atctagaaaa tcctacaaaa    420
aaatgctaaa agaaatggga gaggtagctc cagaatacag gcatgactct cctgattgtg    480
ggatgataat attatgtata gcagcattag taataactaa attagcagca ggggacagat    540
ctggtcttac agccgtgatt aggagagcta ataatgtcct aaaaaatgaa atgaaacgtt    600
acaaaggctt actacccaag gacatagcca acagcttcta tgaagtgttt gaaaaacatc    660
cccactttat agatgttttt gttcattttg gtatagcaca atcttctacc agaggtggca    720
gtagagttga agggattttt gcaggattgt ttatgaatgc ctatggtgca gggcaagtga    780
tgttacggtg gggagtctta gcaaaatcag ttaaaaatat tatgttagga catgctagtg    840
tgcaagcaga aatggaacaa gttgttgagg tttatgaata tgcccaaaaa ttgggtggtg    900
aagcaggatt ctaccatata ttgaacaacc caaaagcatc attattatct ttgactcaat    960
ttcctcactt ctccagtgta gtattaggca atgctgctgg cctaggcata atgggagagt   1020
acagaggtac accgaggaat caagatctat atgatgcagc aaaggcatat gctgaacaac   1080
tcaaagaaaa tggtgtgatt aactacagtg tactagactt gacagcagaa gaactaaccc   1140
tcaagacaac caaaaagat cccaaacctc aaaccactaa atcaaggaa gtacccacca   1200
ccaagcccac agaagagcca accatcaaca ccaccaaaac aaacatcata actacactac   1260
tcacctccaa caccacagga aatccagaac tcacaagtca aatggaaacc ttccactcaa   1320
cttcctccga aggcaatcca agcccttctc aagtctctac aacatccgag tacccatcac   1380
aaccttcatc tccacccaac acaccacgcc agtagttact t                       1421
```

<210> SEQ ID NO 73
<211> LENGTH: 391
<212> TYPE: PRT
<213> ORGANISM: Bovine respiratory syncytial virus

<400> SEQUENCE: 73

```
Met Ala Leu Ser Lys Val Lys Leu Asn Asp Thr Phe Asn Lys Asp Gln
1               5                   10                  15

Leu Leu Ser Thr Ser Lys Tyr Thr Ile Gln Arg Ser Thr Gly Asp Asn
            20                  25                  30

Ile Asp Ile Pro Asn Tyr Asp Val Gln Lys His Leu Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Leu
65                  70                  75                  80

Lys Ile Leu Lys Asp Ala Gly Tyr Gln Val Arg Ala Asn Gly Val Asp
                85                  90                  95

Val Ile Thr His Arg Gln Asp Val Asn Gly Lys Glu Met Lys Phe Glu
            100                 105                 110

Val Leu Thr Leu Val Ser Leu Thr Ser Glu Val Gln Gly Asn Ile Glu
        115                 120                 125
```

```
Ile Glu Ser Arg Lys Ser Tyr Lys Lys Met Leu Lys Glu Met Gly Glu
    130                 135                 140
Val Ala Pro Glu Tyr Arg His Asp Phe Pro Asp Cys Gly Met Ile Val
145                 150                 155                 160
Leu Cys Val Ala Ala Leu Val Ile Thr Lys Leu Ala Ala Gly Asp Arg
                165                 170                 175
Ser Gly Leu Thr Ala Val Ile Arg Arg Ala Asn Asn Val Leu Arg Asn
            180                 185                 190
Glu Met Lys Arg Tyr Lys Gly Leu Ile Pro Lys Asp Ile Ala Asn Ser
        195                 200                 205
Phe Tyr Glu Val Phe Glu Lys Tyr Pro His Tyr Ile Asp Val Phe Val
    210                 215                 220
His Phe Gly Ile Ala Gln Ser Ser Thr Arg Gly Gly Ser Arg Val Glu
225                 230                 235                 240
Gly Ile Phe Ala Gly Leu Phe Met Asn Ala Tyr Gly Ala Gly Gln Val
                245                 250                 255
Met Leu Arg Trp Gly Val Leu Ala Lys Ser Val Lys Asn Ile Met Leu
            260                 265                 270
Gly His Ala Ser Val Gln Ala Glu Met Glu Gln Val Val Glu Val Tyr
        275                 280                 285
Glu Tyr Ala Gln Lys Leu Gly Gly Glu Ala Gly Phe Tyr His Ile Leu
    290                 295                 300
Asn Asn Pro Lys Ala Ser Leu Leu Ser Leu Thr Gln Phe Pro Asn Phe
305                 310                 315                 320
Ser Ser Val Val Leu Gly Asn Ala Ala Gly Leu Gly Ile Met Gly Glu
                325                 330                 335
Tyr Arg Gly Thr Pro Arg Asn Gln Asp Leu Tyr Asp Ala Ala Lys Ala
            340                 345                 350
Tyr Ala Glu Gln Leu Lys Glu Asn Gly Val Ile Asn Tyr Ser Val Leu
        355                 360                 365
Asp Leu Thr Thr Glu Glu Leu Glu Ala Ile Lys Asn Gln Leu Asn Pro
    370                 375                 380
Lys Asp Asn Asp Val Glu Leu
385                 390

<210> SEQ ID NO 74
<211> LENGTH: 1197
<212> TYPE: DNA
<213> ORGANISM: Bovine respiratory syncytial virus
<220> FEATURE:
<221> NAME/KEY: misc_feature
<222> LOCATION: (1)..(1)
<223> OTHER INFORMATION: n is a, c, g, or t

<400> SEQUENCE: 74
ngggcaaata caaaaatggc tcttagcaag gtcaaactaa atgacacttt caacaaggac      60
caactgttgt caaccagcaa atatactatt caacgtagta caggtgacaa cattgatata     120
cccaattacg atgtgcaaaa acatctcaat aagttgtgtg gtatgctatt aataacagaa     180
gatgccaatc ataaatttac aggactgata ggtatgttat atgctatgtc ccgattgggg     240
agagaagata cccttaaaat actcaaagat gcaggctacc aagtgagggc caatggggtt     300
gatgtgataa cacatcgaca ggatgtgaat ggaaaagaaa tgaaatttga agtgctaaca     360
ttagtcagct taacatcaga agttcaaggt aatatagaaa tagagtcaag gaagtcttac     420
aaaaagatgc taaagagat gggagaggta gctccagaat acagacatga ctttcctgat     480
```
tgtggtatga tagtgctatg tgttgctgct ttggttataa caaaattagc agcaggtgat 540
aggtcaggcc tcactgcagt cattaggaga gccaacaatg tactaaggaa tgaaatgaaa 600
cgatacaaag gactcatccc gaaagatata gccaacagct tctatgaagt atttgaaaag 660
taccctcatt acatagatgt attcgtacat tttggcattg ctcaatcctc aactagagga 720
ggtagtaggg tagaaggaat ctttgcaggg ttattcatga atgcatatgg agcaggtcaa 780
gtgatgttaa gatggggtgt gctagccaaa tcagtcaaga acattatgct tggtcatgcc 840
agcgtacaag cagaaatgga acaggttgta gaagtctatg aatatgcaca aaagttaggt 900
ggagaagctg gtttttatca catactgaac aatcctaaag catcattgtt atccttgaca 960
caattcccca acttctctag tgtagtccta ggcaatgctg caggactagg tataatgggt 1020
gagtatagag gtacaccaag aaaccaagac ttgtatgatg ctgccaaagc atatgcagaa 1080
caactaaaag agaatggggt catcaattac agtgtgttgg atctgactac agaggaatta 1140
gaggcaatca agaaccaatt gaatcccaaa gataatgatg tggaattgtg agttaat 1197

<210> SEQ ID NO 75
<211> LENGTH: 515
<212> TYPE: PRT
<213> ORGANISM: Human parainfluenza virus 3

<400> SEQUENCE: 75

Met Leu Ser Leu Phe Asp Thr Phe Asn Ala Arg Arg Gln Glu Asn Ile
1 5 10 15

Thr Lys Ser Ala Gly Gly Ala Ile Ile Pro Gly Gln Lys Asn Thr Val
20 25 30

Ser Ile Phe Ala Leu Gly Pro Thr Ile Thr Asp Asp Asn Glu Lys Met
35 40 45

Thr Leu Ala Leu Leu Phe Leu Ser His Ser Leu Asp Asn Glu Lys Gln
50 55 60

His Ala Gln Arg Ala Gly Phe Leu Val Ser Leu Leu Ser Met Ala Tyr
65 70 75 80

Ala Asn Pro Glu Leu Tyr Leu Thr Thr Asn Gly Ser Asn Ala Asp Val
85 90 95

Lys Tyr Val Ile Tyr Met Ile Glu Lys Asp Leu Lys Arg Gln Lys Tyr
100 105 110

Gly Gly Phe Val Val Lys Thr Arg Glu Met Ile Tyr Glu Lys Thr Thr
115 120 125

Glu Trp Ile Phe Gly Ser Asp Leu Asp Tyr Asp Gln Glu Thr Met Leu
130 135 140

Gln Asn Gly Arg Asn Asn Ser Thr Ile Glu Asp Leu Val His Thr Phe
145 150 155 160

Gly Tyr Pro Ser Cys Leu Gly Ala Leu Ile Ile Gln Ile Trp Ile Val
165 170 175

Leu Val Lys Ala Ile Thr Ser Ile Ser Gly Leu Arg Lys Gly Phe Phe
180 185 190

Thr Arg Leu Glu Ala Phe Arg Gln Asp Gly Thr Val Gln Ala Gly Leu
195 200 205

Val Leu Ser Gly Asp Thr Val Asp Gln Ile Gly Ser Ile Met Arg Ser
210 215 220

Gln Gln Ser Leu Val Thr Leu Met Val Glu Thr Leu Ile Thr Met Asn
225 230 235 240

Thr Ser Arg Asn Asp Leu Thr Thr Ile Glu Lys Asn Ile Gln Ile Val
245 250 255

```
Gly Asn Tyr Ile Arg Asp Ala Gly Leu Ala Ser Phe Phe Asn Thr Ile
            260                 265                 270
Arg Tyr Gly Ile Glu Thr Arg Met Ala Ala Leu Thr Leu Ser Thr Leu
        275                 280                 285
Arg Pro Asp Ile Asn Arg Leu Lys Ala Leu Met Glu Leu Tyr Leu Ser
    290                 295                 300
Lys Gly Pro Arg Ala Pro Phe Ile Cys Ile Leu Arg Asp Pro Ile His
305                 310                 315                 320
Gly Glu Phe Ala Pro Gly Asn Tyr Pro Ala Ile Trp Ser Tyr Ala Met
                325                 330                 335
Gly Val Ala Val Val Gln Asn Arg Ala Met Gln Gln Tyr Val Thr Gly
            340                 345                 350
Arg Ser Tyr Leu Asp Ile Asp Met Phe Gln Leu Gly Gln Ala Val Ala
        355                 360                 365
Arg Asp Ala Glu Ala Gln Met Ser Ser Thr Leu Glu Asp Glu Leu Gly
    370                 375                 380
Val Thr His Glu Ala Lys Glu Ser Leu Lys Arg His Ile Arg Asn Ile
385                 390                 395                 400
Asn Ser Ser Glu Thr Ser Phe His Lys Pro Thr Gly Gly Ser Ala Ile
                405                 410                 415
Glu Met Ala Ile Asp Glu Glu Pro Glu Gln Phe Glu His Arg Ala Asp
            420                 425                 430
Gln Glu Gln Asp Gly Glu Pro Gln Ser Ser Ile Ile Gln Tyr Ala Trp
        435                 440                 445
Ala Glu Gly Asn Arg Ser Asp Asp Arg Thr Glu Gln Ala Thr Glu Ser
    450                 455                 460
Asp Asn Ile Lys Thr Glu Gln Gln Asn Ile Arg Asp Arg Leu Asn Lys
465                 470                 475                 480
Arg Leu Asn Asp Lys Lys Lys Gln Gly Ser Gln Pro Ser Thr Asn Pro
                485                 490                 495
Thr Asn Arg Thr Asn Gln Asp Glu Ile Asp Asp Leu Phe Asn Ala Phe
            500                 505                 510
Gly Ser Asn
        515

<210> SEQ ID NO 76
<211> LENGTH: 1642
<212> TYPE: DNA
<213> ORGANISM: Human parainfluenza virus 3

<400> SEQUENCE: 76
gaggattaaa gacattgact agaaggtcaa gaaaagggaa ctctataatt tcaaaaatgt      60
tgagcctatt tgatacattt aatgcacgta ggcaagaaaa cataacaaaa tcagctggtg     120
gagctatcat tcctggacag aaaaatactg tctccatatt tgcccttgga ccgacaataa     180
ctgatgacaa tgagaaaatg acattagctc ttctatttct atctcattca ctagataatg     240
agaaacaaca tgcacaaagg gcagggttct tggtgtcttt attgtcaatg gcttatgcca     300
atccagagct ttacctgaca caaatggaa gtaatgcaga tgttaaatat gtcatatata     360
tgattgagaa agatctaaaa cggcaaaagt atggaggatt tgtggttaag acgagagaga     420
tgatatatga aaagacaact gagtggatat ttggaagtga cctggattat gaccaggaaa     480
ctatgctgca gaacggcaga aacaattcaa cgattgaaga tcttgttcac acatttgggt     540
atccatcatg tttaggagct cttataatac agatctggat agtttggtc aaagccatca     600 ctagcatctc agggtaaga aaaggctttt tcactcgatt agaggctttc agacaagatg     660
```

```
gaacagtgca agcagggctg gtattgagcg gtgacacagt ggatcagatt gggtcaatca    720
tgcggtctca acagagcttg gtaactctta tggttgagac attaataaca atgaatacta    780
gcagaaatga cctcacaacc atagaaaaga atatacaaat tgttggtaac tacataagag    840
atgcaggtct tgcttcattc ttcaatacaa tcaggtatgg aattgagact agaatggcag    900
ctttgactct atctactctc agaccagata tcaatagatt aaaagctctg atggaattgt    960
atttatcaaa gggaccacgc gctccttta tctgtatcct cagagatcct atacatggtg   1020
agttcgcacc aggcaactat cctgccatat ggagttatgc aatggggtg gcagttgtac   1080 aaaacagagc catgcaacag tatgtgacgg aagatcata tctagatatt gatatgttcc   1140
agctgggaca agcagtagca cgtgatgctg aagctcagat gagctcaaca ctggaagatg   1200
aacttggagt gacacacgaa gccaaagaaa gcttgaaaag acatataagg aacataaaca   1260
gttcagagac atctttccac aaaccaacag gcggatcagc catagagatg caatagatg   1320 aagagccaga acaatttgaa cacagagcag atcaagaaca agatggagaa cctcaatcat   1380
ctataatcca atatgcttgg gcagaaggaa acagaagtga tgatcggacc gagcaagcta   1440
cagaatccga caatatcaag actgaacaac aaaacatcag agacagacta aacaagagac   1500
tcaacgacaa gaagaaacaa ggcagtcaac catccaccaa tcccacaaac agaacgaacc   1560
aggacgaaat agacgatctg ttcaatgcat ttggaagcaa ctaactgagt caacattttg   1620
atctaaatca ataataaata ag                                            1642

<210> SEQ ID NO 77
<211> LENGTH: 539
<212> TYPE: PRT
<213> ORGANISM: Human parainfluenza virus 3

<400> SEQUENCE: 77

Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
                20                  25                  30

Asn Ser Ser Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
```

-continued

```
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Ala Leu Gln Val Arg Leu Pro Leu Leu Thr Arg Leu
        275                 280                 285

Leu Asn Thr Gln Ile Tyr Arg Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Val Val
        355                 360                 365

Lys Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Val Leu Ile Met Ile Ile Ile Leu Phe Ile Ile Asn Val Thr Ile Ile
            500                 505                 510

Ile Ile Ala Val Lys Tyr Tyr Arg Ile Gln Lys Arg Asn Arg Val Asp
        515                 520                 525

Gln Asn Asp Lys Pro Tyr Val Leu Thr Asn Lys
    530                 535
```

<210> SEQ ID NO 78
<211> LENGTH: 1845
<212> TYPE: DNA
<213> ORGANISM: Human parainfluenza virus 3

<400> SEQUENCE: 78

```
aggacaaaag aagtcaatac caacaactat tagcagccac actcgctgga acaagaaaga      60
agggataaaa aaagtttaac agaagaaaca aaaacaaaaa gcacagaaca ccagaacaac     120
aagatcaaaa cacccaaccc actcaaaacg aaaatctcaa aagagattgg caacacaaca     180
aacactgaac atcatgccaa cctcaatact gctaattatt acaaccatga ttatggcatc     240
```

```
tttctgccaa atagatatca caaaactaca gcatgtaggt gtattggtta acagttccaa    300
agggatgaag atatcacaaa actttgaaac aagatatcta attttgagcc tcataccaaa    360
aatagaagat tctaactctt gtggtgacca acagatcaag caatacaaga ggttattgga    420
tagactgatc attcctttat atgatggatt aagattacag aaggatgtga tagtgtccaa    480
tcaagaatcc aatgaaaaca ctgacccag aacaaaacga ttctttggag gggtaattgg     540
aactattgct ctgggagtgg caacctcagc acaaattaca gcggcagttg ctctggttga    600
agccaagcag gcaagatcag acattgaaaa actcaaggaa gcaatcaggg acacaaacaa    660
agcagtgcag tcagtccaga gctccatagg aaatttgata gtagcaatta aatcggtcca    720
ggattatgtc aacaaagaaa tcgtgccatc aattgcgaga ttaggttgtg aagcagcagg    780
acttcagtta ggaattgcat aacacagca ttactcagaa ttaacaaaca tattcggtga     840
taacatagga tcgttacaag aaaagggat aaaattacaa ggtatagcat cattataccg     900
cacaaatatc acagagatat tcacaacatc aacagttgat aaatatgata tttatgatct   960
attatttaca gaatcaataa aggtgagagt tatagatgtt gacttgaatg attactcgat   1020
cgccctccaa gtcagactcc ctttattaac tagactgctg aacacccaga tttacagagt  1080
agattccata tcatataaca tccaaaacag gaatggtat atccctcttc ccagccacat   1140
catgacaaaa ggggcatttc taggtggagc agatgtcaaa gaatgtatag aagcattcag  1200
cagttatata tgcccttctg atccaggatt tgtactaaac catgaaatgg agagctgttt   1260
atcaggaaac atatcccaat gtccaagaac cgtggttaaa tcagacattg ttccaagata  1320
tgcatttgtc aatggaggag tggttgcaaa ttgtataaca accacatgta catgcaacgg  1380
tatcggtaat agaatcaatc aaccacctga tcaaggagta aaaattataa cacataaaga  1440
atgtaataca ataggtatca acggaatgct gttcaataca aataaagaag gaactcttgc  1500
attttacaca ccaaatgata taacattaaa caattctgtt gcacttgatc caattgacat   1560
atcaatcgag ctcaataagg ccaaatcaga tctagaagag tcaaaagaat ggataagaag  1620
gtcaaatcaa aaactagatt ccattggaaa ttggcatcaa tctagcacca caatcataat  1680
tgttttgata atgataatta tattgtttat aattaatgta acgataatta taattgcagt   1740
taagtattac agaattcaaa agagaaatcg agtggatcaa aatgataaac catatgtatt   1800
aacaaacaaa tgacagatct atagatcatt agatattaaa attat                   1845

<210> SEQ ID NO 79
<211> LENGTH: 539
<212> TYPE: PRT
<213> ORGANISM: Guinea pig parainfluenza virus TS-9

<400> SEQUENCE: 79

Met Pro Ile Ser Ile Leu Leu Ile Ile Thr Thr Met Ile Met Ala Ser
1               5                   10                  15

Phe Cys Gln Ile Asp Ile Thr Lys Leu His His Val Gly Val Leu Val
                20                  25                  30

Asn Ser Pro Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Arg Gln Tyr Lys Lys Leu Leu Asp Arg Leu Ile Ile
65                  70                  75                  80

Pro Leu Tyr Asp Gly Leu Arg Leu Gln Lys Asp Val Ile Val Thr Asn
                85                  90                  95
```

```
Gln Glu Ser Asn Glu Asn Thr Asp Pro Arg Thr Lys Arg Phe Phe Gly
        100                 105                 110

Gly Val Ile Gly Thr Ile Ala Leu Gly Val Ala Thr Ser Ala Gln Ile
            115                 120                 125

Thr Ala Ala Val Ala Leu Val Glu Ala Lys Gln Ala Arg Ser Asp Ile
130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
                195                 200                 205

Glu Leu Thr Asn Ile Phe Gly Asp Asn Ile Gly Ser Leu Gln Glu Lys
        210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
        290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Ile
            340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Ile Lys Ile Ile Thr His Lys Glu
                405                 410                 415

Cys Ser Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
        450                 455                 460

Ser Asp Leu Lys Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Leu Phe Ile Ile Asn Val Thr Ile Ile
            500                 505                 510

Thr Ile Ala Ile Lys Tyr Tyr Arg Ile Gln Lys Arg Asn Arg Val Asp
```

```
                 515                 520                 525
Gln Asn Asp Glu Pro Tyr Val Leu Thr Asn Lys
    530                 535

<210> SEQ ID NO 80
<211> LENGTH: 1851
<212> TYPE: DNA
<213> ORGANISM: Guinea pig parainfluenza virus TS-9

<400> SEQUENCE: 80
aggacaaaag aggtcaatac caacaactat tagcagtcat actcacaaga ataagaaaga      60
agggatttaa aaagttaaat aggagaaata aaaacaaaaa gtacagaaca ccagagcgat     120
aaaatcaaaa catctaactc actcaaaaca aaaattccaa agagaccgg  taatacaaca     180 agcattgagc acaatgccaa tttcaatact gctgattatt acaaccatga tcatggcatc     240
cttctgtcaa atagatatca caaaactaca tcatgtaggt gtattggtca atagtcccaa     300
agggatgaag atatcacaaa actttgaaac aagatatctg attttgagcc tcataccaaa     360
aatagaagac tctaactctt gtggtgacca acagatcagg caatacaaga agctattgga     420
tagactgatc atccctttat atgatggatt aagattacaa aaagatgtga tagtaactaa     480
tcaagaatcc aatgaaaaca ctgatcctag aacaaaacga ttctttggag gggtaattgg     540
aactattgct ctgggagtag caacctcagc acaaattaca gcagcagttg ctttggtcga     600
agccaagcag gcaagatcag acatcgaaaa acttaaagaa gcaattaggg acacaaataa     660
agcagtgcag tcagttcaga gctccatagg aaatctaata gtagcaatta aatcagtcca     720
ggattatgtt aacaaagaaa tcgtgccatc gattgcaagg ctaggttgtg aagcagcagg     780
acttcaatta ggaattgcat taacacagca ttactcagaa ttaacaaaca tatttggtga     840
taacatagga tcgttacaag aaaaaggaat aaaattacaa ggtatagcat cattataccg     900
cacaaacatc acagaaatat tcacaacatc aacagttgat aaatatgata tttatgatct     960
gttatttaca gaatcaataa aggtgagagt tatagatgtt gacttgaatg attactcaat    1020
caccctccaa gtcagactcc ctttattaac tagattgctg aacactcaga tctacaaagt    1080
agattccata tcatacaaca tccaaaacag agaatggtat atccctcttc ccagccacat    1140
catgacgaaa ggggcatttc taggtggagc agatgtcaaa gaatgcatag aagcattcag    1200
cagctatata tgcccttctg atccaggatt tgtattaaac catgaaatag agagctgctt    1260
atcaggaaat atatctcaat gtccaagaac cacagtcaca tcagacattg ttccaagata    1320
tgcatttgtc aatggaggag tggttgcaaa ctgtataaca accacttgta catgcaacgg    1380
aatcggtaat agaatcaatc aaccacctga tcaaggaata aaaattataa cacataaaga    1440
atgtagtaca ataggtatca acggaatgct gttcaataca aataagaag  gaactcttgc    1500 attctacaca ccaaatgata taacactaaa caattctgtt gcacttgatc caattgacat    1560
atcaatcgag ctcaacaagg ccaaatcaga tctaaaagaa tcaaaagaat ggataagaag    1620
gtcaaatcaa aaactagatt ccattggaaa ttggcatcaa tctagcacta caatcataat    1680 tatttttgata tgatcattat tattatttat aattaatgta acgataatta caattgcaat    1740
taagtattac agaattcaaa agagaaatcg agtggatcaa aatgatgagc catatgtact    1800
aacaaacaaa taacatatct acagatcatt agatattaaa attataaaaa a             1851

<210> SEQ ID NO 81
<211> LENGTH: 353
<212> TYPE: PRT
<213> ORGANISM: Human parainfluenza virus 3
```

<400> SEQUENCE: 81

```
Met Ser Ile Thr Asn Ser Ala Ile Tyr Thr Phe Pro Glu Ser Ser Phe
1               5                   10                  15
Ser Glu Asn Gly His Ile Glu Pro Leu Pro Leu Lys Val Asn Glu Gln
            20                  25                  30
Arg Lys Ala Val Pro His Ile Arg Val Ala Lys Ile Gly Asn Pro Pro
        35                  40                  45
Lys His Gly Ser Arg Tyr Leu Asp Val Phe Leu Leu Gly Phe Phe Glu
    50                  55                  60
Met Glu Arg Ile Lys Asp Lys Tyr Gly Ser Val Asn Asp Leu Asp Asn
65                  70                  75                  80
Asp Pro Gly Tyr Lys Val Cys Gly Ser Gly Leu Pro Ile Gly Leu
                85                  90                  95
Val Lys Tyr Thr Gly Asn Ile Gln Glu Leu Leu Gln Ala Ala Thr Lys
            100                 105                 110
Leu Asp Ile Glu Val Arg Arg Thr Val Lys Ala Lys Glu Met Ile Val
            115                 120                 125
Tyr Thr Val Gln Asn Ile Lys Pro Glu Leu Tyr Pro Trp Ser Ser Arg
            130                 135                 140
Leu Arg Lys Gly Met Leu Phe Asp Ala Asn Lys Val Ala Leu Ala Pro
145                 150                 155                 160
Gln Cys Leu Pro Leu Asp Arg Ser Ile Lys Phe Arg Val Ile Phe Val
                165                 170                 175
Asn Cys Thr Ala Ile Gly Ser Ile Thr Leu Phe Lys Ile Pro Lys Ser
            180                 185                 190
Met Ala Ser Leu Ser Leu Pro Ser Thr Ile Ser Ile Asn Leu Gln Val
            195                 200                 205
His Ile Lys Thr Gly Val Gln Thr Asp Ser Lys Gly Ile Val Gln Ile
            210                 215                 220
Leu Asp Glu Lys Gly Glu Lys Ser Leu Asn Phe Met Val His Leu Gly
225                 230                 235                 240
Leu Ile Lys Arg Lys Val Gly Arg Met Tyr Ser Val Glu Tyr Cys Lys
                245                 250                 255
Gln Lys Ile Glu Lys Met Arg Leu Ile Phe Ser Leu Gly Ser Val Gly
            260                 265                 270
Gly Ile Ser Leu His Val Asn Ala Thr Gly Ser Ile Ser Lys Thr Leu
            275                 280                 285
Ala Ser Gln Leu Val Phe Lys Arg Glu Ile Cys Tyr Pro Leu Met Asp
            290                 295                 300
Leu Asn Pro His Leu Asn Leu Val Ile Trp Ala Ser Ser Val Glu Ile
305                 310                 315                 320
Thr Arg Val Asp Ala Ile Phe Gln Pro Ser Leu Pro Gly Glu Phe Arg
                325                 330                 335
Tyr Tyr Pro Asn Ile Ile Ala Lys Gly Val Gly Lys Ile Lys Gln Trp
            340                 345                 350
Asn
```

<210> SEQ ID NO 82
<211> LENGTH: 1150
<212> TYPE: DNA
<213> ORGANISM: Human parainfluenza virus 3

<400> SEQUENCE: 82

```
aggattaaag aataaattaa tccttgtcca aaatgagtat aactaactct gcaatataca      60
```

```
cattcccgga gtcatcattc tctgagaatg gtcatataga accattacca ctcaaagtca    120
atgaacagag aaaagcagta cctcacatta gagttgccaa atcggaaat ccaccaaaac    180 atggatcccg gtatttggat gtcttcttac tcggcttctt cgagatggaa cgaatcaaag    240
acaaatacgg gagtgtgaat gatcttgaca atgacccggg ttacaaagtt tgtggctctg    300
gatcattacc aatcggatta gttaaataca ctgggaatat ccaggaatta ttacaggcag    360
caactaaact ggacatagaa gtgagaagaa cagtcaaagc gaaagaaatg attgtttata    420
cggtacaaaa tataaaacca gaactgtacc catggtccag tagactaaga aaaggaatgt    480
tgttcgatgc aacaaagtt gctcttgctc ctcaatgtct tccactagat aggagcataa    540
aattcagagt aatcttcgtt aattgtacgg caattggatc aataaccttg tttaaaattc    600
ccaagtcaat ggcatcacta tctctaccca gcacaatatc aatcaatctg caggtacaca    660
tcaaaacagg ggttcagact gattctaaag ggatagttca aatttttggat gagaagggtg    720 aaaaatcact gaatttcatg gtccatctcg gattgatcaa agaaaagta ggcagaatgt    780 actctgtcga gtactgtaaa cagaaaatcg agaaatgag attgatattt tctttgggat    840
cagttggagg aatcagtctt catgtcaatg caactggatc tatatcaaaa acactagcaa    900
gtcagctggt attcaaaagg gagatttgtt atcccttaat ggatctaaat ccacatctca    960
atctagttat ctgggcttca tcagtagaga ttacaagagt ggatgcaatt ttccaacctt   1020
ctttacctgg cgagttcaga tactatccta acattattgc aaaaggagtt gggaaaatca   1080
aacaatggaa ctagtaatct ctattttgat ctggatatat ctattaagcc aaagcaaata   1140
agagataatc                                                          1150

<210> SEQ ID NO 83
<211> LENGTH: 572
<212> TYPE: PRT
<213> ORGANISM: Human parainfluenza virus 3

<400> SEQUENCE: 83

Met Glu Tyr Trp Lys His Thr Asn His Gly Lys Asp Ala Gly Asn Glu
1               5                   10                  15

Pro Glu Thr Ser Thr Ala Thr Asn Gly Asn Lys Leu Thr Asn Lys Ile
            20                  25                  30

Thr Tyr Ile Leu Trp Thr Ile Thr Leu Met Leu Leu Ser Ile Ile Phe
        35                  40                  45

Ile Ile Val Leu Ile Asn Ser Ile Lys Ser Glu Lys Ala Arg Glu Ser
    50                  55                  60

Leu Leu Gln Asp Ile Asn Asn Glu Phe Met Glu Val Thr Glu Lys Ile
65                  70                  75                  80

Gln Val Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Ile Ser Asp Leu Arg Lys Phe Ile Ser Glu Ile
        115                 120                 125

Thr Ile Arg Asn Asp Asn Gln Glu Val Pro Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175
```

```
Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Ser Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Ala Ile Cys Asn Thr
            340                 345                 350

Thr Gly Cys Pro Gly Lys Thr Gln Arg Asp Cys Asn Gln Ala Ser His
        355                 360                 365

Ser Pro Trp Phe Ser Asp Arg Arg Met Val Asn Ser Ile Ile Val Val
    370                 375                 380

Asp Lys Gly Leu Asn Ser Val Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Ser Pro Val Ile Thr Tyr Ser Thr Ala
            500                 505                 510

Thr Glu Arg Val Asn Glu Leu Ala Ile Arg Asn Lys Thr Leu Ser Ala
        515                 520                 525

Gly Tyr Thr Ala Thr Ser Cys Ile Thr His Tyr Asn Lys Gly Tyr Cys
    530                 535                 540

Phe His Ile Val Glu Ile Asn His Lys Ser Leu Ile Thr Phe Gln Pro
545                 550                 555                 560

Met Leu Phe Lys Thr Glu Ile Pro Lys Ser Cys Ser
                565                 570

<210> SEQ ID NO 84
<211> LENGTH: 1719
<212> TYPE: DNA
<213> ORGANISM: Human parainfluenza virus 3
```

<400> SEQUENCE: 84
atggaatact ggaagcacac caatcacgga aaggatgctg gtaatgagcc ggagacatcc 60
acagccacta atggcaacaa gctcaccaac aagataacat atatattatg gacgataacc 120
ctgatgttat tatcaataat cttcatcata gtgctaatta attccatcaa aagtgaaaag 180
gcccgcgaat cattgctaca agacataaat aatgagttta tggaagttac agaaaagatc 240
caagtggcat cggataatac taatgatcta atacaatcag gagtaaatac aaggcttctt 300
acaattcaga gtcatgtcca gaattatata ccaatatcat tgacacaaca aatatcggat 360
cttaggaaat tcattagtga aattacaatt agaaatgata atcaagaagt gccaccacaa 420
agaataacac atgatgtggg tataaaacct ttaaatccag atgatttctg gagatgcaca 480
tctggtcttc catctttgat gaaaactcca aaaataagat taatgccggg gccaggatta 540
ttagctatgc caacgactgt tgatggctgt gtcagaactc cgtccttagt gataaatgat 600
ctgatttatg cttacacctc aaatctaatc actcgaggtt gccaagatat agggaaatca 660
tatcaagtgt tacagatagg gataataact gtaaactcag acttggtacc tgacttaaat 720
cccaggatct ctcatacctt caacataaat gacaatagaa agtcatgttc tctagcactc 780
ctaaacacag atgtatatca actgtgttca actcccaaag ttgatgaaag atcagattat 840
gcatcatcag gcatagaaga tattgtactt gatattgtca attatgatag ctcaatctca 900
acaacaagat ttaagaataa taatataagt tttgaccaac catatgcggc attataccca 960
tctgttggac cagggatata ctacaaaggc aaaataatat ttcttgggta tggaggtctt 1020
gaacatccaa taaatgagaa tgcaatctgc aacacaactg ggtgtcctgg gaaaacacag 1080
agagactgca atcaagcatc tcatagtcca tggttttcag atagaaggat ggtcaactct 1140
atcattgttg ttgacaaggg tttaaactca gttccaaaat tgaaggtatg gacgatatcg 1200
atgagacaaa attactgggg gtcagaagga agattacttc tactaggtaa caagatctac 1260
atatacacaa gatctacaag ttggcacagc aagttacaat taggaataat tgacattact 1320
gactacagtg atataaggat aaaatggaca tggcataatg tgctatcaag accaggaaac 1380
aatgaatgtc catggggaca ttcatgtccg gatggatgta taacaggagt atatactgat 1440
gcatatccac tcaatcccac aggaagcatt gtatcatctg tcatattaga ctcacaaaaa 1500
tcgagagtca gcccagtcat aacttactca acagcaaccg aaagggtaaa cgagctggcc 1560
atccgaaaca aaacactctc agctgggtat acagcaacaa gctgcattac acactataac 1620
aaaggatatt gttttcatat agtagaaata aatcataaaa gcttaatcac atttcaacct 1680
atgttgttca aaacagagat tccaaaaagc tgcagttaa 1719

<210> SEQ ID NO 85
<211> LENGTH: 572
<212> TYPE: PRT
<213> ORGANISM: Human parainfluenza virus 3

<400> SEQUENCE: 85

Met Glu Tyr Trp Lys His Thr Asn His Gly Lys Asp Val Gly Asn Glu
1 5 10 15

Leu Glu Thr Ser Thr Ala Thr His Gly Asn Lys Leu Thr Asn Lys Ile
20 25 30

Thr Tyr Ile Leu Trp Thr Ile Thr Leu Val Leu Leu Ser Ile Val Phe
35 40 45

Ile Ile Val Leu Thr Asn Ser Ile Lys Ser Glu Lys Ala Arg Glu Ser
50 55 60

```
Leu Leu Gln Asp Ile Asn Asn Glu Phe Met Glu Val Thr Glu Lys Ile
 65                  70                  75                  80

Gln Val Ala Ser Asp Asn Thr Asn Asp Leu Ile Gln Ser Gly Val Asn
             85                  90                  95

Thr Arg Leu Leu Thr Ile Gln Ser His Val Gln Asn Tyr Ile Pro Ile
                100                 105                 110

Ser Leu Thr Gln Gln Ile Ser Asp Leu Arg Lys Phe Ile Ser Glu Ile
            115                 120                 125

Thr Ile Arg Asn Asp Asn Gln Glu Val Pro Gln Arg Ile Thr His
130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
                180                 185                 190

Thr Pro Ser Leu Val Ile Asn Asp Leu Ile Tyr Ala Tyr Thr Ser Asn
            195                 200                 205

Leu Ile Thr Arg Gly Cys Gln Asp Ile Gly Lys Ser Tyr Gln Val Leu
        210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
                260                 265                 270

Lys Val Asp Glu Arg Ser Asp Tyr Ala Ser Ser Gly Ile Glu Asp Leu
            275                 280                 285

Val Leu Asp Ile Val Asn Tyr Asp Gly Ser Ile Ser Thr Thr Arg Phe
        290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Ala Ile Cys Asn Thr
                340                 345                 350

Thr Glu Cys Pro Gly Lys Thr Gln Arg Asp Cys Asn Gln Ala Ser His
                355                 360                 365

Ser Pro Trp Phe Ser Asp Arg Arg Met Val Asn Ser Ile Ile Val Val
370                 375                 380

Asp Lys Gly Leu Asn Ser Val Pro Lys Leu Lys Val Trp Ser Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
                420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
```

```
                    485                 490                 495
Asp Ser Gln Lys Ser Arg Val Asn Pro Val Ile Thr Tyr Ser Thr Ala
                500                 505                 510

Thr Glu Arg Val Asn Glu Leu Ala Ile Arg Asn Glu Thr Leu Ser Ala
            515                 520                 525

Gly Tyr Thr Thr Thr Ser Cys Ile Thr His Tyr Asn Lys Gly Tyr Cys
        530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570
```

<210> SEQ ID NO 86
<211> LENGTH: 1719
<212> TYPE: DNA
<213> ORGANISM: Human parainfluenza virus 3

<400> SEQUENCE: 86

```
atggaatact ggaagcacac caaccacgga aaggatgttg gtaatgagct ggaaacatcc      60
acagccactc atggcaacaa gctcaccaac aagataacat atatattatg gacgataacc     120
ctggtgttat tatcaatagt cttcatcata gtgctaacta attccatcaa aagtgaaaag     180
gcccgcgaat cattgctaca agacataaat aatgagttta tggaagttac agaaaagatc     240
caagtggcat ctgataatac taatgatcta atacagtcag gagtgaatac aaggcttctt     300
acaattcaga gtcatgtcca gaattatata ccaatatcat tgacacaaca aatatcggat     360
cttaggaaat tcattagtga aattacaatt agaaatgata tcaagaagt gccaccacaa     420
agaataacac atgatgtagg tataaaacct ttaaatccag atgatttctg agatgcacg     480
tctggtcttc catctttaat gaaaactcca aaaataagat taatgccggg cccaggatta     540
ttagctatgc caacgactgt tgatggctgt gtcagaaccc cgtccttagt gataaatgat     600
ctgatttatg cttacacctc aaatctaatt actcgaggtt gccaggatat agggaaatca     660
tatcaagtat tacagatagg gataataact gtaaactcag acttggtacc tgacttaaat     720
cctaggatct ctcatacctt caacataaat gacaatagaa agtcatgttc tctagcactc     780
ctaaatacag atgtatatca actgtgttca actccaaaag ttgatgaaag atcagattat     840
gcatcatcag gcatagaaga tcttgtactt gatattgtca attatgatgg ctcaatctca     900
acaacaagat ttaagaataa taatataagt tttgatcaac catatgcggc attatacccat    960
tctgttggac cagggatata ctacaaaggc aaaataatat ttctcgggta tggaggtctt    1020
gaacatccaa taaatgagaa tgcaatctgc aacacaactg agtgtcctgg aaaacacag    1080
agagactgca atcaggcatc tcacagtcca tggttttcag atagaaggat ggtcaactct    1140
ataattgttg ttgacaaggg tttaaactca gttccaaaat tgaaggtatg gtcgatatct    1200
atgagacaaa attactgggg gtcagaagga agattacttc tactaggtaa caagatctac    1260
atatacacaa gatctacaag ttggcacagc aagttacaat taggaataat tgacattact    1320
gactacagtg atataaggat aaaatggaca tggcataatg tgctatcaag accaggaaac    1380
aatgaatgtc catggggaca ttcatgtccg gatggatgta taacgggagt atatactgat    1440
gcatatcccc tcaatcccac aggaagcatt gtatcatctg tcatattgga ctcacaaaa    1500
tcgagagtca acccagtcat aacttactca acagcaaccg aaagggtaaa cgagctggcc    1560
atccgaaacg aaacactctc agctgggtat acaacaacaa gttgcattac acactataac    1620
aaagggtatt gttttcatat agtagaaata aatcataaaa gcttaaacac atttcaaccc    1680
```
atgttgttca aaacagagat tccaaaaagc tgcagttaa 1719

<210> SEQ ID NO 87
<211> LENGTH: 572
<212> TYPE: PRT
<213> ORGANISM: Human parainfluenza virus 3

<400> SEQUENCE: 87

Met Glu Tyr Trp Lys His Thr Asn His Gly Lys Asp Ala Gly Asn Glu
1               5                   10                  15

Leu Glu Thr Ser Met Ala Thr Asn Gly Asn Lys Leu Thr Asn Lys Ile
            20                  25                  30

Thr Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Ile Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
        355                 360                 365

```
Ser Pro Trp Phe Ser Asp Arg Arg Met Val Asn Ser Ile Ile Val Val
        370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
                420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
        450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Arg Asn Arg Thr Leu Ser Ala
        515                 520                 525

Gly Tyr Thr Thr Thr Ser Cys Ile Thr His Tyr Asn Lys Gly Tyr Cys
        530                 535                 540

Phe His Ile Val Glu Ile Asn Gln Lys Ser Leu Asn Thr Leu Gln Pro
545                 550                 555                 560

Met Leu Phe Lys Thr Glu Val Pro Lys Ser Cys Ser
                565                 570

<210> SEQ ID NO 88
<211> LENGTH: 1832
<212> TYPE: DNA
<213> ORGANISM: Human parainfluenza virus 3

<400> SEQUENCE: 88
gacaaatcca aattcgagat ggaatactgg aagcatacca atcacggaaa ggatgctggc      60
aatgagctgg agacgtccat ggctactaat ggcaacaagc tcaccaataa gataacatat     120
atattatgga caataatcct ggtgttatta tcaatagtct tcatcatagt gctaattaat     180
tccatcaaaa gtgaaaaggc tcatgaatca ttgctgcaag acataaataa tgagtttatg     240
gaaattacag aaaagatcca aatggcatcg gataatacca atgatctaat acagtcagga     300
gtgaatacaa ggcttcttac aattcagagt catgtccaga ttatatacc aatatcactg     360 acacaacaga tgtcagatct taggaaattc attagtgaaa ttacaattag aaatgataat     420
caagaagtgc tgccacaaag aataacacat gatgtgggta taaaaccttt aaatccagat     480 gattttttgga gatgcacgtc tggtcttcca tctttaatga aaactccaaa ataaggtta     540 atgccagggc cgggattatt agctatgcca acgactgttg atggctgtat cagaactccg     600
tccttagtta taaatgatct gatttatgct tatacctcaa atctaattac tcgaggttgt     660
caggatatag gaaaatcata tcaagtctta cagatagggga taataactgt aaactcagac     720
ttggtacctg acttaaatcc aggatctct catacttta acataaatga caataggaag     780
tcatgttctc tagcactcct aaatacagat gtatatcaac tgtgttcaac tcccaaagtt     840
gatgaaagat cagattatgc atcatcaggc atagaagata ttgtacttga tattgtcaat     900
tatgatggct caatctcaac aacaagattt aagaataata cataagctt tgatcaacct     960 tatgctgcac tatacccatc tgttggacca gggatatact acaaaggcaa aataatattt    1020
```

-continued

```
ctcgggtatg gaggtcttga acatccaata aatgagaatg taatctgcaa cacaactggg      1080
tgtcccggga aaacacagag agactgcaat caggcatctc atagtccatg gttttcagat      1140
aggaggatgg tcaactctat cattgttgtt gacaaaggct taaactcaat tccaaaattg      1200
aaggtatgga cgatatctat gagacagaat tactgggggt cagaaggaag gttacttcta      1260
ctaggtaaca agatctatat atatacaaga tccacaagtt ggcatagcaa gttacaatta      1320 ggataattg atattactga ttacagtgat ataaggataa aatggacatg gcataatgtg       1380
ctatcaagac caggaaacaa tgaatgtcca tggggacatt catgtccaga tggatgtata      1440
acaggagtat atactgatgc atatccactc aatcccacag ggagcattgt gtcatctgtc      1500
atattagatt cacaaaaatc gagagtgaac ccagtcataa cttactcaac agcaaccgaa      1560
agagtaaacg agctggccat ccgaaacaga acactctcag ctggatatac aacaacaagc      1620
tgcatcacac actataacaa aggatattgt tttcatatag tagaaataaa tcagaaaagc      1680
ttaaacacac ttcaacccat gttgttcaag acagaggttc caaaaagctg cagttaatca      1740
taattaaccg caatatgcat taacctatct ataatacaag tatatgataa gtaatcagca      1800
atcagacaat agacaaaagg gaaatataaa aa                                    1832
```

<210> SEQ ID NO 89
<211> LENGTH: 12
<212> TYPE: DNA
<213> ORGANISM: Artificial Sequence
<220> FEATURE:
<223> OTHER INFORMATION: Synthetic

<400> SEQUENCE: 89
gacgacgaca ag                                                            12

<210> SEQ ID NO 90
<211> LENGTH: 14
<212> TYPE: DNA
<213> ORGANISM: Artificial Sequence
<220> FEATURE:
<223> OTHER INFORMATION: Synthetic

<400> SEQUENCE: 90
gaggagaagc ccgg                                                          14

<210> SEQ ID NO 91
<211> LENGTH: 6
<212> TYPE: PRT
<213> ORGANISM: Artificial Sequence
<220> FEATURE:
<223> OTHER INFORMATION: Synthetic

<400> SEQUENCE: 91

His His His His His His
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic

<400> SEQUENCE: 92

Glu Gln Lys Leu Ile Ser Glu Glu Asp Leu
1               5                   10

```
<210> SEQ ID NO 93
<211> LENGTH: 8
<212> TYPE: PRT
<213> ORGANISM: Artificial Sequence
<220> FEATURE:
<223> OTHER INFORMATION: Synthetic

<400> SEQUENCE: 93

Asp Tyr Lys Asp Asp Asp Asp Lys
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Trp Ser His Pro Gln Phe Glu Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Tyr Pro Tyr Asp Val Pro Asp Tyr Ala
1               5

<210> SEQ ID NO 96
<211> LENGTH: 15
<212> TYPE: DNA
<213> ORGANISM: Artificial Sequence
<220> FEATURE:
<223> OTHER INFORMATION: Synthetic

<400> SEQUENCE: 96
gacgacgaca agatg                                               15

<210> SEQ ID NO 97
<211> LENGTH: 17
<212> TYPE: DNA
<213> ORGANISM: Artificial Sequence
<220> FEATURE:
<223> OTHER INFORMATION: Synthetic

<400> SEQUENCE: 97
taaccgggct tctcctc                                             17

<210> SEQ ID NO 98
<211> LENGTH: 17
<212> TYPE: DNA
<213> ORGANISM: Artificial Sequence
<220> FEATURE:
<223> OTHER INFORMATION: Synthetic

<400> SEQUENCE: 98
gaggagaagc ccggtta                                             17

<210> SEQ ID NO 99
<211> LENGTH: 15
<212> TYPE: DNA
<213> ORGANISM: Artificial Sequence
<220> FEATURE:
```

```
<223> OTHER INFORMATION: Synthetic

<400> SEQUENCE: 99
catcttgtcg tcgtc                                                        15

<210> SEQ ID NO 100
<211> LENGTH: 15
<212> TYPE: DNA
<213> ORGANISM: Artificial Sequence
<220> FEATURE:
<223> OTHER INFORMATION: Synthetic

<400> SEQUENCE: 100
ccgggcttct cctca                                                        15

<210> SEQ ID NO 101
<211> LENGTH: 16
<212> TYPE: DNA
<213> ORGANISM: Artificial Sequence
<220> FEATURE:
<223> OTHER INFORMATION: Synthetic

<400> SEQUENCE: 101
tcttgtcgtc gtcatc                                                       16

<210> SEQ ID NO 102
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(18)

<400> SEQUENCE: 102 gat gac gac gac aag atg                                                 18
Asp Asp Asp Asp Lys Met
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Construct

<400> SEQUENCE: 103

Asp Asp Asp Asp Lys Met
1               5

<210> SEQ ID NO 104
<211> LENGTH: 18
<212> TYPE: DNA
<213> ORGANISM: Artificial Sequence
<220> FEATURE:
<223> OTHER INFORMATION: Synthetic

<400> SEQUENCE: 104
taaccgggct tctcctca                                                     18

<210> SEQ ID NO 105
<211> LENGTH: 18
<212> TYPE: DNA
<213> ORGANISM: Artificial Sequence
<220> FEATURE:
<223> OTHER INFORMATION: Synthetic
```

-continued

```
<400> SEQUENCE: 105
tgaggagaag cccggtta                                                 18

<210> SEQ ID NO 106
<211> LENGTH: 18
<212> TYPE: DNA
<213> ORGANISM: Artificial Sequence
<220> FEATURE:
<223> OTHER INFORMATION: Synthetic

<400> SEQUENCE: 106
catcttgtcg tcgtcatc                                                 18

<210> SEQ ID NO 107
<211> LENGTH: 12
<212> TYPE: PRT
<213> ORGANISM: Artificial Sequence
<220> FEATURE:
<223> OTHER INFORMATION: Synthetic

<400> SEQUENCE: 107

Val Gly Val Asp Pro Lys Ser Pro Leu Val Lys Ser
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic

<400> SEQUENCE: 108

Asp Ser Gly Tyr Tyr Ala Asn Leu Phe Leu His Ile
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic

<400> SEQUENCE: 109

Val Gly Val Asp Ala Lys Ser Ala Leu Val Lys Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

Asp Ser Gly Tyr Tyr Ala Asn Leu Phe Leu His Ile
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic

<400> SEQUENCE: 111

Val Gly Val Asp Pro Lys Ser Pro Leu Val Lys Ser
1               5                   10
```

```
<210> SEQ ID NO 112
<211> LENGTH: 12
<212> TYPE: PRT
<213> ORGANISM: Artificial Sequence
<220> FEATURE:
<223> OTHER INFORMATION: Synthetic

<400> SEQUENCE: 112

Asp Ser Gly Tyr Ala Ala Asn Ala Phe Leu His Ile
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Val Gly Val Asp Pro Lys Ser Pro Leu Val Lys Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic

<400> SEQUENCE: 114

Asp Ser Gly Tyr Tyr Pro Asp Leu Phe Leu His Ile
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic

<400> SEQUENCE: 115

Val Gly Val Asp Pro Lys Ser Pro Leu Val Lys Ser
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic

<400> SEQUENCE: 116

Asp Ser Gly Tyr Pro Thr Ala Pro Phe Leu His Ile
1               5                   10

<210> SEQ ID NO 117
<211> LENGTH: 4
<212> TYPE: PRT
<213> ORGANISM: Artificial Sequence
<220> FEATURE:
<223> OTHER INFORMATION: Synthetic

<400> SEQUENCE: 117

Pro Lys Ser Pro
1
```

```
<210> SEQ ID NO 118
<211> LENGTH: 4
<212> TYPE: PRT
<213> ORGANISM: Artificial Sequence
<220> FEATURE:
<223> OTHER INFORMATION: Synthetic

<400> SEQUENCE: 118

Tyr Ala Asn Leu
1

<210> SEQ ID NO 119
<211> LENGTH: 4
<212> TYPE: PRT
<213> ORGANISM: Artificial Sequence
<220> FEATURE:
<223> OTHER INFORMATION: Synthetic

<400> SEQUENCE: 119

Tyr Pro Asp Leu
1

<210> SEQ ID NO 120
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 120

Tyr Pro Xaa Leu
1

<210> SEQ ID NO 121
<211> LENGTH: 4
<212> TYPE: PRT
<213> ORGANISM: Artificial Sequence
<220> FEATURE:
<223> OTHER INFORMATION: Synthetic

<400> SEQUENCE: 121

Tyr Arg Lys Leu
1

<210> SEQ ID NO 122
<211> LENGTH: 4
<212> TYPE: PRT
<213> ORGANISM: Artificial Sequence
<220> FEATURE:
<223> OTHER INFORMATION: Synthetic

<400> SEQUENCE: 122

Tyr Leu Asp Leu
1

<210> SEQ ID NO 123
<211> LENGTH: 4
<212> TYPE: PRT
<213> ORGANISM: Artificial Sequence
```

-continued

```
<220> FEATURE:
<223> OTHER INFORMATION: Synthetic

<400> SEQUENCE: 123

Tyr Pro Leu Leu
1
```